US012065495B2

(12) United States Patent
Burman et al.

(10) Patent No.: US 12,065,495 B2
(45) Date of Patent: Aug. 20, 2024

(54) COMPOSITIONS AND METHODS COMPRISING ANTI-NRP2 ANTIBODIES

(71) Applicant: aTyr Pharma, Inc., San Diego, CA (US)

(72) Inventors: Luke G. Burman, San Diego, CA (US); Yee Ting (Esther) Chong, San Diego, CA (US); Yanyan Geng, San Diego, CA (US); Leslie Nangle Greene, San Diego, CA (US); Kristina Hamel, San Diego, CA (US); David King, Encinitas, CA (US); Ann Menefee, San Diego, CA (US); Kaitlyn Rauch, San Diego, CA (US); Zhiwen Xu, La Jolla, CA (US); Liting Zhai, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 0 days.

(21) Appl. No.: 18/048,345

(22) Filed: Oct. 20, 2022

(65) Prior Publication Data

US 2023/0312730 A1     Oct. 5, 2023

Related U.S. Application Data

(62) Division of application No. 16/376,979, filed on Apr. 5, 2019, now Pat. No. 11,505,610.

(60) Provisional application No. 62/653,823, filed on Apr. 6, 2018.

(51) Int. Cl.
    *A61K 39/395*   (2006.01)
    *A61K 45/06*    (2006.01)
    *C07K 16/28*    (2006.01)
    *G01N 33/68*    (2006.01)

(52) U.S. Cl.
    CPC ...... *C07K 16/2863* (2013.01); *A61K 39/3955* (2013.01); *A61K 45/06* (2013.01); *G01N 33/6854* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/71* (2013.01); *C07K 2317/72* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| | | |
|---|---|---|
| 6,428,965 B1 | 8/2002 | Ginty et al. |
| 7,736,655 B2 | 6/2010 | Klagsbrun et al. |
| 8,318,163 B2 | 11/2012 | Appleton et al. |
| 8,466,264 B2 | 6/2013 | Appleton et al. |
| 8,529,905 B2 | 9/2013 | Klagsbrun et al. |
| 8,648,173 B2 | 2/2014 | Wu et al. |
| 8,722,043 B2 | 5/2014 | Borg et al. |
| 8,920,805 B2 | 12/2014 | Wu et al. |
| 8,956,622 B2 | 2/2015 | Bagnard et al. |
| 11,505,610 B2 | 11/2022 | Burman et al. |
| 11,807,687 B2 | 11/2023 | Burman et al. |
| 2002/0127227 A1 | 9/2002 | Holmes et al. |
| 2003/0045691 A1 | 3/2003 | Ono et al. |
| 2003/0088075 A1 | 5/2003 | Shitara et al. |
| 2003/0113324 A1 | 6/2003 | Alitalo et al. |
| 2004/0005647 A1 | 1/2004 | Denardo et al. |
| 2004/0028685 A1 | 2/2004 | Kinch et al. |
| 2004/0038339 A1 | 2/2004 | Kufer et al. |
| 2004/0214766 A1 | 10/2004 | Alitalo et al. |
| 2005/0064518 A1 | 3/2005 | Albone et al. |
| 2006/0280747 A1 | 12/2006 | Fuh et al. |
| 2007/0189962 A1 | 8/2007 | Pastan et al. |
| 2009/0196850 A1 | 8/2009 | Romagne et al. |
| 2010/0130904 A1 | 5/2010 | Kirber |
| 2010/0172921 A1 | 7/2010 | Wu et al. |
| 2010/0310573 A1 | 12/2010 | Nakagawa et al. |
| 2011/0064670 A1 | 3/2011 | Gogineni et al. |
| 2011/0091377 A1 | 4/2011 | Alani et al. |
| 2011/0091384 A1 | 4/2011 | Alani et al. |
| 2011/0243932 A1 | 10/2011 | Barrett et al. |
| 2012/0027779 A1 | 2/2012 | Borg et al. |
| 2012/0282637 A1 | 11/2012 | Huber et al. |
| 2013/0131319 A1 | 5/2013 | Igawa et al. |

(Continued)

FOREIGN PATENT DOCUMENTS

| | | |
|---|---|---|
| CN | 1726226 A | 1/2006 |
| CN | 101326196 A | 12/2008 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294: 151-162.*
Rudikoff et al. (1982). PNAS. 79:1979-1983.*
Alto, L. T. et al., "Semaphorins and their signaling mechanisms," Methods. Mol. Biol. 1493:1-25 (2017).

(Continued)

*Primary Examiner* — Christine J Saoud
*Assistant Examiner* — Jon M Lockard
(74) *Attorney, Agent, or Firm* — COOLEY LLP

(57) ABSTRACT

Provided are antibodies and antigen-binding fragments thereof that specifically bind to human neuropilin-2 (NRP2) polypeptides, including those that modulate binding interactions between human NRP2 and at least one NRP2 ligand, for example, human histidyl-tRNA synthetase (HRS), and which thereby modulate subsequent NRP2-mediated downstream signaling events, including related therapeutic compositions and methods for modulating NRP2 activity and treating diseases such as NRP2-associated diseases.

15 Claims, 25 Drawing Sheets

Specification includes a Sequence Listing.

(56) References Cited

U.S. PATENT DOCUMENTS

| | | |
|---|---|---|
| 2013/0266517 A1 | 10/2013 | Saldanha et al. |
| 2014/0193420 A1 | 7/2014 | Aburatani et al. |
| 2014/0234312 A1 | 8/2014 | Wu et al. |
| 2015/0030600 A1 | 1/2015 | Marks et al. |
| 2015/0218267 A1 | 8/2015 | Brodeur et al. |
| 2015/0307589 A1 | 10/2015 | Bagnard et al. |
| 2016/0000873 A1 | 1/2016 | Long et al. |
| 2016/0017041 A1 | 1/2016 | Violette et al. |
| 2016/0046711 A1 | 2/2016 | Bialucha et al. |
| 2016/0108113 A1 | 4/2016 | Ayalon et al. |
| 2016/0108131 A1 | 4/2016 | Berne et al. |
| 2016/0312300 A1 | 10/2016 | Alani et al. |
| 2017/0100456 A1 | 4/2017 | Briscoe et al. |
| 2018/0193454 A1 | 7/2018 | Rothstein et al. |
| 2019/0309076 A1 | 10/2019 | Burman et al. |
| 2021/0163606 A1 | 6/2021 | Burman et al. |

FOREIGN PATENT DOCUMENTS

| | | |
|---|---|---|
| CN | 101754771 A | 6/2010 |
| CN | 102597776 A | 7/2012 |
| CN | 102667484 A | 9/2012 |
| CN | 103459422 A | 12/2013 |
| CN | 104203268 A | 12/2014 |
| CN | 105407891 A | 3/2016 |
| EP | 1968565 B1 | 11/2015 |
| EP | 3024460 B1 | 7/2020 |
| JP | 2010527350 A | 8/2010 |
| JP | 2013507641 A | 3/2013 |
| WO | WO-9929729 A2 | 6/1999 |
| WO | WO-9929858 A1 | 6/1999 |
| WO | WO-9930157 A2 | 6/1999 |
| WO | WO-2004/035537 A2 | 4/2004 |
| WO | WO-2006057500 A1 | 6/2006 |
| WO | WO-2007020075 A1 | 2/2007 |
| WO | WO-2007056470 A2 | 5/2007 |
| WO | WO-2007095749 A1 | 8/2007 |
| WO | WO-2008143665 A1 | 11/2008 |
| WO | WO-2009043933 A1 | 4/2009 |
| WO | WO-2010102251 A2 | 9/2010 |
| WO | WO-2010119704 A1 | 10/2010 |
| WO | WO-2011032013 A1 | 3/2011 |
| WO | WO-2011047033 A2 | 4/2011 |
| WO | WO-2012069557 A1 | 5/2012 |
| WO | WO-2013106765 A1 | 7/2013 |
| WO | WO-2013116742 A1 | 8/2013 |
| WO | WO-2014105810 A1 | 7/2014 |
| WO | WO-2015136471 A1 | 9/2015 |
| WO | WO-2017205377 A2 | 11/2017 |
| WO | WO-2018102589 A2 | 6/2018 |
| WO | WO-2018195302 A1 | 10/2018 |
| WO | WO-2019075472 A1 | 4/2019 |
| WO | WO-2019086351 A1 | 5/2019 |
| WO | WO-2019195770 A1 | 10/2019 |
| WO | WO-2020200196 A1 | 10/2020 |
| WO | WO-2021058548 A1 | 4/2021 |
| WO | WO-2021067761 A1 | 4/2021 |
| WO | WO-2021202590 A1 | 10/2021 |
| WO | WO-2023063208 A1 | 4/2023 |
| WO | WO-2023076998 A1 | 5/2023 |
| WO | WO-2023245117 A2 | 12/2023 |

OTHER PUBLICATIONS

Appleton, B. A. et al., "Structural studies of neuropilin/antibody complexes provide insights into semaphorin and VEGF binding," The EMBO Journal, 26(23):4902-4912 (Nov. 2007).

Aung, N. Y. et al., "Specific neuropilins expression in alveolar macrophages among tissue-specific macrophages," PLoS ONE 11(2):e0147358 (2016).

Bannerman, P. et al., "Peripheral nerve regeneration is delayed in neuropilin 2-deficient mice," J. Neurosci. Res. 86(14):3163-3169 (2008).

Bielenberg, D. R. et al., "Increased smooth muscle contractility in mice deficient for neuropilin 2," Am. J. Path. 181(2):548-559 (2012).

Bielenberg, D. R. et al., "Neuropilins in neoplasms: Expression, regulation, and function," Exp. Cell. Res. 312:584-593 (2006).

Binch, A. L. A. et al., "Class 3 semaphorins expression and association with innervation and angiogenesis within the degenerate human intervertebral disc," Oncotarget 6(21):18338-18354 (2015).

Bogan and Thorn, "Anatomy of hot spots in protein interfaces." J Mol Biol. Jul. 3, 1998; 280(1): 1-9.

Boscolo, E. et al., " AKT hyper-phosphorylation associated with PI3K mutations in lymphatic endothelial cells from a patient with lymphatic malformation," Angiogenesis 18(2):151-162 (2015).

Cao, Y. et al., "Neuropilin-2 promotes extravasation and metastasis by interacting with endothelial 5 integrin," Cancer. Res. 73(14):4579-4590 (2013).

Casset F., et al., "A Peptide Mimetic of an Anti-cd4 Monoclonal Antibody by Rational Design," Biochemical and Biophysical Research Communications, Jul. 2003, vol. 307 (1), pp. 198-205.

Caunt, M. et al., "Blocking neuropilin-2 function inhibits tumor cell metastasis," Cancer Cell, vol. 13, No. 4, Apr. 2008, pp. 331-342.

Chen, L. et al., "131I-labeled monoclonal antibody targeting neuropilin receptor type-2 for tumor SPECT imaging," Int. J. Oncol. 50:649-659 (2017).

Chen Y., et al., "Selection and Analysis of an Optimized Anti-vegf Antibody: Crystal Structure of an Affinity-matured Fab in Complex With Antigen," Journal of Molecular Biology, Nov. 1999, vol. 293 (4), pp. 865-881.

Chong, Y. E. et al., "ATYR2810, a Neuropilin-2 antibody, selectively blocks the NRP2/VEGFR signaling axis and sensitizes aggressive cancers to chemotherapy," Jan. 2021, Retrieved from the Internet: URL: https://atyrpharma.com/wp-content/uploads/2021/05/2021-Keystone_CSC_poster_vS.pdf [retrieved on Dec. 6, 2021], 1 page.

Corliss, B. A. et al., "Macrophages: An inflammatory link between angiogenesis and lymphangiogenesis," Microcirculation 23(2):95-121 (2016).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, Sep. 2002, vol. 169, No. 6, pp. 3076-3084.

Dong, X. et al., "Elevated expression of neuropilin-2 associated with unfavorable prognosis in hepatocellular carcinoma," OncoTargets and Therapy 10:3827-3833 (2017).

Drabkin, H. A. et al., "A triad of NRP2, Dlx and p53 proteins in lung cancer metastasis," Oncotarget 8(57):96464-96465 (2017).

Dutta, S. et al., "Neuropilin-2 regulates endosomal maturation and EGFR trafficking to support cancer cell pathobiology," Cancer Res. 76(2):418-428 (2016).

Dutta, S. et al., "NRP2 transcriptionally regulates its downstream effector WDFY1," Scientific Reports 6, 23588; doi:10.1038/srep23588 (2016).

Elaimy, A. L. et al., "VEGF-neuropilin-2 signaling promotes stem-like traits in breast cancer cells by TAZ-mediated repression of the Rac GAP 2-chimaerin," Sci. Signal 11:eaao6897 (2018).

Elpek, G. O., "Neuropilins and liver," World J. Gastroent. 21(23):7065-7073 (2015).

Extended European Search Report for European Application No. 19781711.7, mailed Dec. 16, 2021, 11 pages.

Fassold, A. et al., "Soluble neuropilin-2, a nerve repellent receptor, is increased in rheumatoid arthritis synovium and aggravates sympathetic fiber repulsion and arthritis," Arthritis & Rheum. 60(10):2892-2901 (2009).

Forsyth, et al., "Deep mutational scanning of an antibody against epidermal growth factor receptor using mammalian cell display and massively parallel pyrosequencing." Mabs (Jul. 1, 2013); 5(4): 523-532. Published online May 29, 2013.

Fujita, H. et al., "Expressions of neuropilin-1, neuropilin-2 and semaphorin 3A Mrna in the rat brain after middle cerebral artery occlusion," Brain Research 914(1-2):1-14 (2001).

(56) References Cited

OTHER PUBLICATIONS

Fusco, F. et al., "Progressive bladder remodeling due to bladder outlet obstruction: a systematic review of morphological and molecular evidences in humans," BMC Urology 18:15 (2018).
Gemmill, R. M. et al., "The neuropilin 2 isoform NRP2b uniquely supports TGF-mediated progression in lung cancer," Sci. Signal. 10, eaag0528 (2017).
Goel, H. L. et al., "Enhancing integrin function by VEGF/neuropilin signaling," Cell Adhesion & Migration, 6(6):554-560 (2012).
Goel, H. L. et al., "GLI1 regulates a novel neuropilin-2/ß1 integrin based autocrine pathway that contributes to breast cancer initiation," EMBO Mol. Med. 5:488-508 (2013).
Goel, H. L. et al., "VEGF/Neuropilin-2 regulation of Bmi-1 and consequent repression of IGF-1R define a novel mechanism of aggressive prostate cancer," Cancer Discov. 2(10):906-921 (2012).
Gogineni, A. et al., "Inhibition of VEGF-C modulates distal lymphatic remodeling and secondary metastasis," PloS One 8(7):e68755 (2013).
Grandclement, C. et al., "Neuropilin-2 Expression Promotes TGF-1-Mediated Epithelial to Mesenchymal Transition in Colorectal Cancer Cells," PLoS One 6(7):e20444 (2011).
Guo, H. H. et al. (Jun. 2004), "Protein tolerance to random amino acid change," Proc Natl Acad Sci USA, vol. 101, No. 25, pp. 9205-9210. Epub Jun. 14, 2004.
Guo, H-F. et al., "Neuropilin functions as an essential cell surface receptor," J. Biol. Chem. 290(49):29120-29126 (2015).
Harding, J. et al., "Lymphangiogenesis is induced by mycobacterial granulomas via vascular endothelial growth factor receptor-3 and supports systemic T-Cell responses against mycobacterial antigen," Am. J. Path. 185(2):432-445 (2015).
Henno, A. et al., "Altered expression of angiogenesis and lymphangiogenesis markers in the uninvolved skin of plaque-type psoriasis," Br. J. Derm., 160:581-590 (2009).
Hey-Cunningham, A. J. et al., "Dysregulation of vascular endothelial growth factors and their neuropilin receptors in the eutopic endometrium of women with endometriosis," Repro. Sci. 20(11):1382-1389 (2013).
Huang, Z-L. et al., "Establishment of a bead-based duplex assay for the simultaneous quantitative detection of Neuropilin-1 and Neuropilin-2 using xMAP technology and its clinical application," J. Clin. Lab. Anal. 2019:e22850; DOI: 10.1002/jcla.22850.
Immormino, R. M. et al., "Neuropilin-2 regulates airway inflammatory responses to inhaled lipopolysaccharide," Am J Physiol Lung Cell Mol Physiol., 315(2):L202-L211 (Aug. 2018).
International Search Report and Written Opinion for International Application No. PCT/US2019/026128, mailed Aug. 12, 2019, 12 pages.
International Search Report and Written Opinion for International Application No. PCT/US2020/054017, mailed Feb. 25, 2021, 13 pages.
International Search Report and Written Opinion for International Application No. PCT/US2022/078780 dated Mar. 15, 2023, 18 pages.
Karkkainen, M. J. et al., "A model for gene therapy of human hereditary lymphedema," PNAS 98(22):12677-12682 (2001).
Karpanen, T. et al., "Functional interaction of VEGF-C and VEGF-D with neuropilin receptors," The FASEB J. 20(9):1462-1472 (2007).
Lippow, et al., "Computational design of antibody-affinity improvement beyond in vivo maturation." Nat Biotechnol. (Oct. 2007); 25(10): 1171-1176. Epub Sep. 23, 2007.
Liu, B. et al., "Identification of prognostic biomarkers by combined mRNA and miRNA expression microarray analysis in pancreatic cancer," Trans. Onc. 11(3):700-714 (2018).
Lu, Y. et al., "Identification of circulating neuropilin-1 and dose-dependent elevation following anti-neuropilin-1 antibody administration," mAbs 1(4):364-369 (2009).
Maccallum R.M., et al., "Antibody-Antigen Interactions: Contact Analysis and Binding Site Topography," Journal of Molecular Biology, Oct. 11, 1996, vol. 262, No. 5, pp. 732-745.
Makinen, T. et al., "Inhibition of lymphangiogenesis with resulting lymphedema in transgenic mice expressing soluble VEGF receptor-3," Nature Med. 7(2):199-205 (2001).
Matthews, B. W., "Structural and genetic analysis of protein stability," Annu. Rev. Biochem., 62:139-160 (1993).
Mendes-Da-Cruz, D. A. et al., "Semaphorin 3F and Neuropilin-2 Control the Migration of Human T-Cell Precursors," PloS One 9(7):e103405 (2014).
Mercurio, A. M., "VEGF/Neuropilin signaling in cancer stem cells," Int. J. Mol. Sci., 20(3):490 (2019).
Meyer, L. A. T. et al., "Current drug design to target the semaphorin/neuropilin/plexin complexes," Cell Adhes. & Migration 10(6):700-708 (2016).
Miaskowski, C. et al., "Lymphatic and angiogenic candidate genes predict the development of secondary lymphedema following breast cancer surgery," PloS One 8(4):e60164 (2013).
Moran, T. P. et al., "Neuropilin-2 is a negative regulator of allergic airway inflammation," J. Allergy Clin. Immunol., AB180 Abstracts, 568 (Feb. 2018).
Mucka, P. et al., "Inflammation and lymphedema are exacerbated and prolonged by neuropilin 2 deficiency," Am. J. Path. 186(11):2803-2812 (2016).
Nakayama, H. et al., "Regulation of mTOR signalling by semaphorin 3F-neuropilin 2 interactions in vitro and in vivo," Scientific Reports 5, 11789; doi: 10.1038/srep11789 (2015).
Napolitano, V. et al., "Neuropilins controlling cancer therapy responsiveness," Int. J. Mol. Sci., 20(8):2049 (2019).
Nasarre, P. et al., "Semaphorin SEMA3F and VEGF have opposing effects on cell attachment and spreading," Neoplasia 5(1):83-92 (2003).
Nasarre, P. et al., "The emerging role of class-3 semaphorins and their neuropilin receptors in oncology," Oncotargets and Therapy 7:1663-1687 (2014).
Neufeld, G. et al., "Semaphorins in angiogenesis and tumor progression," Cold Spring Harbor Perspect in Med. 2:a006718 (2012).
Ng and Henikoff, "Predicting the Effects of Amino Acid Substitutions on Protein Function". Annu Rev Genomics Hum Genet. (2006); 7: 61-80.
Ng, T. et al., "Neuropilin 2 signaling is involved in cell positioning of adult-born neurons through glycogen synthase kinase-3," J.Biol. Chem. 291(48):25088-25095 (2016).
Niland, S. et al., "Neuropilins in the context of tumor vasculature," Int. J. Mol. Sci., 20(3):639 (2019).
Ogata, F. et al., "Excess lymphangiogenesis cooperatively induced by macrophages and CD4+ T cells drives the pathogenesis of lymphedema," J. Inves. Derm. 136:706-714 (2016).
Papadopoulou, K. et al., "Genotyping and mRNA profiling reveal actionable molecular targets in biliary tract cancers," Am. J. Cancer Res. 8(1):2-15 (2018).
Parker, M. W. et al., "Furin processing of semaphorin 3F determines its anti-angiogenic activity by regulating direct binding and competition for neuropilin," Biochemistry 49(19):4068-4075 (2010).
Parker, M. W. et al., "Microplate-based screening for small molecule inhibitors of Neuropilin-2/VEGF-C interactions," Anal. Biochem. 453:4-6 (May 2014).
Parker, M. W. et al., "Structural basis for VEGF-C binding to neuropilin-2 and sequestration by a soluble splice form," Structure, 23(4):677-687 (2015).
Pavlakovic, H., "Soluble VEGFR2: an anti-lymphatic variant of VEGF receptors," Ann. N.Y. Acad. Sci 1207(Suppl 1):E7-E15 (2010).
Pellet-Many, C. et al., "Neuropilins: structure, function and role in disease," Biochemical Journal, vol. 411, No. 2, Apr. 2008, pp. 211-226.
Prud'homme, G. J. et al., "Neuropilins are multifunctional coreceptors involved in tumor initiation, growth, metastasis and immunity," Oncotarget 3(9):921-939 (2012).
Raaben, M. et al., "NRP2 and CD63 are host factors for Lujo virus cell entry," Cell Host Microbe 22(5):688-695.e5 (2017).
Rey-Gallardo, A. et al., "Polysialylated neuropilin-2 enhances human dendritic cell migration through the basic C-terminal region of CCL21," Glycobiology 20(9):1139-1146 (2010).

(56) References Cited

OTHER PUBLICATIONS

Rizzolio, S. et al., "Downregulating neuropilin-2 triggers a novel mechanism enabling EGFR-dependent resistance to oncogene-targeted therapies," Cancer. Res. 78(4):1058-1068 (2017).
Rollenhagen, M. et al., "Polysialic acid on neuropilin-2 is exclusively synthesized by the polysialytransferase ST8SialV and attached to mucin-type O-glycans located between the b2 and c domain," The J. Biol. Chem. 288(32):22880-22892 (2013).
Roy, S. et al., "Multifaceted role of neuropilins in the immune system: Potential targets for immunotherapy," Front. Immunol. 8:1228. doi: 10.3389/fimmu.2017.01228 (Oct. 2017).
Rudikoff, S. et al. "Single amino acid substitution altering antigen-binding specificity", Proc Natl Acad Sci, (Mar. 1982); 79:1979-1983.
Saban, M. R. et al., "VEGF signaling mediates bladder neuroplasticity and inflammation in response to BCG," BMC Physiology 11(16):1-20 (2011).
Saban, R. "Angiogenic factors, bladder neuroplasticity and interstitial cystitis-new pathobiological insights," Trans. Androl. Urol. 4(5):555-562 (2015).
Sainz-Jaspeado, M. et al., "Cytokines regulating lymphangiogenesis," Curr. Opin. Immunol. 53:58-63 (2018).
Sarabipour, S. et al., "VEGF-A121a bindng to Neuropilins—A concept revisited," Cell Adhes. & Migration 12(3):204-214 (2018).
Schellenburg, S. et al., "Role of neuropilin-2 in the immune system," Molecular Immunology, 90:239-244 (2017).
Schwarz, Q. et al., "Neuropilin, you gotta let me know, Should I stay or should I go?" Cell Adhesion & Migration 4(1):61-66 (2010).
Simeon et al., In vitro-engineered non-antibody protein therapeutics, Protein Cell 2018, 9(1 ):3-14, doi:1 0.1 007/s13238-017-0386-6, 2018.
Stanton, M. J. et al., "Angiogenic growth factor axis in autophagy regulation," Autophagy 9(5):789-790 (2013).
Stine, M. J. et al., "Integration of genotypic and phenotypic screening reveals molecular mediators of melanoma-stromal interaction," Cancer. Res. 71(7):2433-2444 (Apr. 2011).
Sulpice, E. et al., "Neuropilin-1 and neuropilin-2 act as coreceptors, potentiating proangiogenic activity," Blood 111(4):2036-2045 (2008).
Tu, D-G. et al., "Promotion of metastasis of thyroid cancer cells via NRP-2 mediated induction," Oncol. Lett. 12:4224-4230 (2016).
Uni Prot Database, P01857, IGHG1_Human, Retrieved online:< u rl: https://www.uniprot.org/uniprotkb/P01857/entry#structure, Retrieved on Jan. 12, 2023, pp. 1 , 2 and 11 , 2023.
UniProtKB Accession No. A0A1COYHRO, Uncharacterized protein, Nov. 2, 2016 [online] 1-3; [Retrieved on May 15, 2023]. Retrieved from the internet: URL: https://www.uniprot.org/uniprot/A0A1C0YHR0 Entire document; amino acid sequence residues 21-31, 4 pages.
Vaahtomeri, K. et al., "Lymphangiogenesis guidance by paracrine and pericellular factors," Genes & Dev 31:1615-1634 (2017).
Vasquez, E. et al., "Deletion of neuropilin 2 enhances detrusor contractility following bladder outlet obstruction," JCI Insight 2(3):e90617 (2017).
Verlinden, L. et al., "Nrp2 deficiency leads to trabecular bone loss and is accompanied by enhanced osteoclast and reduced osteoblast numbers," Bone 55:465-475 (2013).
Wang, J. et al., "NRP-2 in tumor lymphangiogenesis and lymphatic metastasis," Cancer. Lett. 418:176-184 (2018).
Werneburg, S. et al., "Polysialylation and lipopolysaccharide-induced shedding of E-selectin ligand-1 and neuropilin-2 by microglia and THP1 macrophages," GLIA 64:1314-1330 (2016).
Wild, J. R. L. et al., "Neuropilins: expression and roles in the epithelium," Int. J. Exp. Path. 93:81-103 (2012).
Wittmann, P. et al., Neuropilin-2 induced by transforming growth factor—augments migration of hepatocellular carcinoma cells, BMC Cancer 15:909 DOI 10.1186/s128885-015-1919-0 (2015).
Wu, H., et al., "Humanization of a murine monoclonal antibody by simultaneous optimization of framework and CDR residues", Journal of Molecular Biology (1999); 294(1): 151-162.
Xu, Y. et al., "Neuropilin-2 mediates VEGF-C-induced lymphatic sprouting together with VEGFR3," J. Cell. Biol. 188(1):115-130 (2010).
Yang, F. et al., "Understanding lyphangiogenesis in knockout models, the cornea, and ocular diseases for the development of therapeutic interventions," Surv. Ophthalmol., 61(3):272-296 (May-Jun. 2016).
Yang, Y. et al., "Preparation, Purification, and Identification of a Monoclonal Antibody Against NRP2 b1b2 Domain," Monoclonal Antibodies in Immunodiagnosis and Immunotherapy, vol. 34, No. 5, Oct. 2015, pp. 354-359.
Yasuoka, H. et al., "Neuropilin-2 expression in breast cancer: correlation with lymph node metastasis, poor prognosis, and regulation of CXCR4 expression," BMC Cancer 9:220 doi: 10.1 186/1471-2407-9-220 (2009).
Yelland, T. et al., "Crystal structure of the neuropilin-1 MAM domain: completing the neuropilin-1 ectodomain picture," Structure 24(11):2008-2015 (2016).
Yuan, L. et al., "Abnormal lymphatic vessel development in neuropilin 2 mutant mice," Development 129:4797-4806 (2002).
Zhu, H. et al., "VEGF-C inhibition reverses resistance of bladder cancer cells to cisplatin via upregulating maspin," Mol. Med. Reports, 12:3163-3169 (2015).
Anonymous, "aTyr Pharma Presents Preclinical Research Characterizing Effects of ATYR2810 in Highly Aggressive Tumor Subtypes at the 2022 AACR Annual Meeting : BioSpace," Apr. 11, 2022, 3 pages, Retrieved from the Internet: URL:https://www.biospace.com/article/releases/atyr-pharma-presents-preclinical-research-characterizing-effects-of-atyr2810-in-highly-aggressive-tumor-subtypes-at-the-2022-aacr-annual-meeting/.
Guan, J., et al., "The U4 Antibody Epitope on Human Papillomavirus 16 Identified by Cryo-electron Microscopy," Journal of Virology, Sep. 23, 2015, vol. 89, No. 23, pp. 12108-12117.
International Search Report and Written Opinion for International Application No. PCT/US2023/063208, mailed Jul. 18, 2023, 11 pages.
Li, J., et al., "Repertoire diversification in mice with an IgH-locus-targeted transgene for the 1-3 rearranged VH domain of a physiologically selected anti-ssDNA antibody," Molecular Immunology, Mar. 5, 2005, vol. 42, No. 12, pp. 1475-1484.
Partial European Search Report for European Application No. EP20870841.2, mailed Oct. 5, 2023, 15 pages.
Samuel, S., et al., "Neuropilin-2 Mediated [beta]-Catenin Signaling and Survival in Human Gastro-Intestinal Cancer Cell Lines," PLOS ONE, Oct. 20, 2011, vol. 6, No. 10, e23208, 11 pages.
Extended European Search Report for European Application No. EP20870841.2, mailed on Jan. 11, 2024, 12 pages.
International Search Report and Written Opinion for International Application No. PCT/US2023/068511, mailed on Jan. 10, 2024, 12 pages.

\* cited by examiner

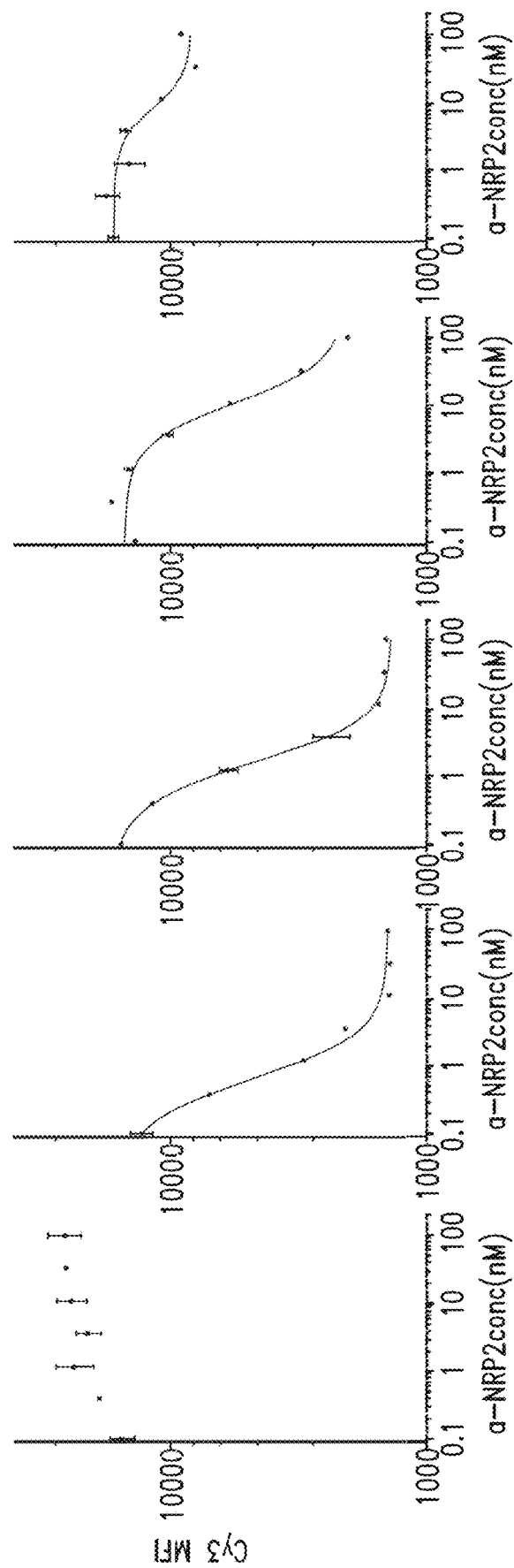

COMPOSITIONS AND METHODS COMPRISING ANTI-NRP2 ANTIBODIES

CROSS-REFERENCE TO RELATED APPLICATIONS

This application is a divisional of U.S. application Ser. No. 16/376,979 filed Apr. 5, 2019, now U.S. Pat. No. 11,505,610, issued Nov. 22, 2022; which application claims the benefit under 35 U.S.C. § 119(e) of U.S. Patent Application No. 62/653,823, filed Apr. 6, 2018, each of which is incorporated by reference in its entirety.

STATEMENT REGARDING SEQUENCE LISTING

The Sequence Listing XML associated with this application is provided in XML file format and is hereby incorporated by reference into the specification. The name of the XML file containing the Sequence Listing XML is ATYR_134_02US_ST26.xml. The XML file is 168,544 bytes, was created on Oct. 20, 2022, and is being submitted electronically via U.S. Patent Center.

BACKGROUND

Technical Field

Embodiments of the present disclosure relate to antibodies and antigen-binding fragments thereof that specifically bind to human neuropilin-2 (NRP2) polypeptides, including those that modulate binding interactions between human NRP2 and at least one NRP2 ligand, for example, human histidyl-tRNA synthetase (HRS), and which thereby modulate subsequent NRP2-mediated downstream signaling events, including related therapeutic compositions and methods for modulating NRP2 activity and treating diseases such as NRP2-associated diseases.

Description of the Related Art

Recent research developments suggest that tRNA synthetases play important roles in cellular responses beyond their well-characterized role in protein synthesis. In particular, there is a growing recognition that tRNA synthetases participate in a range of previously-unrecognized roles in responding to cellular stress and tissue homeostasis, in both intracellular and extracellular environments.

The Resokine family of proteins (HRS Polypeptides) are derived from the histidyl-tRNA synthetase gene (HARS) via proteolysis or alternative splicing, and are important modulators of both intracellular and extracellular activity. Extracellular HARS is readily detectable in the circulation in normal healthy volunteers, and autoantibodies to HARS (Jo-1 antibodies) have been characterized in inflammatory myopathies (IM) and in subjects with inflammatory lung disease (ILD). While the role of Jo-1 antibodies in disease progression is not yet well understood, subjects with Jo-1 antibodies tend to be less susceptible to cancer compared to subjects with inflammatory myopathies without Jo-1 antibodies (see, e.g., Lu et al., PLOS ONE 9(4) e94128, 2014; Modan et al., Clin. Exp. Dermatol. 34(5) 561-565, 2009; and Shi et al., J. Rheum 44 (7) doi 10.3899/jrheum.161480).

Significant progress has been made in elucidating the role of extracellular HARS derived proteins, including the identification of a putative cellular receptor, neuropilin-2 (NRP2 or NRP-2). Interactions of HARS with NRP2 appear to be mediated by the N-terminal region of HARS, and can lead to important changes in the cellular function of NRP2.

Accordingly, the current discovery of the Resokine/neuropilin-2 axis represents a previously unknown mechanism, which acts as a central regulator of cellular processes, including, for example, axonal guidance, endocytosis, cell migration, proliferation, survival, apoptosis, lymphangiogenesis, cellular differentiation, and cell attachment with direct relevance to cancer initiation, growth and metastasis, as wells as muscular, vascular, neuronal, bone, and immune homeostasis. The deregulation of any of these processes may lead to a spectrum of diseases, which may be addressed by the development of anti-NRP2 antibodies that selectively target the Resokine/neuropilin-2 axis. The present disclosure provides such antibodies and related embodiments.

BRIEF SUMMARY

Embodiments of the present disclosure include therapeutic compositions, comprising at least one antibody or antigen-binding fragment thereof that specifically binds to a human neuropilin-2 (NRP2) polypeptide (anti-NRP2 antibody).

In some embodiments, the at least one antibody or antigen-binding fragment thereof specifically binds to a full-length human NRP2 polypeptide or a human NRP2 polypeptide selected from Table N1, optionally with an affinity of about 10 pM to about 500 pM or to about 50 nM, or about, at least about, or no more than about 10, 20, 30, 40, 50, 60, 70, 80, 90, 100, 110, 120, 130, 140, 150, 160, 170, 180, 190, 200, 300, 400, 500, 600, 700, 800, 900 pM, 1 nM, 10 nM, 25 nM, or 50 nM, or optionally with an affinity that ranges from about 10 pM to about 500 pM, about 10 pM to about 400 pM, about 10 pM to about 300 pM, about 10 pM to about 200 pM, about 10 pM to about 100 pM, about 10 pM to about 50 pM, or about 20 pM to about 500 pM, about 20 pM to about 400 pM, about 20 pM to about 300 pM, about 20 pM to about 200 pM, about 20 pM to about 100 pM, about 20 pM to about 50 pM, or about 30 pM to about 500 pM, about 30 pM to about 400 pM, about 30 pM to about 300 pM, about 30 pM to about 200 pM, about 30 pM to about 100 pM, about 30 pM to about 50 pM, or about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 1 nM to about 5 nM, about 5 nM to about 10 nM, about 10 nM to 25 nM, or about 25 nM to about 50 nM. In some instances, the at least one antibody or antigen-binding fragment thereof specifically binds to the human NRP2 polypeptide in its native form but does not substantially bind to the human NRP2 polypeptide in its denatured form.

In some embodiments, the at least one antibody or antigen-binding fragment thereof that specifically binds to at least one epitope in a neuropilin domain selected from one or more of the neuropilin A1 domain, neuropilin A2 domain, neuropilin B1 domain, neuropilin B2 domain, neuropilin C domain, neuropilin A1/A2 combined domain, neuropilin B1/B2 combined domain, neuropilin A2/B1 combined domain, neuropilin B2/C combined domain, neuropilin A2/B1/B2 combined domain, neuropilin A2/B1/B2/C combined domain, neuropilin A1/A2/B1 combined domain, neuropilin A1/A2/B1/B2 combined domain, neuropilin A1/A2/B1/B2/C combined domain, and the neuropilin B1/B2/C combined domain, optionally with an affinity of about 10 pM to about 500 pM or to about 50 nM, or about, at least about, or no more than about 10, 20, 30, 40, 50, 60, 70, 80, 90, 100, 110, 120, 130, 140, 150, 160, 170, 180, 190, 200, 300, 400, 500, 600, 700, 800, 900 pM, 1 nM, 10 nM, 25 nM, or 50 nM, or optionally with an affinity that ranges from about 10 pM to about 500 pM, about 10 pM to about 400 pM, about 10 pM to about 300 pM, about 10 pM to about 200 pM, about 10 pM to about 100 pM, about 10 pM to about 50 pM, or about 20 pM to about 500 pM, about 20 pM to about 400 pM, about 20 pM to about 300 pM, about 20 pM to about 200 pM, about 20 pM to about 100 pM, about 20 pM to about 50 pM, or about 30 pM to about 500 pM, about 30 pM to about 400 pM, about 30 pM to about 300 pM, about 30 pM to about 200 pM, about 30 pM to about 100 pM, about 30 pM to about 50 pM, or about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 1 nM to about 5 nM, about 5 nM to about 10 nM, about 10 nM to 25 nM, or about 25 nM to about 50 nM.

In some embodiments, the at least one antibody or antigen-binding fragment thereof specifically binds to at least one epitope in the neuropilin A1 domain, the neuropilin A2 domain, and/or the neuropilin A1A2 combined domain, including adjacent linker regions, for example, at about residues;

(neuropilin A1 domain) 20-148, 30-141, 40-141, 50-141, 60-141, 70-141, 80-141, 90-141, 100-141, 110-141, 120-141, 130-141; 20-130, 20-120, 20-110, 20-100, 20-90, 20-80, 20-70, 20-60, 20-50, 20-40, or 20-30 as defined by SEQ ID NO:1 (FL human NRP2); or (neuropilin A2 domain) 142-280, 150-265, 160-265, 170-265, 180-265, 190-265, 200-265, 210-265, 220-265, 230-265, 240-265, 250-265, 260-265, 141-270, 141-260, 141-250, 141-240, 141-230, 141-220, 141-210, 141-200, 141-190, 141-180, 141-170, 141-160, 141-150, 200-250, 210-250, 220-250, 230-250, 200-240, 210-240, 220-240, 230-240, 227-247, 228-247, 229-247, 230-247, 231-247, 232-247, 233-247, 234-247, 235-247, 236-247; 227-246, 227-245, 227-244, 227-243, 227-242, 227-241, 227-240, 227-239, 227-238; 235-240, 236-239, 236-238, or residue 237 as defined by SEQ ID NO:1 (FL human NRP2); or (combined A1A2 domain) 20-280, 30-280, 40-280, 50-280, 60-280, 70-280, 80-280, 90-280, 100-280, 110-280, 120-280, 130-280, 140-280, 150-280, 160-280, 170-280, 180-280, 190-280, 200-280, 210-280, 220-280, 230-280, 240-280, 260-280, 270-280, 20-270, 20-260, 20-250, 20-240, 20-230, 20-220, 20-210, 20-200, 20-190, 20-180, 20-170, 20-160, 20-150, 20-140, 20-130, 20-120, 20-110, 20-100, 20-90, 20-80, 20-70, 20-60, 20-50, 20-40, or 20-30 as defined by SEQ ID NO:1 (FL human NRP2).

In some embodiments, the at least one antibody or antigen-binding fragment thereof specifically binds to at least one epitope in the neuropilin B1 domain (SEQ ID NO:12), the neuropilin B2 domain (SEQ ID NO:13), and/or the neuropilin B1/B2 combined domain (SEQ ID NO:20), including adjacent linker regions; for example, at about residues;

(neuropilin B1 domain) 266-426, 280-426, 290-426, 300-426, 310-426, 320-426, 330-426, 340-426, 350-426, 360-426, 370-426, 380-426, 390-426, 400-426, 410-426, 420-426, 280-420, 280-410, 280-400, 280-390, 280-380, 280-370, 280-360, 280-350, 280-340, 280-330, 280-320, 280-310, 280-300, or 280-290 as defined by SEQ ID NO:1 (FL human NRP2);

(neuropilin B2 domain) 438-591, 450-591, 460-591, 470-591, 480-591, 490-591, 500-591, 510-591, 520-591, 530-591, 540-591, 550-591, 560-591, 570-591, 580-591, 438-590, 438-580, 438-570, 438-560, 438-550, 438-540, 438-530, 438-520, 438-510, 438-500, 438-490, 438-480, 438-470, 438-460, or 438-450 as defined by SEQ ID NO:1 (FL human NRP2); or (neuropilin B1/B2 combined domain) 266-591, 276-591, 286-591, 296-591, 306-591, 316-591, 326-591, 336-591, 346-591, 356-591, 366-591, 376-591, 386-591, 396-591, 406-591, 416-591, 426-591, 436-591, 446-591, 456-591, 466-591, 476-591, 486-591, 498-591, 508-591, 518-591, 528-591, 538-591, 548-591, 558-591, 568-591, 578-591, 588-591, 266-581, 266-571, 266-561, 266-551, 266-541, 266-531, 266-521, 266-511, 266-501, 266-491, 266-481, 266-471, 266-461, 266-451, 266-441, 266-431, 266-421, 266-411, 266-401, 266-391, 266-381, 266-371, 266-361, 266-351, 266-341, 266-331, 266-321, 266-311, 266-301, 266-291, 266-281, or 266-271 as defined by SEQ ID NO:1 (FL human NRP2).

In some embodiments, the at least one antibody or antigen-binding fragment thereof specifically binds to at least one epitope in the neuropilin A2/B1 combined domain and/or the neuropilin B2C combined domain, including adjacent linker regions, for example, at about residues;

(neuropilin A2B1 combined domain) 149-437, 159-426, 169-426, 179-426, 189-426, 199-426, 209-426, 219-426, 229-426, 239-426, 249-426, 259-426, 269-426, 279-426, 289-426, 299-426, 309-426, 319-426, 329-426, 339-426, 349-426, 359-426, 369-426, 379-426, 389-426, 399-426, 409-426, 419-426, 149-436, 149-426, 149-416, 149-406, 149-396, 149-386, 149-376, 149-366, 149-356, 149-346, 149-336, 149-326, 149-316, 149-306, 149-296, 149-286, 149-276, 149-266, 149-256, 149-246, 149-236, 149-226, 149-216, 149-206, 149-196, 146-186, 146-176, 146-166, or 146-155 as defined by SEQ ID NO:1 (FL human NRP2); or (neuropilin B2C combined domain) 438-794, 448-794, 458-794, 468-794, 478-794, 487-794, 497-794, 507-794, 517-794, 527-794, 537-794, 547-794, 557-794, 567-794, 587-794, 597-794, 607-794, 617-794, 627-794, 637-794, 647-794, 657-794, 667-794, 677-794, 687-794, 697-794, 707-794, 717-794, 727-794, 737-794, 747-794, 757-794, 767-794, 777-794, 787-794, 427-794, 438-784, 438-774, 438-764, 438-754, 438-744, 438-734, 438-728, 438-714, 438-704, 438-694, 438-684, 438-674, 438-664, 438-654, 438-644, 438-634, 438-624, 438-614, 438-604, 438-596, 438-586, 438-576, 438-566, 438-556, 438-546, 438-536, 438-526, 438-516, 438-506, 438-494, 438-484, 438-474, 438-464, 438-454, 438-444 as defined by SEQ ID NO:1 (FL human NRP2).

In some embodiments, the at least one antibody or antigen-binding fragment thereof specifically binds to at least one epitope in the neuropilin C domain, including adjacent linker regions, for example, at about residues 591-794, 600-794, 610-794, 620-794, 630-794, 640-794, 650-794, 660-794, 670-794, 680-794, 690-794, 700-794, 710-794, 720-794, 730-794, 740-794, 750-794, 760-794, 770-794, 780-794, 790-794, 591-790, 591-780, 591-770, 591-760, 591-750, 591-740, 591-730, 591-720, 591-710, 591-700, 591-690, 591-680, 591-670, 591-660, 591-650, 591-640, 591-630, 591-620, 591-610, or 591-600 as defined by SEQ ID NO:1 (FL human NRP2).

In some embodiments, the at least one antibody or antigen-binding fragment thereof specifically binds to at least one epitope in the neuropilin B1/B2/C combined domain, including adjacent linker regions, for example, at about residues 276-794, 286-794, 296-794, 306-794, 316-794, 326-794, 336-794, 346-794, 356-794, 366-794, 376-794, 387-794, 396-794, 406-794, 416-794, 426-794, 436-794, 446-794, 456-794, 466-794, 476-794, 486-794, 496-794, 506-794, 516-794, 526-794, 536-794, 546-794, 556-794, 566-794, 576-794, 586-794, 596-794, 606-794, 616-794, 626-794, 636-794, 646-794, 656-794, 666-794, 676-794, 686-794, 696-794, 706-794, 716-794, 726-794, 736-794, 746-794, 756-794, 766-794, 776-794, 786-794, 266-794, 276-784, 276-774, 276-764, 276-754, 276-744, 276-734, 276-724, 276-714, 276-704, 276-694, 276-684, 276-674, 276-664, 276-654, 276-644, 276-634, 276-624, 276-614, 276-604, 276-594, 276-584, 276-574, 276-564, 276-554, 276-544, 276-534, 276-524, 276-514, 276-504, 276-594, 276-584, 276-574, 276-564, 276-554, 276-544, 276-534, 276-524, 276-514, 276-504, or 276-496 as defined by SEQ ID NO:1 (FL human NRP2).

In some embodiments, the at least one antibody or antigen-binding fragment thereof specifically binds to a conformational epitope composed of two or more discontinuous epitope regions. In some embodiments, the at least one antibody or antigen-binding fragment thereof specifically binds to a conformational epitope comprising or consisting of:

(a) a first epitope region within the A1 domain, and second epitope region within the A2 domain of the human NPR2 polypeptide;
(b) a first epitope region within the A1 domain, and second epitope region within the B1 domain of the human NPR2 polypeptide;
(c) a first epitope region within the A1 domain, and second epitope region within the B2 domain of the human NPR2 polypeptide;
(d) a first epitope region within the A1 domain, and second epitope region within the C domain of the human NPR2 polypeptide;
(e) a first epitope region within the A2 domain, and second epitope region within the B1 domain of the human NPR2 polypeptide;
(f) a first epitope region within the A2 domain, and second epitope region within the B2 domain of the human NPR2 polypeptide;
(g) a first epitope region within the A2 domain, and second epitope region within the C domain of the human NPR2 polypeptide;
(h) a first epitope region within the B1 domain, and second epitope region within the B2 domain of the human NPR2 polypeptide;
(i) a first epitope region within the B1 domain, and second epitope region within the C domain of the human NPR2 polypeptide; or
(j) a first epitope region within the B2 domain, and second epitope region within the C domain of the human NPR2 polypeptide.

In some embodiments, the at least one antibody or antigen-binding fragment thereof modulates (e.g., interferes with) binding of the human NRP2 polypeptide to at least one NRP2 ligand (for example, an NRP2 ligand selected from Table N2 or Table N3 and/or a human histidyl-tRNA synthetase (HRS) polypeptide selected from Table H1). In some embodiments, the at least NRP2 ligand is an HRS splice variant selected from Table H1, for example, a HRS splice variant selected from one or more of SV9 (HRS(1-60)), SV11 (HRS(1-60)+(399-509)) and SV14 (HRS(1-100)+(399-509)).

In some embodiments, the at least one antibody or antigen-binding fragment thereof is a blocking antibody which inhibits about or at least about 80-100% of the theoretical maximal binding between the human NRP2 polypeptide and the at least one NRP2 ligand after pre-incubation with the human NRP2 polypeptide in a stoichiometrically equivalent amount, optionally about or at least about 80, 85, 90, 95, or 100% of the theoretical maximal binding.

In some embodiments, the at least one antibody or antigen-binding fragment thereof is a partial blocking antibody which inhibits about or at least about 20-80% of the theoretical maximal binding between the human NRP2 polypeptide and the at least one NRP2 ligand after pre-incubation with the human NRP2 polypeptide in a stoichiometrically equivalent amount, optionally about or at least about 20, 25, 30, 35, 40, 45, 50, 55, 60, 65, 70, 75, or 80% of the theoretical maximal binding.

In some embodiments, the at least one antibody or antigen-binding fragment thereof specifically binds to an HRS polypeptide-interacting region of the NRP2 polypeptide, and mimics or agonizes one or more signaling activities of the HRS polypeptide binding to the NRP2 polypeptide.

In some embodiments, the at least one antibody or antigen-binding fragment thereof specifically binds to an HRS polypeptide-interacting region of the NRP2 polypeptide, and modulates binding/signaling activity between the NRP2 polypeptide and at least one NRP2 ligand. In some embodiments, the at least one antibody or antigen-binding fragment thereof antagonizes the binding/signaling activity between the NRP2 polypeptide and the at least one NRP2 ligand. In some embodiments, the at least one antibody or antigen-binding fragment thereof agonizes or enhances the binding/signaling activity between the NRP2 polypeptide and the at least one NRP2 ligand.

In some embodiments, the at least one NRP2 ligand is selected from one or more of:
a VEGF selected from one or more of VEGF-A145, VEGF-A165, VEGF-C, VEGF-D and PIGF-2;
a VEGF receptor (VEGFR) selected from VEGFR2 and VEGFR3;
a semaphorin selected from one or more of SEMA-3B, SEMA-3C, SEMA-3D SEMA-3F, and SEMA-3G;
a plexin selected from one or more of plexin A1, A2, A3, A4, and D1;
a growth factor selected from one or more of fibroblast growth factor (FGF), hepatocyte growth factor (HGF), and platelet derived growth factor (PDGF);
a growth factor receptor selected from one or more of a fibroblast growth factor receptor (FGFR), a hepatocyte growth factor receptor (HGFR), and a platelet derived growth factor receptor (PDGF);
a galectin or a galectin receptor
a transcription factor selected from FAC1 and bromoprotein PHD finger transcription factor;
an adaptor protein selected from one or more of GIPC1, GIPC2 and GIPC3;
an integrin selected from Table N3, optionally one or more of $\alpha_v\beta_1$, $\alpha_v\beta_3$, $\alpha_v\beta_5$, $\alpha_v\beta_6$, $\alpha_v\beta_8$, $\alpha_6\beta_1$ and $\alpha_6\beta_4$;
a transforming growth factor beta selected from one or more of TGFβ1, TGFβ2, TGFβ3, and their corresponding TGFβ receptors; and
an HRS polypeptide selected from Table H1, optionally an HRS splice variant selected from one or more of HisRS$^{N1}$, HisRS$^{N2}$, HisRS$^{N3}$, HisRS$^{N4}$ (SV9), His- RS$^{N5}$, HisRS$^{C1}$, HisRS$^{C2}$, HisRS$^{C3}$, HisRS$^{C4}$, HisRS$^{C5}$, HisRS$^{C6}$, HisRS$^{C7}$, HisRS$^{C8}$(SV11), and HisRS$^{C9}$ (SV14).

In some embodiments, the at least one antibody or antigen-binding fragment thereof antagonizes the binding/signaling activity between the NRP2 polypeptide and a plexin receptor and/or a semaphorin without substantially modulating the binding/signaling activity between the NRP2 polypeptide and VEGFR3 or VEGF-C.

In some embodiments, the at least one antibody or antigen-binding fragment thereof antagonizes the binding/signaling activity between the NRP2 polypeptide and a plexin receptor and/or semaphorin without substantially modulating the binding/signaling activity between the NRP2 polypeptide and a HRS polypeptide.

In some embodiments, the at least one antibody or antigen-binding fragment thereof antagonizes the binding/signaling activity between the NRP2 polypeptide and a plexin receptor and/or a semaphorin without substantially modulating the binding/signaling activity between the NRP2 polypeptide and a HRS polypeptide, and without substantially modulating the binding/signaling activity between the NRP2 polypeptide and VEGFR3 or VEGF-C.

In some embodiments, the at least one antibody or antigen-binding fragment thereof antagonizes the binding/signaling activity between the NRP2 polypeptide and VEGR3 without substantially modulating the binding/signaling activity between the NRP2 polypeptide and a plexin receptor and/or a semaphorin.

In some embodiments, the at least one antibody or antigen-binding fragment thereof antagonizes the binding/signaling activity between the NRP2 polypeptide and VEGR3 or VEGF-C without substantially modulating the binding/signaling activity between the NRP2 polypeptide and a HRS polypeptide.

In some embodiments, the at least one antibody or antigen-binding fragment thereof antagonizes the binding/signaling activity between the NRP2 polypeptide and a plexin receptor without substantially modulating the ligand binding of semaphorin 3 to NRP2.

In some embodiments, the plexin receptor is selected from plexin A1, A2, A3, A4, and D1. In some embodiments, the semaphorin is selected from semaphorin 3B, 3C, 3D, 3F, and 3G.

In some embodiments, the at least one antibody or antigen-binding fragment thereof specifically binds to an epitope within the human NRP2 A2 domain which comprises at least 5 contiguous amino acids of SEQ ID NO: 11, wherein the at least one antibody or antigen-binding fragment thereof selectively inhibits receptor dimerization between NRP2 and plexin A1 without substantially inhibiting dimerization between NRP2 and FLT4 (VEGFR3). In some embodiments, the at least one antibody or antigen-binding fragment thereof specifically binds to an epitope within amino acids 232-242 of human NRP2 SEQ ID NO: 1.

In some embodiments, the at least one antibody or antigen-binding fragment thereof specifically binds to an epitope within the human NRP2 B1 domain which comprises at least 5 contiguous amino acids of SEQ ID NO: 12, wherein the at least one antibody or antigen-binding fragment thereof selectively inhibits receptor dimerization between NRP2 and FLT4 (VEGFR3) without substantially inhibiting dimerization between NRP2 and plexin A1.

In some embodiments, the at least one antibody or antigen-binding fragment thereof specifically binds to an epitope within the human NRP2 B2 domain which comprises at least 5 contiguous amino acids of SEQ ID NO: 13, wherein the at least one antibody or antigen-binding fragment thereof inhibits receptor dimerization between NRP2 and FLT4 (VEGFR3) and inhibits dimerization between NRP2 and plexin A1.

In some embodiments, the at least one antibody or antigen-binding fragment thereof specifically binds to an epitope within the human NRP2 C domain which comprises at least 5 contiguous amino acids of SEQ ID NO: 14, wherein the at least one antibody or antigen-binding fragment thereof inhibits receptor dimerization between NRP2 and plexin A1 and partially inhibits dimerization between NRP2 and FLT4 (VEGFR3).

In some embodiments, the at least one antibody or antigen-binding fragment thereof has an affinity (Kd or EC$_{50}$) for each of (i) a human NRP2 polypeptide and (ii) the corresponding region of a cynomolgus monkey NRP2 polypeptide, wherein the affinity for (i) and (ii) is within the range of about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 0.4 to about 1.2 nM, about 0.9 to about 5.5 nM, about 0.9 to about 5 nM, or about 1 nM to about 10 nM.

In some embodiments, the at least one antibody or antigen-binding fragment thereof has an affinity (Kd or EC$_{50}$) for each of (i) a human NRP2 polypeptide and (ii) the corresponding region of a murine NRP2 polypeptide, wherein the affinity for (i) and (ii) is within the range of about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, or about 1 nM to about 10 nM.

In certain embodiments, the at least one antibody or antigen-binding fragment thereof comprises:
  a heavy chain variable region (V$_H$) sequence that comprises complementary determining region V$_H$CDR1, V$_H$CDR2, and V$_H$CDR3 sequences selected from Table A1 and variants thereof which specifically bind to the human NRP2 polypeptide; and
  a light chain variable region (V$_L$) sequence that comprises complementary determining region V$_L$CDR1, V$_L$CDR2, and V$_L$CDR3 sequences selected from Table A1 and variants thereof which specifically bind to the human NRP2 polypeptide,
  including affinity matured variants of the foregoing which specifically bind to the human NRP2 polypeptide.

In specific embodiments:
  the V$_H$CDR1, V$_H$CDR2, and V$_H$CDR3 sequences comprise SEQ ID NOs: 23-25, respectively, and the V$_L$CDR1, V$_L$CDR2, and V$_L$CDR3 sequences comprise SEQ ID NOs: 26-28, respectively, including variants thereof with 1, 2, 3, 4, or 5 alterations in the CDR(s) and which specifically bind to the human NRP2 polypeptide;
  the V$_H$CDR1, V$_H$CDR2, and V$_H$CDR3 sequences comprise SEQ ID NOs: 29-31, respectively, and the V$_L$CDR1, V$_L$CDR2, and V$_L$CDR3 sequences comprise SEQ ID NOs: 32-34, respectively, including variants thereof with 1, 2, 3, 4, or 5 alterations in the CDR(s) and which specifically bind to the human NRP2 polypeptide;
  the V$_H$CDR1, V$_H$CDR2, and V$_H$CDR3 sequences comprise SEQ ID NOs: 35-37, respectively, and the V$_L$CDR1, V$_L$CDR2, and V$_L$CDR3 sequences comprise SEQ ID NOs: 38-40, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 41-43, respectively, and the V$_L$CDR1, V$_L$CDR2, and V$_L$CDR3 sequences comprise SEQ ID NOs: 44-46, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 47-49, respectively, and the V$_L$CDR1, V$_L$CDR2, and V$_L$CDR3 sequences comprise SEQ ID NOs: 50-52, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 53-55, respectively, and the V$_L$CDR1, V$_L$CDR2, and V$_L$CDR3 sequences comprise SEQ ID NOs: 56-58, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 59-61, respectively, and the V$_L$CDR1, V$_L$CDR2, and V$_L$CDR3 sequences comprise SEQ ID NOs: 62-64, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 65-67, respectively, and the V$_L$CDR1, V$_L$CDR2, and V$_L$CDR3 sequences comprise SEQ ID NOs: 68-70, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 71-73, respectively, and the V$_L$CDR1, V$_L$CDR2, and V$_L$CDR3 sequences comprise SEQ ID NOs: 74-76, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 77-79, respectively, and the V$_L$CDR1, V$_L$CDR2, and V$_L$CDR3 sequences comprise SEQ ID NOs: 80-82, respectively, including variants thereof with 1, 2, 3, 4, or 5 alterations in the CDR(s) and which specifically bind to the human NRP2 polypeptide;

the V$_H$CDR1, V$_H$CDR2, and V$_H$CDR3 sequences comprise SEQ ID NOs: 83-85, respectively, and the V$_L$CDR1, V$_L$CDR2, and V$_L$CDR3 sequences comprise SEQ ID NOs: 86-88, respectively, including variants thereof with 1, 2, 3, 4, or 5 alterations in the CDR(s) and which specifically bind to the human NRP2 polypeptide.

In some embodiments, the at least one antibody or antigen-binding fragment thereof comprises an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof. In some embodiments, the at least one antibody or antigen-binding fragment thereof comprises an IgG Fc domain with high effector function in humans, optionally an IgG1 or IgG3 Fc domain. In some embodiments, the at least one antibody or antigen-binding fragment thereof comprises an IgG Fc domain with low effector function in humans, optionally an IgG2 or IgG4 Fc domain. In some embodiments, the at least one antibody or antigen-binding fragment thereof comprises an IgG1 or IgG4 Fc domain, optionally selected from Table F1.

In some embodiments, the at least one antibody or antigen-binding fragment thereof is a monoclonal antibody. In some embodiments, the at least one antibody or antigen-binding fragment thereof is a humanized antibody. In some embodiments, the at least one antibody or antigen-binding fragment thereof is an Fv fragment, a single chain Fv (scFv) polypeptide, an adnectin, an anticalin, an aptamer, an avimer, a camelid antibody, a designed ankyrin repeat protein (DARPin), a minibody, a nanobody, or a unibody.

In some embodiments, the composition has a purity of at least about 80%, 85%, 90%, 95%, 98%, or 99% on a protein basis with respect to the at least one antibody or antigen-binding fragment, and is substantially aggregate-free. In some embodiments, the therapeutic composition is substantially endotoxin-free.

In some embodiments, the therapeutic composition is a sterile, injectable solution, optionally suitable for intravenous, intramuscular, subcutaneous, or intraperitoneal administration.

In certain embodiments, the therapeutic composition further comprises at least one additional agent selected from one or more of a cancer immunotherapy agent, a chemotherapeutic agent, a hormonal therapeutic agent, and a kinase inhibitor. In some embodiments, the cancer immunotherapy agent is selected from one or more of an immune checkpoint modulatory agent, a cancer vaccine, an oncolytic virus, a cytokine, and a cell-based immunotherapies. In some embodiments, the immune checkpoint modulatory agent is a polypeptide, optionally an antibody or antigen-binding fragment thereof or a ligand, or a small molecule. In some embodiments, the immune checkpoint modulatory agent comprises
(a) an antagonist of a inhibitory immune checkpoint molecule; or
(b) an agonist of a stimulatory immune checkpoint molecule,
for instance, wherein the immune checkpoint modulatory agent specifically binds to the immune checkpoint molecule.

In some embodiments, the inhibitory immune checkpoint molecule is selected from one or more of Programmed Death-Ligand 1 (PD-L1), Programmed Death 1 (PD-1), Programmed Death-Ligand 2 (PD-L2), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, Herpes Virus Entry Mediator (HVEM), and T-cell immunoreceptor with Ig and ITIM domains (TIGIT).

In some embodiments, the antagonist is a PD-L1 and/or PD-L2 antagonist optionally selected from one or more of an antibody or antigen-binding fragment or small molecule that specifically binds thereto, atezolizumab (MPDL3280A), avelumab (MSB0010718C), and durvalumab (MED14736);
the antagonist is a PD-1 antagonist optionally selected from one or more of an antibody or antigen-binding fragment or small molecule that specifically binds thereto, nivolumab, pembrolizumab, MK-3475, AMP-224, AMP-514, PDR001, and pidilizumab;

the antagonist is a CTLA-4 antagonist optionally selected from one or more of an antibody or antigen-binding fragment or small molecule that specifically binds thereto, ipilimumab, and tremelimumab;

the antagonist is an IDO antagonist optionally selected from one or more of an antibody or antigen-binding fragment or small molecule that specifically binds thereto, indoximod (NLG-8189), 1-methyl-tryptophan (1MT), β-Carboline (norharmane; 9H-pyrido[3,4-b]indole), rosmarinic acid, and epacadostat;

the antagonist is a TDO antagonist optionally selected from one or more of an antibody or antigen-binding fragment or small molecule that specifically binds thereto, 680C91, and LM10;

the antagonist is a TIM-3 antagonist optionally selected from one or more of an antibody or antigen-binding fragment or small molecule that specifically binds thereto;

the antagonist is a LAG-3 antagonist optionally selected from one or more of an antibody or antigen-binding fragment or small molecule that specifically binds thereto, and BMS-986016;

the antagonist is a VISTA antagonist optionally selected from one or more of an antibody or antigen-binding fragment or small molecule that specifically binds thereto;

the antagonist is a BTLA, CD160, and/or HVEM antagonist optionally selected from one or more of an antibody or antigen-binding fragment or small molecule that specifically binds thereto; and/or the antagonist is a TIGIT antagonist optionally selected from one or more of an antibody or antigen-binding fragment or small molecule that specifically binds thereto.

In some embodiments, the stimulatory immune checkpoint molecule is selected from one or more of OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agonist is an OX40 agonist optionally selected from one or more of an antibody or antigen-binding fragment or small molecule or ligand that specifically binds thereto, OX86, Fc-OX40L, and GSK3174998;

the agonist is a CD40 agonist optionally selected from one or more of an antibody or antigen-binding fragment or small molecule or ligand that specifically binds thereto, CP-870,893, dacetuzumab, Chi Lob 7/4, ADC-1013, and rhCD40L;

the agonist is a GITR agonist optionally selected from one or more of an antibody or antigen-binding fragment or small molecule or ligand that specifically binds thereto, INCAGN01876, DTA-1, and MED11873;

the agonist is a CD137 agonist optionally selected from one or more of an antibody or antigen-binding fragment or small molecule or ligand that specifically binds thereto, utomilumab, and 4-1BB ligand;

the agonist is a CD27 agonist optionally selected from one or more of an antibody or antigen-binding fragment or small molecule or ligand that specifically binds thereto, varlilumab, and CDX-1127 (1F5);

the agonist is a CD28 agonist optionally selected from one or more of an antibody or antigen-binding fragment or small molecule or ligand that specifically binds thereto, and TAB08; and/or the agonist is an HVEM agonist optionally selected from one or more of an antibody or antigen-binding fragment or small molecule or ligand that specifically binds thereto.

In some embodiments, the cancer vaccine is selected from one or more of Oncophage, a human papillomavirus HPV vaccine optionally Gardasil or Cervarix, a hepatitis B vaccine optionally Engerix-B, Recombivax HB, or Twinrix, and sipuleucel-T (Provenge), or comprises a cancer antigen selected from one or more of human Her2/neu, HerVEGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin αvβ3, integrin α5β1, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In some embodiments, the oncolytic virus selected from one or more of talimogene laherparepvec (T-VEC), coxsackievirus A21 (CAVATAK™), Oncorine (H101), pelareorep (REOLYSIN®), Seneca Valley virus (NTX-010), Senecavirus SVV-001, ColoAd1, SEPREHVIR (HSV-1716), CGTG-102 (Ad5/3-D24-GMCSF), GL-ONC1, MV-NIS, and DNX-2401. In some embodiments, the cytokine selected from one or more of interferon (IFN)-a, IL-2, IL-12, IL-7, IL-21, and Granulocyte-macrophage colony-stimulating factor (GM-CSF). In some embodiments, the cell-based immunotherapy agent comprises cancer antigen-specific T-cells, optionally ex vivo-derived T-cells. In some embodiments, the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells.

In some embodiments, the at least one chemotherapeutic agent is selected from one or more of an alkylating agent, an anti-metabolite, a cytotoxic antibiotic, a topoisomerase inhibitor (type 1 or type II), and an anti-microtubule agent.

In some embodiments, the alkylating agent is selected from one or more of nitrogen mustards (optionally mechlorethamine, cyclophosphamide, mustine, melphalan, chlorambucil, ifosfamide, and busulfan), nitrosoureas (optionally N-Nitroso-N-methylurea (MNU), carmustine (BCNU), lomustine (CCNU), semustine (MeCCNU), fotemustine, and streptozotocin), tetrazines (optionally dacarbazine, mitozolomide, and temozolomide), aziridines (optionally thiotepa, mytomycin, and diaziquone (AZQ)), cisplatins and derivatives thereof (optionally carboplatin and oxaliplatin), and non-classical alkylating agents (optionally procarbazine and hexamethylmelamine);

the anti-metabolite is selected from one or more of anti-folates (optionally methotrexate and pemetrexed), fluoropyrimidines (optionally 5-fluorouracil and capecitabine), deoxynucleoside analogues (optionally ancitabine, enocitabine, cytarabine, gemcitabine, decitabine, azacitidine, fludarabine, nelarabine, cladribine, clofarabine, fludarabine, and pentostatin), and thiopurines (optionally thioguanine and mercaptopurine);

the cytotoxic antibiotic is selected from one or more of anthracyclines (optionally doxorubicin, daunorubicin, epirubicin, idarubicin, pirarubicin, aclarubicin, and mitoxantrone), bleomycins, mitomycin C, mitoxantrone, and actinomycin;

the topoisomerase inhibitor is selected from one or more of camptothecin, irinotecan, topotecan, etoposide, doxorubicin, mitoxantrone, teniposide, novobiocin, merbarone, and aclarubicin; and/or the anti-microtubule agent is selected from one or more of taxanes (optionally paclitaxel and docetaxel) and vinca alkaloids (optionally vinblastine, vincristine, vindesine, vinorelbine).

In some embodiments, the at least one hormonal therapeutic agent is a hormonal agonist or a hormonal antagonist. In some embodiments, the hormonal agonist is selected from one or more of a progestogen (progestin), a corticosteroid (optionally prednisolone, methylprednisolone, or dexamethasone), insulin like growth factors, VEGF derived angiogenic and lymphangiogenic factors (optionally VEGF-A, VEGF-A145, VEGF-A165, VEGF-C, VEGF-D, PIGF-2), fibroblast growth factor (FGF), galectin, hepatocyte growth factor (HGF), platelet derived growth factor (PDGF), transforming growth factor (TGF)-beta, an androgen, an estrogen, and a somatostatin analog. In some embodiments, the hormonal antagonist is selected from one or more of a hormone synthesis inhibitor, optionally an aromatase inhibitor or a gonadotropin-releasing hormone (GnRH) or an analog thereof, and a hormone receptor antagonist, optionally a selective estrogen receptor modulator (SERM) or an anti-androgen, or an antibody directed against a hormonal receptor, optionally cixutumumab, dalotuzumab, figitumumab, ganitumab, istiratumab, robatumumab, alacizumab pegol, bevacizumab, icrucumab, ramucirumab, fresolimumab, metelimumab, naxitamab, cetuximab, depatuxizumab mafodotin, futuximab, imgatuzumab, laprituximab emtansine, matuzumab, modotuximab, necitumumab, nimotuzumab, panitumumab, tomuzotuximab, zalutumumab, aprutumab ixadotin, bemarituzumab, olaratumab, or tovetumab.

In some embodiments, the kinase inhibitor is selected from one or more of adavosertib, afanitib, aflibercept, axitinib, bevacizumab, bosutinib, cabozantinib, cetuximab, cobimetinib, crizotinib, dasatinib, entrectinib, erdafitinib, erlotinib, fostamitinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, SU6656, tofacitinib, trastuzumab, vandetanib, and vemuafenib.

Also included are methods of treating a disease or condition in a subject in need thereof, comprising administering to the subject a therapeutic composition comprising at least one antibody or antigen-binding fragment thereof that specifically binds to a human neuropilin-2 (NRP2) polypeptide, wherein the at least one antibody or antigen-binding fragment thereof modulates (e.g., interferes with) binding of the human NRP2 polypeptide to at least one NRP2 ligand (for example, an NRP2 ligand from Table N2 or Table N3 and/or a human histidyl-tRNA synthetase (HRS) polypeptide from Table H1), for example, as a therapeutic composition described herein.

In some embodiments, the disease or condition is an NRP2-associated disease or condition. In some embodiments, the NRP2-associated disease or condition is selected from one or more of cancer and diseases and pathways associated with cancer, including cancer cell growth, initiation, migration, adhesion, invasion, and/or metastasis; diseases associated with inflammation, autoimmunity, and related inflammatory diseases, including diseases associated with inappropriate immune cell activation or migration such as Graft versus host disease (GVHD); diseases associated with lymphatic development, lymphangiogenesis, and lymphatic damage, including, for example, edema, lymphedema, secondary lymphedema, inappropriate fat absorption and deposition, excess fat deposition, and vascular permeability; diseases associated with infections, including latent infections; diseases associated with allergic disorders/diseases, allergic responses, including, for example, chronic obstructive pulmonary disorder (COPD), neutrophilic asthma, antineutrophil cytoplasmic antibody (ANCA)-associated systemic vasculitis, systemic lupus erythematosus, rheumatoid arthritis, inflammasome-related diseases, and skin-related neutrophil-mediated diseases such as pyoderma gangrenosum; diseases associated with granulomatous inflammatory diseases, including sarcoidosis and granulomas; diseases associated with fibrosis including fibrotic diseases, fibrosis, endothelial to mesenchymal transition (EMT), and wound healing; diseases associated with inappropriate smooth muscle contractility, and inappropriate vascular smooth muscle cell migration and adhesion; diseases associated with inappropriate autophagy, phagocytosis, and efferocytosis; diseases associated with inappropriate migratory cell movement; diseases associated with neuronal diseases, peripheral nervous system remodeling, and pain perception; and diseases associated with bone development and bone remodeling.

In some embodiments, the disease is a cancer, for example, wherein the cancer expresses or overexpresses NRP2. In some embodiments, the cancer displays NRP2-dependent growth, NRP2-dependent adhesion, NRP2-dependent migration, and/or NRP2-dependent invasion. In some embodiments the cancer expresses or overexpresses NRP2 but does not substantially express neuropilin-1 (NRP1).

Also included are methods for reducing or preventing re-emergence of a cancer in a subject in need thereof, wherein administration of the therapeutic composition enables generation of an immune memory to the cancer. In some embodiments, the subject has or is at risk for developing diabetes.

Certain methods comprise administering to the subject at least one additional agent selected from one or more of a cancer immunotherapy agent, a chemotherapeutic agent, a hormonal therapeutic agent, and a kinase inhibitor, for example, as described herein. In some embodiments, the at least one anti-NRP2 antibody or antigen-binding fragment thereof and the at least one agent are administered separately, as separate compositions. In some embodiments, the at least one anti-NRP2 antibody and the at least one agent are administered together as part of the same therapeutic composition, for instance, as a therapeutic composition described herein.

In some embodiments, the cancer immunotherapy agent is selected from one or more of an immune checkpoint modulatory agent, a cancer vaccine, an oncolytic virus, a cytokine, and a cell-based immunotherapies. In some embodiments, the immune checkpoint modulatory agent is a polypeptide, optionally an antibody or antigen-binding fragment thereof or a ligand, or a small molecule. In some embodiments, the immune checkpoint modulatory agent comprises (a) an antagonist of a inhibitory immune checkpoint molecule; or (b) an agonist of a stimulatory immune checkpoint molecule.

for example, wherein the immune checkpoint modulatory agent specifically binds to the In some embodiments, the inhibitory immune checkpoint molecule is selected from one or more of Programmed Death-Ligand 1 (PD-L1), Programmed Death 1 (PD-1), Programmed Death-Ligand 2 (PD-L2), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, Herpes Virus Entry Mediator (HVEM), and T-cell immunoreceptor with Ig and ITIM domains (TIGIT).

In some embodiments, the antagonist is a PD-L1 and/or PD-L2 antagonist optionally selected from one or more of an antibody or antigen-binding fragment or small molecule that specifically binds thereto, atezolizumab (MPDL3280A), avelumab (MSB0010718C), and durvalumab (MED14736), optionally wherein the cancer is selected from one or more of colorectal cancer, melanoma, breast cancer, non-small-cell lung carcinoma, bladder cancer, and renal cell carcinoma;

the antagonist is a PD-1 antagonist optionally selected from one or more of an antibody or antigen-binding fragment or small molecule that specifically binds thereto, nivolumab, pembrolizumab, MK-3475, AMP-224, AMP-514PDR001, and pidilizumab, optionally wherein the PD-1 antagonist is nivolumab and the cancer is optionally selected from one or more of Hodgkin's lymphoma, melanoma, non-small cell lung cancer, hepatocellular carcinoma, renal cell carcinoma, and ovarian cancer;

the PD-1 antagonist is pembrolizumab and the cancer is optionally selected from one or more of melanoma, non-small cell lung cancer, small cell lung cancer, head and neck cancer, and urothelial cancer;

the antagonist is a CTLA-4 antagonist optionally selected from one or more of an antibody or antigen-binding fragment or small molecule that specifically binds thereto, ipilimumab, tremelimumab, optionally wherein the cancer is selected from one or more of melanoma, prostate cancer, lung cancer, and bladder cancer;

the antagonist is an IDO antagonist optionally selected from one or more of an antibody or antigen-binding fragment or small molecule that specifically binds thereto, indoximod (NLG-8189), 1-methyl-tryptophan (1MT), β-Carboline (norharmane; 9H-pyrido[3,4-b]indole), rosmarinic acid, and epacadostat, and wherein the cancer is optionally selected from one or more of metastatic breast cancer and brain cancer optionally glioblastoma multiforme, glioma, gliosarcoma or malignant brain tumor;

the antagonist is a TDO antagonist optionally selected from one or more of an antibody or antigen-binding fragment or small molecule that specifically binds thereto, 680C91, and LM10;

the antagonist is a TIM-3 antagonist optionally selected from one or more of an antibody or antigen-binding fragment or small molecule that specifically binds thereto;

the antagonist is a LAG-3 antagonist optionally selected from one or more of an antibody or antigen-binding fragment or small molecule that specifically binds thereto, and BMS-986016;

the antagonist is a VISTA antagonist optionally selected from one or more of an antibody or antigen-binding fragment or small molecule that specifically binds thereto;

the antagonist is a BTLA, CD160, and/or HVEM antagonist optionally selected from one or more of an antibody or antigen-binding fragment or small molecule that specifically binds thereto;

the antagonist is a TIGIT antagonist optionally selected from one or more of an antibody or antigen-binding fragment or small molecule that specifically binds thereto.

In some embodiments, the stimulatory immune checkpoint molecule is selected from one or more of OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agonist is an OX40 agonist optionally selected from one or more of an antibody or antigen-binding fragment or small molecule or ligand that specifically binds thereto, OX86, Fc-OX40L, and GSK3174998;

the agonist is a CD40 agonist optionally selected from one or more of an antibody or antigen-binding fragment or small molecule or ligand that specifically binds thereto, CP-870,893, dacetuzumab, Chi Lob 7/4, ADC-1013, and rhCD40L, and wherein the cancer is optionally selected from one or more of melanoma, pancreatic carcinoma, mesothelioma, and hematological cancers optionally lymphoma such as Non-Hodgkin's lymphoma;

the agonist is a GITR agonist optionally selected from one or more of an antibody or antigen-binding fragment or small molecule or ligand that specifically binds thereto, INCAGN01876, DTA-1, and MED11873;

the agonist is a CD137 agonist optionally selected from one or more of an antibody or antigen-binding fragment or small molecule or ligand that specifically binds thereto, utomilumab, and 4-1BB ligand;

the agonist is a CD27 agonist optionally selected from one or more of an antibody or antigen-binding fragment or small molecule or ligand that specifically binds thereto, varlilumab, and CDX-1127 (1F5);

the agonist is a CD28 agonist optionally selected from one or more of an antibody or antigen-binding fragment or small molecule or ligand that specifically binds thereto, and TAB08; and/or the agonist is an HVEM agonist optionally selected from one or more of an antibody or antigen-binding fragment or small molecule or ligand that specifically binds thereto.

In some embodiments, the cancer vaccine is selected from one or more of Oncophage, a human papillomavirus HPV vaccine optionally Gardasil or Cervarix, a hepatitis B vaccine optionally Engerix-B, Recombivax HB, or Twinrix, and sipuleucel-T (Provenge), or comprises a cancer antigen selected from one or more of human Her2/neu, HerVEGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v\beta 3$, integrin $\alpha 5\beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin, optionally wherein the subject has or is at risk for having a cancer that comprises the corresponding cancer antigen.

In some embodiments, the oncolytic virus selected from one or more of talimogene laherparepvec (T-VEC), coxsackievirus A21 (CAVATAK™), Oncorine (H101), pelareorep (REOLYSIN®), Seneca Valley virus (NTX-010), Senecavirus SVV-001, ColoAd1, SEPREHVIR (HSV-1716), CGTG-102 (Ad5/3-D24-GMCSF), GL-ONC1, MV-NIS, and DNX-2401. In some embodiments, the cytokine selected from one or more of interferon (IFN)-a, IL-2, IL-12, IL-7, IL-21, and Granulocyte-macrophage colony-stimulating factor (GM-CSF). In some embodiments, the cell-based immunotherapy agent comprises cancer antigen-specific T-cells, optionally ex vivo-derived T-cells. In some embodiments, the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells.

In some embodiments, the at least one chemotherapeutic agent is selected from one or more of an alkylating agent, an anti-metabolite, a cytotoxic antibiotic, a topoisomerase inhibitor (type 1 or type II), and an anti-microtubule agent.

In some embodiments, the alkylating agent is selected from one or more of nitrogen mustards (optionally mechlorethamine, cyclophosphamide, mustine, melphalan, chlorambucil, ifosfamide, and busulfan), nitrosoureas (optionally N-Nitroso-N-methylurea (MNU), carmustine (BCNU), lomustine (CCNU), semustine (MeCCNU), fotemustine, and streptozotocin), tetrazines (optionally dacarbazine, mitozolomide, and temozolomide), aziridines (optionally thiotepa, mytomycin, and diaziquone (AZQ)), cisplatins and derivatives thereof (optionally carboplatin and oxaliplatin), and non-classical alkylating agents (optionally procarbazine and hexamethylmelamine);

the anti-metabolite is selected from one or more of anti-folates (optionally methotrexate and pemetrexed), fluoropyrimidines (optionally 5-fluorouracil and capecitabine), deoxynucleoside analogues (optionally ancitabine, enocitabine, cytarabine, gemcitabine, decitabine, azacitidine, fludarabine, nelarabine, cladribine, clofarabine, fludarabine, and pentostatin), and thiopurines (optionally thioguanine and mercaptopurine);

the cytotoxic antibiotic is selected from one or more of anthracyclines (optionally doxorubicin, daunorubicin, epirubicin, idarubicin, pirarubicin, aclarubicin, and mitoxantrone), bleomycins, mitomycin C, mitoxantrone, and actinomycin;

the topoisomerase inhibitor is selected from one or more of camptothecin, irinotecan, topotecan, etoposide, doxorubicin, mitoxantrone, teniposide, novobiocin, merbarone, and aclarubicin; and/or the anti-microtubule agent is selected from one or more of taxanes (optionally paclitaxel and docetaxel) and *vinca* alkaloids (optionally vinblastine, vincristine, vindesine, vinorelbine).

In some embodiments, the at least one hormonal therapeutic agent is a hormonal agonist or a hormonal antagonist. In some embodiments, the hormonal agonist is selected from one or more of a progestogen (progestin), a corticosteroid (optionally prednisolone, methylprednisolone, or dexamethasone), insulin like growth factors, VEGF derived angiogenic and lymphangiogenic factors (optionally VEGF-A, VEGF-A145, VEGF-A165, VEGF-C, VEGF-D, PIGF-2), fibroblast growth factor (FGF), galectin, hepatocyte growth factor (HGF), platelet derived growth factor (PDGF), transforming growth factor (TGF)-beta, an androgen, an estrogen, and a somatostatin analog. In some embodiments, the hormonal antagonist is selected from one or more of a hormone synthesis inhibitor, optionally an aromatase inhibitor or a gonadotropin-releasing hormone (GnRH) or an analog thereof, and a hormone receptor antagonist, optionally a selective estrogen receptor modulator (SERM) or an anti-androgen, or an antibody directed against a hormonal receptor, optionally cixutumumab, dalotuzumab, figitumumab, ganitumab, istiratumab, robatumumab, alacizumab pegol, bevacizumab, icrucumab, ramucirumab, fresolimumab, metelimumab, naxitamab, cetuximab, depatuxizumab mafodotin, futuximab, imgatuzumab, laprituximab emtansine, matuzumab, modotuximab, necitumumab, nimotuzumab, panitumumab, tomuzotuximab, zalutumumab, aprutumab ixadotin, bemarituzumab, olaratumab, or tovetumab.

In some embodiments, the kinase inhibitor is selected from one or more of adavosertib, afanitib, aflibercept, axitinib, bevacizumab, bosutinib, cabozantinib, cetuximab, cobimetinib, crizotinib, dasatinib, entrectinib, erdafitinib, erlotinib, fostamitinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, SU6656, tofacitinib, trastuzumab, vandetanib, and vemuafenib. In some embodiments, the cancer is a primary cancer. In some embodiments, the cancer is a metastatic cancer, for example, a metastatic cancer that expresses NRP2 and/or NRP2B. In some embodiments, the cancer is selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, the metastatic cancer is selected from one or more of:
(a) a bladder cancer which has metastasized to the bone, liver, and/or lungs;
(b) a breast cancer which has metastasized to the bone, brain, liver, and/or lungs;
(c) a colorectal cancer which has metastasized to the liver, lungs, and/or peritoneum;
(d) a kidney cancer which has metastasized to the adrenal glands, bone, brain, liver, and/or lungs;
(e) a lung cancer which has metastasized to the adrenal glands, bone, brain, liver, and/or other lung sites;
(f) a melanoma which has metastasized to the bone, brain, liver, lung, and/or skin/muscle;
(g) a ovarian cancer which has metastasized to the liver, lung, and/or peritoneum;
(h) a pancreatic cancer which has metastasized to the liver, lung, and/or peritoneum;
(i) a prostate cancer which has metastasized to the adrenal glands, bone, liver, and/or lungs;
(j) a stomach cancer which has metastasized to the liver, lung, and/or peritoneum;
(l) a thyroid cancer which has metastasized to the bone, liver, and/or lungs; and
(m) a uterine cancer which has metastasized to the bone, liver, lung, peritoneum, and/or vagina.

In some embodiments, the subject has, and/or is selected for treatment based on having, increased circulating or serum levels of at least one NRP2 ligand (for example, an NRP2 ligand from Table N2 or Table N3 and/or an HRS polypeptide from Table H1), either bound or free, relative to the levels of a healthy control or matched control standard or population of subject(s), optionally about or at least about 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 3000, 4000, or 5000 pM of the at least one NRP2 ligand (for example, HRS polypeptide), or about or at least about 30-100, 40-100, 50-100, 30-2000, 40-2000, 50-2000, 60-2000, 70-2000, 80-2000, 90-2000, 100-2000, 200-2000, 300-2000, 400-2000, 500-2000, 600-2000, 700-2000, 800-2000, 900-2000, 1000-2000, 2000-3000, 3000-4000, or 4000-5000 pM of the at least one NRP2 ligand.

In some embodiments, the subject has, and/or is selected for treatment based on having, a disease associated with increased levels or expression of at least one NRP2 ligand (for example, an NRP2 ligand from Table N2 or Table N3 and/or an HRS polypeptide from Table H1) and/or a coding mRNA thereof relative to a healthy control or matched control standard or population of subject(s), optionally a cancer which has increased levels or expression of the at least one NRP2 ligand and/or a coding mRNA thereof relative to a non-cancerous control cell or tissue, optionally relative to a non-cancerous cell or tissue of the same type as the cancer, optionally wherein the HRS polypeptide is a splice variant selected from $HisRS^{N1}$, $HisRS^{N2}$, $HisRS^{N3}$, $HisRS^{N4}$, $HisRS^{N5}$, $HisRS^{C1}$, $HisRS^{C2}$, $HisRS^{C3}$, $HisRS^{C4}$, $HisRS^{C5}$, $HisRS^{C6}$, $HisRS^{C7}$, $HisRS^{C8}$, and $HisRS^{C9}$.

In some embodiments, the subject has, and/or is selected for treatment based on having, increased circulating or serum levels of a soluble neuropilin 2 (NRP2) polypeptide (for example, selected from Table N1), either bound or free, relative to the levels of a healthy control or matched control standard or population of subject(s), optionally circulating or serum levels of about or at least about 10, 20, 30, 50, 100, 200, 300, 400, 500, 600, 700, 800, 900, 1000, 1100, 1200, 1300, 1400, 1500, 1600, 1700, 1800, 1900, 2000, 3000, 4000, 5000 pM of the soluble NRP2 polypeptide, or optionally circulating or serum levels about 30-50, 50-100, 100-2000, 200-2000, 300-2000, 400-2000, 500-2000, 600-2000, 700-2000, 800-2000, 900-2000, 1000-2000, 2000-3000, 3000-4000, 4000-5000 pM of the soluble NRP2 polypeptide.

In some embodiments, the subject has, and/or is selected for treatment based on having, a disease associated with increased levels or expression of an NRP2 polypeptide (for example, selected from Table N1) and/or a coding mRNA thereof relative to a healthy control or matched control standard or population of subject(s), optionally a cancer which has increased levels or expression of an NRP2 polypeptide (for example, selected from Table N1) and/or a coding mRNA thereof relative to a control cell or tissue, optionally relative to a non-cancerous cell or tissue of the same type as the cancer.

In some embodiments, the subject has, and/or is selected for treatment based on having, a disease associated with increased levels or expression of NRP2A and/or NRP2B, or an altered ratio of NRP2A:NRP2B expression, relative to a healthy control or matched control standard or population of subject(s). In some embodiments, the subject has significantly higher expression or levels of NRP2B relative to a healthy control or matched control standard or population of subject(s). In some embodiments, the levels of NRP2B are increased by about or at least about 10%, 20%, 30%, 40%, 50%, 100%, 200%, 300%, 400%, 500%, 600%, 700%, 800%, 900%, 1000% compared to a healthy control or matched control standard or population of subject(s).

In some embodiments, the subject has, and/or is selected for treatment based on having, increased circulating levels of HRS:NRP2 complexes relative to a healthy or matched control standard or population of subject(s).

In some embodiments, the healthy control or matched control standard or population of subject(s) comprises average ranges for age-matched samples of cancerous or non-cancerous cells or tissue of the same type as the cancer, which comprise specific characteristics such as drug resistance, metastatic potential, aggressiveness, genetic signature (e.g., p53 mutations, PTEN deletion, IGFR expression), and/or expression patterns.

Certain embodiments comprise administering the at least one anti-NRP2 antibody in an amount and at a frequency sufficient to achieve an average, sustained serum or circulating levels of a soluble NRP2 polypeptide of about or less than about 500 pM, 400 pM, 300 pM, 200 pM, 100 pM, 50 pm, 40 pM, 30 pM, 20 pM, or 10 pM.

Certain embodiments comprise administering the at least one anti-NRP2 antibody in an amount and at a frequency sufficient to achieve a reduction in the circulating levels of HRS:NRP2 complexes, optionally a reduction of about or at least about 5, 10, 15, 20, 25, 30, 35, 40, 45, 50, 60, 70, 80, 90, 95, 99, or 100%.

In some embodiments, the at least one anti-NRP2 antibody enhances the immune response to the cancer by about, or at least about, 5, 10, 15, 20, 25, 30, 35, 40, 45, 50, 60, 70, 80, 90, 100, 200, 300, 400, 500, 600, 700, 800, 900, 1000, 2000% or more, relative to a control.

In some embodiments, the at least one anti-NRP2 antibody reduces the rate of in vitro growth of the cancer by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody reduces the in vitro adhesiveness of the cancer to a substrate by about or at least about, 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the substrate comprises laminin.

In some embodiments, the at least one anti-NRP2 antibody reduces the invasiveness of the cancer by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody inhibits the rate of migration or motility of the cancer by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody inhibits the rate of autophagy or endosome maturation (for example, endosome acidification) of the cancer or associated immune cells by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody enhances the susceptibility of the cancer to a chemotherapeutic agent, hormonal therapeutic agent, or kinase inhibitor, by about or at least about 5, 10, 15, 20, 25, 30, 35, 40, 45, 50, 60, 70, 80, 90, 100, 200, 300, 400, 500, 600, 700, 800, 900, 1000, 2000% or more relative to the chemotherapeutic agent alone.

In some embodiments, the at least one anti-NRP2 antibody enhances an anti-tumor and/or immunostimulatory activity of the cancer immunotherapy agent by about, or at least about, 5, 10, 15, 20, 25, 30, 35, 40, 45, 50, 60, 70, 80, 90, 100, 200, 300, 400, 500, 600, 700, 800, 900, 1000, 2000% or more, relative to the cancer immunotherapy agent alone.

Certain embodiments comprise administering the at least one anti-NRP2 antibody in an amount and at a frequency sufficient to achieve a steady state concentration, or average circulating concentration, of the at least one anti-NRP2 antibody of between about 1 nM and about 1 µM, between about 1 nM and about 100 nM, between about 1 nM and about 10 nM, or between about 1 nM and about 3 µM.

Also included are patient care kits, comprising:
(a) at least one antibody or antigen-binding fragment thereof that specifically binds to a human neuropilin-2 (NRP2) polypeptide, as described herein; and optionally
(b) at least one additional agent selected from one or more of a cancer immunotherapy agent, a chemotherapeutic agent, a hormonal therapeutic agent, and a kinase inhibitor.

In some embodiments, (a) and (b) are in separate therapeutic compositions. In some embodiments, (a) and (b) are in the same therapeutic composition, as described herein.

In some patient care kits, the at least one chemotherapeutic agent is selected from one or more of an alkylating agent, an anti-metabolite, a cytotoxic antibiotic, a topoisomerase inhibitor (type 1 or type II), and an anti-microtubule agent.

In some patient care kits, the alkylating agent is selected from one or more of nitrogen mustards (optionally mechlorethamine, cyclophosphamide, mustine, melphalan, chlorambucil, ifosfamide, and busulfan), nitrosoureas (optionally N-Nitroso-N-methylurea (MNU), carmustine (BCNU), lomustine (CCNU), semustine (MeCCNU), fotemustine, and streptozotocin), tetrazines (optionally dacarbazine, mitozolomide, and temozolomide), aziridines (optionally thiotepa, mytomycin, and diaziquone (AZQ)), cisplatins and derivatives thereof (optionally carboplatin and oxaliplatin), and non-classical alkylating agents (optionally procarbazine and hexamethylmelamine);

the anti-metabolite is selected from one or more of anti-folates (optionally methotrexate and pemetrexed), fluoropyrimidines (optionally 5-fluorouracil and capecitabine), deoxynucleoside analogues (optionally ancitabine, enocitabine, cytarabine, gemcitabine, decitabine, azacitidine, fludarabine, nelarabine, cladribine, clofarabine, fludarabine, and pentostatin), and thiopurines (optionally thioguanine and mercaptopurine);

the cytotoxic antibiotic is selected from one or more of anthracyclines (optionally doxorubicin, daunorubicin, epirubicin, idarubicin, pirarubicin, aclarubicin, and mitoxantrone), bleomycins, mitomycin C, mitoxantrone, and actinomycin;

the topoisomerase inhibitor is selected from one or more of camptothecin, irinotecan, topotecan, etoposide, doxorubicin, mitoxantrone, teniposide, novobiocin, merbarone, and aclarubicin; and/or the anti-microtubule agent is selected from one or more of taxanes (optionally paclitaxel and docetaxel) and *vinca* alkaloids (optionally vinblastine, vincristine, vindesine, vinorelbine).

In some patient care kits, the at least one hormonal therapeutic agent is a hormonal agonist or a hormonal antagonist. In some patient care kits, the hormonal agonist is selected from one or more of a progestogen (progestin), a corticosteroid (optionally prednisolone, methylprednisolone, or dexamethasone), insulin like growth factors, VEGF derived angiogenic and lymphangiogenic factors (optionally VEGF-A, VEGF-A145, VEGF-A165, VEGF-C, VEGF-D, PIGF-2), fibroblast growth factor (FGF), galectin, hepatocyte growth factor (HGF), platelet derived growth factor (PDGF), transforming growth factor (TGF)-beta, an androgen, an estrogen, and a somatostatin analog.

In some patient care kits, the hormonal antagonist is selected from one or more of a hormone synthesis inhibitor, optionally an aromatase inhibitor or a gonadotropin-releasing hormone (GnRH) or an analog thereof, and a hormone receptor antagonist, optionally a selective estrogen receptor modulator (SERM) or an anti-androgen, or an antibody directed against a hormonal receptor, optionally cixutumumab, dalotuzumab, figitumumab, ganitumab, istiratumab, robatumumab, alacizumab pegol, bevacizumab, icrucumab, ramucirumab, fresolimumab, metelimumab, naxitamab, cetuximab, depatuxizumab mafodotin, futuximab, imgatuzumab, laprituximab emtansine, matuzumab, modotuximab, necitumumab, nimotuzumab, panitumumab, tomuzotuximab, zalutumumab, aprutumab ixadotin, bemarituzumab, olaratumab, or tovetumab.

In some patient care kits, the kinase inhibitor is selected from one or more of adavosertib, afanitib, aflibercept, axitinib, bevacizumab, bosutinib, cabozantinib, cetuximab, cobimetinib, crizotinib, dasatinib, entrectinib, erdafitinib, erlotinib, fostamitinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, SU6656, tofacitinib, trastuzumab, vandetanib, and vemuafenib Also included are bioassay systems, comprising a substantially pure anti-NRP2 antibody or antigen-binding fragment thereof, optionally as defined herein, and a host cell line that expresses a human NRP2 polypeptide on the cell surface.

In some embodiments, the NRP2 polypeptide is labeled with a detectable label. In some embodiments, the anti- NRP2 antibody is labeled with a detectable label. In some embodiments, the NRP2 polypeptide is functionally coupled to a readout or indicator, such as a fluorescent or luminescent indicator of biological activity of the NRP2 polypeptide. In some embodiments, the NRP2 polypeptide is selected from Table N1. Some bioassay systems comprise at least one NRP2 ligand (for example, an NRP2 ligand from Table N2 or Table N3 and/or a human histidyl-tRNA synthetase (HRS) polypeptide from Table H1), for example, wherein the host cell expresses the at least one NRP2 ligand. In some embodiments, the HRS polypeptide is selected from Table H1, for example, wherein the HRS polypeptide comprises a HRS splice variant, optionally selected from $HisRS^{N1}$, $HisRS^{N2}$, $HisRS^{N3}$, $HisRS^{N4}$, $HisRS^{N5}$, $HisRS^{C1}$, $HisRS^{C2}$, $HisRS^{C3}$, $HisRS^{C4}$, $HisRS^{C5}$, $HisRS^{C6}$, $HisRS^{C7}$, $HisRS^{C8}$, and $HisRS^{C9}$. In some embodiments, the at least one NRP2 ligand is selected from Table N2 or Table N3.

Some embodiments include a detection system, comprising a cell that expresses a human neuropilin 2 (NRP2) polypeptide and at least one NRP2 ligand (for example, a recombinant NRP2 ligand selected from Table N2 or Table N3 and/or a human histidyl-tRNA synthetase (HRS) polypeptide from Table H1), and a human or humanized anti-NRP2 antibody or antigen-binding fragment thereof, as described herein, which modulates the interaction between the NRP2 polypeptide and the at least one NRP2 ligand. In some embodiments, the anti-NRP2 antibody is labeled with a detectable label. In some embodiments, the NRP2 polypeptide is selected from Table N1. In some embodiments, the HRS polypeptide is selected from Table H1, for example, wherein the HRS polypeptide comprises a HRS splice variant, optionally selected from $HisRS^{N1}$, $HisRS^{N2}$, $HisRS^{N3}$, $HisRS^{N4}$, $HisRS^{N5}$, $HisRS^{C1}$, $HisRS^{C2}$, $HisRS^{C3}$, $HisRS^{C4}$, $HisRS^{C5}$, $HisRS^{C6}$, $HisRS^{C7}$, $HisRS^{C8}$, and $HisRS^{C9}$. In some embodiments, the at least one NRP2 ligand is selected from Table N2 or Table N3. In some embodiments, the NRP2 polypeptide and/or the at least one NRP2 ligand (for example, an NRP2 ligand from Table N2 or Table N3 and/or an HRS polypeptide from Table H1) is/are functionally coupled to a readout or indicator, such as a fluorescent or luminescent indicator of biological activity of the NRP2 polypeptide or the at least one NRP2 ligand.

Also included are diagnostic systems, comprising a cell that comprises a neuropilin 2 (NRP2) polypeptide, and at least one NRP2 ligand that specifically binds to the NRP2 polypeptide (for example, an NRP2 ligand selected from Table N2 or Table N3 and/or a human histidyl-tRNA synthetase (HRS) polypeptide selected from Table H1), wherein the cell comprises an indicator molecule that indicates a change in the levels or activity of the NRP2 polypeptide in response to interaction with the at least one NRP2 ligand.

Also included are cellular compositions, comprising an engineered population of cells in which at least one cell comprises one or more polynucleotides encoding a human or humanized anti-NRP2 antibody or antigen-binding fragment thereof, as described herein, wherein the cells are capable of growing in a serum-free medium.

Also included are cellular growth devices, comprising a human or humanized anti-NRP2 antibody or antigen-binding fragment thereof, as described herein, an engineered population of cells in which at least one cell comprises one or more polynucleotides encoding said anti-NRP2 antibody or antigen-binding fragment thereof, at least about 10 liters of a serum-free growth medium, and a sterile container.

BRIEF DESCRIPTION OF THE DRAWINGS

FIG. 4A shows antibody binding to U251 cells, FIG. 4B shows antibody binding to HUVEC cells, FIG. 4C shows antibody binding to THP-1 M1cells, and FIG. 4D shows antibody binding to HLEC cells.

FIG. 5A shows antibody binding to HUVEC cells with antibody concentrations ranging from 0.06 nM-1000 nM. FIG. 5B shows binding to U251 cells, with antibody concentrations ranging from 0.01 nM-1000 nM. FIG. 5C shows binding to A549 cells with antibody concentrations ranging from 0.01 nM-1000 nM. FIG. 5D shows binding to THP-1 M1cells, with antibody concentrations ranging from 0.01 nM-1000 nM. Antibodies 14v2 (aNRP2-14), 10v2 (aNRP2-10), 11v2(aNRP2-11), 2v2(aNRP2-2), and isotype control (cMOPC21) were incubated with cells at the indicated concentrations as described in the examples.

FIG. 6A shows antibody concentrations over the range 0.05-30 nM, and FIG. 6B shows the results with antibody concentrations tested over the range 0.02-10 nM, both with a 3-fold antibody dilution. Antibody binding was detected using an AF647-conjugated goat anti-mouse IgG secondary antibody (GaM AF647). Antibodies 8v2(aNRP2-8) #1328, 9v2(aNRP2-9) #1329, 10v2(aNRP2-10) #1330, 14v2, 11v2 (aNRP2-11) #1331, 14v2(aNRP2-14), #1344, 15v2(aNRP2-15) #1347 and isotype control (cMOPC21) (data not shown) were incubated with cells at the indicated concentrations as described in the Examples.

FIG. 7A shows the FACS binding curve using VEGF-C(R&D systems), using rabbit detection antibody (Abcam) and a goat antibody AF647 labeled secondary antibody. FIG. 7B shows the flow cytometry scatter plots. From left to right, the curves in FIG. 7B show (a-R AF647); (Rb Iso_Ctl+a-R AF647); (a-VEGFc+a-R AF647); and (VEGFc 100 nM+a-VEGFc+a-R AF647).

FIGS. 8A-8M show anti-NRP2 antibody blocking, displacement curves for the indicated antibodies on VEGF-C binding to Expi293-hNRP2 clonal cells over expressing human NRP2. FIG. 8A shows the results with the isotype control antibody, FIG. 8B shows the results with antibody 8v2(aNRP2-8) #1328, FIG. 8C shows the results with antibody 9v2(aNRP2-9) #1329, FIG. 8D shows the results with antibody 11v2(aNRP2-11) #1331, FIG. 8E shows the results with antibody 14v2(aNRP2-14) #1344, FIG. 8F shows the results with antibody 2v1(aNRP2-1) #1326, FIG. 8G shows the results with antibody 2v2(aNRP2-2) #1327, FIG. 8H shows the results with antibody 2v10(aNRP2-10) #1330, FIG. 8I shows the results with antibody #1333, FIG. 8J shows the results with antibody #1334, FIG. 8K shows the results with antibody 2v7(aNRP2-7) #1335, FIG. 8L shows the results with antibody 2v12(aNRP2-12) #1336, and FIG. 8M shows the results with antibody #1337.

FIG. 9 shows the FACS binding curve using Sema 3F-p95 or p65 (in house), using an anti-myc detection antibody as described in the Examples.

FIG. 10A shows the results with the isotype control antibody, FIG. 10B shows the results with antibody 14v2(aNRP2-14) #1344, FIG. 10C shows the results with antibody 8v2(aNRP2-8) #1328, FIG. 10D shows the results with antibody 9v2(aNRP2-9) #1329, FIG. 10E shows the results with antibody 2v10(aNRP2-10) #1330, FIG. 10F shows the results with antibody 15v2 (aNRP2-15) #1347, FIG. 10G shows the results with antibody 11v2(aNRP2-11) #1331, and FIG. 10H shows the results with antibody 2v2(aNRP2-2) #1327.

FIG. 11A shows the results with antibody 14v2(aNRP2-14) #1344, FIG. 11B shows the results with antibody 8v2(aNRP2-8) #1328, FIG. 11C shows the results with antibody 9v2(aNRP2-9) #1329, FIG. 11D shows the results with antibody 2v10(aNRP2-10) #1330, FIG. 11E shows the results with antibody 15v2(aNRP2-15) #1347, and FIG. 11F shows the results with antibody 11v2 (aNRP2-11) #1331.

DETAILED DESCRIPTION

Figure 1A:
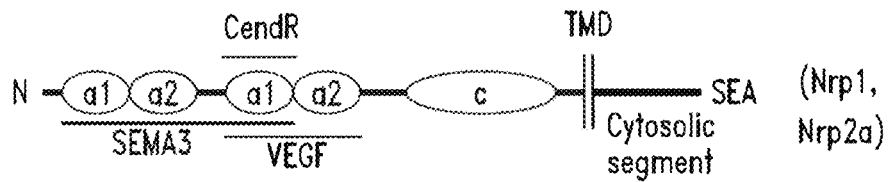
FIGS. 1A-1B illustrate the general domain structure of neuropilins (1A) and exemplary neuropilin co-receptor functions (1B).

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" includes "one element", "one or more elements" and/or "at least one element".

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes. As used herein, the term "antigen" includes substances that are capable, under appropriate conditions, of inducing an immune response to the substance and of reacting with the products of the immune response. For example, an antigen can be recognized by antibodies (humoral immune response) or sensitized T-lymphocytes (T helper or cell-mediated immune response), or both. Antigens can be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" includes any substance to which an antibody binds, or for which antibodies are desired, regardless of whether the substance is immunogenic. For such antigens, antibodies can be identified by recombinant methods, independently of any immune response.

An "antagonist" refers to biological structure or chemical agent that interferes with or otherwise reduces the physiological action of another agent or molecule. In some instances, the antagonist specifically binds to the other agent or molecule. Included are full and partial antagonists.

An "agonist" refers to biological structure or chemical agent that increases or enhances the physiological action of another agent or molecule. In some instances, the agonist specifically binds to the other agent or molecule. Included are full and partial agonists.

The term "anergy" refers to the functional inactivation of a T-cell, or B-cell response to re-stimulation by antigen.

As used herein, the term "amino acid" is intended to mean both naturally occurring and non-naturally occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. Certain features and characteristics of antibodies (and antigen-binding fragments thereof) are described in greater detail herein.

An antibody or antigen-binding fragment can be of essentially any type. As is well known in the art, an antibody is an immunoglobulin molecule capable of specific binding to a target, such as an immune checkpoint molecule, through at least one epitope recognition site, located in the variable region of the immunoglobulin molecule.

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise 1, 2, 3, 4, 5, or all 6 CDRs of a V H and V L sequence from antibodies that bind to a target molecule.

The binding properties of antibodies and antigen-binding fragments thereof can be quantified using methods well known in the art (see Davies et al., Annual Rev. Biochem. 59:439-473, 1990). In some embodiments, an antibody or antigen-binding fragment thereof specifically binds to a target molecule, for example, an NRP2 polypeptide or an epitope or complex thereof, with an equilibrium dissociation constant that is about or ranges from about $\leq 1.0^{-7}$ M to about $10^{-8}$ M. In some embodiments, the equilibrium dissociation constant is about or ranges from about $\leq 1.0^{-9}$ M to about $\leq 1.0^{-10}$ M. In certain illustrative embodiments, an antibody or antigen-binding fragment thereof has an affinity (Kd or $EC_{50}$) for a target molecule (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

A molecule such as a polypeptide or antibody is said to exhibit "specific binding" or "preferential binding" if it reacts or associates more frequently, more rapidly, with greater duration and/or with greater affinity with a particular cell, substance, or particular epitope than it does with alternative cells or substances, or epitopes. An antibody "specifically binds" or "preferentially binds" to a target molecule or epitope if it binds with greater affinity, avidity, more readily, and/or with greater duration than it binds to other substances or epitopes, for example, by a statistically significant amount. Typically one member of the pair of molecules that exhibit specific binding has an area on its surface, or a cavity, which specifically binds to and is therefore complementary to a particular spatial and/or polar organization of the other member of the pair of molecules. Thus, the members of the pair have the property of binding specifically to each other. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. The term is also applicable where, for example, an antibody is specific for a particular epitope which is carried by a number of antigens, in which case the specific binding member carrying the antigen-binding fragment or domain will be able to bind to the various antigens carrying the epitope; for example, it may be cross reactive to a number of different forms of a target antigen from multiple species that share a common epitope Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant (Kd) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd. As used herein, the term "affinity" includes the equilibrium constant for the reversible binding of two agents and is expressed as Kd or $EC_{50}$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. In some embodiments, affinity is expressed in the terms of the half maximal effective concentration ($EC_{50}$), which refers to the concentration of an agent, such as an antibody, or an anti-NRP2 antibody, as disclosed herein, which induces a response halfway between the baseline and maximum after a specified exposure time. The $EC_{50}$ is commonly used as a measure of an antibody's potency.

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. See Inbar et al., PNAS USA. 69:2659-2662, 1972; Hochman et al., Biochem. 15:2706-2710, 1976; and Ehrlich et al., Biochem. 19:4091-4096, 1980.

In certain embodiments, single chain Fv (scFV) antibodies are contemplated. For example, Kappa bodies (III et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (scFv) polypeptide is a covalently linked VH::VL heterodimer which is expressed from a gene fusion including VH- and VL-encoding genes linked by a peptide-encoding linker. Huston et al. (PNAS USA. 85(16): 5879-5883, 1988). A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments described herein are in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associate with each other to form an antigen-binding site: antigen-binding sites are formed by the association of the first domain of one polypeptide within the multimer with the second domain of another polypeptide within the multimer (WO94/13804). A dAb fragment of an antibody consists of a VH domain (Ward et al., Nature 341:544-546, 1989). Diabodies and other multivalent or multispecific fragments can be constructed, for example, by gene fusion (see WO94/13804; and Holliger et al., PNAS USA. 90:6444-6448, 1993)).

Minibodies comprising a scFv joined to a CH3 domain are also included (see Hu et al., Cancer Res. 56:3055-3061, 1996). See also Ward et al., Nature. 341:544-546, 1989; Bird et al., Science. 242:423-426, 1988; Huston et al., PNAS USA. 85:5879-5883, 1988); PCT/US92/09965; WO94/13804; and Reiter et al., Nature Biotech. 14:1239-1245, 1996.

Where bispecific antibodies are to be used, these may be conventional bispecific antibodies, which can be manufactured in a variety of ways (Holliger and Winter, Current Opinion Biotechnol. 4:446-449, 1993), e.g., prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., Protein Eng., 9:616-621, 1996).

In certain embodiments, the antibodies or antigen-binding fragments described herein are in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies and antigen-binding fragments described herein are in the form of a nanobody. Minibodies are encoded by single genes and are efficiently produced in almost all prokaryotic and eukaryotic hosts, for example, *E. coli* (see U.S. Pat. No. 6,765,087), molds (for example *Aspergillus* or *Trichoderma*) and yeast (for example *Saccharomyces, Kluyvermyces, Hansenula* or *Pichia* (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B-cells.

In some embodiments, the antibodies or antigen-binding fragments described herein are in the form of an aptamer (see, e.g., Ellington et al., Nature. 346, 818-22, 1990; and Tuerk et al., Science. 249, 505-10, 1990, incorporated by reference). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620, incorporated by reference.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments utilize the bacterial protein Thioredoxin-A as a scaffold protein, the variable loop being inserted within the reducing active site (-Cys-Gly-Pro-Cys-loop in the wild protein), with the two cysteines lateral chains being able to form a disulfide bridge. Methods for identifying peptide aptamers are described, for example, in U.S. Application No. 2003/0108532, incorporated by reference. Peptide aptamer selection can be performed using different systems known in the art, including the yeast two-hybrid system.

In some embodiments, the antibodies or antigen-binding fragments described herein are in the form of an avimer. Avimers refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., Nature Biotechnology. 23:1556-1561, 2005; U.S. Pat. No. 7,166,697; and U.S. Application Nos. 2004/0175756, 2005/0048512, 2005/0053973, 2005/0089932 and 2005/0221384, incorporated by reference.

In some embodiments, the antibodies or antigen-binding fragments described herein are in the form of an adnectin. Adnectins refer to a class of targeted biologics derived from human fibronectin, an abundant extracellular protein that naturally binds to other proteins. See, e.g., U.S. Application Nos. 2007/0082365; 2008/0139791; and 2008/0220049, incorporated by reference. Adnectins typically consists of a natural fibronectin backbone, as well as the multiple targeting domains of a specific portion of human fibronectin. The targeting domains can be engineered to enable an adnectin to specifically recognize an NRP2 polypeptide or an epitope thereof.

In some embodiments, the antibodies or antigen-binding fragments described herein are in the form of an anticalin. Anticalins refer to a class of antibody mimetics that are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable (3-barrel scaffold) that are pairwise connected by four peptide loops and an attached α-helix. In certain aspects, conformational deviations to achieve specific binding are made in the hypervariable loop region(s). See, e.g., Skerra, FEBS J. 275:2677-83, 2008, incorporated by reference.

In some embodiments, the antibodies or antigen-binding fragments described herein are in the form of a designed ankyrin repeat protein (DARPin). DARPins include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins. See, e.g., Stumpp et al., Curr Opin Drug Discov Devel. 10:153-159, 2007; U.S. Application No. 2009/0082274; and PCT/EP2001/10454, incorporated by reference.

Also included are heavy chain dimers, such as antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains).

In camelids, the diversity of antibody repertoire is determined by the complementary determining regions (CDR) 1, 2, and 3 in the VH or VHH regions. The CDR3 in the camel VHH region is characterized by its relatively long length averaging 16 amino acids (Muyldermans et al., 1994, Protein Engineering 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421, published Feb. 17, 2005

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies are "chimeric" antibodies. In this regard, a chimeric antibody is comprised of an antigen-binding fragment of an antibody operably linked or otherwise fused to a heterologous Fc portion of a different antibody. In certain embodiments, the Fc domain or heterologous Fc domain is of human origin. In certain embodiments, the Fc domain or heterologous Fc domain is of mouse origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

As used herein, a subject "at risk" of developing a disease, or adverse reaction may or may not have detectable disease, or symptoms of disease, and may or may not have displayed detectable disease or symptoms of disease prior to the treatment methods described herein. "At risk" denotes that a subject has one or more risk factors, which are measurable parameters that correlate with development of a disease, as described herein and known in the art. A subject having one or more of these risk factors has a higher probability of developing disease, or an adverse reaction than a subject without one or more of these risk factor(s).

"Biocompatible" refers to materials or compounds which are generally not injurious to biological functions of a cell or subject and which will not result in any degree of unacceptable toxicity, including allergenic and disease states.

The term "binding" refers to a direct association between two molecules, due to, for example, covalent, electrostatic, hydrophobic, and ionic and/or hydrogen-bond interactions, including interactions such as salt bridges and water bridges.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "effector function", or "ADCC effector function" in the context of antibodies refers to the ability of that antibody to engage with other arms of the immune system, including for example, the activation of the classical complement pathway, or through engagement of Fc receptors. Complement dependent pathways are primarily driven by the interaction of C1q with the C1 complex with clustered antibody Fc domains. Antibody dependent cellular cytotoxicity (ADCC), is primarily driven by the interaction of Fc receptors (FcRs) on the surface of effector cells (natural killer cells, macrophages, monocytes and eosinophils) which bind to the Fc region of an IgG which itself is bound to a target cell. Fc receptors (FcRs) are key immune regulatory receptors connecting the antibody mediated (humoral) immune response to cellular effector functions. Receptors for all classes of immunoglobulins have been identified, including FcγR (IgG), Fc∈RI (IgE), FcαRI (IgA), FcμR (IgM) and FcδR (IgD). There are at least three classes of receptors for human IgG found on leukocytes: CD64 (FcγRI), CD32 (FcγRIIa, FcγRIIb and FcγRIIc) and CD16 (FcγRIIIa and FcγRIIIb). FcγRI is classed as a high affinity receptor (nanomolar range KD) while FcγRII and FcγRIII are low to intermediate affinity (micromolar range KD). Upon Fc binding a signaling pathway is triggered which results in the secretion of various substances, such as lytic enzymes, perform, granzymes and tumour necrosis factor, which mediate in the destruction of the target cell. The level of ADCC effector function various for human IgG subtypes. Although this is dependent on the allotype and specific FcvR, in simple terms ADCC effector function is "high" for human IgG1 and IgG3, and "low" for IgG2 and IgG4.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The term "epitope" includes any determinant, preferably a polypeptide determinant, capable of specific binding to an immunoglobulin or T-cell receptor. An epitope includes a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen, for example, an NRP2 polypeptide. In particular embodiments, an epitope comprises, consists, or consists essentially of about, at least about, or no more than about 3, 4, 5, 6, 7, 8, 9, 10, 11, 12, 13, 14, 15, 16, 17, 18, 19, or 20 contiguous amino acids (i.e., a linear epitope) or non-contiguous amino acids (i.e., conformational epitope) of a reference sequence (see, e.g., Table N1) or target molecule described herein.

An "epitope" includes that portion of an antigen or other macromolecule capable of forming a binding interaction that interacts with the variable region binding pocket of a binding protein. Such binding interaction can be manifested as an intermolecular contact with one or more amino acid residues of a CDR. Antigen binding can involve a CDR3 or a CDR3 pair. An epitope can be a linear peptide sequence (i.e., "continuous") or can be composed of noncontiguous amino acid sequences (i.e., "conformational" or "discontinuous"). A binding protein can recognize one or more amino acid sequences; therefore an epitope can define more than one distinct amino acid sequence. Epitopes recognized by binding protein can be determined by peptide mapping and sequence analysis techniques well known to one of skill in the art. A "cryptic epitope" or a "cryptic binding site" is an epitope or binding site of a protein sequence that is not exposed or substantially protected from recognition within an unmodified polypeptide, but is capable of being recognized by a binding protein of a denatured or proteolyzed polypeptide. Amino acid sequences that are not exposed, or are only partially exposed, in the unmodified polypeptide structure are potential cryptic epitopes. If an epitope is not exposed, or only partially exposed, then it is likely that it is buried within the interior of the polypeptide. Candidate cryptic epitopes can be identified, for example, by examining the three-dimensional structure of an unmodified polypeptide.

The term "half maximal effective concentration" or "$EC_{50}$" refers to the concentration of an agent (e.g., antibody) as described herein at which it induces a response halfway between the baseline and maximum after some specified exposure time; the $EC_{50}$ of a graded dose response curve therefore represents the concentration of a compound at which 50% of its maximal effect is observed. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an agent (e.g., antibody) is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, an agent will have an $EC_{50}$ value of about 1 nM or less.

"Immune response" means any immunological response originating from immune system, including responses from the cellular and humeral, innate and adaptive immune systems. Exemplary cellular immune cells include for example, lymphocytes, macrophages, T cells, B cells, NK cells, neutrophils, eosinophils, dendritic cells, mast cells, monocytes, and all subsets thereof. Cellular responses include for example, effector function, cytokine release, phagocytosis, efferocytosis, translocation, trafficking, proliferation, differentiation, activation, repression, cell-cell interactions, apoptosis, etc. Humeral responses include for example IgG, IgM, IgA, IgE, responses and their corresponding effector functions.

The "half-life" of an agent such as an antibody can refer to the time it takes for the agent to lose half of its pharmacologic, physiologic, or other activity, relative to such activity at the time of administration into the serum or tissue of an organism, or relative to any other defined time-point. "Half-life" can also refer to the time it takes for the amount or concentration of an agent to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30, 40, 50, 60, 70, 80, 90, 100 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The term "migratory cells" refers to cells that are capable of movement from one place to another in response to a stimulus. Exemplary migratory cells include immune cells such as monocytes, Natural Killer (NK) cells, dendritic cells (immature or mature), subsets of dendritic cells including myeloid, plasmacytoid (also called lymphoid) and Langerhans cells, macrophages such as histiocytes, tissue resident macrophages such as Kupffer's cells, microglia cells in the CNS, alveolar macrophages, and peritoneal macrophages, macrophage subtypes such as M0, M1, Mox, M2a, M2b, and M2c macrophages, neutrophils, eosinophils, mast cells, basophils, B cells including plasma B cells, memory B cells, B-1 cells, and B-2 cells, CD45RO (naive T) cells, CD45RA (memory T) cells, CD4 Helper T Cells including Th1, Th2, and Tr1/Th3 cells, CD8 Cytotoxic T Cells, Regulatory T Cells, Gamma Delta T Cells, and thymocytes. Additional examples of migratory cells include fibroblasts, fibrocytes, tumor cells, and stem cells. The term "cell migration" refers to the movement of migratory cells, and the term "modulation of cell migration" refers to the modulation of the movement of any such migratory cells.

The terms "polypeptide," "protein" and "peptide" are used interchangeably and mean a polymer of amino acids not limited to any particular length. The term "enzyme" includes polypeptide or protein catalysts. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "polynucleotide" and "nucleic acid" includes mRNA, RNA, cRNA, cDNA, and DNA. The term typically refers to polymeric form of nucleotides of at least 10 bases in length, either ribonucleotides or deoxynucleotides or a modified form of either type of nucleotide. The term includes single and double stranded forms of DNA. The terms "isolated DNA" and "isolated polynucleotide" and "isolated nucleic acid" refer to a molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode a polypeptide. Also included are recombinant vectors, including, for example, expression vectors, viral vectors, plasmids, cosmids, phagemids, phage, viruses, and the like.

Additional coding or non-coding sequences may, but need not, be present within a polynucleotide described herein, and a polynucleotide may, but need not, be linked to other molecules and/or support materials. Hence, a polynucleotide or expressible polynucleotides, regardless of the length of the coding sequence itself, may be combined with other sequences, for example, expression control sequences.

"Expression control sequences" include regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, which have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-REx™ system (Invitrogen Carlsbad, CA), LacSwitch® (Stratagene, (San Diego, CA) and the Cre-ERT tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

An "expressible polynucleotide" includes a cDNA, RNA, mRNA or other polynucleotide that comprises at least one coding sequence and optionally at least one expression control sequence, for example, a transcriptional and/or translational regulatory element, and which can express an encoded polypeptide upon introduction into a cell, for example, a cell in a subject.

Various viral vectors that can be utilized to deliver an expressible polynucleotide include adenoviral vectors, herpes virus vectors, vaccinia virus vectors, adeno-associated virus (AAV) vectors, and retroviral vectors. In some instances, the retroviral vector is a derivative of a murine or avian retrovirus, or is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein. Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector.

In particular embodiments, the expressible polynucleotide is a modified RNA or modified mRNA polynucleotide, for example, a non-naturally occurring RNA analog. In certain embodiments, the modified RNA or mRNA polypeptide comprises one or more modified or non-natural bases, for example, a nucleotide base other than adenine (A), guanine (G), cytosine (C), thymine (T), and/or uracil (U). In some embodiments, the modified mRNA comprises one or more modified or non-natural internucleotide linkages. Expressible RNA polynucleotides for delivering an encoded therapeutic polypeptide are described, for example, in Kormann et al., Nat Biotechnol. 29:154-7, 2011; and U.S. Application Nos. 2015/0111248; 2014/0243399; 2014/0147454; and 2013/0245104, which are incorporated by reference in their entireties.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., polypeptide such as an antibody) in a composition may be defined. For instance, certain compositions may comprise an agent such as a polypeptide agent that is at least 80%, 85%, 90%, 91%, 92%, 93%, 94%, 95%, 96%, 97%, 98%, 99%, or 100% pure on a protein basis or a weight-weight basis, including all decimals and ranges in between, as measured, for example and by no means limiting, by high performance liquid chromatography (HPLC), a well-known form of column chromatography used frequently in biochemistry and analytical chemistry to separate, identify, and quantify compounds.

A "lipid nanoparticle" or "solid lipid nanoparticle" refers to one or more spherical nanoparticles with an average diameter of between about 10 to about 1000 nanometers, and which comprise a solid lipid core matrix that can solubilize lipophilic molecules. The lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, which are incorporated by reference in their entireties. Certain compositions described herein are formulated with one or more lipid nanoparticles.

The terms or "Neuropilin 2-associated disease" or "NRP2-associated disease" refer to diseases and conditions in which NRP2 activity, expression, and/or spatial distribution plays a role in the pathophysiology of that disease or condition. In some instances, NRP2 associated diseases are modulated by the anti-NRP2 antibodies of the present disclosure by altering the interaction of NRP2 with at least one NRP2 ligand to impact NRP2 activity, signaling, expression, and/or spatial distribution. Exemplary NRP2-associated diseases and conditions include without limitation, cancer and diseases or pathologies associated with cancer including cancer cell growth, cancer initiation, cancer migration, cancer cell adhesion, invasion, and metastasis. Also included are diseases associated with inflammation and autoimmunity, and related inflammatory diseases, including disease associated with inappropriate immune cell activation or migration such as graft versus host disease (GVHD). Additional examples include diseases associated with lymphatic development, lymphangiogenesis, and lymphatic damage, including edema, lymphedema, secondary lymphedema, inappropriate fat absorption and deposition, excess fat deposition, and vascular permeability. Also included are diseases associated with infections including latent infections, and diseases associated with allergic disorders/diseases and allergic responses, including chronic obstructive pulmonary disorder (COPD), neutrophilic asthma, antineutrophil cytoplasmic antibody (ANCA)-associated systemic vasculitis, systemic lupus erythematosus, rheumatoid arthritis, inflammasome-related disease(s), and skin-related neutrophil-mediated disease(s) such as pyoderma gangrenosum. Additional examples include diseases associated with granulomatous inflammatory diseases including sarcoidosis and granulomas, and fibrotic diseases including endometriosis, fibrosis, endothelial to mesenchymal transition (EMT), and wound healing, among others. Also included are diseases associated with inappropriate smooth muscle contractility and vascular smooth muscle cell migration and/or adhesion, and diseases associated with inappropriate autophagy, phagocytosis, and efferocytosis. Also included are diseases associated with inappropriate migratory cell movement, as described herein. Additional examples include neuronal diseases, including diseases associated with peripheral nervous system remodeling and pain perception. Also included are diseases associated with bone development and/or bone remodeling. Typically, the term "inappropriate" refers to an activity or characteristic that associates with or causes a pathology or disease state.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

Certain embodiments include biologically active "variants" and "fragments" of the polypeptides (e.g., antibodies) described herein, and the polynucleotides that encode the same. "Variants" contain one or more substitutions, additions, deletions, and/or insertions relative to a reference polypeptide or polynucleotide (see, e.g., the Tables and the Sequence Listing). A variant polypeptide or polynucleotide comprises an amino acid or nucleotide sequence with at least about 50%, 55%, 60%, 65%, 70%, 75%, 80%, 85%, 90%, 91%, 92%, 93%, 94%, 95%, 96%, 97%, 98%, 99% or more sequence identity or similarity or homology to a reference sequence, as described herein, and substantially retains the activity of that reference sequence. Also included are sequences that consist of or differ from a reference sequences by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids or nucleotides and which substantially retain the activity of that reference sequence. In certain embodiments, the additions or deletions include C-terminal and/or N-terminal additions and/or deletions.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (e.g., antibody) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without $NaPO_4$). In specific embodiments, solubility is measured at relatively lower pH (e.g., pH 6.0) and relatively higher salt (e.g., 500 mM NaCl and 10 mM $NaPO_4$). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, the terms "therapeutically effective amount", "therapeutic dose," "prophylactically effective amount," or "diagnostically effective amount" is the amount of an agent (e.g., anti-NRP2 antibody, immunotherapy agent) needed to elicit the desired biological response following administration.

As used herein, "treatment" of a subject (e.g., a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied to every other embodiment unless expressly stated otherwise.

Anti-NRP2 Antibodies

Certain embodiments include antibodies, and antigen-binding fragments thereof, which specifically bind to a human neuropilin 2 (NRP2) polypeptide. In some embodiments, the at least one antibody or antigen-binding fragment thereof modulates (e.g., interferes with) binding of the human NRP2 polypeptide to at least one NRP2 ligand, such as a human histidyl-tRNA synthetase (HRS) polypeptide or other NRP2 ligand.

Neuropilin-2 is a cell surface receptor protein that modulates a broad range of cellular functions through its roles as an essential cell surface receptor and co-receptor for a variety of ligands (see, e.g., Guo and Vander Kooi, J. Cell. Biol. 290 No 49: 29120-29126. 2015). For instance, it functions during epithelial to mesenchymal transition (EMT), for example, by promoting TGF-β1-mediated EMT in colorectal and other cancer cells (see, e.g., Grandclement et al., PLoS ONE 6(7) e20444, 2011), and by mediating EMT or endo-EMT in fibroblasts, myofibroblasts, and endothelial cells to promote fibrosis formation (see, e.g., Pardali et al., Int. J. Mol. Sci. 18:2157, 2017).

Neuropilin-2 expression promotes lymphangiogenesis (see, e.g., Doci et al., Cancer Res. 75:2937-2948, 2015) single nucleotide polymorphisms (SNPs) in NRP2 are associated with lymphedema (see, e.g., Miaskowski et al., PLoS ONE 8(4) e60164, 2013). NRP2 also regulates smooth muscle contractility (see, e.g., Bielenberg et al., Amer. J. Path. 181:548-559, 2012), regulates autophagy, for example, in cancer (see, e.g., Stanton et al., Cancer Res. 73:160-171, 2013), contributes to tumor initiation, survival, and metastasis (see, e.g., Goel et al., EMBO Mol. Med. 5:488-508, 2013; and Samuel et al., PLoS ONE 6(10) e23208, 2011), and regulates immune cell activation and migration (see, e.g., Mendes-da-Cruz et al., PLoS ONE 9(7) e103405, 2014). Neuropilins are also multifunctional co-receptors involved in tumor initiation, growth, metastasis and immunity (see, e.g., Prud'homme et al., Oncotarget 3:921-939, 2012).

Neuropilin-2 is expressed in various cells of the immune system, including lymphoid cells such as B and T cells, and myeloid cells such as basophils, eosinophil, monocytes, dendritic cells, neutrophils, and macrophages, including tissue-specific macrophages, for example, alveolar macrophages. It is also expressed in endothelial and epithelial cells in the lung and other tissues, and in muscle cells [see, e.g., Bielenberg et al., Amer. J. Path. 181:548-559, 2012; Aung, et al., PLoS ONE 11(2) e0147358, 2016; Schellenburg et al., Mol. Imm 90:239-244, 2017; and Wild et al., Int. J. Exp. Path. 93:81-103, 2012).

Neuropilin-2 also plays a key role in endosome development, for example, by regulating late endosomal maturation, an important aspect of phagocytosis and efferocytosis, which respectively contribute to clearance of infections and apoptotic cells (See, e.g., Diaz-Vera et al., J. Cell. Sci. 130:697-711, 2017; Dutta et al., Cancer Res. 76:418-428, 2016).

Figure 1B:
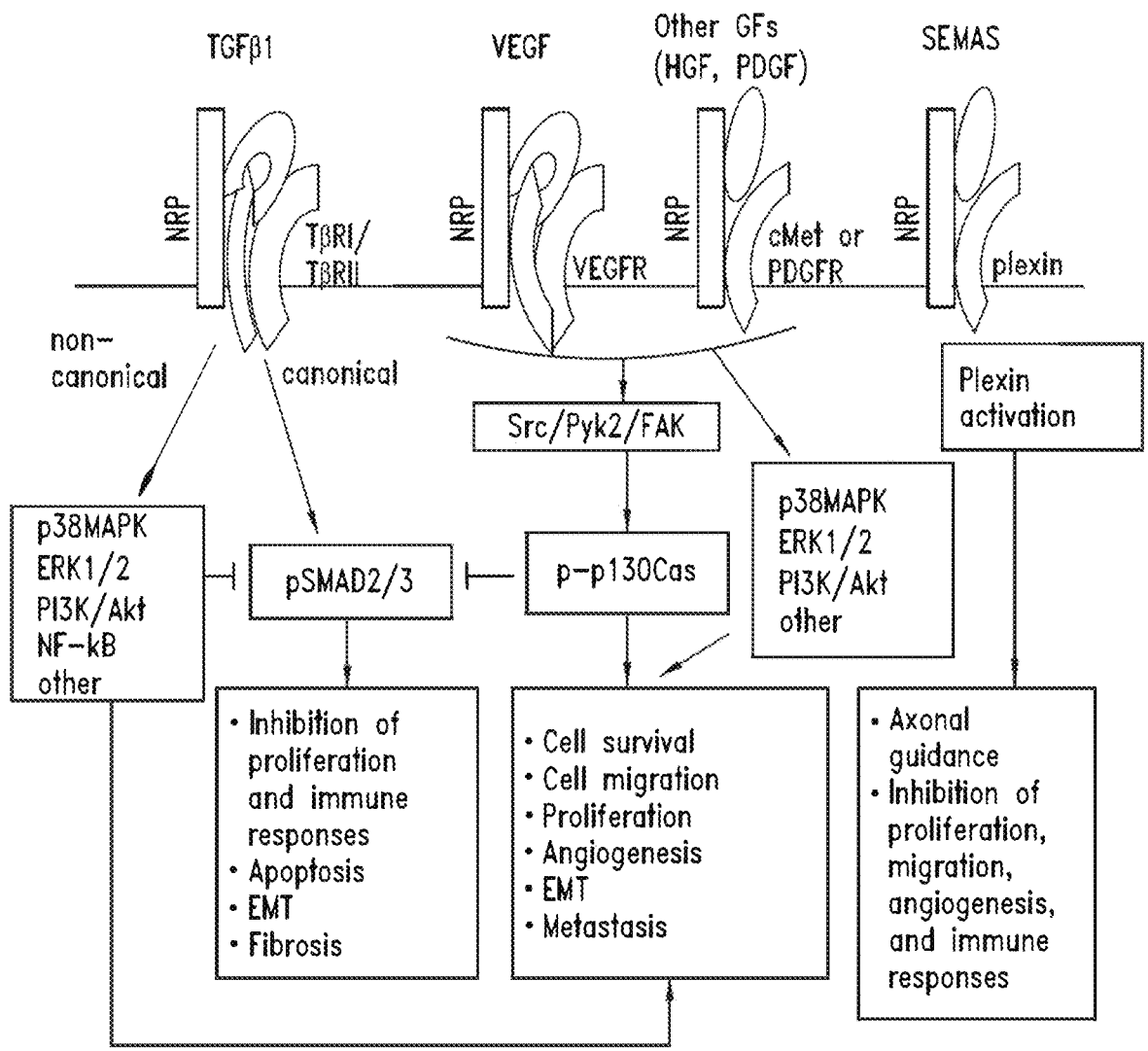
Figure 2:
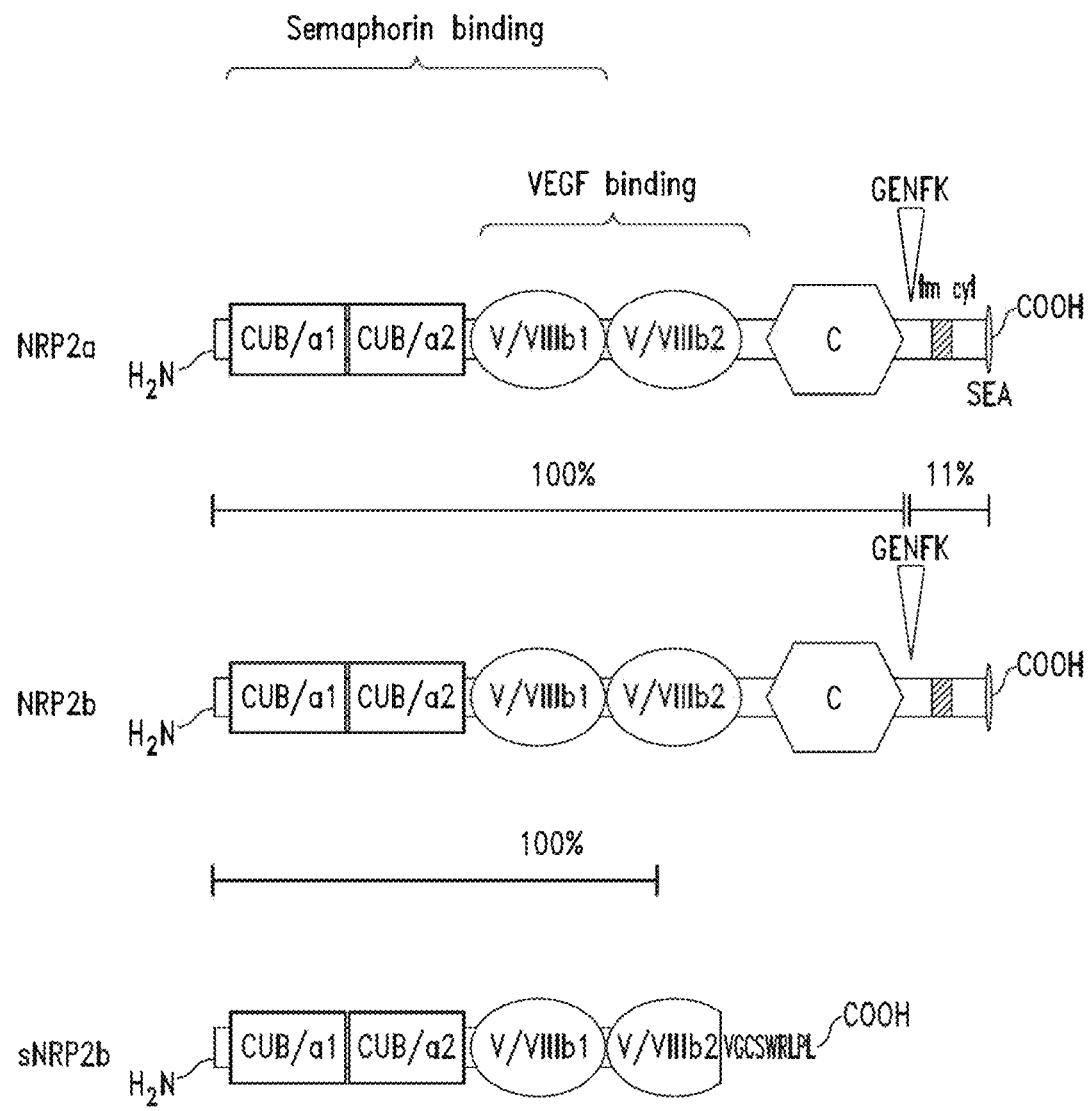
FIG. 2 illustrates the domain structure of certain NRP2 isoforms and exemplary NRP2 ligand binding domains.

Neuropilin-2 is known to be a key player in the pathophysiology of many diseases (e.g., "NRP2-associated diseases") and interacts with a broad array of soluble ligands including semaphorin 3F, VEGF-C and D, and TGF-beta (see, for example, Table N2 and Table N3), and an array of cellular receptors and co-factors (see, for example, FIGS. 1A-1B and FIG. 2). NRP2 is also polysialated on dendritic cells, and actively interacts with the chemokine CCL21 to mediate immune cell migration, and for which single nucleotide polymorphisms associated with ILD and RA have been described (see, e.g., Rey-Gallardo et al., Glycobiology 20:1139-1146, 2010; Stahl et al., Nat. Genet. 42:508-514, 2013; and Miller et al., Arthritis Rheum. 65:3239-3247). Additionally, soluble, circulating forms of NRP-2 are known (see, e.g., Parker et al., Structure 23(4) 677-687, 2015), and internal studies have confirmed the existence of circulating complexes of HRS polypeptides and NRP-2 polypeptides in circulation. Accordingly, given the central role played by NRP2 in pathophysiology in a broad range of diseases, it is evident that interactions between NRP2 and NRP2 ligand(s) (for example, NRP2 ligands from Table N2 and Table N3), and the modulation of those interactions with antibodies against NRP2 to selectively change the corresponding biological activities, provides broad potential for the treatment of diseases, including NRP2 associated diseases.

NRP2 is a single transmembrane receptor with a predominant extracellular region containing two CUB domains (A1/A2 combined domain), two Factor V/VIII homology domains (B1/B2 combined domain), and a MAM domain (C domain) (see FIGS. 1A-1B). The A1A2 combined domain interacts with sema region of the semaphorins, and the B1 domain interacts with the semaphorin PSI and Ig-like domains. NRP2 has a higher affinity for SEMA3F and 3G; in contrast, SEMAs 3A, 3B and 3E preferentially interact with NRP1. Both NRP1 and NRP2 have similar affinity for SEMA 3C. The B1B2 combined domain interacts with several growth factors containing heparin-binding domains, including VEGF C & D, placenta growth factor (PIGF)-2, fibroblast growth factor (FGF), galectin, hepatocyte growth factor (HGF), platelet derived growth factor (PDGF), and transforming growth factor (TGF)-beta (see, for example, Prud'homme et al., Oncotarget. 3:921-939, 2012). NRP2 also interacts with various growth factor-specific receptors, and interactions with these receptors occur independently of binding to SEMAs. In this context, integrins and growth factor receptors like VEGF receptor, TGF-beta receptor, c-Met, EGFR, FGFR, PDGFR, have been shown to interact with NRPs and in general appear to increase the affinity of each ligand for its receptor and to modulate down stream signaling. The C domain (Mam) domain does not appear to be required for ligand binding, but appears essential for signaling Accordingly, anti-NRP2 antibodies that bind to the A1 and/or A2 domains of NRP2 have the potential to selectively modulate semaphorin binding. Likewise, anti-NRP2 antibodies that bind to the B1 domain have the potential to modulating both semaphorin and VEGF and growth factor binding, and anti-NRP2 antibodies that bind to the B2 domain have the potential to selectively modulate VEGF and growth factor binding. Antibodies that bind to the C domain might not directly impact NRP2 ligand binding, but have the potential to modulate NRP2 downstream signaling. Additional diversity in the functional effects of specific anti-NRP2 antibodies may be expected based on their binding mode, and as a result of steric effects, which may indirectly impact ligand binding.

NRP2 can form homodimers as well as heterodimers, and is heavily glycosylated. NRP2 has different splice variants which are between about 551 and 926 amino acids long. Two major variants for NRP2 are categorized as NRP2a and NRP2b. These differ in their intracellular C terminal part (FIGS. 1A-1B) in which for NRP2a, the c-terminal domain comprises 42 amino acids and a PDZ-binding domain with the C-terminal SEA amino acid sequence. By contrast, NRP2b comprises a 46 amino acid C terminal domain which shares about 11% of the intracellular and transmembrane sequence of NRP2a. Between the MAM domain and the transmembrane domain, additional splicing can occur and 5 additional amino acids (GENFK) can be added to either the NRP2a, or NRP2b forms—these variants are named based on the number additional amino acids added through alternative splicing. Thus the two additional variants of NRP2 are named NRP2a(17) and NRP2a(22) and the two different transmembrane variants for NRP2b are named NRP2b(0) and NRP2b(5). Additionally, a soluble form called sNRP2b can be generated. Exemplary NRP2 polypeptide sequences are provided in Table N1 below.

TABLE N1

Exemplary Human NRP2 Polypeptides

| Name | Residues | Sequence | SEQ ID NO: |
|---|---|---|---|
| Human full length NRP2 Variant 1 NRP2a(22) | 1-931 | MDMFPLTWVFLALYFSRHQVRGQPDPPCGGRLNSKDAGYITS PGYPQDYPSHQNCEWIVYAPEPNQKIVLNFNPHFEIEKHDCK YDFIEIRDGDSESADLLGKHCGNIAPPTIISSGSMLYIRFTS DYARQGAGFSLRYEIFKTGSEDCSKNFTSPNGTIESPGFPEK YPHNLDCTFTILAKPKMEIILQFLIFDLEHDPLQVGEGDCKY DWLDIWDGIPHVGPLIGKYCGTKTPSELRSSTGILSLTFHTD MAVAKDGFSARYYLVHQEPLENFQCNVPLGMESGRIANEQIS ASSTYSDGRWTPQQSRLHGDDNGWTPNLDSNKEYLQVDLRFL TMLTAIATQGAISRETQNGYYVKSYKLEVSTNGEDWMVYRHG KNHKVFQANNDATEVVLNKLHAPLLTRFVRIRPQTWHSGIAL RLELFGCRVTDAPCSNMLGMLSGLIADSQISASSTQEYLWSP SAARLVSSRSGWFPRIPQAQPGEEWLQVDLGTPKTVKGVIIQ GARGGDSITAVEARAFVRKFKVSYSLNGKDWEYIQDPRTQQP KLFEGNMHYDTPDIRRFDPIPAQYVRVYPERWSPAGIGMRLE VLGCDWTDSKPTVETLGPTVKSEETTTPYPTEEEATECGENC SFEDDKDLQLPSGFNCNFDFLEEPCGWMYDHAKWLRTTWASS SSPNDRTFPDDRNFLRLQSDSQREGQYARLISPPVHLPRSPV CMEFQYQATGGRGVALQVVREASQESKLLWVIREDQGGEWKH GRIILPSYDMEYQIVFEGVIGKGRSGEIAIDDIRISTDVPLE NCMEPISAFAGENPFKVDIPEIHEREGYEDEIDDEYEVDWSNS SSATSGSGAPSTDKEKSWLYTLDPILITIIAMSSLGVLLGAT CAGLLLYCTCSYSGLSSRSCTTLENYNFELYDGLKHKVKMNH QKCCSEA | 1 |
| Human NRP2 Variant 2 precursor NRP2a(17) | 1-926 | MDMFPLTWVFLALYFSRHQVRGQPDPPCGGRLNSKDAGYITS PGYPQDYPSHQNCEWIVYAPEPNQKIVLNFNPHFEIEKHDCK YDFIEIRDGDSESADLLGKHCGNIAPPTIISSGSMLYIKFTS DYARQGAGFSLRYEIFKTGSEDCSKNFTSPNGTIESPGFPEK YPHNLDCTFTILAKPKMEIILQFLIFDLEHDPLQVGEGDCKY DWLDIWDGIPHVGPLIGKYCGTKTPSELRSSTGILSLTFHTD MAVAKDGFSARYYLVHQEPLENFQCNVPLGMESGRIANEQIS ASSTYSDGRWTPQQSRLHGDDNGWTPNLDSNKEYLQVDLRFL TMLTAIATQGAISRETQNGYYVKSYKLEVSTNGEDWMVYRHG KNHKVFQANNDATEVVLNKLHAPLLTRFVRIRPQTWHSGIAL RLELFGCRVTDAPCSNMLGMLSGLIADSQISASSTQEYLWSP SAARLVSSRSGWFPRIPQAQPGEEWLQVDLGTPKTVKGVIIQ GARGGDSITAVEARAFVRKFKVSYSLNGKDWEYIQDPRTQQP KLFEGNMHYDTPDIRRFDPIPAQYVRVYPERWSPAGIGMRLE VLGCDWTDSKPTVETLGPTVKSEETTTPYPTEEEATECGENC SFEDDKDLQLPSGFNCNFDFLEEPCGWMYDHAKWLRTTWASS SSPNDRTFPDDRNFLRLQSDSQREGQYARLISPPVHLPRSPV CMEFQYQATGGRGVALQVVREASQESKLLWVIREDQGGEWKH GRIILPSYDMEYQIVFEGVIGKGRSGEIAIDDIRISTDVPLE NCMEPISAFAVDIPEIHEREGYEDEIDDEYEVDWSNSSSATS GSGAPSTDKEKSWLYTLDPILITIIAMSSLGVLLGATCAGLL LYCTCSYSGLSSRSCTTLENYNFELYDGLKHKVKMNHQKCCS EA | 2 |
| Human NRP2 Variant 3 precursor NRP2a(0) | 1-909 | MDMFPLTWVFLALYFSRHQVRGQPDPPCGGRLNSKDAGYITS PGYPQDYPSHQNCEWIVYAPEPNQKIVLNFNPHFEIEKHDCK YDFIEIRDGDSESADLLGKHCGNIAPPTIISSGSMLYIKFTS DYARQGAGFSLRYEIFKTGSEDCSKNFTSPNGTIESPGFPEK YPHNLDCTFTILAKPKMEIILQFLIFDLEHDPLQVGEGDCKY DWLDIWDGIPHVGPLIGKYCGTKTPSELRSSTGILSLTFHTD MAVAKDGFSARYYLVHQEPLENFQCNVPLGMESGRIANEQIS ASSTYSDGRWTPQQSRLHGDDNGWTPNLDSNKEYLQVDLRFL TMLTAIATQGAISRETQNGYYVKSYKLEVSTNGEDWMVYRHG KNHKVFQANNDATEVVLNKLHAPLLTRFVRIRPQTWHSGIAL RLELFGCRVTDAPCSNMLGMLSGLIADSQISASSTQEYLWSP SAARLVSSRSGWFPRIPQAQPGEEWLQVDLGTPKTVKGVIIQ GARGGDSITAVEARAFVRKFKVSYSLNGKDWEYIQDPRTQQP KLFEGNMHYDTPDIRRFDPIPAQYVRVYPERWSPAGIGMRLE VLGCDWTDSKPTVETLGPTVKSEETTTPYPTEEEATECGENC SFEDDKDLQLPSGFNCNFDFLEEPCGWMYDHAKWLRTTWASS SSPNDRTFPDDRNFLRLQSDSQREGQYARLISPPVHLPRSPV CMEFQYQATGGRGVALQVVREASQESKLLWVIREDQGGEWKH GRIILPSYDMEYQIVFEGVIGKGRSGEIAIDDIRISTDVPLE NCMEPISAFADEYEVDWSNSSSATSGSGAPSTDKEKSWLYTL DPILITIIAMSSLGVLLGATCAGLLLYCTCSYSGLSSRSCTT LENYNFELYDGLKHKVKMNHQKCCSEA | 3 |
| Human NRP2 Variant 4 precursor NRP2b(5) | 1-906 | MDMFPLTWVFLALYFSRHQVRGQPDPPCGGRLNSKDAGYITS PGYPQDYPSHQNCEWIVYAPEPNQKIVLNFNPHFEIEKHDCK YDFIEIRDGDSESADLLGKHCGNIAPPTIISSGSMLYIKFTS DYARQGAGFSLRYEIFKTGSEDCSKNFTSPNGTIESPGFPEK | 4 |

TABLE N1-continued

Exemplary Human NRP2 Polypeptides

| Name | Residues | Sequence | SEQ ID NO: |
|---|---|---|---|
| | | YPHNLDCTFTILAKPKMEIILQFLIFDLEHDPLQVGEGDCKY DWLDIWDGIPHVGPLIGKYCGTKTPSELRSSTGILSLTFHTD MAVAKDGFSARYYLVHQEPLENFQCNVPLGMESGRIANEQIS ASSTYSDGRWTPQQSRLHGDDNGWTPNLDSNKEYLQVDLRFL TMLTAIATQGAISRETQNGYYVKSYKLEVSTNGEDWMVYRHG KNHKVFQANNDATEVVLNKLHAPLLTRFVRIRPQTWHSGIAL RLELFGCRVTDAPCSNMLGMLSGLIADSQISASSTQEYLWSP SAARLVSSRSGWFPRIPQAQPGEEWLQVDLGTPKTVKGVIIQ GARGGDSITAVEARAFVRKFKVSYSLNGKDWEYIQDPRTQQP KLFEGNMHYDTPDIRRFDPIPAQYVRVYPERWSPAGIGMRLE VLGCDWTDSKPTVETLGPTVKSEETTTPYPTEEEATECGENC SFEDDKDLQLPSGFNCNFDFLEEPCGWMYDHAKWLRTTWASS SSPNDRTFPDDRNFLRLQSDSQREGQYARLISPPVHLPRSPV CMEFQYQATGGRGVALQVVREASQESKLLWVIREDQGGEWKH GRIILPSYDMEYQIVFEGVIGKGRSGEIAIDDIRISTDVPLE NCMEPISAFAGENFKGGTLLPGTEPTVDTVPMQPIPAYWYYV MAAGGAVLVLVSVALALVLHYHRFRYAAKKTDHSITYKTSHY TNGAPLAVEPTLTIKLEQDRGSHC | |
| Human NRP2 Variant 5 precursor NRP2b(0) | 1-901 | MDMFPLTWVFLALYFSRHQVRGQPDPPCGGRLNSKDAGYI TSPGYPQDYPSHQNCEWIVYAPEPNQKIVLNFNPHFEIEK HDCKYDFIEIRDGDSESADLLGKHCGNIAPPTIISSGSMLYI KFTSDYARQGAGFSLRYEIFKTGSEDCSKNFTSPNGTIESPG FPEKYPHNLDCTFTILAKPKMEIILQFLIFDLEHDPLQVGEG DCKYDWLDIWDGIPHVGPLIGKYCGTKTPSELRSSTGILSLT FHTDMAVAKDGFSARYYLVHQEPLENFQCNVPLGMESGRIAN EQISASSTYSDGRWTPQQSRLHGDDNGWTPNLDSNKEYLQVD LRFLTMLTAIATQGAISRETQNGYYVKSYKLEVSTNGEDWMV YRHGKNHKVFQANNDATEVVLNKLHAPLLTRFVRIRPQTWHS GIALRLELFGCRVTDAPCSNMLGMLSGLIADSQISASSTQEY LWSPSAARLVSSRSGWFPRIPQAQPGEEWLQVDLGTPKTVKG VIIQGARGGDSITAVEARAFVRKFKVSYSLNGKDWEYIQDPR TQQPKLFEGNMHYDTPDIRRFDPIPAQYVRVYPERWSPAGIG MRLEVLGCDWTDSKPTVETLGPTVKSEETTTPYPTEEEATEC GENCSFEDDKDLQLPSGFNCNFDFLEEPCGWMYDHAKWLRTT WASSSSPNDRTFPDDRNFLRLQSDSQREGQYARLISPPVHLP RSPVCMEFQYQATGGRGVALQVVREASQESKLLWVIREDQGG EWKHGRIILPSYDMEYQIVFEGVIGKGRSGEIAIDDIRISTD VPLENCMEPISAFAGGTLLPGTEPTVDTVPMQPIPAYWYYVM AAGGAVLVLVSVALALVLHYHRFRYAAKKTDHSITYKTSHYT NGAPLAVEPTLTIKLEQDRGSHC | 5 |
| Human NRP2 Variant 6 precursor S9NRP2b Soluble NRP2 | 1-555 | MDMFPLTWVFLALYFSRHQVRGQPDPPCGGRLNSKDAGYITS PGYPQDYPSHQNCEWIVYAPEPNQKIVLNFNPHFEIEKHDCK YDFIEIRDGDSESADLLGKHCGNIAPPTIISSGSMLYIKFTS DYARQGAGFSLRYEIFKTGSEDCSKNFTSPNGTIESPGFPEK YPHNLDCTFTILAKPKMEIILQFLIFDLEHDPLQVGEGDCKY DWLDIWDGIPHVGPLIGKYCGTKTPSELRSSTGILSLTFHTD MAVAKDGFSARYYLVHQEPLENFQCNVPLGMESGRIANEQIS ASSTYSDGRWTPQQSRLHGDDNGWTPNLDSNKEYLQVDLRFL TMLTAIATQGAISRETQNGYYVKSYKLEVSTNGEDWMVYRHG KNHKVFQANNDATEVVLNKLHAPLLTRFVRIRPQTWHSGIAL RLELFGCRVTDAPCSNMLGMLSGLIADSQISASSTQEYLWSP SAARLVSSRSGWFPRIPQAQPGEEWLQVDLGTPKTVKGVIIQ GARGGDSITAVEARAFVRKFKVSYSLNGKDWEYIQDPRTQQP KVGCSWRPL | 6 |
| Human NRP2 Variant 2 NRP2a(17) | 23-926 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK | 7 |

TABLE N1-continued

Exemplary Human NRP2 Polypeptides

| Name | Residues | Sequence | SEQ ID NO: |
|---|---|---|---|
| | | GRSGEIAIDDIRISTDVPLENCMEPISAFAVDIPEIHEREGY EDEIDDEYEVDWSNSSSATSGSGAPSTDKEKSWLYTLDPILI TIIAMSSLGVLLGATCAGLLLYCTCSYSGLSSRSCTTLENYN FELYDGLKHKVKMNHQKCCSEA | |
| NRP2 splice variant 5 NRP2b(0) | 23-901 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCMEPISAFAGGTLLPGTEPTV DTVPMQPIPAYWYYVMAAGGAVLVLVSVALALVLHYHRFRYA AKKTDHSITYKTSHYTNGAPLAVEPTLTIKLEQDRGSHC | 8 |
| Soluble NRP2 S9Nrp-2b | 23-555 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKVGCSWRPL | 9 |
| NRP2 A1 domain | 28-141 | CGGRLNSKDAGYITSPGYPQDYPSHQNCEWIVYAPEPNQKIV LNFNPHFEIEKHDCKYDFIEIRDGDSESADLLGKHCGNIAPP TIISSGSMLYIKFTSDYARQGAGFSLRYEI | 10 |
| NRP2 A2 domain | 149-265 | CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYY | 11 |
| NRP2 B1 domain | 280-426 | PLGMESGRIANEQISASSTYSDGRWTPQQSRLHGDDNGWTPN LDSNKEYLQVDLRFLTMLTAIATQGAISRETQNGYYVKSYKL EVSTNGEDWMVYRHGKNHKVFQANNDATEVVLNKLHAPLLTR FVRIRPQTWHSGIALRLELFG | 12 |
| NRP2 B2 domain | 438-591 | LGMLSGLIADSQISASSTQEYLWSPSAARLVSSRSGWFPRIP QAQPGEEWLQVDLGTPKTVKGVIIQGARGGDSITAVEARAFV RKFKVSYSLNGKDWEYIQDPRTQQPKLFEGNMHYDTPDIRRF DPIPAQYVRVYPERWSPAGIGMRLEVLG | 13 |
| NRP2 C domain | 641-794 | PSGFNCNFDFLEEPCGWMYDHAKWLRTTWASSSSPNDRTFPD DRNFLRLQSDSQREGQYARLISPPVHLPRSPVCMEFQYQATG GRGVALQVVREASQESKLLWVIREDQGGEWKHGRIILPSYDM EYQIVFEGVIGKGRSGEIAIDDIRISTD | 14 |
| NRP2 A1A2 combined domains | 23-265 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYY | 15 |
| NRP2 A2B1 combined domains | 149-426 | CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN | 16 |

TABLE N1-continued

Exemplary Human NRP2 Polypeptides

| Name | Residues | Sequence | SEQ ID NO: |
|---|---|---|---|
| | | GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFG | |
| NRP2 A1A2B1 combined domains | 23-426 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFG | 17 |
| NRP2 A1A2B1B2 combined domains | 23-595 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWT | 18 |
| NRP2 A2B1B2 combined domains | 145-595 | GSEDCSKNFTSPNGTIESPGFPEKYPHNLDCTFTILAKPKME IILQFLIFDLEHDPLQVGEGDCKYDWLDIWDGIPHVGPLIGK YCGTKTPSELRSSTGILSLTFHTDMAVAKDGFSARYYLVHQE PLENFQCNVPLGMESGRIANEQISASSTYSDGRWTPQQSRLH GDDNGWTPNLDSNKEYLQVDLRFLTMLTAIATQGAISRETQN GYYVKSYKLEVSTNGEDWMVYRHGKNHKVFQANNDATEVVLN KLHAPLLTRFVRIRPQTWHSGIALRLELFGCRVTDAPCSNML GMLSGLIADSQISASSTQEYLWSPSAARLVSSRSGWFPRIPQ AQPGEEWLQVDLGTPKTVKGVIIQGARGGDSITAVEARAFVR KFKVSYSLNGKDWEYIQDPRTQQPKLFEGNMHYDTPDIRRFD PIPAQYVRVYPERWSPAGIGMRLEVLGCDWT | 19 |
| NRP2 B1B2 combined domains | 276-595 | QCNVPLGMESGRIANEQISASSTYSDGRWTPQQSRLHGDDNG WTPNLDSNKEYLQVDLRFLTMLTAIATQGAISRETQNGYYVK SYKLEVSTNGEDWMVYRHGKNHKVFQANNDATEVVLNKLHAP LLTRFVRIRPQTWHSGIALRLELFGCRVTDAPCSNMLGMLSG LIADSQISASSTQEYLWSPSAARLVSSRSGWFPRIPQAQPGE EWLQVDLGTPKTVKGVIIQGARGGDSITAVEARAFVRKFKVS YSLNGKDWEYIQDPRTQQPKLFEGNMHYDTPDIRRFDPIPAQ YVRVYPERWSPAGIGMRLEVLGCDWT | 20 |
| NRP2 v2-Fc fusion protein | 23-855 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCMEPISAFAVDIPEIHEREGY EDEIDDEYEVDWSNSSSATSGSGAPSTDKEKSWLYDKTHTCP PCPAPELLGGPSVFLFPPKPKDTLMISRTPEVTCVVVDVSHE DPEVKFNWYVDGVEVHNAKTKPREEQYNSTYRVVSVLTVLHQ DWLNGKEYKCKVSNKALPAPIEKTISKAKGQPREPQVYTLPP SRDELTKNQVSLTCLVKGFYPSDIAVEWESNGQPENNYKTTP | 21 |

TABLE N1-continued

Exemplary Human NRP2 Polypeptides

| Name | Residues | Sequence | SEQ ID NO: |
|---|---|---|---|
| | | PVLDSDGSFFLYSKLTVDKSRWQQGNVFSCSVMHEALHNHYT QKSLSLSPGK | |
| NRP2 A2B1B2-Fc | 145-595 | GSEDCSKNFTSPNGTIESPGFPEKYPHNLDCTFTILAKPKME IILQFLIFDLEHDPLQVGEGDCKYDWLDIWDGIPHVGPLIGK YCGTKTPSELRSSTGILSLTFHTDMAVAKDGFSARYYLVHQE PLENFQCNVPLGMESGRIANEQISASSTYSDGRWTPQQSRLH GDDNGWTPNLDSNKEYLQVDLRFLTMLTAIATQGAISRETQN GYYVKSYKLEVSTNGEDWMVYRHGKNHKVFQANNDATEVVLN KLHAPLLTRFVRIRPQTWHSGIALRLELFGCRVTDAPCSNML GMLSGLIADSQISASSTQEYLWSPSAARLVSSRSGWFPRIPQ AQPGEEWLQVDLGTPKTVKGVIIQGARGGDSITAVEARAFVR KFKVSYSLNGKDWEYIQDPRTQQPKLFEGNMHYDTPDIRRFD PIPAQYVRVYPERWSPAGIGMRLEVLGCDWTDKTHTCPPCPA PELLGGPSVFLFPPKPKDTLMISRTPEVTCVVVDVSHEDPEV KFNWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVLD SDGSFFLYSKLTVDKSRWQQGNVFSCSVMHEALHNHYTQKSL SLSPGK | 22 |
| NRP2 B2C combined domains | 438-794 | LGMLSGLIADSQISASSTQEYLWSPSAARLVSSRSGWFPRIP QAQPGEEWLQVDLGTPKTVKGVIIQGARGGDSITAVEARAFV RKFKVSYSLNGKDWEYIQDPRTQQPKLFEGNMHYDTPDIRRF DPIPAQYVRVYPERWSPAGIGMRLEVLGCDWTDSKPTVETLG PTVKSEETTTPYPTEEEATECGENCSFEDDKDLQLPSGFNCN FDFLEEPCGWMYDHAKWLRTTWASSSSPNDRTFPDDRNFLRL QSDSQREGQYARLISPPVHLPRSPVCMEFQYQATGGRGVALQ VVREASQESKLLWVIREDQGGEWKHGRIILPSYDMEYQIVFE GVIGKGRSGEIAIDDIRISTD | 89 |
| NRP2 B1B2C combined domains | 276-794 | QCNVPLGMESGRIANEQISASSTYSDGRWTPQQSRLHGDDNG WTPNLDSNKEYLQVDLRFLTMLTAIATQGAISRETQNGYYVK SYKLEVSTNGEDWMVYRHGKNHKVFQANNDATEVVLNKLHAP LLTRFVRIRPQTWHSGIALRLELFGCRVTDAPCSNMLGMLSG LIADSQISASSTQEYLWSPSAARLVSSRSGWFPRIPQAQPGE EWLQVDLGTPKTVKGVIIQGARGGDSITAVEARAFVRKFKVS YSLNGKDWEYIQDPRTQQPKLFEGNMHYDTPDIRRFDPIPAQ YVRVYPERWSPAGIGMRLEVLGCDWTDSKPTVETLGPTVKSE ETTTPYPTEEEATECGENCSFEDDKDLQLPSGFNCNFDFLEE PCGWMYDHAKWLRTTWASSSSPNDRTFPDDRNFLRLQSDSQR EGQYARLISPPVHLPRSPVCMEFQYQATGGRGVALQVVREAS QESKLLWVIREDQGGEWKHGRIILPSYDMEYQIVFEGVIGKG RSGEIAIDDIRISTD | 90 |
| NRP2 A2B1B2C combined domains | 149-802 | CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCME | 121 |
| NRP2 A1A2B1B2C combined domains | 23-802 | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA | 122 |

TABLE N1-continued

Exemplary Human NRP2 Polypeptides

| Name | Residues | Sequence | SEQ ID NO: |
|---|---|---|---|
| | | QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCME | |
| NRP2A A1A2B1B2C combined domains + juxta-membrane | | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCMEPISAFAVDIPEIHEREGY EDEIDDEYEVDWSNSSSATSGSGAPSTDKEKSWLYTLDP | 123 |
| NRP2B A1A2B1B2C combined domains + juxta-membrane | | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDSKPTVETLGPTVKS EETTTPYPTEEEATECGENCSFEDDKDLQLPSGFNCNFDFLE EPCGWMYDHAKWLRTTWASSSSPNDRTFPDDRNFLRLQSDSQ REGQYARLISPPVHLPRSPVCMEFQYQATGGRGVALQVVREA SQESKLLWVIREDQGGEWKHGRIILPSYDMEYQIVFEGVIGK GRSGEIAIDDIRISTDVPLENCMEPISAFAGGTLLPGTEPTV DTVPMQPIPAY | 124 |
| NRP2 (23-595)-Fc | | QPDPPCGGRLNSKDAGYITSPGYPQDYPSHQNCEWIVYAPEP NQKIVLNFNPHFEIEKHDCKYDFIEIRDGDSESADLLGKHCG NIAPPTIISSGSMLYIKFTSDYARQGAGFSLRYEIFKTGSED CSKNFTSPNGTIESPGFPEKYPHNLDCTFTILAKPKMEIILQ FLIFDLEHDPLQVGEGDCKYDWLDIWDGIPHVGPLIGKYCGT KTPSELRSSTGILSLTFHTDMAVAKDGFSARYYLVHQEPLEN FQCNVPLGMESGRIANEQISASSTYSDGRWTPQQSRLHGDDN GWTPNLDSNKEYLQVDLRFLTMLTAIATQGAISRETQNGYYV KSYKLEVSTNGEDWMVYRHGKNHKVFQANNDATEVVLNKLHA PLLTRFVRIRPQTWHSGIALRLELFGCRVTDAPCSNMLGMLS GLIADSQISASSTQEYLWSPSAARLVSSRSGWFPRIPQAQPG EEWLQVDLGTPKTVKGVIIQGARGGDSITAVEARAFVRKFKV SYSLNGKDWEYIQDPRTQQPKLFEGNMHYDTPDIRRFDPIPA QYVRVYPERWSPAGIGMRLEVLGCDWTDKTHTCPPCPAPELL GGPSVFLFPPKPKDTLMISRTPEVTCVVVDVSHEDPEVKFNW YVDGVEVHNAKTKPREEQYNSTYRVVSVLTVLHQDWLNGKEY KCKVSNKALPAPIEKTISKAKGQPREPQVYTLPPSRDELTKN QVSLTCLVKGFYPSDIAVEWESNGQPENNYKTTPPVLDSDGS FFLYSKLTVDKSRWQQGNVFSCSVMHEALHNHYTQKSLSLSP GK | 120 |

In certain embodiments, the at least one antibody or antigen-binding fragment thereof specifically binds to a full-length human NRP2 polypeptide or a human NRP2 polypeptide selected from Table N1. In some embodiments, the antibody or antigen-binding fragment thereof binds to the human NRP2 polypeptide with an affinity of about 10 pM to about 500 pM or to about 50 nM, or about, at least about, or no more than about 10, 20, 30, 40, 50, 60, 70, 80, 90, 100, 110, 120, 130, 140, 150, 160, 170, 180, 190, 200, 300, 400, 500, 600, 700, 800, 900 pM, 1 nM, 10 nM, 25 nM, or 50 nM, or optionally with an affinity that ranges from about 10 pM to about 500 pM, about 10 pM to about 400 pM, about 10 pM to about 300 pM, about 10 pM to about 200 pM, about 10 pM to about 100 pM, about 10 pM to about 50 pM, or about 20 pM to about 500 pM, about 20 pM to about 400 pM, about 20 pM to about 300 pM, about 20 pM to about 200 pM, about 20 pM to about 100 pM, about 20 pM to about 50 pM, or about 30 pM to about 500 pM, about 30 pM to about 400 pM, about 30 pM to about 300 pM, about 30 pM to about 200 pM, about 30 pM to about 100 pM, about 30 pM to about 50 pM, or about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 1 nM to about 5 nM, about 5 nM to about 10 nM, about 10 nM to about 25 nM, or about 25 nM to about 50 nM.

In some embodiments, the at least one antibody or antigen-binding fragment thereof that specifically binds to at least one epitope in at least one neuropilin domain. Exemplary neuropilin domains include one or more of the neuropilin A1 domain (SEQ ID NO:10), neuropilin A2 domain (SEQ ID NO:11), neuropilin B1 domain (SEQ ID NO:12), neuropilin B2 domain (SEQ ID NO:13), neuropilin C domain (SEQ ID NO:14), neuropilin A1/A2 combined domain (SEQ ID NO:15), neuropilin B1/B2 combined domain (SEQ ID NO:20), neuropilin A2/B1 combined domain (SEQ ID NO:16), neuropilin B2/C combined domain (SEQ ID NO:89), neuropilin A2/B1/B2 combined domain (SEQ ID NO:19), neuropilin A2/B1/B2/C combined domain (SEQ ID NO:121), neuropilin A1/A2/B1 combined domain (SEQ ID NO:17), neuropilin A1/A2/B1/B2 combined domain (SEQ ID NO:18), neuropilin A1/A2/B1/B2/C combined domain (SEQ ID NO:122), and the neuropilin B1/B2/C combined domain (SEQ ID NO: 90). In specific embodiments, the at least one antibody or antigen-binding fragment thereof specifically binds to at least one epitope in the neuropilin B1 domain, the neuropilin B2 domain, and/or the neuropilin B1/B2 combined domain (see Table N1). In particular embodiments, the antibody or antigen-binding fragment thereof binds to the at least one domain (or at least one epitope therein) with an affinity of about 10 pM to about 500 pM or to about 50 nM, or about, at least about, or no more than about 10, 20, 30, 40, 50, 60, 70, 80, 90, 100, 110, 120, 130, 140, 150, 160, 170, 180, 190, 200, 300, 400, 500, 600, 700, 800, 900 pM, 1 nM, 10 nM, 25 nM, or 50 nM, or optionally with an affinity that ranges from about 10 pM to about 500 pM, about 10 pM to about 400 pM, about 10 pM to about 300 pM, about 10 pM to about 200 pM, about 10 pM to about 100 pM, about 10 pM to about 50 pM, or about 20 pM to about 500 pM, about 20 pM to about 400 pM, about 20 pM to about 300 pM, about 20 pM to about 200 pM, about 20 pM to about 100 pM, about 20 pM to about 50 pM, or about 30 pM to about 500 pM, about 30 pM to about 400 pM, about 30 pM to about 300 pM, about 30 pM to about 200 pM, about 30 pM to about 100 pM, about 30 pM to about 50 pM, or about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 1 nM to about 5 nM, about 5 nM to about 10 nM, about 10 nM to 25 nM, or about 25 nM to about 50 nM.

In some embodiments, the at least one antibody or antigen-binding fragment thereof specifically binds to at least one epitope in the neuropilin A1 domain, the neuropilin A2 domain, and/or the neuropilin A1A2 combined domain, including adjacent linker regions, for example, at about residues (neuropilin A1 domain) 20-148, 30-141, 40-141, 50-141, 60-141, 70-141, 80-141, 90-141, 100-141, 110-141, 120-141, 130-141; 20-130, 20-120, 20-110, 20-100, 20-90, 20-80, 20-70, 20-60, 20-50, 20-40, or 20-30 as defined by SEQ ID NO:1 (FL human NRP2); or, for example, at about residues (neuropilin A2 domain) 142-280, 150-265, 160-265, 170-265, 180-265, 190-265, 200-265, 210-265, 220-265, 230-265, 240-265, 250-265, 260-265, 141-270, 141-260, 141-250, 141-240, 141-230, 141-220, 141-210, 141-200, 141-190, 141-180, 141-170, 141-160, 141-150, 200-250, 210-250, 220-250, 230-250, 200-240, 210-240, 220-240, 230-240, 227-247, 228-247, 229-247, 230-247, 231-247, 232-247, 233-247, 234-247, 235-247, 236-247; 227-246, 227-245, 227-244, 227-243, 227-242, 227-241, 227-240, 227-239, 227-238; 235-240, 236-239, 236-238, or residue 237 as defined by SEQ ID NO:1 (FL human NRP2); or, for example, at about residues (combined A1A2 domain) 20-280, 30-280, 40-280, 50-280, 60-280, 70-280, 80-280, 90-280, 100-280, 110-280, 120-280, 130-280, 140-280, 150-280, 160-280, 170-280, 180-280, 190-280, 200-280, 210-280, 220-280, 230-280, 240-280, 260-280, 270-280, 20-270, 20-260, 20-250, 20-240, 20-230, 20-220, 20-210, 20-200, 20-190, 20-180, 20-170, 20-160, 20-150, 20-140, 20-130, 20-120, 20-110, 20-100, 20-90, 20-80, 20-70, 20-60, 20-50, 20-40, or 20-30 as defined by SEQ ID NO:1 (FL human NRP2).

In particular embodiments, the at least one antibody or antigen-binding fragment thereof specifically binds to at least one epitope in the neuropilin B1 domain (SEQ ID NO:12), the neuropilin B2 domain (SEQ ID NO:13), and/or the neuropilin B1/B2 combined domain (SEQ ID NO:20), including adjacent linker regions, for example, at about residues (neuropilin B1 domain) 266-426, 280-426, 290-426, 300-426, 310-426, 320-426, 330-426, 340-426, 350-426, 360-426, 370-426, 380-426, 390-426, 400-426, 410-426, 420-426, 280-420, 280-410, 280-400, 280-390, 280-380, 280-370, 280-360, 280-350, 280-340, 280-330, 280-320, 280-310, 280-300, or 280-290 as defined by SEQ ID NO:1 (FL human NRP2); (neuropilin B2 domain) 438-591, 450-591, 460-591, 470-591, 480-591, 490-591, 500-591, 510-591, 520-591, 530-591, 540-591, 550-591, 560-591, 570-591, 580-591, 438-590, 438-580, 438-570, 438-560, 438-550, 438-540, 438-530, 438-520, 438-510, 438-500, 438-490, 438-480, 438-470, 438-460, 438-450 as defined by SEQ ID NO:1 (FL human NRP2); or (neuropilin B1/B2 combined domain) 266-591, 276-591, 286-591, 296-591, 306-591, 316-591, 326-591, 336-591, 346-591, 356-591, 366-591, 376-591, 386-591, 396-591, 406-591, 416-591, 426-591, 436-591, 446-591, 456-591, 466-591, 476-591, 486-591, 498-591, 508-591, 518-591, 528-591, 538-591, 548-591, 558-591, 568-591, 578-591, 588-591, 266-581, 266-571, 266-561, 266-551, 266-541, 266-531, 266-521, 266-511, 266-501, 266-491, 266-481, 266-471, 266-461, 266-451, 266-441, 266-431, 266-421, 266-411, 266-401, 266-391, 266-381, 266-371, 266-361, 266-351, 266-341, 266-331, 266-321, 266-311, 266-301, 266-291, 266-281, or 266-271 as defined by SEQ ID NO:1 (FL human NRP2).

In some embodiments, the at least one antibody or antigen-binding fragment thereof specifically binds to at least one epitope in the neuropilin A2/B1 combined domain and/or the neuropilin B2C combined domain, including adjacent linker regions, for example, at about residues (neuropilin A2B1 combined domain) 149-437, 159-426, 169-426, 179-426, 189-426, 199-426, 209-426, 219-426, 229-426, 239-426, 249-426, 259-426, 269-426, 279-426, 289-426, 299-426, 309-426, 319-426, 329-426, 339-426, 349-426, 359-426, 369-426, 379-426, 389-426, 399-426, 409-426, 419-426, 149-436, 149-426, 149-416, 149-406, 149-396, 149-386, 149-376, 149-366, 149-356, 149-346, 149-336, 149-326, 149-316, 149-306, 149-296, 149-286, 149-276, 149-266, 149-256, 149-246, 149-236, 149-226, 149-216, 149-206, 149-196, 146-186, 146-176, 146-166, or 146-155 as defined by SEQ ID NO:1 (FL human NRP2); or, for example, at about residues (neuropilin B2C combined domain) 438-794, 448-794, 458-794, 468-794, 478-794, 487-794, 497-794, 507-794, 517-794, 527-794, 537-794, 547-794, 557-794, 567-794, 587-794, 597-794, 607-794, 617-794, 627-794, 637-794, 647-794, 657-794, 667-794, 677-794, 687-794, 697-794, 707-794, 717-794, 727-794, 737-794, 747-794, 757-794, 767-794, 777-794, 787-794, 427-794, 438-784, 438-774, 438-764, 438-754, 438-744, 438-734, 438-728, 438-714, 438-704, 438-694, 438-684, 438-674, 438-664, 438-654, 438-644, 438-634, 438-624, 438-614, 438-604, 438-596, 438-586, 438-576, 438-566, 438-556, 438-546, 438-536, 438-526, 438-516, 438-506, 438-494, 438-484, 438-474, 438-464, 438-454, 438-444 as defined by SEQ ID NO:1 (FL human NRP2).

In some embodiments, the at least one antibody or antigen-binding fragment thereof specifically binds to at least one epitope in the neuropilin C domain, including adjacent linker regions, for example, at about residues 591-794, 600-794, 610-794, 620-794, 630-794, 640-794, 650-794, 660-794, 670-794, 680-794, 690-794, 700-794, 710-794, 720-794, 730-794, 740-794, 750-794, 760-794, 770-794, 780-794, 790-794, 591-790, 591-780, 591-770, 591-760, 591-750, 591-740, 591-730, 591-720, 591-710, 591-700, 591-690, 591-680, 591-670, 591-660, 591-650, 591-640, 591-630, 591-620, 591-610, or 591-600 as defined by SEQ ID NO:1 (FL human NRP2).

In some embodiments, the at least one antibody or antigen-binding fragment thereof specifically binds to at least one epitope in the neuropilin B1/B2/C combined domain, including adjacent linker regions, for example, at about residues 276-794, 286-794, 296-794, 306-794, 316-794, 326-794, 336-794, 346-794, 356-794, 366-794, 376-794, 387-794, 396-794, 406-794, 416-794, 426-794, 436-794, 446-794, 456-794, 466-794, 476-794, 486-794, 496-794, 506-794, 516-794, 526-794, 536-794, 546-794, 556-794, 566-794, 576-794, 586-794, 596-794, 606-794, 616-794, 626-794, 636-794, 646-794, 656-794, 666-794, 676-794, 686-794, 696-794, 706-794, 716-794, 726-794, 736-794, 746-794, 756-794, 766-794, 776-794, 786-794, 266-794, 276-784, 276-774, 276-764, 276-754, 276-744, 276-734, 276-724, 276-714, 276-704, 276-694, 276-684, 276-674, 276-664, 276-654, 276-644, 276-634, 276-624, 276-614, 276-604, 276-594, 276-584, 276-574, 276-564, 276-554, 276-544, 276-534, 276-524, 276-514, 276-504, 276-594, 276-584, 276-574, 276-564, 276-554, 276-544, 276-534, 276-524, 276-514, 276-504, or 276-496 as defined by SEQ ID NO:1 (FL human NRP2).

In some embodiments, the at least one antibody or antigen-binding fragment thereof specifically binds to a conformational epitope composed of two or more discontinuous epitope regions. In some embodiments, the at least one antibody or antigen-binding fragment thereof specifically binds to a conformational epitope comprising or consisting of:

(a) a first epitope region within the A1 domain, and second epitope region within the A2 domain of the human NPR2 polypeptide;

(b) a first epitope region within the A1 domain, and second epitope region within the B1 domain of the human NPR2 polypeptide;

(c) a first epitope region within the A1 domain, and second epitope region within the B2 domain of the human NPR2 polypeptide;

(d) a first epitope region within the A1 domain, and second epitope region within the C domain of the human NPR2 polypeptide;

(e) a first epitope region within the A2 domain, and second epitope region within the B1 domain of the human NPR2 polypeptide;

(f) a first epitope region within the A2 domain, and second epitope region within the B2 domain of the human NPR2 polypeptide;

(g) a first epitope region within the A2 domain, and second epitope region within the C domain of the human NPR2 polypeptide;

(h) a first epitope region within the B1 domain, and second epitope region within the B2 domain of the human NPR2 polypeptide;

(i) a first epitope region within the B1 domain, and second epitope region within the C domain of the human NPR2 polypeptide; or (j) a first epitope region within the B2 domain, and second epitope region within the C domain of the human NPR2 polypeptide.

In some embodiments, the antibody or antigen-binding fragment thereof specifically binds to at least one epitope within a region of a human NRP2 polypeptide that binds to or interacts with at least one "NRP2 ligand", including any molecule that interacts with or binds reversibly to human NRP2. General examples of "NRP2 ligands" include polypeptides such as HRS polypeptides, soluble ligands, receptors (e.g., cell surface receptors), including growth factors, growth factor receptors, and others, and specific examples of NRP2 ligands are detailed herein. In some embodiments, the at least one antibody or antigen-binding fragment thereof modulates (e.g., antagonizes, interferes with, agonizes, enhances) binding of the human NRP2 polypeptide to at least one "NRP2 ligand".

As noted above, in certain embodiments the at least one NRP2 ligand is an HRS polypeptide. Thus, in certain embodiments, an antibody or antigen-binding fragment thereof specifically binds to at least one epitope within a region of a human NRP2 polypeptide that binds to or interacts with at least one human HRS polypeptide, and thereby modulates binding of the human NRP2 polypeptide to the human HRS polypeptide. Exemplary HRS polypeptides are provided in Table H1 below.

TABLE H1

Exemplary Human HRS polypeptides

| Name | Residues | Sequence | SEQ ID NO: |
|---|---|---|---|
| FL cytosolic wild type | 1-509 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKLIYDLKDQGGE LLSLRYDLTVPFARYLAMNKLTNIKRYHIAKVYRRDNPAMT RGRYREFYQCDFDIAGNFDPMIPDAECLKIMCEILSSLQIG DFLVKVNDRRILDGMFAICGVSDSKFRTICSSVDKLDKVSW EEVKNEMVGEKGLAPEVADRIGDYVQQHGGVSLVEQLLQDP KLSQNKQALEGLGDLKLLFEYLTLFGIDDKISFDLSLARGL DYYTGVIYEAVLLQTPAQAGEEPLGVGSVAAGGRYDGLVGM FDPKGRKVPCVGLSIGVERIFSIVEQRLEALEEKIRTTETQ VLVASAQKKLLEERLKLVSELWDAGIKAELLYKKNPKLLNQ LQYCEEAGIPLVAIIGEQELKDGVIKLRSVTSREEVDVRRE DLVEEIKRRTGQPLCIC | 91 |
| HisRS1$^{N1}$ | 1-141 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKLIYDLKDQGGE LLSLRYDLTVPFARYLAM | 92 |
| HisRS1$^{N2}$ | 1-408 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKLIYDLKDQGGE LLSLRYDLTVPFARYLAMNKLTNIKRYHIAKVYRRDNPAMT RGRYREFYQCDFDIAGNFDPMIPDAECLKIMCEILSSLQIG DFLVKVNDRRILDGMFAICGVSDSKFRTICSSVDKLDKVSW EEVKNEMVGEKGLAPEVADRIGDYVQQHGGVSLVEQLLQDP KLSQNKQALEGLGDLKLLFEYLTLFGIDDKISFDLSLARGL DYYTGVIYEAVLLQTPAQAGEEPLGVGSVAAGGRYDGLVGM FDPKGRKVPCVGLSIGVERIFSIVEQRLEALEEKIRTTE | 93 |
| HisRS1$^{N3}$ | 1-113 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKL | 94 |
| HisRS1$^{N4}$ | 1-60 | MAERAALEELVKLQGERVRGLKQQKASAELIEEEVAKLLKL KAQLGPDESKQKFVLKTPK | 95 |
| HisRS1$^{N5}$ | 1-243 + 27 aa | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKLIYDLKDQGGE LLSLRYDLTVPFARYLAMNKLTNIKRYHIAKVYRRDNPAMT RGRYREFYQCDFDIAGNFDPMIPDAECLKIMCEILSSLQIG DFLVKVNDRRILDGMFAICGVSDSKFRTICSSVDKLDKVGY PWWNSCSRILNYPKTSRPWRAWET | 96 |
| HisRS1$^{C1}$ | 405-509 | RTTETQVLVASAQKKLLEERLKLVSELWDAGIKAELLYKKN PKLLNQLQYCEEAGIPLVAIIGEQELKDGVIKLRSVTSREE VDVRREDLVEEIKRRTGQPLCIC | 97 |
| HisRS1$^{C2}$ | 1-60 + 175-509 | MAERAALEELVKLQGERVRGLKQQKASAELIEEEVAKLLKL KAQLGPDESKQKFVLKTPKDFDIAGNFDPMIPDAECLKIMC EILSSLQIGDFLVKVNDRRILDGMFAICGVSDSKFRTICSS VDKLDKVSWEEVKNEMVGEKGLAPEVADRIGDYVQQHGGVS LVEQLLQDPKLSQNKQALEGLGDLKLLFEYLTLFGIDDKIS FDLSLARGLDYYTGVIYEAVLLQTPAQAGEEPLGVGSVAAG GRYDGLVGMFDPKGRKVPCVGLSIGVERIFSIVEQRLEALE EKIRTTETQVLVASAQKKLLEERLKLVSELWDAGIKAELLY KKNPKLLNQLQYCEEAGIPLVAIIGEQELKDGVIKLRSVTS REEVDVRREDLVEEIKRRTGQPLCIC | 98 |
| HisRS1$^{C3}$ | 1-60 + 211-509 | MAERAALEELVKLQGERVRGLKQQKASAELIEEEVAKLLKL KAQLGPDESKQKFVLKTPKVNDRRILDGMFAICGVSDSKFR TICSSVDKLDKVSWEEVKNEMVGEKGLAPEVADRIGDYVQQ HGGVSLVEQLLQDPKLSQNKQALEGLGDLKLLFEYLTLFGI DDKISFDLSLARGLDYYTGVIYEAVLLQTPAQAGEEPLGVG SVAAGGRYDGLVGMFDPKGRKVPCVGLSIGVERIFSIVEQR LEALEEKIRTTETQVLVASAQKKLLEERLKLVSELWDAGIK AELLYKKNPKLLNQLQYCEEAGIPLVAIIGEQELKDGVIKL RSVTSREEVDVRREDLVEEIKRRTGQPLCIC | 99 |
| HisRS1$^{C4}$ | 1-100 + 211-509 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKVNDRRILDGMFAICGVSDSKFRT ICSSVDKLDKVSWEEVKNEMVGEKGLAPEVADRIGDYVQQH GGVSLVEQLLQDPKLSQNKQALEGLGDLKLLFEYLTLFGID | 99 |

TABLE H1-continued

Exemplary Human HRS polypeptides

| Name | Residues | Sequence | SEQ ID NO: |
|---|---|---|---|
| | | DKISFDLSLARGLDYYTGVIYEAVLLQTPAQAGEEPLGVGS VAAGGRYDGLVGMFDPKGRKVPCVGLSIGVERIFSIVEQRL EALEEKIRTTETQVLVASAQKKLLEERLKLVSELWDAGIKA ELLYKKNPKLLNQLQYCEEAGIPLVAIIGEQELKDGVIKLR SVTSREEVDVRREDLVEEIKRRTGQPLCIC | |
| HisRS1$^{C5}$ | 1-174 + 211-509 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKETLMGKYGEDSKLIYDLKDQGGE LLSLRYDLTVPFARYLAMNKLTNIKRYHIAKVYRRDNPAMT RGRYREFYQCVNDRRILDGMFAICGVSDSKFRTICSSVDKL DKVSWEEVKNEMVGEKGLAPEVADRIGDYVQQHGGVSLVEQ LLQDPKLSQNKQALEGLGDLKLLFEYLTLFGIDDKISFDLS LARGLDYYTGVIYEAVLLQTPAQAGEEPLGVGSVAAGGRYD GLVGMFDPKGRKVPCVGLSIGVERIFSIVEQRLEALEEKIR TTETQVLVASAQKKLLEERLKLVSELWDAGIKAELLYKKNP KLLNQLQYCEEAGIPLVAIIGEQELKDGVIKLRSVTSREEV DVRREDLVEEIKRRTGQPLCIC | 100 |
| HisRS1$^{C6}$ | 1-60 + 101-509 | MAERAALEELVKLQGERVRGLKQQKASAELIEEEVAKLLKL KAQLGPDESKQKFVLKTPKETLMGKYGEDSKLIYDLKDQGG ELLSLRYDLTVPFARYLAMNKLTNIKRYHIAKVYRRDNPAM TRGRYREFYQCDFDIAGNFDPMIPDAECLKIMCEILSSLQI GDFLVKVNDRRILDGMFAICGVSDSKFRTICSSVDKLDKVS WEEVKNEMVGEKGLAPEVADRIGDYVQQHGGVSLVEQLLQD PKLSQNKQALEGLGDLKLLFEYLTLFGIDDKISFDLSLARG LDYYTGVIYEAVLLQTPAQAGEEPLGVGSVAAGGRYDGLVG MFDPKGRKVPCVGLSIGVERIFSIVEQRLEALEEKIRTTET QVLVASAQKKLLEERLKLVSELWDAGIKAELLYKKNPKLLN QLQYCEEAGIPLVAIIGEQELKDGVIKLRSVTSREEVDVRR EDLVEEIKRRTGQPLCIC | 101 |
| HisRS1$^{C7}$ | 1-100 + 175-509 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKDFDIAGNFDPMIPDAECLKIMCE ILSSLQIGDFLVKVNDRRILDGMFAICGVSDSKFRTICSSV DKLDKVSWEEVKNEMVGEKGLAPEVADRIGDYVQQHGGVSL VEQLLQDPKLSQNKQALEGLGDLKLLFEYLTLFGIDDKISF DLSLARGLDYYTGVIYEAVLLQTPAQAGEEPLGVGSVAAGG RYDGLVGMFDPKGRKVPCVGLSIGVERIFSIVEQRLEALEE KIRTTETQVLVASAQKKLLEERLKLVSELWDAGIKAELLYK KNPKLLNQLQYCEEAGIPLVAIIGEQELKDGVIKLRSVTSR EEVDVRREDLVEEIKRRTGQPLCIC | 102 |
| HisRS1$^{C8}$ | 1-60 + 399-509 | MAERAALEELVKLQGERVRGLKQQKASAELIEEEVAKLLKL KAQLGPDESKQKFVLKTPKALEEKIRTTETQVLVASAQKKL LEERLKLVSELWDAGIKAELLYKKNPKLLNQLQYCEEAGIP LVAIIGEQELKDGVIKLRSVTSREEVDVRREDLVEEIKRRT GQPLCIC | 103 |
| HisRS1$^{C9}$ | 1-100 + 399-509 | MAERAALEELVKLQGERVRGLKQQKASAELIEEEVAKLLKL KAQLGPDESKQKFVLKTPKGTRDYSPRQMAVREKVFDVIIR CFKRHGAEVIDTPVFELKALEEKIRTTETQVLVASAQKKLL EERLKLVSELWDAGIKAELLYKKNPKLLNQLQYCEEAGIPL VAIIGEQELKDGVIKLRSVTSREEVDVRREDLVEEIKRRTG QPLCIC | 104 |
| HisRS1$^{C10}$ | 369-509 | MFDPKGRKVPCVGLSIGVERIFSIVEQRLEALEEKIRTTET QVLVASAQKKLLEERLKLVSELWDAGIKAELLYKKNPKLLN QLQYCEEAGIPLVAIIGEQELKDGVIKLRSVTSREEVDVRR EDLVEEIKRRTGQPLCIC | 105 |
| HisRS1$^{I1}$ | 191-333 | CLKIMCEILSSLQIGDFLVKVNDRRILDGMFAICGVSDSKF RTICSSVDKLDKVSWEEVKNEMVGEKGLAPEVADRIGDYVQ QHGGVSLVEQLLQDPKLSQNKQALEGLGDLKLLFEYLTLFG IDDKISFDLSLARGLDYYTG | 106 |
| FL mito. wild type | 1-506 | MPLLGLLPRRAWASLLSQLLRPPCASCTGAVRCQSQVAEAV LTSQLKAHQEKPNFIIKTPKGTRDLSPQHMVVREKILDLVI SCFKRHGAKGMDTPAFELKETLTEKYGEDSGLMYDLKDQGG ELLSLRYDLTVPFARYLAMNKVKKMKRYHVGKVWRRESPTI VQGRYREFCQCDFDIAGQFDPMIPDAECLKIMCEILSGLQL GDFLIKVNDRRIVDGMFAVCGVPESKFRAICSSIDKLDKMA WKDVRHEMVVKKGLAPEVADRIGDYVQCHGGVSLVEQMFQD PRLSQNKQALEGLGDLKLLFEYLTLFGIADKISFDLSLARG | 107 |

TABLE H1-continued

Exemplary Human HRS polypeptides

| Name | Residues | Sequence | SEQ ID NO: |
|---|---|---|---|
| | | LDYYTGVIYEAVLLQTPTQAGEEPLNVGSVAAGGRYDGLVG MFDPKGHKVPCVGLSIGVERIFYIVEQRMKTKGEKVRTTET QVFVATPQKNFLQERLKLIAELWDSGIKAEMLYKNNPKLLT QLHYCESTGIPLVVIIGEQELKEGVIKIRSVASREEVAIKR ENFVAEIQKRLSES | |
| | 152-398 | HVGKVWRRESPTIVQGRYREFCQCDFDIAGQFDPMIPDAEC LKIMCEILSGLQLGDFLIKVNDRRIVDGMFAVCGVPESKFR AICSSIDKLDKMAWKDVRHEMVVKKGLAPEVADRIGDYVQC HGGVSLVEQMFQDPRLSQNKQALEGLGDLKLLFEYLTLFGI ADKISFDLSLARGLDYYTGVIYEAVLLQTPTQAGEEPLNVG SVAAGGRYDGLVGMFDPKGHKVPCVGLSIGVERIFYIVEQR M | 108 |
| | 294-372 | QALEGLGDLKLLFEYLTLFGIDDKISFDLSLARGLDYYTGV IYEAVLLQTPAQAGEEPLGVGSVAAGGRYDGLVGMFDP | 109 |
| Amino-acylation domain and anticodon binding domain | 54-509 | FVLKTPKGTRDYSPRQMAVREKVFDVIIRCFKRHGAEVIDT PVFELKETLMGKYGEDSKLIYDLKDQGGELLSLRYDLTVPF ARYLAMNKLTNIKRYHIAKVYRRDNPAMTRGRYREFYQCDF DIAGNFDPMIPDAECLKIMCEILSSLQIGDFLVKVNDRRIL DGMFAICGVSDSKFRTICSSVDKLDKVSWEEVKNEMVGEKG LAPEVADRIGDYVQQHGGVSLVEQLLQDPKLSQNKQALEGL GDLKLLFEYLTLFGIDDKISFDLSLARGLDYYTGVIYEAVL LQTPAQAGEEPLGVGSVAAGGRYDGLVGMFDPKGRKVPCVG LSIGVERIFSIVEQRLEALEEKIRTTETQVLVASAQKKLLE ERLKLVSELWDAGIKAELLYKKNPKLLNQLQYCEEAGIPLV AIIGEQELKDGVIKLRSVTSREEVDVRREDLVEEIKRRTGQ PLCIC | 110 |
| Amino-acylation domain | 54-398 | FVLKTPKGTRDYSPRQMAVREKVFDVIIRCFKRHGAEVIDT PVFELKETLMGKYGEDSKLIYDLKDQGGELLSLRYDLTVPF ARYLAMNKLTNIKRYHIAKVYRRDNPAMTRGRYREFYQCDF DIAGNFDPMIPDAECLKIMCEILSSLQIGDFLVKVNDRRIL DGMFAICGVSDSKFRTICSSVDKLDKVSWEEVKNEMVGEKG LAPEVADRIGDYVQQHGGVSLVEQLLQDPKLSQNKQALEGL GDLKLLFEYLTLFGIDDKISFDLSLARGLDYYTGVIYEAVL LQTPAQAGEEPLGVGSVAAGGRYDGLVGMFDPKGRKVPCVG LSIGVERIFSIVEQRLE | 111 |
| Amino-acylation (core) domain | 61-398 | GTRDYSPRQMAVREKVFDVIIRCFKRHGAEVIDTPVFELKE TLMGKYGEDSKLIYDLKDQGGELLSLRYDLTVPFARYLAMN KLTNIKRYHIAKVYRRDNPAMTRGRYREFYQCDFDIAGNFD PMIPDAECLKIMCEILSSLQIGDFLVKVNDRRILDGMFAIC GVSDSKFRTICSSVDKLDKVSWEEVKNEMVGEKGLAPEVAD RIGDYVQQHGGVSLVEQLLQDPKLSQNKQALEGLGDLKLLF EYLTLFGIDDKISFDLSLARGLDYYTGVIYEAVLLQTPAQA GEEPLGVGSVAAGGRYDGLVGMFDPKGRKVPCVGLSIGVER IFSIVEQRLE | 112 |
| Anticodon binding domain | 399-509 | ALEEKIRTTETQVLVASAQKKLLEERLKLVSELWDAGIKAE LLYKKNPKLLNQLQYCEEAGIPLVAIIGEQELKDGVIKLRS VTSREEVDVRREDLVEEIKRRTGQPLCIC | 113 |
| Anticodon binding (core) domain | 406-501 | TTETQVLVASAQKKLLEERLKLVSELWDAGIKAELLYKKNP KLLNQLQYCEEAGIPLVAIIGEQELKDGVIKLRSVTSREEV DVRREDLVEEIKRR | 114 |
| HRS WHEP consensus | | $X_A$-L-$X_B$-Q-G-X-X-V-R-X-L-K-X-X-K-A-$X_C$-V-X-X-L-L-X-L-K-$X_D$<br>Where:<br>X is any amino acid<br>$X_A$ is 0-50 amino acids<br>$X_B$ is about 5-7 amino acids, preferably 6 amino acids<br>$X_C$ is about 7-9 amino acids, preferably 8 amino acids<br>$X_D$ is 0-50 amino acids | 115 |

Thus, in certain embodiments, the at least one NRP2 ligand is selected from Table H1, and the anti-NRP2 antibody or antigen-binding fragment thereof modulates (e.g., interferes with) binding of a human NRP2 polypeptide (for example, a human NRP2 polypeptide selected from Table N1) to a human HRS polypeptide selected from Table H1. In some embodiments, the anti-NRP2 antibody or antigen-binding fragment specifically binds to an HRS polypeptide-interacting region of the NRP2 polypeptide, and in some instances mimics one or more signaling activities of the HRS polypeptide binding to the NRP2 polypeptide, for example, as an agonist antibody. An "HRS polypeptide-interacting region" includes a region or domain of a human NRP2 polypeptide that interacts with a region or domain of human HRS polypeptide, for example, at a ligand binding site for a different NRP2 ligand (examples of which are provided herein), a dimerization domain, a protein-protein interaction domain, or at a site which is allosterically sensitive within a NRP2 polypeptide to modulate the activity of the NRP2 polypeptide.

In certain embodiments, an antibody or antigen-binding fragment thereof is a "blocking antibody", which fully or substantially inhibits the binding between a human NRP2 polypeptide (selected, for example, from Table N1) and an NRP2 ligand such as a human HRS polypeptide (selected, for example, from Table H1) or other NRP2 ligand (for example, selected from Table N2 or Table N3). In some embodiments, a "blocking antibody" inhibits about or at least about 80-100% (e.g., 80, 85, 90, 95, or 100%) of the theoretical maximal binding between the NRP2 polypeptide and the NRP2 ligand (for example, HRS polypeptide) after pre-incubation of the "blocking antibody" with the NRP2 polypeptide in a substantially stoichiometrically equivalent amount. As used herein, a "stoichiometrically equivalent amount" refers to a situation where the number of moles of one substance (e.g., anti-NRP2 antibody) is equivalent or substantially equivalent to the number of moles at least one other substance (e.g., NRP2 polypeptide) in a given equation or reaction.

In certain embodiments, an antibody or antigen-binding fragment thereof is a "partial-blocking antibody", which at least partially but not fully inhibits the binding between a human NRP2 polypeptide (selected, for example, from Table N1) and an NRP2 ligand such as a human HRS polypeptide (selected, for example, from Table H1) or other NRP2 ligand (for example, selected from Table N2 or Table N3). In some embodiments, a "partial-blocking antibody" inhibits about or at least about 20-80% (e.g., 20, 25, 30, 35, 40, 45, 50, 55, 60, 65, 70, 75, or 80%) of the theoretical maximal binding between the NRP2 polypeptide and the NRP2 ligand (for example, HRS polypeptide) after pre-incubation of the "partial-blocking antibody" with the NRP2 polypeptide in a stoichiometric amount.

In specific embodiments, the at least one antibody or antigen-binding fragment thereof specifically inhibits or otherwise reduces the binding between a human NRP2 polypeptide and a HRS polypeptide splice variant selected from Table H1, for example, a HRS splice variant selected from one or more of $HisRS^{N1}$, $HisRS^{N2}$, $HisRS^{N3}$, $HisRS^{N2}$ (SV9), $HisRS^{N5}$, $HisRS^{C1}$, $HisRS^{C2}$, $HisRS^{C3}$, $HisRS^{C4}$, $HisRS^{C5}$, $HisRS^{C6}$, $HisRS^{C7}$, $HisRS^{C8}$ (SV11), and $HisRS^{C9}$ (SV14).

As noted above, NRP2 interacts with multiple NRP2 ligands other than HRS, which mediate downstream signaling events. Additional examples of NRP2 ligands are provided in Table N2 and Table N3 below.

TABLE N2

Exemplary Neuropilin Ligands

| Ligand | NRP1 | NRP2 |
|---|---|---|
| VEGF-A121 | + | |
| VEGF-A145 | | + |
| VEGF-A165 | + | + |
| VEGF-B167 | + | |
| VEGF-C | + | + |
| VEGF-D | + | + |
| VEGF-E | + | |
| PlGF-2 | + | + |
| VEGFR | +R1 and R2 | +R1, R2, R3 |
| Heparin | + | + |
| SEMA3A | + | |
| SEMA 3B, C, D, F, G | + | + |
| Plexins A1, A2, A3, A4, D1 | + | + |
| GIPC1 | + | + |
| TGF-β1, β2, β3, and LAP | + | + |
| TbRI and TbRII | + | + |
| FGF-1, 2, 4, and 7 | + | + |
| FGF receptor 1 | + | + |
| Integrins (see Table N3) | + | + |
| Fibronectin | + | |
| Galectin-1 and Galectin Receptors | + | + |
| Li-CAM | + | + |
| Glat-1 | + | |
| HRS polypeptides (see Table H1) | | + |

TABLE N3

Vertebrate integrins as NRP2 ligands

| Name | Synonyms | Distribution | Ligands |
|---|---|---|---|
| $α_1β_1$ | VLA-1 | Many | Collagens, laminins |
| $α_2β_1$ | VLA-2 | Many | Collagens, laminins |
| $α_3β_1$ | VLA-3 | Many | Laminin-5 |
| $α_4β_1$ | VLA-4 | Hematopoietic cells | Fibronectin, VCAM-1 |
| $α_5β_1$ | VLA-5; fibronectin receptor | widespread | fibronectin and proteinases |
| $α_6β_1$ | VLA-6; laminin receptor | widespread | laminins |
| $α_7β_1$ | | muscle, glioma | laminins |
| $α_Lβ_2$ | LFA-1 | T-lymphocytes | ICAM-1, ICAM-2 |
| $α_Mβ_2$ | Mac-1, CR3 | Neutrophils and monocytes | Serum proteins, ICAM-1 |
| $α_{IIb}β_3$ | Fibrinogen receptor; gpIIbIIIa | Platelets | fibrinogen, fibronectin[24] |
| $α_vβ_1$ | | ocular melanoma; neurological tumors | vitronectin; fibrinogen |
| $α_vβ_3$ | vitronectin receptor | activated endothelial cells, melanoma, glioblastoma | vitronectin, fibronectin, fibrinogen, osteopontin, Cyr61, thyroxine, TETRAC |
| $α_vβ_5$ | | widespread, esp. fibroblasts, epithelial cells | vitronectin and adenovirus |
| $α_vβ_6$ | | proliferating epithelia, esp. lung and mammary gland | fibronectin; TGFβ1 + 3 |
| $α_vβ_8$ | | neural tissue; periphera lnerve | fibronectin; TGFβ1 + 3 |
| $α_6β_4$ | | Epithelial cells | Laminin |

Thus, in certain embodiments, the at least one NRP2 ligand is selected from Table N2 and/or Table N3.

For example, in some aspects, the at least one NRP2 ligand is a VEGF (vascular endothelial growth factor) ligand selected from VEGF-A145, VEGF-A165, VEGF-C, VEGF-D, and PlGF-2. VEGF-VEGFR2/3-NRP2 interactions are associated with promoting cell migration, cell growth, cell survival, and cell attachment, and also with lymphangiogenesis, increasing vascular permeability, activating integrin signaling, promoting vesicular trafficking and internalization, and slowing cellular differentiation. Accordingly anti-NRP2 antibodies which modulate VEGF related NRP2 ligands would be expected find utility in modulating one or more of these pathways.

In certain aspects, the at least one NRP2 ligand is a semaphorin selected from one or more of SEMA-3B, SEMA-3C, SEMA-3D, SEMA-3F, and SEMA-3B, or a plexin receptor selected from one or more of plexins A1, A2, A3, A4, and D1. SEMAs typically antagonize the effects of VEGF-C, through there is a close dynamic interplay between VEGF and Sema signaling pathways. SEMAs typically function in the immune system to control cell movement, cell migration, cell-cell communication, and cell activation. SEMA Plexin-NRP2 interactions are associated with inhibiting cell migration, inhibiting cell growth, promoting apoptosis, inhibiting cell attachment, inhibiting integrin signaling, promoting cellular differentiation, inhibiting lymphangiogenesis, reducing vascular permeability, promoting microtubule destabilization, mediating the collapse of actin cytoskeleton & cell contraction including growth cone collapse and actomyosin contraction, and preventing neuronal cell spreading and inhibiting axon outgrowth. Accordingly anti-NRP2 antibodies which modulate SEMA-related NRP2 ligands would be expected find utility in modulating one or more of these pathways.

In some aspects, the at least one NRP2 ligand is an integrin selected from one or more of αVβ1, αVβ3, αVβ5, αVβ6, αVβ8, α6β1 and a6β4. Integrin-NRP2 interactions are generally associated with increased cell adhesion, cell growth, cancer growth and invasiveness. Accordingly anti-NRP2 antibodies which modulate integrin related NRP2 ligands would be expected find utility in modulating one or more of these pathways.

In some aspects, the at least one NRP2 ligand is selected from TGFβ1, TGFβ2, TGFβ3, and their corresponding TGFβ receptors. TGF-β signaling is strongly involved in the regulation of EMT in cancer, and also in fibrosis development (see, for example, Gemmill et al., Sci. Signal. 10 eaag0528, 2017). NRP2B expression is preferentially upregulated by TGF-β signaling in abnormal lungs, and shows little or no expression in normal lung. NRP2B expression enhances migration, invasion, metastasis, and tumor-sphere formation, and also enhances acquired EGFR inhibitor resistance associated with EMT in cancer cells. Accordingly anti-NRP2 antibodies which modulate TGF-β related NRP2 ligands would be expected find utility in modulating one or more of these pathways. Thus, in certain embodiments, an anti-NRP2 antibody or antigen-binding fragment thereof modulates binding/signaling activity between an NRP2 polypeptide and at least one of the NRP2 ligands from Table N2 and/or Table N3, for example, by specifically binding to an NRP2 ligand-interacting region of the NRP2 polypeptide.

In some instances, the at least one antibody or antigen-binding fragment thereof antagonizes the binding/signaling activity between the NRP2 polypeptide and the at least one NRP2 ligand. For example, in some embodiments, the anti-NRP2 antibody antagonizes or reduces about or at least about 20-100% (e.g., about 20, 25, 30, 35, 40, 45, 50, 55, 60, 65, 70, 75, 80, 90, or 100%) of the theoretical maximal binding/signaling between the NRP2 polypeptide and the NRP2 ligand after pre-incubation of the anti-NRP2 antibody with the NRP2 polypeptide in a substantially stoichiometrically equivalent amount.

In some instances, the at least one antibody or antigen-binding fragment thereof agonizes or enhances the binding/signaling activity between the NRP2 polypeptide and the at least one NRP2 ligand. For instance, in some embodiments, the anti-NRP2 antibody agonizes or enhances by about or at least about 20%-500% (e.g., about 20, 30, 40, 50, 60, 70, 80, 90, 100, 200, 300, 400 or 500%) the theoretical maximal binding/signaling activity between the NRP2 polypeptide and the at least one NRP2 ligand after pre-incubation of the anti-NRP2 antibody with the NRP2 polypeptide in a substantially stoichiometrically equivalent amount.

In some embodiments, the at least one antibody or antigen-binding fragment thereof selectively modulates the binding and/or signaling of semaphorins to, or via, the NRP2 polypeptide. In some aspects, such antibodies do not substantially block the interaction of VEGF-C or related NRP2 ligands. In some aspects, such antibodies are agonistic antibodies with respect to semaphorin signaling. In some aspects, such antibodies are antagonistic antibodies with respect to semaphorin signaling.

In some embodiments, the at least one antibody or antigen-binding fragment thereof selectively modulates the binding and/or signaling of VEGF-C or related NRP2 ligands to, or via, the NRP2 polypeptide. In some aspects, such antibodies do not substantially block the interaction of semaphorins. In some embodiments, such antibodies selectively modulate both the binding of VEGF-C or related NRP2 ligands and semaphorins to the NRP2 polypeptide. In some embodiments, such antibodies are agonistic antibodies with respect to VEGF-C signaling. In some aspects, such antibodies are antagonistic antibodies with respect to VEGF-C signaling.

In some embodiments, the at least one antibody or antigen-binding fragment thereof selectively modulates the binding and/or signaling of integrins or related NRP2 ligands to the NRP2 polypeptide.

In some embodiments, the at least one antibody or antigen-binding fragment thereof selectively modulates the binding and/or signaling of TGFβ1, TGFβ2, TGFβ3, or their corresponding TGFβ receptors to the NRP2 polypeptide.

In some embodiments, the at least one antibody or antigen-binding fragment thereof selectively modulates the binding and/or signaling of fibroblast growth factor (FGF), galectin, hepatocyte growth factor (HGF), platelet derived growth factor, and/or their corresponding receptors to the NRP2 polypeptide.

In some embodiments, the at least one antibody or antigen-binding fragment thereof antagonizes the binding/signaling activity between the NRP2 polypeptide and a plexin receptor and/or a semaphorin without substantially modulating the binding/signaling activity between the NRP2 polypeptide and VEGFR3 or VEGF-C.

In some embodiments, the at least one antibody or antigen-binding fragment thereof antagonizes the binding/signaling activity between the NRP2 polypeptide and a plexin receptor and/or semaphorin without substantially modulating the binding/signaling activity between the NRP2 polypeptide and a HRS polypeptide.

In some embodiments, the at least one antibody or antigen-binding fragment thereof antagonizes the binding/signaling activity between the NRP2 polypeptide and a plexin receptor and/or a semaphorin without substantially modulating the binding/signaling activity between the NRP2 polypeptide and a HRS polypeptide, and without substantially modulating the binding/signaling activity between the NRP2 polypeptide and VEGFR3 or VEGF-C.

In some embodiments, the at least one antibody or antigen-binding fragment thereof antagonizes the binding/signaling activity between the NRP2 polypeptide and VEGR3 without substantially modulating the binding/signaling activity between the NRP2 polypeptide and a plexin receptor and/or a semaphorin.

In some embodiments, the at least one antibody or antigen-binding fragment thereof antagonizes the binding/signaling activity between the NRP2 polypeptide and VEGR3 or VEGF-C without substantially modulating the binding/signaling activity between the NRP2 polypeptide and a HRS polypeptide.

In some embodiments, the at least one antibody or antigen-binding fragment thereof antagonizes the binding/signaling activity between the NRP2 polypeptide and a plexin receptor without substantially modulating the ligand binding of semaphorin 3 to NRP2.

In some embodiments, the plexin receptor is selected from plexin A1, A2, A3, A4, and D1. In some embodiments, the semaphorin is selected from semaphorin 3B, 3C, 3D, 3F, and 3G.

In some embodiments, the at least one antibody or antigen-binding fragment thereof specifically binds to an epitope within the human NRP2 A2 domain which comprises at least 5 contiguous amino acids of SEQ ID NO: 11, wherein the at least one antibody or antigen-binding fragment thereof selectively inhibits receptor dimerization between NRP2 and plexin A1 without substantially inhibiting dimerization between NRP2 and FLT4 (VEGFR3). In some embodiments, the at least one antibody or antigen-binding fragment thereof specifically binds to an epitope within amino acids 232-242 of human NRP2 SEQ ID NO: 1.

In some embodiments, the at least one antibody or antigen-binding fragment thereof specifically binds to an epitope within the human NRP2 B1 domain which comprises at least 5 contiguous amino acids of SEQ ID NO: 12, wherein the at least one antibody or antigen-binding fragment thereof selectively inhibits receptor dimerization between NRP2 and FLT4 (VEGFR3) without substantially inhibiting dimerization between NRP2 and plexin A1.

In some embodiments, the at least one antibody or antigen-binding fragment thereof specifically binds to an epitope within the human NRP2 B2 domain which comprises at least 5 contiguous amino acids of SEQ ID NO: 13, wherein the at least one antibody or antigen-binding fragment thereof inhibits receptor dimerization between NRP2 and FLT4 (VEGFR3) and inhibits dimerization between NRP2 and plexin A1.

In some embodiments, the at least one antibody or antigen-binding fragment thereof specifically binds to an epitope within the human NRP2 C domain which comprises at least 5 contiguous amino acids of SEQ ID NO: 14, wherein the at least one antibody or antigen-binding fragment thereof inhibits receptor dimerization between NRP2 and plexin A1 and partially inhibits dimerization between NRP2 and FLT4 (VEGFR3).

In some embodiments, the at least one antibody or antigen-binding fragment thereof has an affinity (Kd or $EC_{50}$) for each of (i) a human NRP2 polypeptide and (ii) the corresponding region of a cynomolgus monkey NRP2 polypeptide, wherein the affinity for (i) and (ii) is within the range of about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, about 0.4 to about 1.2 nM, about 0.9 to about 5.5 nM, about 0.9 to about 5 nM, or about 1 nM to about 10 nM.

In some embodiments, the at least one antibody or antigen-binding fragment thereof has an affinity (Kd or $EC_{50}$) for each of (i) a human NRP2 polypeptide and (ii) the corresponding region of a murine NRP2 polypeptide, wherein the affinity for (i) and (ii) is within the range of about 20 pM to about 200 pM, about 30 pM to about 300 pM, about 40 pM to about 400 pM, about 50 pM to about 500 pM, about 60 pM to about 600 pM, about 70 pM to about 700 pM, about 80 pM to about 800 pM, about 90 pM to about 900 pM, about 100 pM to about 1 nM, or about 1 nM to about 10 nM.

In certain embodiments, an antibody or antigen-binding fragment thereof is characterized by or comprises a heavy chain variable region ($V_H$) sequence that comprises complementary determining region $V_H$CDR1, $V_H$CDR2, and $V_H$CDR3 sequences, and a light chain variable region ($V_L$) sequence that comprises complementary determining region $V_L$CDR1, $V_L$CDR2, and $V_L$CDR3 sequences. Exemplary $V_H$, $V_H$CDR1, $V_H$CDR2, $V_H$CDR3, $V_L$, $V_L$CDR1, $V_L$CDR2, and $V_L$CDR3 sequences are provided in Table A1 below.

TABLE A1

Exemplary CDR Sequences

| Description | Sequence | SEQ ID NO: |
|---|---|---|
| Clone 17F7 | | |
| $V_H$CDR1 Ab/clone aNRP2-1 | GYTFTSYWMH | 23 |
| $V_H$CDR2 Ab/clone aNRP2-1 | AIYPGNSDTSYNQQFKGKA | 24 |
| $V_H$CDR3 Ab/clone aNRP2-1 | RGGGYFDY | 25 |
| $V_L$CDR1 Ab/clone aNRP2-1 | KASQNVGAAVA | 26 |
| $V_L$CDR2 Ab/clone aNRP2-1 | aASNRYT | 27 |
| $V_L$CDR3 Ab/clone aNRP2-1 | QQYSSYPLLT | 28 |
| Clone 3F2 | | |
| $V_H$CDR1 Ab/clone aNRP2-2 | GYTFTSYWMH | 29 |
| $V_H$CDR2 Ab/clone aNRP2-2 | VIHPNSASTFYNERFKT | 30 |
| $V_H$CDR3 Ab/clone aNRP2-2 | PGTVRRSDY | 31 |
| $V_L$CDR1 Ab/clone aNRP2-2 | RSSQNIVHSTGNTYLE | 32 |
| $V_L$CDR2 Ab/clone aNRP2-2 | KVSNRFS | 33 |
| $V_L$CDR3 Ab/clone aNRP2-2 | FQGSHVPWT | 34 |
| Clone 8E2 | | |
| $V_H$CDR1 Ab/clone aNRP2-6 | GFNIKDYYIH | 35 |

TABLE A1-continued

Exemplary CDR Sequences

| Description | Sequence | SEQ ID NO: |
|---|---|---|
| V$_H$CDR2 Ab/clone aNRP2-6 | RIDVEDDETKYAPKFQG | 36 |
| V$_H$CDR3 Ab/clone aNRP2-6 | PIYGSREAWFAY | 37 |
| V$_L$CDR1 Ab/clone aNRP2-6 | TASSSVSSSYLH | 38 |
| V$_L$CDR2 Ab/clone aNRP2-6 | RTSNLAS | 39 |
| V$_L$CDR3 Ab/clone aNRP2-6 | HQYYRSPPT | 40 |
| Clone 5H11 | | |
| V$_H$CDR1 Ab/clone aNRP2-7 | GFNIKDYYIH | 41 |
| V$_H$CDR2 Ab/clone aNRP2-7 | RIDVEDDETKYAPKFQG | 42 |
| V$_H$CDR3 Ab/clone aNRP2-7 | PIYGSREAFFAY | 43 |
| V$_L$CDR1 Ab/clone aNRP2-7 | TASSSVSSSYLH | 44 |
| V$_L$CDR2 Ab/clone aNRP2-7 | STSNLAS | 45 |
| V$_L$CDR3 Ab/clone aNRP2-7 | HQYYRSPPT | 46 |
| Clone 7G10 | | |
| V$_H$CDR1 Ab/clone aNRP2-8 | GFNVKDYYVH | 47 |
| V$_H$CDR2 Ab/clone aNRP2-8 | RIDVEDDETKYAPKFQG | 48 |
| V$_H$CDR3 Ab/clone aNRP2-8 | PIYGAREAWFAY | 49 |
| V$_L$CDR1 Ab/clone aNRP2-8 | TANSSVSSSYLH | 50 |
| V$_L$CDR2 Ab/clone aNRP2-8 | STSNLAS | 51 |
| V$_L$CDR3 Ab/clone aNRP2-8 | HQYHRSPPT | 52 |
| Clone 9E7 | | |
| V$_H$CDR1 Ab/clone aNRP2-9 | GFSLTNYGVY | 53 |
| V$_H$CDR2 Ab/clone aNRP2-9 | VIWSGGSTDYNAAFIS | 54 |
| V$_H$CDR3 Ab/clone aNRP2-9 | NGPNWDRGYYAMDY | 55 |
| V$_L$CDR1 Ab/clone aNRP2-9 | KSSQSLLNSRNQKNYLA | 56 |
| V$_L$CDR2 Ab/clone aNRP2-9 | FASTRES | 57 |
| V$_L$CDR3 Ab/clone aNRP2-9 | QQHYSTPFT | 58 |
| Clone 1E3 | | |
| V$_H$CDR1 Ab/clone aNRP2-10 | GFNIKDYYIH | 59 |
| V$_H$CDR2 Ab/clone aNRP2-10 | RIDVEDDETKYAPKFQG | 60 |
| V$_H$CDR3 Ab/clone aNRP2-10 | PIYGSREAWFAY | 61 |
| V$_L$CDR1 Ab/clone aNRP2-10 | TASSSVSSSYLH | 62 |
| V$_L$CDR2 Ab/clone aNRP2-10 | STSNLAS | 63 |
| V$_L$CDR3 Ab/clone aNRP2-10 | HQYYRSPPT | 64 |
| Clone 13D7 | | |
| V$_H$CDR1 Ab/clone aNRP2-11 | GYTFTSFGIS | 65 |
| V$_H$CDR2 Ab/clone aNRP2-11 | EIYPRSGNTYYNENFKG | 66 |
| V$_H$CDR3 Ab/clone aNRP2-11 | SSGYYGSTPFPY | 67 |
| V$_L$CDR1 Ab/clone aNRP2-11 | RASQDISNYLN | 68 |
| V$_L$CDR2 Ab/clone aNRP2-11 | YTSRLHS | 69 |
| V$_L$CDR3 Ab/clone aNRP2-11 | QQGNTLPWT | 70 |
| Clone 20F3 | | |
| V$_H$CDR1 Ab/clone aNRP2-12 | GYTFTTSGMS | 71 |
| V$_H$CDR2 Ab/clone aNRP2-12 | WINTYSGVPTYADDFKG | 72 |
| V$_H$CDR3 Ab/clone aNRP2-12 | YYSYYVDFDY | 73 |
| V$_L$CDR1 Ab/clone aNRP2-12 | aASSSVSSSYLY | 74 |
| V$_L$CDR2 Ab/clone aNRP2-12 | STSNLAS | 75 |
| V$_L$CDR3 Ab/clone aNRP2-12 | HQWSSYPRT | 76 |
| Clone 18E8 | | |
| V$_H$CDR1 Ab/clone aNRP2-14 | GFSLTSYGVH | 77 |
| V$_H$CDR2 Ab/clone aNRP2-14 | LIWSGGSTDYSPAFIS | 78 |
| V$_H$CDR3 Ab/clone aNRP2-14 | NSYSSGYYAMDY | 79 |
| V$_L$CDR1 Ab/clone aNRP2-14 | KASQNVGTAVA | 80 |

TABLE A1-continued

Exemplary CDR Sequences

| Description | Sequence | SEQ ID NO: |
|---|---|---|
| V$_L$CDR2 Ab/clone aNRP2-14 | SASNRYT | 81 |
| V$_L$CDR3 Ab/clone aNRP2-14 | QQYSSYPPYT | 82 |
| Clone 19E8 | | |
| V$_H$CDR1 Ab/clone aNRP2-15 | GFNIKDSFIH | 83 |
| V$_H$CDR2 Ab/clone aNRP2-15 | RIDPEDDETKYAPKFQG | 84 |
| V$_H$CDR3 Ab/clone aNRP2-15 | PIYGSREAWFAY | 85 |
| V$_L$CDR1 Ab/clone aNRP2-15 | TASSSVSSSYLH | 86 |
| V$_L$CDR2 Ab/clone aNRP2-15 | RTSNLAS | 87 |
| V$_L$CDR3 Ab/clone aNRP2-15 | HQYYRSPPT | 88 |

Thus, in certain embodiments, an antibody or antigen-binding fragment thereof comprises a heavy chain variable region (V$_H$) sequence that comprises complementary determining region V$_H$CDR1, V$_H$CDR2, and V$_H$CDR3 sequences selected from Table A1 and variants thereof which specifically bind to a human NRP2 polypeptide (selected, for example, from Table N1); and a light chain variable region (V$_L$) sequence that comprises complementary determining region V$_L$CDR1, V$_L$CDR2, and V$_L$CDR3 sequences selected from Table A1 and variants thereof which specifically bind to the human NRP2 polypeptide (selected, for example, from Table N1).

In certain embodiments, the CDR sequences are as follows:
the V$_H$CDR1, V$_H$CDR2, and V$_H$CDR3 sequences comprise SEQ ID NOs: 23-25, respectively, and the V$_L$CDR1, V$_L$CDR2, and V$_L$CDR3 sequences comprise SEQ ID NOs: 26-28, respectively, including variants thereof;
the V$_H$CDR1, V$_H$CDR2, and V$_H$CDR3 sequences comprise SEQ ID NOs: 29-31, respectively, and the V$_L$CDR1, V$_L$CDR2, and V$_L$CDR3 sequences comprise SEQ ID NOs: 32-34, respectively, including variants thereof;
the V$_H$CDR1, V$_H$CDR2, and V$_H$CDR3 sequences comprise SEQ ID NOs: 35-37, respectively, and the V$_L$CDR1, V$_L$CDR2, and V$_L$CDR3 sequences comprise SEQ ID NOs: 38-40, respectively, including variants thereof;
the V$_H$CDR1, V$_H$CDR2, and V$_H$CDR3 sequences comprise SEQ ID NOs: 41-43, respectively, and the V$_L$CDR1, V$_L$CDR2, and V$_L$CDR3 sequences comprise SEQ ID NOs: 44-46, respectively, including variants thereof;
the V$_H$CDR1, V$_H$CDR2, and V$_H$CDR3 sequences comprise SEQ ID NOs: 47-49, respectively, and the V$_L$CDR1, V$_L$CDR2, and V$_L$CDR3 sequences comprise SEQ ID NOs: 50-52, respectively, including variants thereof;
the V$_H$CDR1, V$_H$CDR2, and V$_H$CDR3 sequences comprise SEQ ID NOs: 53-55, respectively, and the V$_L$CDR1, V$_L$CDR2, and V$_L$CDR3 sequences comprise SEQ ID NOs: 56-58, respectively, including variants thereof;
the V$_H$CDR1, V$_H$CDR2, and V$_H$CDR3 sequences comprise SEQ ID NOs: 59-61, respectively, and the V$_L$CDR1, V$_L$CDR2, and V$_L$CDR3 sequences comprise SEQ ID NOs: 62-64, respectively, including variants thereof;
the V$_H$CDR1, V$_H$CDR2, and V$_H$CDR3 sequences comprise SEQ ID NOs: 65-67, respectively, and the V$_L$CDR1, V$_L$CDR2, and V$_L$CDR3 sequences comprise SEQ ID NOs: 68-70, respectively, including variants thereof;
the V$_H$CDR1, V$_H$CDR2, and V$_H$CDR3 sequences comprise SEQ ID NOs: 71-73, respectively, and the V$_L$CDR1, V$_L$CDR2, and V$_L$CDR3 sequences comprise SEQ ID NOs: 74-76, respectively, including variants thereof;
the V$_H$CDR1, V$_H$CDR2, and V$_H$CDR3 sequences comprise SEQ ID NOs: 77-79, respectively, and the V$_L$CDR1, V$_L$CDR2, and V$_L$CDR3 sequences comprise SEQ ID NOs: 80-82, respectively, including variants thereof;
the V$_H$CDR1, V$_H$CDR2, and V$_H$CDR3 sequences comprise SEQ ID NOs: 83-85, respectively, and the V$_L$CDR1, V$_L$CDR2, and V$_L$CDR3 sequences comprise SEQ ID NOs: 86-88, respectively, including variants thereof.

Also included are variants thereof, including affinity matured variants, which bind to human NRP2, for example, variants having 1, 2, 3, 4, 5, or 6 alterations in one or more of the CDR regions, for example, one or more the V$_H$CDR1, V$_H$CDR2, V$_H$CDR3, V$_L$CDR1, V$_L$CDR2, and/or V$_L$CDR3 sequences described herein. Exemplary "alterations" include amino acid substitutions, additions, and deletions.

Merely for illustrative purposes, the binding interactions between a human NRP2 polypeptide and an NRP2 ligand can be detected and quantified using a variety of routine methods, including biacore assays (for example, with appropriately tagged soluble reagents, bound to a sensor chip), FACS analyses with cells expressing a NRP2 polypeptide on the cell surface (either native, or recombinant), immunoassays, fluorescence staining assays, ELISA assays, and microcalorimetry approaches such as ITC (Isothermal Titration calorimetry).

In certain embodiments, an antibody or antigen-binding fragment thereof comprises variant or otherwise modified Fc region(s), including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylation/sialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb, FcRn), its pharmacokinetic properties (e.g., stability or half-life, bioavailability, tissue distribution, volume of distribution, concentration, elimination rate constant, elimination rate, area under the curve (AUC), clearance, $C_{max}$, $t_{max}$, $C_{min}$; fluctuation), its immunogenicity, its complement fixation or activation, and/or the CDC/ADCC/ADCP-related activities of the Fc region, among other properties described herein, relative to a corresponding wild-type Fc sequence of an antibody or antigen-binding fragment thereof. Included are modified Fc regions of human and/or mouse origin.

Also included are antibodies or antigen-binding fragments thereof that comprise hybrid Fc regions, for example, Fc regions that comprise a combination of Fc domains (e.g., hinge, $CH_2$, $CH_3$, $CH_4$) from immunoglobulins of different species (e.g., human, mouse), different Ig classes, and/or different Ig subclasses. General examples include hybrid Fc regions that comprise, consist of, or consist essentially of the following combination of $CH_2/CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgE/IgA1, IgE/IgA2, IgE/IgD, IgE/IgE, IgE/IgG1, IgE/IgG2, IgE/IgG3, IgE/IgG4, IgE/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM, IgM/IgA1, IgM/IgA2, IgM/IgD, IgM/IgE, IgM/IgG1, IgM/IgG2, IgM/IgG3, IgM/IgG4, IgM/IgM (or fragments or variants thereof), and optionally include a hinge from one or more of IgA1, IgA2, IgD, IgG1, IgG2, IgG3, or IgG4, and/or a $CH_4$ domain from IgE and/or IgM. In specific embodiments, the hinge, $CH_2$, $CH_3$, and $CH_4$ domains are from human Ig.

Additional examples include hybrid Fc regions that comprise, consist of, or consist essentially of the following combination of $CH_2/CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_3$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Certain examples include hybrid Fc regions that comprise, consist of, or consist essentially of the following combination of $CH_3/CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_2$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Particular examples include hybrid Fc regions that comprise, consist of, or consist essentially of the following combination of hinge/$CH_2$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_3$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Certain examples include hybrid Fc regions that comprise, consist of, or consist essentially of the following combination of hinge/$CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Some examples include hybrid Fc regions that comprise, consist of, or consist essentially of the following combination of hinge/$CH_4$ domains: IgA1/IgE, IgA1/IgM, IgA2/IgE, IgA2/IgM, IgD/IgE, IgD/IgM, IgG1/IgE, IgG1/IgM, IgG2/IgE, IgG2/IgM, IgG3/IgE, IgG3/IgM, IgG4/IgE, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_3$ domain from one or more of IgA1, IgA2, IgD, IgE, IgG1, IgG2, IgG3, IgG4, or IgM.

Specific examples of hybrid Fc regions can be found, for example, in WO 2008/147143, which are derived from combinations of IgG subclasses or combinations of human IgD and IgG.

Also included are antibodies or antigen-binding fragments thereof having derivatized or otherwise modified Fc regions. In certain aspects, the Fc region may be modified by phosphorylation, sulfation, acrylation, glycosylation, methylation, farnesylation, acetylation, amidation, and the like, for instance, relative to a wild-type or naturally-occurring Fc region. In certain embodiments, the Fc region may comprise wild-type or native glycosylation patterns, or alternatively, it may comprise increased glycosylation relative to a native form, decreased glycosylation relative to a native form, or it may be entirely deglycosylated. As one example of a modified Fc glycoform, decreased glycosylation of an Fc region reduces binding to the C1q region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform can be generated by substituting the Q295 position with a cysteine residue (see, e.g., U.S. Application No.

2010/0080794), according to the Kabat et al. numbering system. Certain embodiments may include Fc regions where about 80-100% of the glycoprotein in Fc region comprises a mature core carbohydrate structure that lacks fructose (see, e.g., U.S. Application No. 2010/0255013). Some embodiments may include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region of an antibody or antigen-binding fragment thereof may comprise oligomannose-type N-glycans, and optionally have one or more of the following: increased ADCC effector activity, increased binding affinity for FcγRIIIA (and certain other FcRs), similar or increased binding specificity for the target of the NRP2 polypeptide, similar or higher binding affinity for the target of the NRP2 polypeptide, and/or similar or lower binding affinity for mannose receptor, relative to a corresponding Fc region that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., Nat Biotechnol. 17:176-180, 1999; Davies et al., Biotechnol Bioeng. 74:288-294, 2001; Shields et al., J Biol Chem. 277:26733-26740, 2002; Shinkawa et al., 2003, J Biol Chem. 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions of an antibody or antigen-binding fragment thereof may have altered binding to one or more FcRs, and/or corresponding changes to effector function, relative to a corresponding, wild-type Fc sequence (e.g., same species, same Ig class, same Ig subclass). For instance, such Fc regions may have increased binding to one or more of Fcγ receptors, Fcα receptors, FcE receptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, FcE receptors, and/or the neonatal Fc receptor, relative to a corresponding, wild-type Fc sequence. Specific FcRs are described elsewhere herein.

In some embodiments, an antibody comprises an Fc domain, comprising one or more mutations to increase binding to one or more of Fcγ receptors, Fcα receptors, FcE receptors, and/or the neonatal Fc receptor, relative to a corresponding, wild-type Fc sequence. In some embodiments, an antibody comprises an IgG1 or IgG3 Fc domain, comprising one or more mutations to increase binding to one or more of Fcγ receptors, Fcα receptors, FcE receptors, and/or the neonatal Fc receptor, relative to a corresponding, wild-type Fc sequence. In some embodiments, an antibody comprises an Fc domain, comprising one or more mutations to increase effector function. In some embodiments the at least one antibody comprises an Fc domain selected from a human IgG1 and IgG3, comprising one or more mutations to increase effector function.

In some embodiments, an antibody is blocking antibody that comprises an Fc domain with high effector activity. In some embodiments, the blocking antibody comprises an Fc domain selected from a human IgG1 and IgG3, comprising one or more mutations to increase effector function. In some embodiments, an antibody is a partial-blocking antibody that comprises an Fc domain with high effector activity. In some embodiments, the partial-blocking antibody comprises an Fc domain selected from a human IgG1 and IgG3, comprising one or more mutations to increase effector function. In some embodiments, an antibody is a non-blocking antibody that comprises an Fc domain with high effector activity. In some embodiments, the non-blocking antibody comprises an Fc domain selected from a human IgG1 or IgG3, comprising one or more mutations to increase effector function.

In some embodiments, an antibody comprises an Fc domain, comprising one or more mutations to decrease binding to one or more of Fcγ receptors, Fcα receptors, FcE receptors, and/or the neonatal Fc receptor, relative to a corresponding, wild-type Fc sequence. In some embodiments, an antibody comprises an IgG1 or IgG3 Fc domain, comprising one or more mutations to decrease binding to one or more of Fcγ receptors, Fcα receptors, FcE receptors, and/or the neonatal Fc receptor, relative to a corresponding, wild-type Fc sequence. In some embodiments, an antibody comprises an Fc domain, comprising one or more mutations to decrease effector function. In some embodiments, an antibody comprises an Fc domain selected from a human IgG2 and IgG4, comprising one or more mutations to decrease effector function.

In some embodiments, an antibody is a blocking antibody comprising an Fc domain with low effector activity. In some embodiments, the blocking antibody comprises an Fc domain selected from a human IgG2 and IgG4, comprising one or more mutations to decrease effector function. In some embodiments, an antibody is a partial-blocking antibody comprising an Fc domain with low effector activity. In some embodiments, the partial-blocking antibody comprises an Fc domain selected from a human IgG2 and IgG4, comprising one or more mutations to decrease effector function. In some embodiments, an antibody is a non-blocking antibody comprising an Fc domain with low effector activity. In some embodiments, the non-blocking antibody comprises an Fc domain selected from a human IgG2 and IgG4, comprising one or more mutations to decrease effector function.

Specific examples of Fc variants having altered (e.g., increased, decreased) effector function/FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/ E333A/K334A triple mutant, which has increased binding to FcγRIIIa, decreased binding to FcγRIIb, and increased ADCC (see, e.g., Shields et al., J Biol Chem. 276:6591-6604, 2001; and Presta et al., Biochem Soc Trans. 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/434S, and 428L/4345 (see U.S. Application Nos. 2009/0163699 and 20060173170), based on the EU index of Kabat et al.

Certain variant, fragment, hybrid, or modified Fc regions may have altered effector functions, relative to a corresponding, wild-type Fc sequence. For example, such Fc regions may have increased complement fixation or activation, increased C1q binding affinity, increased CDC-related activity, increased ADCC-related activity, and/or increased ADCP-related activity, relative to a corresponding, wild-type Fc sequence. In other embodiments, such Fc regions may have decreased complement fixation or activation, decreased C1q binding affinity, decreased CDC-related activity, decreased ADCC-related activity, and/or decreased ADCP-related activity, relative to a corresponding, wild-type Fc sequence. As merely one illustrative example, an Fc region may comprise a deletion or substitution in a complement-binding site, such as a C1q-binding site, and/or a deletion or substitution in an ADCC site. Examples of such deletions/substitutions are described, for example, in U.S. Pat. No. 7,030,226. Many Fc effector functions, such as ADCC, can be assayed according to routine techniques in the art. (see, e.g., Zuckerman et al., CRC Crit Rev Microbiol. 7:1-26, 1978). Useful effector cells for such assays includes, but are not limited to, natural killer (NK) cells, macrophages, and other peripheral blood mononuclear cells (PBMC). Alternatively, or additionally, certain Fc effector functions may be assessed in vivo, for example, by employing an animal model described in Clynes et al. PNAS. 95:652-656, 1998.

Certain variant hybrid, or modified Fc regions may have altered stability or half-life relative to a corresponding, wild-type Fc sequence. In certain embodiments, such Fc regions may have increased half-life relative to a corresponding, wild-type Fc sequence. In other embodiments, variant hybrid, or modified Fc regions may have decreased half-life relative to a corresponding, wild-type Fc sequence. Half-life can be measured in vitro (e.g., under physiological conditions) or in vivo, according to routine techniques in the art, such as radiolabeling, ELISA, or other methods. In vivo measurements of stability or half-life can be measured in one or more bodily fluids, including blood, serum, plasma, urine, or cerebrospinal fluid, or a given tissue, such as the liver, kidneys, muscle, central nervous system tissues, bone, etc. As one example, modifications to an Fc region that alter its ability to bind the FcRn can alter its half-life in vivo. Assays for measuring the in vivo pharmacokinetic properties (e.g., in vivo mean elimination half-life) and non-limiting examples of Fc modifications that alter its binding to the FcRn are described, for example, in U.S. Pat. Nos. 7,217,797 and 7,732,570; and U.S. Application Nos. US 2010/0143254 and 2010/0143254.

Additional non-limiting examples of modifications to alter stability or half-life include substitutions/deletions at one or more of amino acid residues selected from 251-256, 285-290, and 308-314 in the $CH_2$ domain, and 385-389 and 428-436 in the $CH_3$ domain, according to the numbering system of Kabat et al. See U.S. Application No. 2003/0190311. Specific examples include substitution with leucine at position 251, substitution with tyrosine, tryptophan or phenylalanine at position 252, substitution with threonine or serine at position 254, substitution with arginine at position 255, substitution with glutamine, arginine, serine, threonine, or glutamate at position 256, substitution with threonine at position 308, substitution with proline at position 309, substitution with serine at position 311, substitution with aspartate at position 312, substitution with leucine at position 314, substitution with arginine, aspartate or serine at position 385, substitution with threonine or proline at position 386, substitution with arginine or proline at position 387, substitution with proline, asparagine or serine at position 389, substitution with methionine or threonine at position 428, substitution with tyrosine or phenylalanine at position 434, substitution with histidine, arginine, lysine or serine at position 433, and/or substitution with histidine, tyrosine, arginine or threonine at position 436, including any combination thereof. Such modifications optionally increase affinity of the Fc region for the FcRn and thereby increase half-life, relative to a corresponding, wild-type Fc region.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Additional examples of variants include IgG Fc regions having conservative or non-conservative substitutions (as described elsewhere herein) at one or more of positions 250, 314, or 428 of the heavy chain, or in any combination thereof, such as at positions 250 and 428, or at positions 250 and 314, or at positions 314 and 428, or at positions 250, 314, and 428 (see, e.g., U.S. Application No. 2011/0183412). In specific embodiments, the residue at position 250 is substituted with glutamic acid or glutamine, and/or the residue at position 428 is substituted with leucine or phenylalanine. As another illustrative example of an IgG Fc variant, any one or more of the amino acid residues at positions 214 to 238, 297 to 299, 318 to 322, and/or 327 to 331 may be used as a suitable target for modification (e.g., conservative or non-conservative substitution, deletion). In particular embodiments, the IgG Fc variant $CH_2$ domain contains amino acid substitutions at positions 228, 234, 235, and/or 331 (e.g., human IgG4 with Ser228Pro and Leu235Ala mutations) to attenuate the effector functions of the Fc region (see U.S. Pat. No. 7,030,226). Here, the numbering of the residues in the heavy chain is that of the EU index (see Kabat et al., "Sequences of Proteins of Immunological Interest," 5 th Ed., National Institutes of Health, Bethesda, Md. (1991)). Certain of these and related embodiments have altered (e.g., increased, decreased) FcRn binding and/or serum half-life, optionally without reduced effector functions such as ADCC or CDC-related activities.

Additional examples include variant Fc regions that comprise one or more amino acid substitutions at positions 279, 341, 343 or 373 of a wild-type Fc region, or any combination thereof (see, e.g., U.S. Application No. 2007/0224188). The wild-type amino acid residues at these positions for human IgG are valine (279), glycine (341), proline (343) and tyrosine (373). The substation(s) can be conservative or non-conservative, or can include non-naturally occurring amino acids or mimetics, as described herein. Alone or in combination with these substitutions, certain embodiments may also employ a variant Fc region that comprises at least 1, 2, 3, 4, 5, 6, 7, 8, 9, 10 or more amino acid substitutions selected from the following: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283P, 283R, 283T, 283W, 283Y, 285N, 286F, 288N, 288P, 292E, 292F, 292G, 292I, 292L, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339O, 339R, 339S, 339W, 339Y, 341D, 341E, 341F, 341H, 341I, 341K, 341L, 341M, 341N, 341P, 341O, 341R, 341S, 341T, 341V, 341W, 341Y, 343A, 343D, 343E, 343F, 343G, 343H, 343I, 343K, 343L, 343M, 343N, 343O, 343R, 343S, 343T, 343V, 343W, 343Y, 373D, 373E, 373F, 373G, 373H, 373I, 373K, 373L, 373M, 373N, 373O, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379O, 379S, 379T, 380D, 380N, 380S, 380T, 382D, 382F, 382H, 382I, 382K, 382L, 382M, 382N, 382P, 382O, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K. As above, the numbering of the residues in the heavy chain is that of the EU index (see Kabat et al., supra). Such variant Fc regions typically confer an altered effector function or altered serum half-life upon the antibody to which the variant Fc region is operably attached. Preferably the altered effector function is an increase in ADCC, a decrease in ADCC, an increase in CDC, a decrease in CDC, an increase in C1q binding affinity, a decrease in C1q binding affinity, an increase in FcR (preferably FcRn) binding affinity or a decrease in FcR (preferably FcRn) binding affinity as compared to a corresponding Fc region that lacks such amino acid substitution(s).

Additional examples include variant Fc regions that comprise an amino acid substitution at one or more of position(s) 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and/or 428 (see, e.g., U.S. Pat. No. 7,662,925). In specific embodiments, the variant Fc region comprises at least one amino acid substitution selected from the group consisting of: P230A, E233D, L234E, L234Y, L234I, L235D, L235S, L235Y, L235I, S239D, S239E, S239N, S239O, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328O, L328D, L328V, L328T, A330Y, A330L, A330I, I332D, I332E, I332N, I332O, T335D, T335R, and T335Y. In other specific embodiments, the variant Fc region comprises at least one amino acid substitution selected from the group consisting of: V264I, F243L/V264I, L328M, I332E, L328M/I332E, V264I/I332E, S298A/I332E, S239E/I332E, S239O/I332E, S239E, A330Y, I332D, L328I/I332E, L328O/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/I332E, S239O/V264I/I332E, S239E/V264I/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239D/V264I/I332E, S239D/V264I/S298A/I332E, S239D/V264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/V264T, S239D/A330Y/I332E/K326E, and S239D/A330Y/I332E/K326T, In more specific embodiments, the variant Fc region comprises a series of substitutions selected from the group consisting of: N297D/I332E, F241Y/F243Y/V262T/V264T/N297D/I332E, S239D/N297D/I332E, S239E/N297D/I332E, S239D/D265Y/N297D/I332E, S239D/D265H/N297D/I332E, V264E/N297D/I332E, Y296N/N297D/I332E, N297D/A330Y/I332E, S239D/D265V/N297D/I332E, S239D/D265I/N297D/I332E, and N297D/S298A/A330Y/I332E. In specific embodiments, the variant Fc region comprises an amino acid substitution at position 332 (using the numbering of the EU index, Kabat et al., supra). Examples of substitutions include 332A, 332D, 332E, 332F, 332G, 332H, 332K, 332L, 332M, 332N, 332P, 332Q, 332R, 332S, 332T, 332V, 332W and 332Y. The numbering of the residues in the Fc region is that of the EU index of Kabat et al. Among other properties described herein, such variant Fc regions may have increased affinity for an FcγR, increased stability, and/or increased solubility, relative to a corresponding, wild-type Fc region.

Further examples include variant Fc regions that comprise one or more of the following amino acid substitutions: 224N/Y, 225A, 228L, 230S, 239P, 240A, 241L, 243S/V/G/H/A 244L, 246E, 247L/A, 252T, 254T/P, 258K, 261Y, 265V, 266A, 267G/N, 268N, 269K/G, 273A, 276D, 278H, 279M, 280N, 283G, 285R, 288R, 289A, 290E, 291L, 292Q, 297D, 299A, 300H, 301C, 304G, 305A, 306I/F, 311R, 312N, 315D/K/S, 320R, 322E, 323A, 324T, 325S, 326E/R, 332T, 333D/G, 335I, 338R, 339T, 340Q, 341E, 342R, 344Q, 347R, 351S, 352A, 354A, 355W, 356G, 358T, 361D/Y, 362L, 364C, 365Q/P, 370R, 372L, 377V, 378T, 383N, 389S, 390D, 391C, 393A, 394A, 399G, 404S, 408G, 409R, 411I, 412A, 414M, 421S, 422I, 426F/P, 428T, 430K, 431S, 432P, 433P, 438L, 439E/R, 440G, 441F, 442T, 445R, 446A, 447E, optionally where the variant has altered recognition of an Fc ligand and/or altered effector function compared with a parent Fc polypeptide, and wherein the numbering of the residues is that of the EU index as in Kabat et al. Specific examples of these and related embodiments include variant Fc regions that comprise or consist of the following sets of substitutions: (1) N276D, R292Q, V305A, I377V, T394A, V412A and K439E; (2) P244L, K246E, D399G and K409R; (3) S304G, K320R, S324T, K326E and M358T; (4) F243S, P247L, D265V, V266A, S383N and T411I; (5) H224N, F243L, T393A and H433P; (6) V240A, S267G, G341E and E356G; (7) M252T, P291L, P352A, R355W, N390D, S408G, S426F and A431S; (8) P228L, T289A, L365Q, N389S and S440G; (9) F241L, V273A, K340Q and L441F; (10) F241L, T299A, I332T and M428T; (11) E269K, Y300H, Q342R, V422I and G446A; (12) T225A, R301c, S304G, D312N, N315D, L351S and N421S; (13) S254T, L306I, K326R and Q362L; (14) H224Y, P230S, V323A, E333D, K338R and S364C; (15) T335I, K414M and P445R; (16) T335I and K414M; (17) P247A, E258K, D280N, K288R, N297D, T299A, K322E, Q342R, S354A and L365P; (18) H268N, V279M, A339T, N361D and S426P; (19) C261Y, K290E, L306F, Q311R, E333G and Q438L; (20) E283G, N315K, E333G, R344Q, L365P and S442T; (21) Q347R, N361Y and K439R; (22) S239P, S254P, S267N, H285R, N315S, F372L, A378T, N390D, Y391C, F404S, E430K, L432P and K447E; and (23) E269G, Y278H, N325S and K370R, wherein the numbering of the residues is that of the EU index as in Kabat et al. (see, e.g., U.S. Application No. 2010/0184959).

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

In particular embodiments, the Fc region comprises, consists, or consists essentially of the Fc from human IgG1 or IgG4 (see, e.g., Allberse and Schuurman, Immunology. 105:9-19, 2002), or a fragment or variant thereof. Table F1 below provides exemplary sequences (CH1, hinge (underlined), CH2, and CH3 regions) from human IgG1 and IgG4. Examples of variant IgG4 sequences that can be employed are described, for example, in Peters et al., JBC. 287:24525-24533, 2012, and include substitutions at C227, C230, C127 (e.g., C1275), and C131 (e.g., C1315). Other variants that can be used include a L445P substitution in IgG4 (denoted as IgG4-2) or a D356E and L358M substitution in IgG1, (denoted as IgG1m(zf)).

TABLE F1

Exemplary IgG4 Fc Sequences

| Name | Sequence | SEQ ID NO: |
|---|---|---|
| Wild-type IgG4 | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPSCPAPEFLGGPSVFLFPPKPKDTLMISRTPEVTCVVVDVSQED PEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEG NVFSCSVMHEALHNHYTQKSLSLSLGK | 116 |
| S241P | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEG NVFSCSVMHEALHNHYTQKSLSLSLGK | 117 |
| IgG1m(za) GenBank: AH007035.2 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 118 |
| Kappa Km3 | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC | 119 |

As noted above, antibodies having altered Fc regions typically have altered (e.g., improved, increased, decreased) pharmacokinetic properties relative to corresponding wild-type Fc region. Examples of pharmacokinetic properties include stability or half-life, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve (AUC or exposure; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state).

In particular embodiments, an antibody or antigen-binding fragment thereof has a biological half life at about pH 7.4, at about a physiological pH, at about 25° C. or room temperature, and/or at about 37° C. or human body temperature (e.g., in vivo, in serum, in a given tissue, in a given species such as rat, mouse, monkey, or human), of about or at least about 30 minutes, about 1 hour, about 2 hour, about 3 hours, about 4 hours, about 5 hours, about 6 hours, about 12 hours, about 18 hours, about 20 hours, about 24 hours, about 30 hours, about 36 hours, about 40 hours, about 48 hours, about 50 hours, about 60 hours, about 70 hours, about 72 hours, about 80 hours, about 84 hours, about 90 hours, about 96 hours, about 120 hours, or about 144 hours or more, or about 1 week, or about 2 weeks, or about 3 weeks, or about 4 weeks, or about 5 weeks, or about 6 weeks or more, or any intervening half-life, including all ranges in between.

In some embodiments, an antibody or antigen-binding fragment thereof has a T m of about or at least about 60, 62, 64, 66, 68, 70, 72, 74, or 75° C. In some embodiments, an antibody or antigen-binding fragment thereof has a $T_m$ of about 60° C. or greater.

In some embodiments, an antibody or antigen-binding fragment thereof conjugated to one or more cytotoxic or chemotherapeutic agents. General examples of cytotoxic or chemotherapeutic agents include, without limitation, alkylating agents, anti-metabolites, anthracyclines, anti-tumor antibiotics, platinums, type I topoisomerase inhibitors, type II topoisomerase inhibitors, vinca alkaloids, and taxanes. Specific examples of cytotoxic or chemotherapeutic agents include, without limitation, cyclophosphamide, cilengitide, lomustine (CCNU), melphalan, procarbazine, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof. Further examples of cytotoxic or chemotherapeutic agents include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

The antibodies or antigen-binding fragments thereof can be used in any of the compositions, methods, and/or kits described herein, and combined with one or more of the immunotherapy agents described herein.

Additional Therapeutic Agents and Compositions

Immunotherapy Agents. Certain embodiments employ one or more cancer immunotherapy agents. In certain instances, an immunotherapy agent modulates the immune response of a subject, for example, to increase or maintain a cancer-related or cancer-specific immune response, and thereby results in increased immune cell inhibition or reduction of cancer cells. Exemplary immunotherapy agents include polypeptides, for example, antibodies and antigen-binding fragments thereof, ligands, and small peptides, and mixtures thereof. Also include as immunotherapy agents are small molecules, cells (e.g., immune cells such as T-cells), various cancer vaccines, gene therapy or other polynucleotide-based agents, including viral agents such as oncolytic viruses, and others known in the art. Thus, in certain embodiments, the cancer immunotherapy agent is selected from one or more of immune checkpoint modulatory agents, cancer vaccines, oncolytic viruses, cytokines, and a cell-based immunotherapies.

In certain embodiments, the cancer immunotherapy agent is an immune checkpoint modulatory agent. Particular examples include "antagonists" of one or more inhibitory immune checkpoint molecules, and "agonists" of one or more stimulatory immune checkpoint molecules. Generally, immune checkpoint molecules are components of the immune system that either turn up a signal (co-stimulatory molecules) or turn down a signal, the targeting of which has therapeutic potential in cancer because cancer cells can perturb the natural function of immune checkpoint molecules (see, e.g., Sharma and Allison, Science. 348:56-61, 2015; Topalian et al., Cancer Cell. 27:450-461, 2015; Pardoll, Nature Reviews Cancer. 12:252-264, 2012). In some embodiments, the immune checkpoint modulatory agent (e.g., antagonist, agonist) "binds" or "specifically binds" to the one or more immune checkpoint molecules, as described herein.

In particular embodiments, the immune checkpoint modulatory agent is a polypeptide or peptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein Antibodies are also included as polypeptides. Thus, in some embodiments, the immune checkpoint modulatory polypeptide agent is an antibody or "antigen-binding fragment thereof", as described elsewhere herein.

In some embodiments, the agent is or comprises a "ligand," for example, a natural ligand, of the immune checkpoint molecule. A "ligand" refers generally to a substance or molecule that forms a complex with a target molecule (e.g., biomolecule) to serve a biological purpose, and includes a "protein ligand," which generally produces a signal by binding to a site on a target molecule or target protein. Thus, certain agents are protein ligands that, in nature, bind to an immune checkpoint molecule and produce a signal. Also included are "modified ligands," for example, protein ligands that are fused to a pharmacokinetic modifier, for example, an Fc region derived from an immunoglobulin.

The binding properties of polypeptides can be quantified using methods well known in the art (see Davies et al., Annual Rev. Biochem. 59:439-473, 1990). In some embodiments, a polypeptide specifically binds to a target molecule, for example, an immune checkpoint molecule or an epitope thereof, with an equilibrium dissociation constant that is about or ranges from about 1.0-7 to about 10-8 M. In some embodiments, the equilibrium dissociation constant is about or ranges from about 1.0-9 M to about 1.0-10 M. In certain illustrative embodiments, the polypeptide has an affinity (Kd or $EC_{50}$) for a target described herein (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the agent is a "small molecule," which refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of about or less than about 1000-2000 Daltons, typically between about 300 and 700 Daltons, and including about or less than about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described for herein polypeptides such as antibodies. For instance, in some embodiments a small molecule specifically binds to a target, for example, an immune checkpoint molecule, with a binding affinity (Kd or $EC_{50}$) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the immune checkpoint modulatory agent is an antagonist or inhibitor of one or more inhibitory immune checkpoint molecules. Exemplary inhibitory immune checkpoint molecules include Programmed Death-Ligand 1 (PD-L1), Programmed Death-Ligand 2 (PD-L2), Programmed Death 1 (PD-1), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, and T-cell immunoreceptor with Ig and ITIM domains (TIGIT).

In certain embodiments, the agent is a PD-1 (receptor) antagonist or inhibitor, the targeting of which has been shown to restore immune function in the tumor environment (see, e.g., Phillips et al., Int Immunol. 27:39-46, 2015). PD-1 is a cell surface receptor that belongs to the immunoglobulin superfamily and is expressed on T cells and pro-B cells. PD-1 interacts with two ligands, PD-L1 and PD-L2. PD-1 functions as an inhibitory immune checkpoint molecule, for example, by reducing or preventing the activation of T-cells, which in turn reduces autoimmunity and promotes self-tolerance. The inhibitory effect of PD-1 is accomplished at least in part through a dual mechanism of promoting apoptosis in antigen specific T-cells in lymph nodes while also reducing apoptosis in regulatory T cells (suppressor T cells). Some examples of PD-1 antagonists or inhibitors include an antibody or antigen-binding fragment or small molecule that specifically binds to PD-1 and reduces one or more of its immune-suppressive activities, for example, its downstream signaling or its interaction with PD-L1. Specific examples of PD-1 antagonists or inhibitors include the antibodies nivolumab, pembrolizumab, PDR001, MK-3475, AMP-224, AMP-514, and pidilizumab, and antigen-binding fragments thereof (see, e.g., U.S. Pat. Nos. 8,008,449; 8,993,731; 9,073,994; 9,084,776; 9,102,727; 9,102,728; 9,181,342; 9,217,034; 9,387,247; 9,492,539; 9,492,540; and U.S. Application Nos. 2012/0039906; 2015/0203579).

In some embodiments, the agent is a PD-L1 antagonist or inhibitor. As noted above, PD-L1 is one of the natural ligands for the PD-1 receptor. General examples of PD-L1 antagonists or inhibitors include an antibody or antigen-binding fragment or small molecule that specifically binds to PD-L1 and reduces one or more of its immune-suppressive activities, for example, its binding to the PD-1 receptor. Specific examples of PD-L1 antagonists include the antibodies atezolizumab (MPDL3280A), avelumab (MSB0010718C), and durvalumab (MED14736), and antigen-binding fragments thereof (see, e.g., U.S. Pat. Nos. 9,102,725; 9,393,301; 9,402,899; 9,439,962).

In some embodiments, the agent is a PD-L2 antagonist or inhibitor. As noted above, PD-L2 is one of the natural ligands for the PD-1 receptor. General examples of PD-L2 antagonists or inhibitors include an antibody or antigen-binding fragment or small molecule that specifically binds to PD-L2 and reduces one or more of its immune-suppressive activities, for example, its binding to the PD-1 receptor.

In some embodiments, the agent is a CTLA-4 antagonist or inhibitor. CTLA4 or CTLA-4 (cytotoxic T-lymphocyte-associated protein 4), also known as CD152 (cluster of differentiation 152), is a protein receptor that functions as an inhibitory immune checkpoint molecule, for example, by transmitting inhibitory signals to T-cells when it is bound to CD80 or CD86 on the surface of antigen-presenting cells. General examples CTLA-4 antagonists or inhibitors include an antibody or antigen-binding fragment or small molecule that specifically binds to CTLA-4. Particular examples include the antibodies ipilimumab and tremelimumab, and antigen-binding fragments thereof. At least some of the activity of ipilimumab is believed to be mediated by antibody-dependent cell-mediated cytotoxicity (ADCC) killing of suppressor Tregs that express CTLA-4.

In some embodiments, the agent is an IDO antagonist or inhibitor, or a TDO antagonist or inhibitor. IDO and TDO are tryptophan catabolic enzymes with immune-inhibitory properties. For example, IDO is known to suppress T-cells and NK cells, generate and activate Tregs and myeloid-derived suppressor cells, and promote tumor angiogenesis. General examples of IDO and TDO antagonists or inhibitors include an antibody or antigen-binding fragment or small molecule that specifically binds to IDO or TDO (see, e.g., Platten et al., Front Immunol. 5: 673, 2014) and reduces or inhibits one or more immune-suppressive activities. Specific examples of IDO antagonists or inhibitors include indoximod (NLG-8189), 1-methyl-tryptophan (1MT), β-Carboline (norharmane; 9H-pyrido[3,4-b]indole), rosmarinic acid, and epacadostat (see, e.g., Sheridan, Nature Biotechnology. 33:321-322, 2015). Specific examples of TDO antagonists or inhibitors include 680C91 and LM10 (see, e.g., Pilotte et al., PNAS USA. 109:2497-2502, 2012).

In some embodiments, the agent is a TIM-3 antagonist or inhibitor. T-cell Immunoglobulin domain and Mucin domain 3 (TIM-3) is expressed on activated human CD4+ T-cells and regulates Th1 and Th17 cytokines. TIM-3 also acts as a negative regulator of Th1/Tc1 function by triggering cell death upon interaction with its ligand, galectin-9. TIM-3 contributes to the suppressive tumor microenvironment and its overexpression is associated with poor prognosis in a variety of cancers (see, e.g., Li et al., Acta Oncol. 54:1706-13, 2015). General examples of TIM-3 antagonists or inhibitors include an antibody or antigen-binding fragment or small molecule that specifically binds to TIM-3 and reduces or inhibits one or more of its immune-suppressive activities.

In some embodiments, the agent is a LAG-3 antagonist or inhibitor. Lymphocyte Activation Gene-3 (LAG-3) is expressed on activated T-cells, natural killer cells, B-cells and plasmacytoid dendritic cells. It negatively regulates cellular proliferation, activation, and homeostasis of T-cells, in a similar fashion to CTLA-4 and PD-1 (see, e.g., Workman and Vignali. European Journal of Immun. 33: 970-9, 2003; and Workman et al., Journal of Immun. 172: 5450-5, 2004), and has been reported to play a role in Treg suppressive function (see, e.g., Huang et al., Immunity. 21: 503-13, 2004). LAG3 also maintains CD8+ T-cells in a tolerogenic state and combines with PD-1 to maintain CD8 T-cell exhaustion. General examples of LAG-3 antagonists or inhibitors include an antibody or antigen-binding fragment or small molecule that specifically binds to LAG-3 and inhibits one or more of its immune-suppressive activities. Specific examples include the antibody BMS-986016, and antigen-binding fragments thereof.

In some embodiments, the agent is a VISTA antagonist or inhibitor. V-domain Ig suppressor of T cell activation (VISTA) is primarily expressed on hematopoietic cells and is an inhibitory immune checkpoint regulator that suppresses T-cell activation, induces Foxp3 expression, and is highly expressed within the tumor microenvironment where it suppresses anti-tumor T cell responses (see, e.g., Lines et al., Cancer Res. 74:1924-32, 2014). General examples of VISTA antagonists or inhibitors include an antibody or antigen-binding fragment or small molecule that specifically binds to VISTA and reduces one or more of its immune-suppressive activities.

In some embodiments, the agent is a BTLA antagonist or inhibitor. B- and T-lymphocyte attenuator (BTLA; CD272) expression is induced during activation of T-cells, and it inhibits T-cells via interaction with tumor necrosis family receptors (TNF-R) and B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses, for example, by inhibiting the function of human CD8+ cancer-specific T-cells (see, e.g., Derre et al., J Clin Invest 120:157-67, 2009). General examples of BTLA antagonists or inhibitors include an antibody or antigen-binding fragment or small molecule that specifically binds to BTLA-4 and reduce one or more of its immune-suppressive activities.

In some embodiments, the agent is an HVEM antagonist or inhibitor, for example, an antagonist or inhibitor that specifically binds to HVEM and interferes with its interaction with BTLA or CD160. General examples of HVEM antagonists or inhibitors include an antibody or antigen-binding fragment or small molecule that specifically binds to HVEM, optionally reduces the HVEM/BTLA and/or HVEM/CD160 interaction, and thereby reduces one or more of the immune-suppressive activities of HVEM.

In some embodiments, the agent is a CD160 antagonist or inhibitor, for example, an antagonist or inhibitor that specifically binds to CD160 and interferes with its interaction with HVEM. General examples of CD160 antagonists or inhibitors include an antibody or antigen-binding fragment or small molecule that specifically binds to CD160, optionally reduces the CD160/HVEM interaction, and thereby reduces or inhibits one or more of its immune-suppressive activities.

In some embodiments, the agent is a TIGIT antagonist or inhibitor. T cell Ig and ITIM domain (TIGIT) is a co-inhibitory receptor that is found on the surface of a variety of lymphoid cells, and suppresses antitumor immunity, for example, via Tregs (Kurtulus et al., J Clin Invest. 125:4053-4062, 2015). General examples of TIGIT antagonists or inhibitors include an antibody or antigen-binding fragment or small molecule that specifically binds to TIGIT and reduce one or more of its immune-suppressive activities (see, e.g., Johnston et al., Cancer Cell. 26:923-37, 2014).

In certain embodiments, the immune checkpoint modulatory agent is an agonist of one or more stimulatory immune checkpoint molecules. Exemplary stimulatory immune checkpoint molecules include OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agent is an OX40 agonist. OX40 (CD134) promotes the expansion of effector and memory T cells, and suppresses the differentiation and activity of T-regulatory cells (see, e.g., Croft et al., Immunol Rev. 229:173-91, 2009). Its ligand is OX40L (CD252).

Since OX40 signaling influences both T-cell activation and survival, it plays a key role in the initiation of an anti-tumor immune response in the lymph node and in the maintenance of the anti-tumor immune response in the tumor microenvironment. General examples of OX40 agonists include an antibody or antigen-binding fragment or small molecule or ligand that specifically binds to OX40 and increases one or more of its immunostimulatory activities. Specific examples include OX86, OX-40L, Fc-OX40L, GSK3174998, MED10562 (a humanized OX40 agonist), MED16469 (murine OX4 agonist), and MED16383 (an OX40 agonist), and antigen-binding fragments thereof.

In some embodiments, the agent is a CD40 agonist. CD40 is expressed on antigen-presenting cells (APC) and some malignancies. Its ligand is CD40L (CD154). On APC, ligation results in upregulation of costimulatory molecules, potentially bypassing the need for T-cell assistance in an antitumor immune response. CD40 agonist therapy plays an important role in APC maturation and their migration from the tumor to the lymph nodes, resulting in elevated antigen presentation and T cell activation. Anti-CD40 agonist antibodies produce substantial responses and durable anticancer immunity in animal models, an effect mediated at least in part by cytotoxic T-cells (see, e.g., Johnson et al. Clin Cancer Res. 21: 1321-1328, 2015; and Vonderheide and Glennie, Clin Cancer Res. 19:1035-43, 2013). General examples of CD40 agonists include an antibody or antigen-binding fragment or small molecule or ligand that specifically binds to CD40 and increases one or more of its immunostimulatory activities. Specific examples include CP-870,893, dacetuzumab, Chi Lob 7/4, ADC-1013, CD40L, rhCD40L, and antigen-binding fragments thereof.

In some embodiments, the agent is a GITR agonist. Glucocorticoid-Induced TNFR family Related gene (GITR) increases T cell expansion, inhibits the suppressive activity of Tregs, and extends the survival of T-effector cells. GITR agonists have been shown to promote an anti-tumor response through loss of Treg lineage stability (see, e.g., Schaer et al., Cancer Immunol Res. 1:320-31, 2013). These diverse mechanisms show that GITR plays an important role in initiating the immune response in the lymph nodes and in maintaining the immune response in the tumor tissue. Its ligand is GITRL. General examples of GITR agonists include an antibody or antigen-binding fragment or small molecule or ligand that specifically binds to GITR and increases one or more of its immunostimulatory activities. Specific examples include GITRL, INCAGN01876, DTA-1, MED11873, and antigen-binding fragments thereof.

In some embodiments, the agent is a CD137 agonist. CD137 (4-1BB) is a member of the tumor necrosis factor (TNF) receptor family, and crosslinking of CD137 enhances T-cell proliferation, IL-2 secretion, survival, and cytolytic activity. CD137-mediated signaling also protects T-cells such as CD8+ T-cells from activation-induced cell death. General examples of CD137 agonists include an antibody or antigen-binding fragment or small molecule or ligand that specifically binds to CD137 and increases one or more of its immunostimulatory activities. Specific examples include the CD137 (or 4-1BB) ligand (see, e.g., Shao and Schwarz, J Leukoc Biol. 89:21-9, 2011) and the antibody utomilumab, including antigen-binding fragments thereof.

In some embodiments, the agent is a CD27 agonist. Stimulation of CD27 increases antigen-specific expansion of naïve T cells and contributes to T-cell memory and long-term maintenance of T-cell immunity. Its ligand is CD70. The targeting of human CD27 with an agonist antibody stimulates T-cell activation and antitumor immunity (see, e.g., Thomas et al., Oncoimmunology. 2014; 3:e27255. doi:10.4161/onci.27255; and He et al., J Immunol. 191: 4174-83, 2013). General examples of CD27 agonists include an antibody or antigen-binding fragment or small molecule or ligand that specifically binds to CD27 and increases one or more of its immunostimulatory activities. Specific examples include CD70 and the antibodies varlilumab and CDX-1127 (1F5), including antigen-binding fragments thereof.

In some embodiments, the agent is a CD28 agonist. CD28 is constitutively expressed CD4+ T cells some CD8+ T cells. Its ligands include CD80 and CD86, and its stimulation increases T-cell expansion. General examples of CD28 agonists include an antibody or antigen-binding fragment or small molecule or ligand that specifically binds to CD28 and increases one or more of its immunostimulatory activities. Specific examples include CD80, CD86, the antibody TAB08, and antigen-binding fragments thereof.

In some embodiments, the agent is CD226 agonist. CD226 is a stimulating receptor that shares ligands with TIGIT, and opposite to TIGIT, engagement of CD226 enhances T-cell activation (see, e.g., Kurtulus et al., J Clin Invest. 125:4053-4062, 2015; Bottino et al., J Exp Med. 1984:557-567, 2003; and Tahara-Hanaoka et al., Int Immunol. 16:533-538, 2004). General examples of CD226 agonists include an antibody or antigen-binding fragment or small molecule or ligand (e.g., CD112, CD155) that specifically binds to CD226 and increases one or more of its immunostimulatory activities.

In some embodiments, the agent is an HVEM agonist. Herpesvirus entry mediator (HVEM), also known as tumor necrosis factor receptor superfamily member 14 (TNFRSF14), is a human cell surface receptor of the TNF-receptor superfamily. HVEM is found on a variety of cells including T-cells, APCs, and other immune cells. Unlike other receptors, HVEM is expressed at high levels on resting T-cells and down-regulated upon activation. It has been shown that HVEM signaling plays a crucial role in the early phases of T-cell activation and during the expansion of tumor-specific lymphocyte populations in the lymph nodes. General examples of HVEM agonists include an antibody or antigen-binding fragment or small molecule or ligand that specifically binds to HVEM and increases one or more of its immunostimulatory activities.

In certain embodiments, the cancer immunotherapy agent is a cancer vaccine. Exemplary cancer vaccines include Oncophage, human papillomavirus HPV vaccines such Gardasil or Cervarix, hepatitis B vaccines such as Engerix-B, Recombivax HB, or Twinrix, and sipuleucel-T (Provenge). In some embodiments, the cancer vaccine comprises or utilizes one or more cancer antigens, or cancer-associate d antigens. Exemplary cancer antigens include, without limitation, human Her2/neu, HerVEGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, VEGR-3, NRP2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v\beta 3$, integrin $\alpha 5\beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PSMA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In certain embodiments, the cancer immunotherapy agent is an oncolytic virus. An oncolytic virus is a virus that preferentially infects and kills cancer cells. Included are naturally-occurring and man-made or engineered oncolytic viruses. Most oncolytic viruses are engineered for tumor selectivity, although there are naturally-occurring examples such as Reovirus and the SVV-001 Seneca Valley virus. General examples of oncolytic viruses include VSV, Poliovirus, Reovirus, Senecavirus, and RIGVIR, and engineered versions thereof. Non-limiting examples of oncolytic viruses include herpes simplex virus (HSV) and engineered version thereof, talimogene laherparepvec (T-VEC), coxsackievirus A21 (CAVATAK™), Oncorine (H101), pelareorep (REOLYSIN®), Seneca Valley virus (NTX-010), Senecavirus SVV-001, ColoAd1, SEPREHVIR (HSV-1716), CGTG-102 (Ad5/3-D24-GMCSF), GL-ONC1, MV-NIS, and DNX-2401, among others.

In certain embodiments, the cancer immunotherapy agent is a cytokine. Exemplary cytokines include interferon (IFN)-a, IL-2, IL-12, IL-7, IL-21, and Granulocyte-macrophage colony-stimulating factor (GM-CSF).

In certain embodiments, the cancer immunotherapy agent is cell-based immunotherapy, for example, a T-cell based adoptive immunotherapy. In some embodiments, the cell-based immunotherapy comprises cancer antigen-specific T-cells, optionally ex vivo-derived T-cells. In some embodiments, the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells. In specific embodiments, the CAR-modified T-cell is targeted against CD-19 (see, e.g., Maude et al., Blood. 125: 4017-4023, 2015).

In certain instances, the cancer to be treated associates with the cancer antigen, that is, the cancer antigen-specific T-cells are targeted against or enriched for at least one antigen that is known to associate with the cancer to be treated. In some embodiments, the cancer antigen is selected from one or more of CD19, human Her2/neu, HerVEGF receptor (EGFR), Her3, A33 antigen, B7H3, CD5, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-E50-1, p53, survivin, integrin αvβ3, integrin α5β1, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

Additional exemplary cancer antigens include 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R1 7I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B1 6, MAGE-B1 7, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MCI R, M-CSF, ME1/m, mesothelin, MG50/PXDN, MMP1 1, MN/CA IX-antigen, MRP-3, MUC-1, MUC-2, MUM-1/m, MUM-2/m, MUM-3/m, myosin class l/m, NA88-A, N-acetylglucosaminyltransferase-V, Neo-PAP, Neo-PAP/m, NFYC/m, NGEP, NMP22, NPM/ALK, N-Ras/m, NSE, NY-ESO-B, NY-ESO-1, OA1, OFA-iLRP, OGT, OGT/m, OS-9, OS-9/m, osteocalcin, osteopontin, pi 5, p190 minor bcr-abl, p53, p53/m, PAGE-4, PAI-1, PAI-2, PAP, PART-1, PATE, PDEF, Pim-1 Kinase, Pin-1, PmI/PARalpha, POTE, PRAME, PRDX5/m, prostein, proteinase-3, PSA, PSCA, PSGR, PSM, PSMA, PTPRK/m, RAGE-1, RBAF600/m, RHAMM/CD1 68, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AM L1, TGF-beta, TGFbeta RII, TGM-4, TPI/m, TRAG-3, TRG, TRP-1, TRP-2/6b, TRP/INT2, TRP-p8, tyrosinase, UPA, VEGFR1, VEGFR-2/FLK-1, and WT1. Certain preferred antigens include p53, CA125, EGFR, Her2/neu, hTERT, PAP, MAGE-A1, MAGE-A3, Mesothelin, MUC-1, GP100, MART-1, Tyrosinase, PSA, PSCA, PSMA, STEAP-1, Ras, CEA and WT1, and more preferably PAP, MAGE-A3, WT1, and MUC-1.

In some embodiments the antigen is selected from MAGE-A1 (e.g., MAGE-A1 according to accession number M77481), MAGE-A2, MAGE-A3, MAGE-A6 (e.g., MAGE-A6 according to accession number NM_005363), MAGE-C1, MAGE-C2, melan-A (e.g., melan-A according to accession number NM_00551 1), GP100 (e.g., GP100 according to accession number M77348), tyrosinase (e.g., tyrosinase according to accession number NM_000372), survivin (e.g., survivin according to accession number AF077350), CEA (e.g., CEA according to accession number NM_004363), Her-2/neu (e.g., Her-2/neu according to accession number M1 1 730), WT1 (e.g., WT1 according to accession number NM_000378), PRAME (e.g., PRAME according to accession number NM_0061 15), EGFRI (epidermal growth factor receptor 1) (e.g., EGFRI (epidermal growth factor receptor 1) according to accession number AF288738), MUC1, mucin-1 (e.g., mucin-1 according to accession number NM_002456), SEC61 G (e.g., SEC61 G according to accession number NM_014302), hTERT (e.g., hTERT accession number NM_198253), 5T4 (e.g., 5T4 according to accession number NM_006670), TRP-2 (e.g., TRP-2 according to accession number NM_001 922), STEAP1 (Six-transmembrane epithelial antigen of prostate 1), PSCA, PSA, PSMA, etc.

In some embodiments, the cancer antigen is selected from PCA, PSA, PSMA, STEAP, and optionally MUC-1, including fragments, variants, and derivatives thereof. In some embodiments, the cancer antigen selected from NY-ESO-1, MAGE-C1, MAGE-C2, survivin, 5T4, and optionally MUC-1, including fragments, variants, and derivatives thereof.

In some instances, cancer antigens encompass idiotypic antigens associated with a cancer or tumor disease, particularly lymphoma or a lymphoma associated disease, for example, wherein the idiotypic antigen is an immunoglobulin idiotype of a lymphoid blood cell or a T cell receptor idiotype of a lymphoid blood cell.

In some instances, the cancer antigen-specific T-cells are selected from one or more of chimeric antigen receptor (CAR)-modified T-cells (e.g., targeted against a cancer antigen), and T-cell Receptor (TCR)-modified T-cells, tumor infiltrating lymphocytes (TILs), and peptide-induced T-cells.

The skilled artisan will appreciate that the various cancer immunotherapy agents described herein can be combined with any one or more of the various anti-NRP2 antibodies (including antigen-binding fragments thereof) described herein, and used according to any one or more of the methods or compositions described herein.

Chemotherapeutic Agents. Certain embodiments employ one or more chemotherapeutic agents, for example, small molecule chemotherapeutic agents. Non-limiting examples of chemotherapeutic agents include alkylating agents, antimetabolites, cytotoxic antibiotics, topoisomerase inhibitors (type 1 or type II), an anti-microtubule agents, among others.

Examples of alkylating agents include nitrogen mustards (e.g., mechlorethamine, cyclophosphamide, mustine, melphalan, chlorambucil, ifosfamide, and busulfan), nitrosoureas (e.g., N-Nitroso-N-methylurea (MNU), carmustine (BCNU), lomustine (CCNU), semustine (MeCCNU), fotemustine, and streptozotocin), tetrazines (e.g., dacarbazine, mitozolomide, and temozolomide), aziridines (e.g., thiotepa, mytomycin, and diaziquone (AZQ)), cisplatins and derivatives thereof (e.g., carboplatin and oxaliplatin), and non-classical alkylating agents (optionally procarbazine and hexamethylmelamine).

Examples of anti-metabolites include anti-folates (e.g., methotrexate and pemetrexed), fluoropyrimidines (e.g., 5-fluorouracil and capecitabine), deoxynucleoside analogues (e.g., ancitabine, enocitabine, cytarabine, gemcitabine, decitabine, azacitidine, fludarabine, nelarabine, cladribine, clofarabine, fludarabine, and pentostatin), and thiopurines (e.g., thioguanine and mercaptopurine);

Examples of cytotoxic antibiotics include anthracyclines (e.g., doxorubicin, daunorubicin, epirubicin, idarubicin, pirarubicin, aclarubicin, and mitoxantrone), bleomycins, mitomycin C, mitoxantrone, and actinomycin. Examples of topoisomerase inhibitors include camptothecin, irinotecan, topotecan, etoposide, doxorubicin, mitoxantrone, teniposide, novobiocin, merbarone, and aclarubicin.

Examples of anti-microtubule agents include taxanes (e.g., paclitaxel and docetaxel) and *vinca* alkaloids (e.g., vinblastine, vincristine, vindesine, vinorelbine).

The skilled artisan will appreciate that the various chemotherapeutic agents described herein can be combined with any one or more of the various anti-NRP2 antibodies (including antigen-binding fragments thereof) described herein, and used according to any one or more of the methods or compositions described herein.

Hormonal Therapeutic Agents. Certain embodiments employ at least one hormonal therapeutic agent. General examples of hormonal therapeutic agents include hormonal agonists and hormonal antagonists. Particular examples of hormonal agonists include progestogen (progestin), corticosteroids (e.g., prednisolone, methylprednisolone, dexamethasone), insulin like growth factors, VEGF derived angiogenic and lymphangiogenic factors (e.g., VEGF-A, VEGF-A145, VEGF-A165, VEGF-C, VEGF-D, PIGF-2), fibroblast growth factor (FGF), galectin, hepatocyte growth factor (HGF), platelet derived growth factor (PDGF), transforming growth factor (TGF)-beta, androgens, estrogens, and somatostatin analogs. Examples of hormonal antagonists include hormone synthesis inhibitors such as aromatase inhibitors and gonadotropin-releasing hormone (GnRH)s agonists (e.g., leuprolide, goserelin, triptorelin, histrelin) including analogs thereof. Also included are hormone receptor antagonist such as selective estrogen receptor modulators (SERMs; e.g., tamoxifen, raloxifene, toremifene) and anti-androgens (e.g., flutamide, bicalutamide, nilutamide).

Also included are hormonal pathway inhibitors such as antibodies directed against hormonal receptors. Examples include inhibitors of the the IGF receptor (e.g., IGF-IR1) such as cixutumumab, dalotuzumab, figitumumab, ganitumab, istiratumab, and robatumumab; inhibitors of the vascular endothelial growth factor receptors 1, 2 or 3 (VEGFR1, VEGFR2 or VEGFR3) such as alacizumab pegol, bevacizumab, icrucumab, ramucirumab; inhibitors of the TGF-beta receptors R1, R2, and R3 such as fresolimumab and metelimumab; inhibitors of c-Met such as naxitamab; inhibitors of the EGF receptor such as cetuximab, depatuxizumab mafodotin, futuximab, imgatuzumab, laprituximab emtansine, matuzumab, modotuximab, necitumumab, nimotuzumab, panitumumab, tomuzotuximab, and zalutumumab; inhibitors of the FGF receptor such as aprutumab ixadotin and bemarituzumab; and inhibitors of the PDGF receptor such as olaratumab and tovetumab.

The skilled artisan will appreciate that the various hormonal therapeutic agents described herein can be combined with any one or more of the various anti-NRP2 antibodies (including antigen-binding fragments thereof) described herein, and used according to any one or more of the methods or compositions described herein.

Kinase Inhibitors. Certain embodiments employ at least one kinase inhibitor, including tyrosine kinase inhibitors. Examples of kinase inhibitors include, without limitation, adavosertib, afanitib, aflibercept, axitinib, bevacizumab, bosutinib, cabozantinib, cetuximab, cobimetinib, crizotinib, dasatinib, entrectinib, erdafitinib, erlotinib, fostamitinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, SU6656, tofacitinib, trastuzumab, vandetanib, and vemuafenib.

The skilled artisan will appreciate that the various kinase inhibitors described herein can be combined with any one or more of the various anti-NRP2 antibodies (including antigen-binding fragments thereof) described herein, and used according to any one or more of the methods or compositions described herein.

Methods of Use and Therapeutic Compositions

Embodiments of the present disclosure relate to the discovery that human histidyl-tRNA synthetase (HRS) polypeptides have unexpected biological properties which are relevant to treating a broad range of diseases and conditions, and that certain of these properties relate to the interactions between HRS and human neuropilin 2 (NRP2). Accordingly, antibodies directed against human NRP2, which interfere with the binding between NRP2 and NRP2 ligands, including, for example, human HRS, can be used as standalone therapies in the treatment of diseases, including NRP2-associated diseases, or in combination with other therapeutic agents as described herein.

Certain embodiments therefore include methods of treating, ameliorating the symptoms of, and/or reducing the progression of, a disease or condition in a subject in need thereof, comprising administering to the subject at least one antibody or antigen-binding fragment thereof that specifically binds to a human neuropilin-2 (NRP2) polypeptide. In some instances, the at least one antibody or antigen-binding fragment thereof antagonizes the binding/signaling activity between the NRP2 polypeptide and the at least one NRP2 ligand. In some instances, the at least one antibody or antigen-binding fragment thereof mimics or otherwise enhances one or more signaling activities of the NRP2/NRP2 ligand interaction, for example, by acting as an agonist antibody.

In some instances, the at least one antibody or antigen-binding fragment thereof interferes with binding of the human NRP2 polypeptide to a human HRS polypeptide. In some instances, the at least one antibody or antigen-binding fragment thereof mimics one or more signaling activities of the HRS polypeptide binding to the NRP2 polypeptide, for example, by acting as an agonist antibody. Exemplary anti-NRP2 antibodies and therapeutic compositions comprising the same are described elsewhere herein.

In certain embodiments, the disease is or condition is an NRP2-associated disease or condition. In some embodiments, the NRP2-associated disease or condition is selected from one or more of cancer and diseases and pathways associated with cancer, including cancer cell growth, initiation, migration, adhesion, invasion, and/or metastasis; diseases associated with inflammation, autoimmunity, and related inflammatory diseases, including diseases associated with inappropriate immune cell activation or migration such as Graft versus host disease (GVHD); diseases associated with lymphatic development, lymphangiogenesis, and lymphatic damage, including, for example, edema, lymphedema, secondary lymphedema, inappropriate fat absorption and deposition, excess fat deposition, and vascular permeability; diseases associated with infections, including latent infections; diseases associated with allergic disorders/diseases, allergic responses, including, for example, chronic obstructive pulmonary disorder (COPD), neutrophilic asthma, antineutrophil cytoplasmic antibody (ANCA)-associated systemic vasculitis, systemic lupus erythematosus, rheumatoid arthritis, inflammasome-related diseases, and skin-related neutrophil-mediated diseases such as pyoderma gangrenosum; diseases associated with granulomatous inflammatory diseases, including sarcoidosis and granulomas; diseases associated with fibrosis including fibrotic diseases, fibrosis, endothelial to mesenchymal transition (EMT), and wound healing; diseases associated with inappropriate smooth muscle contractility, and inappropriate vascular smooth muscle cell migration and adhesion; diseases associated with inappropriate autophagy, phagocytosis, and efferocytosis; diseases associated with neuronal diseases, peripheral nervous system remodeling, and pain perception; and diseases associated with bone development and bone remodeling.

In some embodiments, the disease is a cancer. Here, upregulation of NRP2 expression is associated with tumorigenesis and in particular tumor metastasis, and is correlated with more aggressive disease in several tumor types. Moreover, the semaphorin/plexin/neuropilin signaling axis influences many of the hallmarks of cancer (see, for example, Franzolin and Tamagnone Int. J. Mol. Sci. 20, 377; doi: 10.3390/ijms20020377, 2019); Nasarre et al., OncoTargets and Therapy 2014:7 1663-1687; Neufeld et al., Cold Spring Harb Perspect Med. 2:a006718, 2012). Consistent with these studies, increased expression of NRP2 in prostate cancer cells is induced by Phosphatase and tensin homolog (PTEN deletion), and its expression correlates with Gleason grade (see, for example, Zhao et al., Thoracic Cancer 8: 203-213, 2017). Additionally, P53 mutations upregulate NRP2 expression via suppression of DLX2 transcription leading to increased cell mobility. About 50% of human tumors and cancers contain a mutation in the p53 gene, with the vast majority of these mutations occurring in the DNA binding domain, and such is linked to poorer prognosis (see, for example, Drabkin et al., Oncotarget. 8 (No 57) 96464-96465, 2017). Additionally, TGF-β signaling is involved in the expression of NRP2B, and up-regulation of EMT in cancer, which may explain why in advanced tumors, higher production of TGF-β is positively associated with tumor aggressiveness and poor prognosis (see, for example, Malfettone et al., Cancer Lett. 392:39-50, 2017).

Certain embodiments thus include methods of treating ameliorating the symptoms of, or inhibiting the progression of, a cancer in a subject in need thereof, comprising administering to the subject at least one antibody or antigen-binding fragment thereof that specifically binds to a human NRP2 polypeptide (an anti-NRP2 antibody), and which modulates (e.g., interferes with) binding of the human NRP2 polypeptide to a NRP2 ligand (for example, an NRP2 ligand from Table N2 or Table N3 and/or a human HRS polypeptide from Table H1). Certain embodiments include reducing or preventing the re-emergence of a cancer in a subject in need thereof, for example, a metastatic cancer, wherein administration of the therapeutic composition enables generation of an immune memory to the cancer. In some embodiments, the subject has or is at risk for developing diabetes, for example, type 1 diabetes or type 2 diabetes.

In some embodiments, the subject has, and/or is selected for treatment based on having, a disease associated with increased levels or expression of at least one NRP2 ligand (for example, an NRP2 ligand from Table N2 or Table N3 and/or an HRS polypeptide from Table H1) and/or a coding mRNA thereof relative to a healthy control. For instance, in some embodiments, the levels of the at least one NRP2 ligand in the diseases subject, cells, or tissue are about or at least about 1.5, 2, 3, 4, 5, 6, 7, 8, 9, 10, 15, 20, 30, 40, 50, 60, 70, 80, 90, 100, 1000 or more times the levels of the at least one NRP2 ligand in a healthy control. In some embodiments, the subject has, and/or is selected for treatment based on having, a cancer which has increased levels or expression of at least one NRP2 ligand (for example, an NRP2 ligand from Table N2 or Table N3 and/or an HRS polypeptide from Table H1) and/or a coding mRNA thereof relative to a non-cancerous control cell or tissue. For instance, in some embodiments, the levels of the at least one NRP2 ligand in the cancer cells or tissue are about or at least about 1.5, 2, 3, 4, 5, 6, 7, 8, 9, 10, 15, 20, 30, 40, 50, 60, 70, 80, 90, 100, 1000 or more times the levels of the NRP2 ligand in a non-cancerous control or standard. Thus, certain embodiments include methods of selecting a subject for treatment, comprising (i) detecting increased expression levels of at least one NRP2 ligand (for example, an NRP2 ligand from Table N2 or Table N3 and/or an HRS polypeptide from Table H1) and/or coding mRNA in the subject relative to a control or reference, and (ii) administering to the subject a therapeutic composition comprising at least one anti-NRP2-antibody, as described herein. In particular embodiments, the HRS polypeptide is a splice variant of full-length HRS. In some embodiments, the HRS splice variant is selected from one or more of HisRS$^{N1}$, HisRS$^{N2}$, HisRS$^{N3}$, HisRS$^{N4}$, HisRS$^{N5}$, HisRS$^{C1}$, HisRS$^{C2}$, HisRS$^{C3}$, HisRS$^{C5}$, HisRS$^{C6}$, HisRS$^{C7}$, HisRS$^{C8}$, and HisRS$^{C9}$.

In some embodiments, the subject has, and/or is selected for treatment based on having, increased circulating or serum levels of a soluble neuropilin 2 (NRP2) polypeptide (selected, for example, from Table N1), either bound to an HRS polypeptide or free, relative to the levels of a healthy or matched control population of subject(s). For instance, in certain embodiments, the circulating or serum levels are about or at least about 10, 20, 30, 50, 100, 200, 300, 400, 500, 600, 700, 800, 900, 1000, 1100, 1200, 1300, 1400, 1500, 1600, 1700, 1800, 1900, 2000, 3000, 4000, 5000 pM of the soluble NRP2 polypeptide, or the circulating or serum levels are about 30-50, 50-100, 100-2000, 200-2000, 300-2000, 400-2000, 500-2000, 600-2000, 700-2000, 800-2000, 900-2000, 1000-2000, 2000-3000, 3000-4000, 4000-5000 pM of the soluble NRP2 polypeptide.

In certain embodiments, the subject has, and/or is selected for treatment based on having, a disease associated with increased levels or expression of an NRP2 polypeptide (optionally selected from Table N1) and/or a coding mRNA thereof relative to a healthy control (e.g., an NRP2-associated disease). For example, in certain embodiments, the levels of the NRP2 polypeptide in the diseased subject, cells, or tissue are about or at least about 1.5, 2, 3, 4, 5, 6, 7, 8, 9, 10, 15, 20, 30, 40, 50, 60, 70, 80, 90, 100 or more times the levels of NRP2 polypeptide in a healthy control. In some embodiments, the subject has, and/or is selected for treatment based on having, a cancer which has increased levels or expression of a NRP2 polypeptide (selected, for example, from Table N1) and/or a coding mRNA thereof relative to a control cell or tissue, optionally relative to a non-cancerous cell or tissue of the same type as the cancer. For instance, in some embodiments, the levels of the NRP2 polypeptide in the cancer cells or tissue are about or at least about 1.5, 2, 3, 4, 5, 6, 7, 8, 9, 10, 15, 20, 30, 40, 50, 60, 70, 80, 90, 100 or more times the levels of NRP2 polypeptide in a non-cancerous control or standard. Some embodiments thus include methods of selecting a subject for treatment, comprising (i) detecting increased expression levels of a NRP2 polypeptide and/or a coding mRNA thereof in the subject relative to a control or reference, and (ii) administering to the subject a therapeutic composition comprising at least one anti-NRP2-antibody, as described herein.

In some embodiments, the subject has, and/or is selected for treatment based on having, a disease associated with increased levels or expression of NRP2A and/or NRP2B, or an altered ratio of NRP2A:NRP2B expression, relative to a healthy control or matched control standard or population of subject(s). In some embodiments, the subject has significantly higher expression or levels of NRP2B relative to a healthy control or matched control standard or population of subject(s). In some embodiments, the levels of NRP2B are increased by about or at least about 10%, 20%, 30%, 40%, 50%, 100%, 200%, 300%, 400%, 500%, 600%, 700%, 800%, 900%, 1000% compared to a healthy control or matched control standard or population of subject(s). In some embodiments, the subject has, and/or is selected for treatment based on having, increased circulating levels of HRS:NRP2 complexes relative to a healthy or matched control standard or population of subject(s). Certain embodiments therefore include methods of selecting a subject for cancer treatment, comprising (i) detecting increased expression levels of HRS:NRP2 complexes in the subject relative to a control or reference, and (ii) administering to the subject a therapeutic composition comprising at least one anti-NRP2-antibody, as described herein.

In some embodiments, the healthy control or matched control standard or population of subject(s) comprises average ranges for age-matched samples of cancerous or non-cancerous cells or tissue of the same type as the cancer, which comprise specific characteristics such as drug resistance, metastatic potential, aggressiveness, genetic signature (e.g., p53 mutations, PTEN deletion, IGFR expression), and/or expression patterns.

Some embodiments comprise administering at least one anti-NRP2 antibody to a subject in an amount and at a frequency sufficient to achieve an average, sustained blood plasma concentration of soluble NRP2 of about or less than about 500 pM, 400 pM, 300 pM, 200 pM, 100 pM, 50 pm, 40 pM, 30 pM, 20 pM, or 10 pM.

Certain embodiments comprise administering at least one anti-NRP2 antibody in an amount and at a frequency sufficient to achieve a reduction in the circulating levels of HRS:NRP2 complexes, for example, a reduction of about or at least about 5, 10, 15, 20, 25, 30, 35, 40, 45, 50, 60, 70, 80, 90, 95, 99, or 100%.

For the treatment of cancer, in some instances, an anti-NRP2 antibody enhances the immune response to the cancer by about, or at least about, 5, 10, 15, 20, 25, 30, 35, 40, 45, 50, 60, 70, 80, 90, 100, 200, 300, 400, 500, 600, 700, 800, 900, 1000, 2000% or more, relative to an untreated control. Exemplary immune responses include increasing or enhancing immune cell invasion of a solid tumor, and increasing the biological activity against the cancer. In certain embodiments, an anti-NRP2 antibody enhances an adaptive immune response to the cancer, and in some embodiments, an anti-NRP2 antibody enhances an innate immune response to the cancer. In some-instances, an anti-NRP2 antibody directly or indirectly enhances a T-cell-mediated response to the cancer. In some-instances, an anti-NRP2 antibody enhances a B-cell-mediated or antibody-mediated response to the cancer. In some-instances, an anti-NRP2 antibody modulates a macrophage responses to the cancer. In some-instances, an anti-NRP2 antibody modulates immune cell, or cancer autophagy. In some-instances, an anti-NRP2 antibody modulates immune cell phagocytosis. In some-instances, an anti-NRP2 antibody modulates cancer cell apoptosis. In some-instances, an anti-NRP2 antibody modulates immune cell efferocytosis and/or cancer cell autophagy.

In some embodiments, an anti-NRP2 antibody enhances macrophage responses to the cancer. In some embodiments, an anti-NRP2 inhibits macrophage responses to the cancer.

In some embodiments of the anti-NRP2 antibody, the antibody enhances autophagy. In some embodiments, an anti-NRP2 inhibits autophagy. In some embodiments, an anti-NRP2 enhances phagocytosis. In some embodiments, an anti-NRP2 inhibits phagocytosis. In some embodiments, an anti-NRP2 enhances apoptosis. In some embodiments of the anti-NRP2 antibody, the antibody inhibits apoptosis. In some embodiments, an anti-NRP2 antibody enhances efferocytosis. In some embodiments, an anti-NRP2 inhibits efferocytosis.

In some-instances, an anti-NRP2 antibody reduces cancer initiation, cancer cell migration, adhesion, or cancer cell metastasis by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some-instances, an anti-NRP2 antibody reduces cancer mediated lymphoangiogenesis by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody reduces the rate of in vitro growth of the cancer (for example, cancer cells isolated from a biopsy or other sample grown in vitro) by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody reduces the adhesiveness of the cancer (for example, cancer cells isolated from a biopsy or other sample grown in vitro) to a substrate by about or at least about, 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the substrate comprises laminin.

In some embodiments, the at least one anti-NRP2 antibody reduces the invasiveness of the cancer (for example, cancer cells isolated from a biopsy or other sample grown in vitro) by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody inhibits the rate of migration or motility of the cancer or a migratory cell (for example, cancer or immune cells isolated from a biopsy or other sample grown in vitro) by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody inhibits the rate of autophagy or endosome maturation (for example, endosome acidification) of the cancer or associated immune cells by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In some embodiments, the at least one anti-NRP2 antibody enhances the susceptibility of the cancer to an additional agent (for example, chemotherapeutic agent, hormonal therapeutic agent, and or kinase inhibitor) by about or at least about 5, 10, 15, 20, 25, 30, 35, 40, 45, 50, 60, 70, 80, 90, 100, 200, 300, 400, 500, 600, 700, 800, 900, 1000, 2000% or more relative to the additional agent alone. In some embodiments, the at least one anti-NRP2 antibody enhances an anti-tumor and/or immunostimulatory activity of a cancer immunotherapy agent by about or at least about 5, 10, 15, 20, 25, 30, 35, 40, 45, 50, 60, 70, 80, 90, 100, 200, 300, 400, 500, 600, 700, 800, 900, 1000, 2000% or more, relative to the cancer immunotherapy agent alone.

Some embodiments include administering the at least one anti-NRP2 antibody in an amount and at a frequency sufficient to achieve a steady state concentration, or average circulating concentration, of the at least one anti-NRP2 antibody of between about 1 nM and about 1 µM, between about 1 nM and about 100 nM, between about 1 nM and about 10 nM, or between about 1 nM and about 3 µM.

Also include are combination therapies for treating cancers, including methods of treating ameliorating the symptoms of, or inhibiting the progression of, a cancer in a subject in need thereof, comprising administering to the subject at least one antibody or antigen-binding fragment thereof that specifically binds to a human NRP2 polypeptide (an anti-NRP2 antibody) in combination with at least one additional agent, for example, a cancer immunotherapy agent, a chemotherapeutic agent, a hormonal therapeutic agent, and/or a kinase inhibitor. Exemplary cancer immunotherapy agents, chemotherapeutic agents, hormonal therapeutic agents, and kinase inhibitors are described elsewhere herein.

In some instances, an anti-NRP2 antibody and the at least one additional agent are administered separately, for example, in separate therapeutic compositions and at the same or different times. In some embodiments, an anti-NRP2 antibody and the at least one additional agent are administered as part of the same therapeutic composition, at the same time.

Particular methods employ one or more anti-NRP2 antibodies, or antigen-binding fragments thereof, as part of (i.e., in addition to) a combination therapy regimen. Exemplary combination regiments are provided in Table M1 below.

TABLE M1

Combination Therapy Regimens

| Cancer Type | Agents | Acronym |
|---|---|---|
| Breast Cancer | Cyclophosphamide, methotrexate, 5-fluorouracil, vinorelbine | CMF |
| | Doxorubicin, cyclophosphamide | AC |
| Hodgkin's lymphoma | Docetaxel, doxorubicin, cyclophosphamide | TAC |
| | Doxorubicin, bleomycin, vinblastine, dacarbazine | ABVD |
| | Mustine, vincristine, procarbazine, prednisolone | MOPP |
| Non-Hodgkin's lymphoma | Cyclophosphamide, doxorubicin, vincristine, prednisolone | CHOP |
| Germ cell tumor | Bleomycin, etoposide, cisplatin | BEP |
| Stomach cancer | Epirubicin, cisplatin, 5-fluorouracil | ECF |
| | Epirubicin, cisplatin, capecitabine | ECX |
| Bladder cancer | Methotrexate, vincristine, doxorubicin, cisplatin | MVAC |
| Lung cancer | Cyclophosphamide, doxorubicin, vincristine, vinorelbine | CAV |
| Colorectal cancer | 5-fluorouracil, folinic acid, oxaliplatin | FOLFOX |
| Pancreatic Cancer | Leucovorin, fluorouracil, irinotecan (Camptosar), oxaliplatin | FOLFIRINOX |
| | Gemcitabine, nabpaclitaxel | ABRAXANE |

In some embodiments, the methods and therapeutic compositions described herein (for example, anti-NRP2 antibody, alone or in combination with at least one additional agent) increase median survival time of a subject by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods and therapeutic compositions described herein (for example, anti-NRP2 antibody, alone or in combination with at least one additional agent) increase median survival time of a subject by 1 year, 2 years, 3 years, or longer. In some embodiments, the methods and therapeutic compositions described herein (for example, anti-NRP2 antibody, alone or in combination with cancer immunotherapy agent) increase progression-free survival by 2 weeks, 3 weeks, 4 weeks, 5 weeks, 6 weeks, 7 weeks, 8 weeks, 9 weeks, 10 weeks or longer. In certain embodiments, the methods or therapeutic compositions described herein increase progression-free survival by 1 year, 2 years, 3 years, or longer.

In certain embodiments, the methods and therapeutic compositions described herein (for example, anti-NRP2 antibody, alone or in combination with at least one additional agent) are sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the methods and therapeutic compositions described herein (for example, anti-NRP2 antibody, alone or in combination with at least one additional agent) are sufficient to result in stable disease. In certain embodiments, the methods and therapeutic compositions described herein (for example, anti-NRP2 antibody, alone or in combination with cancer immunotherapy agent) are sufficient to result in clinically relevant reduction in symptoms of a particular disease indication known to the skilled clinician.

In some embodiments, an anti-NRP2 antibody increases, complements, or otherwise enhances the anti-tumor and/or immunostimulatory activity of the cancer immunotherapy agent, relative to the cancer immunotherapy agent alone. In some embodiments, an anti-NRP2 antibody enhances the anti-tumor and/or immunostimulatory activity of the cancer immunotherapy agent by about, or at least about, 5, 10, 15, 20, 25, 30, 35, 40, 45, 50, 60, 70, 80, 90, 100, 200, 300, 400, 500, 600, 700, 800, 900, 1000, 2000% or more, relative to the cancer immunotherapy agent alone.

The methods and therapeutic compositions described herein can be used in the treatment of any variety of cancers or tumors. In some embodiments, the cancer is a primary cancer, i.e., a cancer growing at the anatomical site where tumor progression began and yielded a cancerous mass. In some embodiments, the cancer is a secondary or metastatic cancer, i.e., a cancer which has spread from the primary site or tissue of origin into one or more different sites or tissues. In some embodiments, the cancer expresses or overexpresses NRP2. In some embodiments, the subject or patient has a cancer selected from one or more of melanoma (e.g., metastatic melanoma), an epithelial or epithelial-derived tumor, pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma or HCC), sarcoma, B-cell malignancy, breast cancer (for example, estrogen receptor positive (ER+), estrogen receptor negative (ER−), Her2 positive (Her2+), Her2 negative (Her2−), or a combination thereof, e.g., ER+/Her2+, ER+/Her2−, ER−/Her2+, or ER−/Her2−; or "triple negative" breast cancer which is estrogen receptor-negative, progesterone receptor-negative, and HER2-negative), ovarian cancer, colorectal cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, stomach cancer, virus-induced tumors such as, for example, papilloma virus-induced carcinomas (e.g., cervical carcinoma, cervical cancer), adenocarcinomas, herpes virus-induced tumors (e.g., Burkitt's lymphoma, EBV-induced B-cell lymphoma), hepatitis B-induced tumors (hepatocellular carcinomas), HTLV-1-indued and HTLV-2-induced lymphomas, acoustic neuroma, lung cancers (e.g., lung carcinoma, bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal cancer (e.g., oesophageal carcinoma), wart involvement, tumors of the small intestine, craniopharyngeomas, ovarian carcinoma, genital tumors, ovarian cancer (e.g., ovarian carcinoma), pancreatic cancer (e.g., pancreatic carcinoma), endometrial carcinoma, liver metastases, penile cancer, tongue cancer, gall bladder cancer, leukaemia, plasmocytoma, and lid tumor.

In some embodiments, as noted above, the cancer or tumor is a metastatic cancer, for example, a metastatic cancer that expresses NRP2 and/or NRP2B. Further to the above cancers, exemplary metastatic cancers include, without limitation, bladder cancers which have metastasized to the bone, liver, and/or lungs; breast cancers which have metastasized to the bone, brain, liver, and/or lungs; colorectal cancers which have metastasized to the liver, lungs, and/or peritoneum; kidney cancers which have metastasized to the adrenal glands, bone, brain, liver, and/or lungs; lung cancers which have metastasized to the adrenal glands, bone, brain, liver, and/or other lung sites; melanomas which have metastasized to the bone, brain, liver, lung, and/or skin/muscle; ovarian cancers which have metastasized to the liver, lung, and/or peritoneum; pancreatic cancers which have metastasized to the liver, lung, and/or peritoneum; prostate cancers which have metastasized to the adrenal glands, bone, liver, and/or lungs; stomach cancers which have metastasized to the liver, lung, and/or peritoneum; thyroid cancers which have metastasized to the bone, liver, and/or lungs; and uterine cancers which have metastasized to the bone, liver, lung, peritoneum, and/or vagina; among others.

In some embodiments, for example, where the cancer immunotherapy agent is a PD-1 or PD-L1 antagonist or inhibitor, the subject has one or more biomarkers (e.g., increased PD-1 or PD-L1 levels in cells such as cancer cells or cancer-specific CTLs) that make the suitable for PD-1 or PD-L1 inhibitor therapy. For instance, in some embodiments, the subject has increased fractions of programmed cell death 1 high/cytotoxic T lymphocyte—associated protein 4 high (e.g., PD-1$^{hi}$CTLA-4$^{hi}$) cells within a tumor-infiltrating CD8+ T cell subset (see, e.g., Daud et al., J Clin Invest. 126:3447-3452, 2016). As another example, in some embodiments, the subject has increased levels of Bim (B cell lymphoma 2-interacting (Bcl2-interacting) mediator) in circulating tumor-reactive (e.g., PD-1$^+$CD11a$^{hi}$CD8$^+$) T cells, and optionally has metastatic melanoma (see, e.g., Dronca et al., JCI Insight. May 5; 1(6): e86014, 2016).

Certain specific combinations include an anti-NRP2 antibody and a PD-L1 antagonist or inhibitor, for example, atezolizumab (MPDL3280A), avelumab (MSB0010718C), and durvalumab (MED14736), for treating a cancer selected from one or more of colorectal cancer, melanoma, breast cancer, non-small-cell lung carcinoma, bladder cancer, and renal cell carcinoma.

Some specific combinations include an anti-NRP2 antibody and a PD-1 antagonist, for example, nivolumab, for treating a cancer selected from one or more of Hodgkin's lymphoma, melanoma, non-small cell lung cancer, hepatocellular carcinoma, renal cell carcinoma, and ovarian cancer.

Particular specific combinations include an anti-NRP2 antibody and a PD-1 antagonist, for example, pembrolizumab, for treating a cancer selected from one or more of melanoma, non-small cell lung cancer, small cell lung cancer, head and neck cancer, and urothelial cancer.

Certain specific combinations include an anti-NRP2 antibody and a CTLA-4 antagonist, for example, ipilimumab and tremelimumab, for treating a cancer selected from one or more of melanoma, prostate cancer, lung cancer, and bladder cancer.

Some specific combinations include an anti-NRP2 antibody and an IDO antagonist, for example, indoximod (NLG-8189), 1-methyl-tryptophan (1MT), β-Carboline (norharmane; 9H-pyrido[3,4-b]indole), rosmarinic acid, or epacadostat, for treating a cancer selected from one or more of metastatic breast cancer and brain cancer optionally Glioblastoma Multiforme, glioma, gliosarcoma or malignant brain tumor.

Certain specific combinations include an anti-NRP2 antibody and the cytokine INF-a for treating melanoma, Kaposi sarcoma, and hematologic cancers. Also included is the combination of an anti-NRP2 antibody and IL-2 (e.g., Aldesleukin) for treating metastatic kidney cancer or metastatic melanoma.

Some specific combinations include an anti-NRP2 antibody and a T-cell based adoptive immunotherapy, for example, comprising CAR-modified T-cells targeted against CD-19, for treating hematological cancers such as acute lymphoblastic leukemia (ALL), chronic lymphocytic leukemia (CLL), and B-cell neoplasms (see, e.g., Maude et al., 2015, supra; Lorentzen and Straten, Scand J Immunol. 82:307-19, 2015; and Ramos et al., Cancer J. 20:112-118, 2014).

The methods for treating cancers can be combined with other therapeutic modalities. For example, a combination therapy described herein can be administered to a subject before, during, or after other therapeutic interventions, including symptomatic care, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions (for example, NRP2-associated diseases or conditions) described herein are known in the art.

For in vivo use, as noted above, for the treatment of human or non-human mammalian disease or testing, the agents described herein are generally incorporated into one or more therapeutic or pharmaceutical compositions prior to administration, including veterinary therapeutic compositions.

Thus, certain embodiments relate to therapeutic compositions that comprise at least one antibody or antigen-binding fragment thereof that specifically binds to a human NRP2 polypeptide, as described herein. In some instances, a therapeutic or pharmaceutical composition comprises one or more of the agents described herein in combination with a pharmaceutically- or physiologically-acceptable carrier or excipient. Certain therapeutic compositions further comprise at least one cancer immunotherapy agent, as described herein.

Some therapeutic compositions comprise (and certain methods utilize) only one anti-NRP2 antibody or antigen-binding fragment thereof. Certain therapeutic compositions comprise (and certain methods utilize) a mixture of at least two, three, four, or five different anti-NRP2 antibodies or antigen-binding fragments thereof.

For instance, certain therapeutic compositions comprise at least two anti-NRP2 antibodies, including a first antibody or antigen-binding fragment thereof that specifically binds to at least one first epitope of a human NRP2 polypeptide, and a second antibody or antigen-binding fragment thereof that specifically binds to at least one second epitope of a human NRP2 polypeptide, wherein the at least one first epitope differs from the at least one second epitope. In some embodiments, the first and the second antibody or antigen-binding fragment thereof specifically and non-competitively bind to the same domain of the NRP2 polypeptide.

In some embodiments, the first and the second antibody or antigen-binding fragment thereof specifically and non-competitively bind to different domains of the NRP2 polypeptide.

In certain embodiments, the first antibody or antigen-binding fragment is an antagonistic antibody (e.g., interferes with one or more signaling activities of the HRS/NRP2 binding interaction), and the second antibody or antigen-binding fragment is an agonist antibody (e.g., mimics or agonizes one or more signaling activities of the HRS/NRP2 binding interaction). In some embodiments, the first antibody antagonizes the binding/signaling activity between the NRP2 polypeptide and the at least one NRP2 ligand. In certain embodiments, the second antibody or antigen-binding fragment thereof agonizes or enhances the binding/signaling activity between the NRP2 polypeptide and at least one NRP2 ligand.

In some embodiments, the first and the second antibody or antigen-binding fragments thereof are both blocking antibodies, for example, for at least two different NRP2 ligands. In some embodiments, the first and the second antibody or antigen-binding fragments thereof are both partial-blocking antibodies, for example, for at least two different NRP2 ligands. In some instances, the first and the second antibodies or antigen-binding fragments thereof are both non-blocking antibodies, for example, with respect to at least two different NRP2 ligands.

In some instances, the first antibody or antigen-binding fragment thereof is a blocking antibody and the second antibody or antigen-binding fragment thereof is a partial-blocking antibody. In certain instances, the first antibody or antigen-binding fragment thereof is a blocking antibody and the second antibody or antigen-binding fragment thereof is a non-blocking antibody.

In some embodiments, the first and the second antibodies or antigen-binding fragments thereof both comprise an IgG Fc domain with high effector function in humans, for example, an IgG1 or IgG3 Fc domain. In some embodiments, the first and the second antibodies or antigen-binding fragments thereof comprise an IgG Fc domain with low effector function in humans, for example, an IgG2 or IgG4 Fc domain.

In some instances, the first antibody or antigen-binding fragment thereof comprises an IgG Fc domain with high effector function in humans, for example, an IgG1 or IgG3 Fc domain, and the second antibody or antigen-binding fragment thereof comprises an IgG Fc domain with low effector function in humans, for example, an IgG2 or IgG4 Fc domain.

In particular embodiments, the therapeutic composition comprising the agents such as antibodies or other polypeptide agents (e.g., anti-NRP2 antibodies) is substantially pure on a protein basis or a weight-weight basis, for example, the composition has a purity of at least about 80%, 85%, 90%, 95%, 98%, or 99% on a protein basis or a weight-weight basis.

In some embodiments, the antibodies (e.g., anti-NRP2 antibodies) or other polypeptide agents provided herein do not form aggregates, have a desired solubility, and/or have an immunogenicity profile that is suitable for use in humans, as described herein and known in the art. Thus, in some embodiments, the therapeutic composition comprising a polypeptide agent (for example, an antibody such as an anti-NRP2 antibody) is substantially aggregate-free. For example, certain compositions comprise less than about 10% (on a protein basis) high molecular weight aggregated proteins, or less than about 5% high molecular weight aggregated proteins, or less than about 4% high molecular weight aggregated proteins, or less than about 3% high molecular weight aggregated proteins, or less than about 2% high molecular weight aggregated proteins, or less than about 1% high molecular weight aggregated proteins. Some compositions comprise a polypeptide agent (e.g., an antibody such as an anti-NRP2 antibody) that is at least about 50%, about 60%, about 70%, about 80%, about 90% or about 95% monodisperse with respect to its apparent molecular mass.

In some embodiments, polypeptide agents such as antibodies (e.g., anti-NRP2 antibodies) are concentrated to about or at least about 0.1 mg/ml, 0.2 mg/ml, 0.3 mg/ml, 0.4 mg/ml, 0.5 mg/ml, 0.6, 0.7, 0.8, 0.9, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11, 12, 13, 14 or 15 mg/ml and are formulated for biotherapeutic uses.

To prepare a therapeutic or pharmaceutical composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate therapeutic or pharmaceutical composition, can be carried out via any of the accepted modes of administration of agents for serving similar utilities. The therapeutic or pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, intramuscular, subcutaneous or topical. Preferred modes of administration depend upon the nature of the condition to be treated or prevented. Particular embodiments include administration by IV infusion.

Carriers can include, for example, pharmaceutically- or physiologically-acceptable carriers, excipients, or stabilizers that are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related therapeutic or pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will typically contain a therapeutically effective amount of an agent described herein, for treatment of a disease or condition of interest.

A therapeutic or pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid therapeutic or pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid therapeutic or pharmaceutical composition intended for either parenteral or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations are prepared so that a parenteral dosage unit contains between 0.01 to 10% by weight of the agent of interest prior to dilution.

The therapeutic or pharmaceutical compositions may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a therapeutic or pharmaceutical composition for topical administration. If intended for transdermal administration, the composition may include a transdermal patch or iontophoresis device.

The therapeutic or pharmaceutical compositions may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The therapeutic or pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The therapeutic or pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The therapeutic or pharmaceutical or IVIG compositions may be administered in a therapeutically effective amount, which will vary depending upon a variety of factors including the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy. In some instances, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g). In some embodiments, the therapeutically effective dose is administered on a weekly, bi-weekly, or monthly basis. In specific embodiments, the therapeutically effective dose is administered on a weekly, bi-weekly, or monthly basis, for example, at a dose of about 1-10 or 1-5 mg/kg, or about 1, 2, 3, 4, 5, 6, 7, 8, 9, or 10 mg/kg.

The combination therapies described herein may include administration of a single pharmaceutical dosage formulation, which contains an anti-NRP2 antibody and an additional therapeutic agent (e.g., immunotherapy agent, chemotherapeutic agent, hormonal therapeutic agent, kinase inhibitor), as well as administration of compositions comprising an anti-NRP2 antibody and an additional therapeutic agent in its own separate pharmaceutical dosage formulation. For example, an anti-NRP2 antibody as described herein and additional therapeutic agent can be administered to the subject together in a single oral dosage composition such as a tablet or capsule, or each agent administered in separate oral dosage formulations. Similarly, an anti-NRP2 antibody as described herein and additional therapeutic agent can be administered to the subject together in a single parenteral dosage composition such as in a saline solution or other physiologically acceptable solution, or each agent administered in separate parenteral dosage formulations. As another example, for cell-based therapies, an anti-NRP2 antibody can be mixed with the cells prior to administration, administered as part of a separate composition, or both. Where separate dosage formulations are used, the compositions can be administered at essentially the same time, i.e., concurrently, or at separately staggered times, i.e., sequentially and in any order; combination therapy is understood to include all these regimens.

Also included are patient care kits, comprising (a) at least one antibody or antigen-binding fragment thereof that specifically binds to a human neuropilin 2 (NRP2) polypeptide (an anti-NRP2 antibody), as described herein; and optionally (b) at least one additional therapeutic agent (e.g., immunotherapy agent, chemotherapeutic agent, hormonal therapeutic agent, kinase inhibitor). In certain kits, (a) and (b) are in separate therapeutic compositions. In some kits, (a) and (b) are in the same therapeutic composition.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an anti-NRP2 antibody and optionally at least one additional therapeutic agent. For example, the kit includes a plurality of syringes, ampules, foil packets, or blister packs, each containing a single unit dose of an anti-NRP2 antibody and optionally at least one additional therapeutic agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

Bioassays and Analytical Assays for Drug Release Assays and Product Specifications, Diagnostics, and Reagents Also included are bioassays that relate to anti-NRP2 antibodies and related agents such as therapeutic and diagnostic reagents. Examples include bioassays and analytical assays that measure purity, biological activity, affinity, solubility, pH, endotoxin levels, among others, many of which are described herein. Also included are assays that establish dose response curves and/or provide one or more bases for comparison between different batches of antibody. Batch comparisons can be based on any one or more of chemical characterization, biological characterization, and clinical characterization. Also included are methods of evaluating the potency, stability, pharmacokinetics, and immunogenicity of a selected antibody. Among other uses, these and other methods can be used for lot releasing testing of biologic or chemical agents, including anti-NRP2 antibodies, described herein.

Certain embodiments include the use of bioaffinity assays. Such assays can be used to assess the binding affinity, for example, between an anti-NRP2 antibody and at least one NRP2 ligand (for example, an NRP2 ligand from Table N2 or Table N3 and/or an HRS polypeptide from Table H1), including its ability to interfere with the interaction between a human NRP2 polypeptide and the at least one NRP2 ligand, or other cellular binding partner. Certain exemplary binding affinity assays may utilize ELISA assays, and other immunoassays as described herein and known in the art. Certain assays utilize high-performance receptor binding chromatography (see, e.g., Roswall et al., Biologicals. 24:25-39, 1996). Other exemplary binding affinity assays may utilize surface plasmon resonance (SPR)-based technologies. Examples include BIACore technologies, certain of which integrate SPR technology with a microfluidics system to monitor molecular interactions in real time at concentrations ranging from pM to mM. Also included are KINEXA™ assays, which provide accurate measurements of binding specificity, binding affinity, and binding kinetics/rate constants.

Certain embodiments relate to immunoassays for evaluating or optimizing the immunogenicity of anti-NRP2 antibodies. Examples include ex vivo human cellular assays and in vitro immuno-enzymatic assays to provide useful information on the immunogenic potential of a therapeutic protein. Ex vivo cell-response assays can be used, for example, to reproduce the cellular co-operation between antigen-presenting cells (APCs) and T-cells, and thereby measure T-cells activation after contact with a protein of interest. Certain in vitro enzymatic assays may utilize a collection of recombinant HLA-DR molecules that cover a significant portion of a relevant human population, and may include automated immuno-enzymatic assays for testing the binding of peptides (stemming from the fragmentation of the therapeutic protein) with the HLA-DR molecules. Also included are methods of reducing the immunogenicity of a selected protein, such as by using these and related methods to identify and then remove or alter one or more T-cell epitopes from an anti-NRP2 antibody.

Also included are biological release assays (e.g., cell-based assays) for measuring parameters such as specific biological activities, including non-canonical biological activities, and cytotoxicity. Certain specific biological assays include, for example, cell-based assays that utilize a cellular binding partner (e.g., cell-surface receptor (for example a NRP2 polypeptide and/or at least one NRP2 ligand (for example, an NRP2 ligand from Table N2 or Table N3) presented on the cell surface), which is either endogenously, or recombinantly expressed on the cell surface), which is functionally coupled to a readout, such as a fluorescent or luminescent indicator of NRP2 or NRP2 ligand binding, or functional activity, as described herein.

For instance, specific embodiments include a cell that either endogenously or recombinantly expresses a human NRP2 polypeptide on the cell surface, which allows assessment of the ability of anti-NRP2 antibody to bind NRP2. In some embodiments, the anti-NRP2 antibody and/or the NRP2 polypeptide is/are functionally coupled to a readout or indicator, such as a fluorescent or luminescent indicator to measure the binding and/or biological activity of the NRP2 polypeptide. In some embodiments, the cell also expresses at least one NRP2 ligand (for example, an NRP2 ligand from Table N2 or Table N3 and/or an HRS polypeptide from Table H1), wherein the at least one NRP2 ligand is coupled to a readout or indicator, such as a fluorescent or luminescent indicator of binding and/or biological activity of the at least one NRP2 ligand.

Also included are in vivo biological assays to characterize the pharmacokinetics of an anti-NRP2 antibody, typically utilizing engineered, or wild type mice, rat, monkey or other mammal (see, e.g., Lee et al., The Journal of Pharmacology. 281:1431-1439, 1997). Examples of cytotoxicity-based biological assays include release assays (e.g., chromium or europium release assays to measure apoptosis; see, e.g., von Zons et al., Clin Diagn Lab Immunol. 4:202-207, 1997), among others, which can assess the cytotoxicity anti-NRP2 antibodies, whether for establishing dose response curves, batch testing, or other properties related to approval by various regulatory agencies, such as the Food and Drug Administration (FDA).

Also included are assays for evaluating the effects of an anti-NRP2 antibody on immune cells. Examples include an assay system, comprising an activated population of T-cells and at least one anti-NRP2 antibody, wherein the at least one anti-NRP2 antibody interferes with binding of NRP2 to at least one NRP2 ligand (for example, an NRP2 ligand from Table N2 or Table N3 and/or an HRS polypeptide from Table H1).

Certain embodiments include an assay system, comprising a single monoclonal anti-NRP2 antibody and at least one human NRP2 polypeptide, wherein the anti-NRP2 antibody binds to the NRP2 polypeptide. In some instances, the at least one antibody comprises an IgG4 Fc domain.

Also included are testing material(s), comprising a purified NRP2 polypeptide, wherein said purified NRP2 polypeptide is bound to a solid substrate in a manner that enables antibody binding detection.

Such assays and materials can be used, for example, to develop a dose response curve for a selected anti-NRP2 antibody, and/or to compare the dose response curve of different batches of proteins or other agents. A dose-response curve is an X-Y graph that relates the magnitude of a stressor to the response of a receptor, such as an NRP2-NRP2 ligand (for example, an NRP2 ligand from Table N2 or Table N3 and/or an HRS polypeptide from Table H1) interaction; the response may be a physiological or biochemical response, such as a non-canonical biological activity in a cell in vitro or in a cell or tissue in vivo, a therapeutically effective amount as measured in vivo (e.g., as measured by $EC_{50}$), or death, whether measured in vitro or in vivo (e.g., cell death, organismal death). Death is usually indicated as an $LD_{50}$, a statistically-derived dose that is lethal to 50% of a modeled population, though it can be indicated by $LC_{01}$ (lethal dose for 1% of the animal test population), $LC_{100}$ (lethal dose for 100% of the animal test population), or $LC_{Lo}$ (lowest dose causing lethality). Almost any desired effect or endpoint can be characterized in this manner.

The measured dose of a response curve is typically plotted on the X axis and the response is plotted on the Y axis. More typically, the logarithm of the dose is plotted on the X axis, most often generating a sigmoidal curve with the steepest portion in the middle. The No Observable Effect Level (NOEL) refers to the lowest experimental dose for which no measurable effect is observed, and the threshold dose refers to the first point along the graph that indicates a response above zero. As a general rule, stronger drugs generate steeper dose response curves. For many drugs, the desired effects are found at doses slightly greater than the threshold dose, often because lower doses are relatively ineffective and higher doses lead to undesired side effects. For in vivo generated dose response curves, a curve can be characterized by values such as µg/kg, mg/kg, or g/kg of body-weight, if desired.

For batch comparisons, it can be useful to calculate the coefficient of variation (CV) between different dose response curves of different batches (e.g., between different batches of anti-NRP2 antibody), in part because the CV allows comparison between data sets with different units or different means. For instance, in certain exemplary embodiments, two or three or more different batches of anti-NRP2 antibodies or other agents have a CV between them of less than about 30%, 20%, 15%, 14%, 13%, 12%, 11%, 10%, 9%, 8%, 7%, 6%, 5%, 4%, 3%, 2%, or 1% for a 4, 5, 6, 7, or 8 point dose curve. In certain embodiments, the dose response curve is measured in a cell-based assay, and its readout relates to an increase or a decrease in a selected activity of an anti-NRP2 antibody. In certain embodiments, the dose response curve is measured in a cell release assay or animal model (e.g., mouse model), and its readout relates to cell death or animal death. Other variations will be apparent to persons skilled in the art.

Expression and Purification Systems

Certain embodiments include methods and related compositions for expressing and purifying an anti-NRP2 antibody or other polypeptide-based agent described herein. Such recombinant anti-NRP2 antibodies can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6. As one general example, anti-NRP2 antibodies may be prepared by a procedure including one or more of the steps of: (a) preparing a construct comprising a polynucleotide sequences that encode an anti-NRP2 antibody heavy and light chain and that are operably linked to a regulatory element; (b) introducing the constructs into a host cell; (c) culturing the host cell to express an anti-NRP2 antibody; and (d) isolating an anti-NRP2 antibody from the host cell.

Anti-NRP2 antibody polynucleotides are described elsewhere herein. In order to express a desired polypeptide, a nucleotide sequence encoding an anti-NRP2 antibody, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, J. Biol. Chem. 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

Certain embodiments may employ E. coli-based expression systems (see, e.g., Structural Genomics Consortium et al., Nature Methods. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in E. coli, such as ROSETTA—(DE3) and Rosetta 2 (DE3) strains. Cell lysis and sample handling may also be improved using reagents sold under the trademarks BENZONASE® nuclease and BUG-BUSTER® Protein Extraction Reagent. For cell culture, auto-inducing media can improve the efficiency of many expression systems, including high-throughput expression systems. Media of this type (e.g., OVERNIGHT EXPRESS' Autoinduction System) gradually elicit protein expression through metabolic shift without the addition of artificial inducing agents such as IPTG. Particular embodiments employ hexahistidine tags (such as those sold under the trademark HISTAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because overexpression of proteins in *Escherichia coli* at low temperature improves their solubility and stability (see, e.g., Qing et al., Nature Biotechnology. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987). Also included are *Pichia pandoris* expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629, 163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., Proc. Natl. Acad. Sci. U.S.A. 91:3224-3227 (1994)). Also included are baculovirus expression systems, including those that utilize SF9, SF21, and *T. ni* cells (see, e.g., Murphy and Piwnica-Worms, Curr Protoc Protein Sci. Chapter 5:Unit5.4, 2001). Insect systems can provide post-translation modifications that are similar to mammalian systems.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is the cell-free expression of proteins. These and related embodiments typically utilize purified RNA polymerase, ribosomes, tRNA and ribonucleotides; these reagents may be produced by extraction from cells or from a cell-based expression system.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results Probl. Cell Differ. 20:125-162 (1994)).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Any number of selection systems may be used to recover transformed or transduced cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., Proc. Natl. Acad. Sci. U.S.A. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). The use of visible markers has gained popularity with such markers as green fluorescent protein (GFP) and other fluorescent proteins (e.g., RFP, YFP), anthocyanins, P-glucuronidase and its substrate GUS, and luciferase and its substrate luciferin, being widely used not only to identify transformants, but also to quantify the amount of transient or stable protein expression attributable to a specific vector system (see, e.g., Rhodes et al., Methods Mol. Biol. 55:121-131 (1995)).

Also included are high-throughput protein production systems, or micro-production systems. Certain aspects may utilize, for example, hexa-histidine fusion tags for protein expression and purification on metal chelate-modified slide surfaces or MagneHis Ni-Particles (see, e.g., Kwon et al., BMC Biotechnol. 9:72, 2009; and Lin et al., Methods Mol Biol. 498:129-41, 2009)). Also included are high-throughput cell-free protein expression systems (see, e.g., Sitaraman et al., Methods Mol Biol. 498:229-44, 2009). These and related embodiments can be used, for example, to generate microarrays of anti-NRP2 antibodies which can then be used for screening libraries to identify antibodies and antigen-binding domains that interact with the NRP2 polypeptide(s) of interest.

A variety of protocols for detecting and measuring the expression of polynucleotide-encoded products, using binding agents or antibodies such as polyclonal or monoclonal antibodies specific for the product, are known in the art. Examples include enzyme-linked immunosorbent assay (ELISA), western immunoblots, radioimmunoassays (RIA), and fluorescence activated cell sorting (FACS). These and other assays are described, among other places, in Hampton et al., Serological Methods, a Laboratory Manual (1990) and Maddox et al., J. Exp. Med. 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can be grown on serum free medium (see, e.g., Rosser et al., Protein Expr. Purif. 40:237-43, 2005; and U.S. Pat. No. 6,210,922).

An antibody, or antigen-binding fragment thereof, produced by a recombinant cell may be secreted or contained intracellularly depending on the sequence and/or the vector used. As will be understood by those of skill in the art, expression vectors containing polynucleotides may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification and/or detection of soluble proteins. Examples of such domains include cleavable and non-cleavable affinity purification and epitope tags such as avidin, FLAG tags, poly-histidine tags (e.g., 6×His), cMyc tags, V5-tags, glutathione S-transferase (GST) tags, and others.

The protein produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating anti-NRP2 antibodies and antigen-binding fragments thereof, and composition comprising concentrated soluble proteins. In different aspects such concentrated solutions of anti-NRP2 antibodies may comprise proteins at a concentration of about 5 mg/mL; or about 8 mg/mL; or about 10 mg/mL; about 15 mg/mL; or about 20 mg/mL.

In some aspects, such compositions may be substantially monodisperse, meaning that an at least one anti-NRP2 antibody exists primarily (i.e., at least about 90%, or greater) in one apparent molecular weight form when assessed for example, by size exclusion chromatography, dynamic light scattering, or analytical ultracentrifugation.

In some aspects, such compositions have a purity (on a protein basis) of at least about 90%, or in some aspects at least about 95% purity, or in some embodiments, at least 98% purity. Purity may be determined via any routine analytical method as known in the art.

In some aspects, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

Examples of concentration approaches contemplated herein include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the reagents, anti-NRP2 antibodies, or related agents have a purity of at least about 90%, as measured according to routine techniques in the art. In certain embodiments, such as diagnostic compositions or certain therapeutic compositions, an anti-NRP2 antibody composition has a purity of at least about 95%. In specific embodiments, such as therapeutic or pharmaceutical compositions, an anti-NRP2 antibody composition has a purity of at least about 97% or 98% or 99%. In other embodiments, such as when being used as reference or research reagents, anti-NRP2 antibodies can be of lesser purity, and may have a purity of at least about 50%, 60%, 70%, or 80%. Purity can be measured overall or in relation to selected components, such as other proteins, e.g., purity on a protein basis.

Purified anti-NRP2 antibodies can also be characterized according to their biological characteristics. Binding affinity and binding kinetics can be measured according to a variety of techniques known in the art, such as Biacore® and related technologies that utilize surface plasmon resonance (SPR), an optical phenomenon that enables detection of unlabeled interactants in real time. SPR-based biosensors can be used in determination of active concentration, screening and characterization in terms of both affinity and kinetics. The presence or levels of one or more canonical or non-canonical biological activities can be measured according to cell-based assays, including those that utilize a cellular binding partner of a selected anti-NRP2 antibody, which is functionally coupled to a readout or indicator, such as a fluorescent or luminescent indicator of biological activity, as described herein.

In certain embodiments, as noted above, an anti-NRP2 antibody composition is substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, an anti-NRP2 antibody composition is made from a eukaryotic cell such as a mammalian or human cell in substantially serum free media. In certain embodiments, as noted herein, an anti-NRP2 antibody composition has an endotoxin content of less than about 10 EU/mg of anti-NRP2 antibody, or less than about 5 EU/mg of anti-NRP2 antibody, less than about 3 EU/mg of anti-NRP2 antibody, or less than about 1 EU/mg of anti-NRP2 antibody.

In certain embodiments, an anti-NRP2 antibody composition comprises less than about 10% wt/wt high molecular weight aggregates, or less than about 5% wt/wt high molecular weight aggregates, or less than about 2% wt/wt high molecular weight aggregates, or less than about or less than about 1% wt/wt high molecular weight aggregates.

Also included are protein-based analytical assays and methods, which can be used to assess, for example, protein purity, size, solubility, and degree of aggregation, among other characteristics. Protein purity can be assessed a number of ways. For instance, purity can be assessed based on primary structure, higher order structure, size, charge, hydrophobicity, and glycosylation. Examples of methods for assessing primary structure include N- and C-terminal sequencing and peptide-mapping (see, e.g., Allen et al., Biologicals. 24:255-275, 1996)). Examples of methods for assessing higher order structure include circular dichroism (see, e.g., Kelly et al., Biochim Biophys Acta. 1751:119-139, 2005), fluorescent spectroscopy (see, e.g., Meagher et al., J. Biol. Chem. 273:23283-89, 1998), FT-IR, amide hydrogen-deuterium exchange kinetics, differential scanning calorimetry, NMR spectroscopy, immunoreactivity with conformationally sensitive antibodies. Higher order structure can also be assessed as a function of a variety of parameters such as pH, temperature, or added salts. Examples of methods for assessing protein characteristics such as size include analytical ultracentrifugation and size exclusion HPLC (SEC-HPLC), and exemplary methods for measuring charge include ion-exchange chromatography and isoelectric focusing. Hydrophobicity can be assessed, for example, by reverse-phase HPLC and hydrophobic interaction chromatography HPLC. Glycosylation can affect pharmacokinetics (e.g., clearance), conformation or stability, receptor binding, and protein function, and can be assessed, for example, by mass spectrometry and nuclear magnetic resonance (NMR) spectroscopy.

As noted above, certain embodiments include the use of SEC-HPLC to assess protein characteristics such as purity, size (e.g., size homogeneity) or degree of aggregation, and/or to purify proteins, among other uses. SEC, also including gel-filtration chromatography (GFC) and gel-permeation chromatography (GPC), refers to a chromatographic method in which molecules in solution are separated in a porous material based on their size, or more specifically their hydrodynamic volume, diffusion coefficient, and/or surface properties. The process is generally used to separate biological molecules, and to determine molecular weights and molecular weight distributions of polymers. Typically, a biological or protein sample (such as a protein extract produced according to the protein expression methods provided herein and known in the art) is loaded into a selected size-exclusion column with a defined stationary phase (the porous material), preferably a phase that does not interact with the proteins in the sample. In certain aspects, the stationary phase is composed of inert particles packed into a dense three-dimensional matrix within a glass or steel column. The mobile phase can be pure water, an aqueous buffer, an organic solvent, or a mixture thereof. The stationary-phase particles typically have small pores and/or channels which only allow molecules below a certain size to enter. Large particles are therefore excluded from these pores and channels, and their limited interaction with the stationary phase leads them to elute as a "totally-excluded" peak at the beginning of the experiment. Smaller molecules, which can fit into the pores, are removed from the flowing mobile phase, and the time they spend immobilized in the stationary-phase pores depends, in part, on how far into the pores they penetrate. Their removal from the mobile phase flow causes them to take longer to elute from the column and results in a separation between the particles based on differences in their size. A given size exclusion column has a range of molecular weights that can be separated. Overall, molecules larger than the upper limit will not be trapped by the stationary phase, molecules smaller than the lower limit will completely enter the solid phase and elute as a single band, and molecules within the range will elute at different rates, defined by their properties such as hydrodynamic volume. For examples of these methods in practice with pharmaceutical proteins, see Bruner et al., Journal of Pharmaceutical and Biomedical Analysis. 15: 1929-1935, 1997.

Protein purity for clinical applications is also discussed, for example, by Anicetti et al. (Trends in Biotechnology. 7:342-349, 1989). More recent techniques for analyzing protein purity include, without limitation, the LabChip GXII, an automated platform for rapid analysis of proteins and nucleic acids, which provides high throughput analysis of titer, sizing, and purity analysis of proteins. In certain non-limiting embodiments, clinical grade proteins such as protein fragments and antibodies can be obtained by utilizing a combination of chromatographic materials in at least two orthogonal steps, among other methods (see, e.g., Therapeutic Proteins: Methods and Protocols. Vol. 308, Eds., Smales and James, Humana Press Inc., 2005). Typically, protein agents (e.g., anti-NRP2 antibodies, and antigen-binding fragments) are substantially endotoxin-free, as measured according to techniques known in the art and described herein.

Protein solubility assays are also included. Such assays can be utilized, for example, to determine optimal growth and purification conditions for recombinant production, to optimize the choice of buffer(s), and to optimize the choice of anti-NRP2 antibodies or variants thereof. Solubility or aggregation can be evaluated according to a variety of parameters, including temperature, pH, salts, and the presence or absence of other additives. Examples of solubility screening assays include, without limitation, microplate-based methods of measuring protein solubility using turbidity or other measure as an end point, high-throughput assays for analysis of the solubility of purified recombinant proteins (see, e.g., Stenvall et al., Biochim Biophys Acta. 1752:6-10, 2005), assays that use structural complementation of a genetic marker protein to monitor and measure protein folding and solubility in vivo (see, e.g., Wigley et al., Nature Biotechnology. 19:131-136, 2001), and electrochemical screening of recombinant protein solubility in *Escherichia coli* using scanning electrochemical microscopy (SECM) (see, e.g., Nagamine et al., Biotechnology and Bioengineering. 96:1008-1013, 2006), among others. Anti-NRP2 antibodies with increased solubility (or reduced aggregation) can be identified or selected for according to routine techniques in the art, including simple in vivo assays for protein solubility (see, e.g., Maxwell et al., Protein Sci. 8:1908-11, 1999).

Protein solubility and aggregation can also be measured by dynamic light scattering techniques. Aggregation is a general term that encompasses several types of interactions or characteristics, including soluble/insoluble, covalent/non-covalent, reversible/irreversible, and native/denatured interactions and characteristics. For protein therapeutics, the presence of aggregates is typically considered undesirable because of the concern that aggregates may cause an immunogenic reaction (e.g., small aggregates), or may cause adverse events on administration (e.g., particulates). Dynamic light scattering refers to a technique that can be used to determine the size distribution profile of small particles in suspension or polymers such as proteins in solution. This technique, also referred to as photon correlation spectroscopy (PCS) or quasi-elastic light scattering (QELS), uses scattered light to measure the rate of diffusion of the protein particles. Fluctuations of the scattering intensity can be observed due to the Brownian motion of the molecules and particles in solution. This motion data can be conventionally processed to derive a size distribution for the sample, wherein the size is given by the Stokes radius or hydrodynamic radius of the protein particle. The hydrodynamic size depends on both mass and shape (conformation). Dynamic scattering can detect the presence of very small amounts of aggregated protein (<0.01% by weight), even in samples that contain a large range of masses. It can also be used to compare the stability of different formulations, including, for example, applications that rely on real-time monitoring of changes at elevated temperatures. Accordingly, certain embodiments include the use of dynamic light scattering to analyze the solubility and/or presence of aggregates in a sample that contains an anti-NRP2 antibody of the present disclosure.

Although the foregoing embodiments have been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLE 1

Generation of Antibodies to Human Neuropilin 2

Antibody generation. The anti-NRP2 antibodies listed in Table E1 were generated by immunizing mice via an IP administration with $1 \times 10^6$ Expi293 cells stably over expressing human NRP2A variant 2 (Origene Technologies Cat #RC220706), (prepared as more fully described below) using standard methodologies. Titers were boosted via S.C. administration of 10 μg/mouse of the corresponding recombinant NRP2 polypeptides listed in Table E2, using either IFA or Magic Mouse as the adjuvant. Mice were boosted every 2-3 weeks and then screened for initial titer and specificity using the NRP2 polypeptides listed in Table E2.

TABLE E1

Antibodies

| Antibody | Immunogen # | Clone | Isotype | Target domain |
|---|---|---|---|---|
| aNRP2-1 | 1023 | 17f7 | mIgG1k | b2 |
| aNRP2-2 | 1085 | 3f2 | mIgG2ak | c |
| aNRP2-6 | 1024 | 8e2 | mIgG1k | b1 |
| aNRP2-7 | 1024 | 5h11 | mIgG1k | b1 |
| aNRP2-8 | 1024 | 7g10 | mIgG1k | b1 |
| aNRP2-9 | 1024 | 9e7 | mIgG1k | b1 |
| aNRP2-10 | 1024 | 1e3 | mIgG1k | b1 |
| aNRP2-11 | 1024 | 13d7 | mIgG2ak | b2 |
| aNRP2-12 | 1085 | 20f3 | mIgG2ak | c |
| aNRP2-14 | 1024 | 18b8 | mIgG1k | a2 |
| aNRP2-15 | 1024 | 19e8 | mIgG2bk | b1 |

TABLE E2

NRP2 Immunogens

| Immunogen | # | Sequence | SEQ ID NO: |
|---|---|---|---|
| NRP2 (23-595)-Fc | 1023 | QPDPPCGGRLNSKDAGYITSPGYPQDYPSHQNCEWIVYAPEPNQK IVLNFNPHFEIEKHDCKYDFIEIRDGDSESADLLGKHCGNIAPPT IISSGSMLYIKFTSDYARQGAGFSLRYEIFKTGSEDCSKNFTSPN GTIESPGFPEKYPHNLDCTFTILAKPKMEIILQFLIFDLEHDPLQ VGEGDCKYDWLDIWDGIPHVGPLIGKYCGTKTPSELRSSTGILSL TFHTDMAVAKDGFSARYYLVHQEPLENFQCNVPLGMESGRIANEQ ISASSTYSDGRWTPQQSRLHGDDNGWTPNLDSNKEYLQVDLRFLT MLTAIATQGAISRETQNGYYVKSYKLEVSTNGEDWMVYRHGKNHK VFQANNDATEVVLNKLHAPLLTRFVRIRPQTWHSGIALRLELFGC RVTDAPCSNMLGMLSGLIADSQISASSTQEYLWSPSAARLVSSRS GWFPRIPQAQPGEEWLQVDLGTPKTVKGVIIQGARGGDSITAVEA RAFVRKFKVSYSLNGKDWEYIQDPRTQQPKLFEGNMHYDTPDIRR FDPIPAQYVRVYPERWSPAGIGMRLEVLGCDWTDKTHTCPPCPAP ELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTC LVKGFYPSDIAVEWESNGQPENNYKTTPPVLDSDGSFFLYSKLTV DKSRWQQGNVFSCSVMHEALHNHYTQKSLSLSPGK | 120 |
| NRP2 (145-595)-Fc | | GSEDCSKNFTSPNGTIESPGFPEKYPHNLDCTFTILAKPKMEIIL QFLIFDLEHDPLQVGEGDCKYDWLDIWDGIPHVGPLIGKYCGTKT PSELRSSTGILSLTFHTDMAVAKDGFSARYYLVHQEPLENFQCNV PLGMESGRIANEQISASSTYSDGRWTPQQSRLHGDDNGWTPNLDS NKEYLQVDLRFLTMLTAIATQGAISRETQNGYYVKSYKLEVSTNG EDWMVYRHGKNHKVFQANNDATEVVLNKLHAPLLTRFVRIRPQTW HSGIALRLELFGCRVTDAPCSNMLGMLSGLIADSQISASSTQEYL WSPSAARLVSSRSGWFPRIPQAQPGEEWLQVDLGTPKTVKGVIIQ GARGGDSITAVEARAFVRKFKVSYSLNGKDWEYIQDPRTQQPKLF EGNMHYDTPDIRRFDPIPAQYVRVYPERWSPAGIGMRLEVLGCDW TDKTHTCPPCPAPELLGGPSVFLFPPKPKDTLMISRTPEVTCVVV DVSHEDPEVKFNWYVDGVEVHNAKTKPREEQYNSTYRVVSVLTVL HQDWLNGKEYKCKVSNKALPAPIEKTISKAKGQPREPQVYTLPPS RDELTKNQVSLTCLVKGFYPSDIAVEWESNGQPENNYKTTPPVLD SDGSFFLYSKLTVDKSRWQQGNVFSCSVMHEALHNHYTQKSISIS PGK | 22 |
| NRP2 (23-855)-Fc | 1085 | QPDPPCGGRLNSKDAGYITSPGYPQDYPSHQNCEWIVYAPEPNQK IVLNFNPHFEIEKHDCKYDFIEIRDGDSESADLLGKHCGNIAPPT IISSGSMLYIKFTSDYARQGAGFSLRYEIFKTGSEDCSKNFTSPN GTIESPGFPEKYPHNLDCTFTILAKPKMEIILQFLIFDLEHDPLQ VGEGDCKYDWLDIWDGIPHVGPLIGKYCGTKTPSELRSSTGILSL TFHTDMAVAKDGFSARYYLVHQEPLENFQCNVPLGMESGRIANEQ ISASSTYSDGRWTPQQSRLHGDDNGWTPNLDSNKEYLQVDLRFLT MLTAIATQGAISRETQNGYYVKSYKLEVSTNGEDWMVYRHGKNHK VFQANNDATEVVLNKLHAPLLTRFVRIRPQTWHSGIALRLELFGC RVTDAPCSNMLGMLSGLIADSQISASSTQEYLWSPSAARLVSSRS GWFPRIPQAQPGEEWLQVDLGTPKTVKGVIIQGARGGDSITAVEA RAFVRKFKVSYSLNGKDWEYIQDPRTQQPKLFEGNMHYDTPDIRR FDPIPAQYVRVYPERWSPAGIGMRLEVLGCDWTDKSKPTVETLGPT VKSEETTTPYPTEEEATECGENCSFEDDKDLQLPSGFNCNFDFLE | 21 |

TABLE E2-continued

NRP2 Immunogens

| Immunogen # | Sequence | SEQ ID NO: |
|---|---|---|
| | EPCGWMYDHAKWLRTTWASSSSPNDRTFPDDRNFLRLQSDSQREG | |
| | QYARLISPPVHLPRSPVCMEFQYQATGGRGVALQVVREASQESKL | |
| | LWVIREDQGGEWKHGRIILPSYDMEYQIVFEGVIGKGRSGEIAID | |
| | DIRISTDVPLENCMEPISAFAVDIPEIHEREGYEDEIDDEYEVDW | |
| | SNSSSATSGSGAPSTDKEKSWLYDKTHTCPPCPAPELLGGPSVFL | |
| | FPPKPKDTLMISRTPEVTCVVVDVSHEDPEVKFNWYVDGVEVHNA | |
| | KTKPREEQYNSTYRVVSVLTVLHQDWLNGKEYKCKVSNKALPAPI | |
| | EKTISKAKGQPREPQVYTLPPSRDELTKNQVSLTCLVKGFYPSDI | |
| | AVEWESNGQPENNYKTTPPVLDSDGSFFLYSKLTVDKSRWQQGNV | |
| | FSCSVMHEALHNHYTQKSISISPGK | |

For all antibodies, spleens were isolated from immunized animals and fusion with mouse myeloma cells was performed to generate hybridomas using standard techniques. Fusion, plating into 96-well plates, ELISA screening of hybridomas, expansion and characterization of positive hybridomas (titer and isotype) and freezing of up to 15 hybridomas per antigen, was performed at The Scripps Research Institute (TSRI) Center for Antibody Development and Production. Antibody variable domain sequences were obtained using standard sequencing approaches performed at Lake Pharma, and are listed in Table A1.

Recombinant antibodies were produced from hybridoma cells after expansion and purified from conditioned medium starting at 2 weeks of culture by flowing over a Protein A affinity column, eluting and storing in Phosphate Buffered Saline (1×PBS), pH 7.4. Each lot was tested for protein concentration, purity, and endotoxin level. Purity by SDS-PAGE was routinely >90%.

EXAMPLE 2

Characterization of Anti-Human Neuropilin 2 Antibodies

Initial assessments of binding affinity as measured by enzyme-linked immunosorbent assay (ELISA), surface plasmon resonance (SPR), and flow cytometry (FACS) binding to cell lines expressing recombinant NRP2, as well as the ability of the antibodies to block Fc-HRS(2-60), VEGF-C binding, or Semaphorin 3F are presented in Table E3.

Anti-NRP2 antibody binding and affinity measurements. Surface plasmon resonance (SPR) methods were used to demonstrate binding of anti-NRP2 antibodies to human NRP2 antigen and to measure binding affinities as summarized in Table E3. SPR experiments were conducted on a Bio-Rad ProteOn XPR36 Protein Interaction Array instrument. Goat anti-mouse antibody was immobilized on ProteOn GLC sensor chips by amine coupling. Anti-NRP2 antibodies were subsequently flowed over and captured by the anti-mouse antibody. Human NRP2 antigen protein was flowed over the captured antibody at varying concentrations (150, 50, 16.67, 5.56, 1.85 nM). The sensor chip surface was regenerated between each analyte run to remove anti-NRP2 antibodies and NRP2 protein. Data was double referenced against a surface with no anti-NRP2 antibody captured (immobilized goat anti-mouse antibody only) and a buffer only blank. Affinity constants were derived by globally fitting sensorgrams to a Langmuir (1:1) interaction model in the ProteOn manager software. For each anti-NRP2 antibody, data from the multiple NRP2 concentrations was fit as a single data set with dissociation rate constant ($k_d$), association rate constant ($k_a$) and R max values as global parameters. The reported binding affinity is the equilibrium dissociation constant ($K_D$) calculated from $k_d/k_a$.

Running buffer: 50 mM HEPES, 300 mM NaCl, 5 mM CaCl$_2$, 0.005% Tween-20, pH 7.4

Amine coupling: ProteOn Amine Coupling Kit (Bio-Rad #1762410)

Antibody coupling buffer: 10 mM sodium acetate pH 5.5

Immobilized antibody:

AffiniPure Goat Anti-Mouse IgG, Fcγ Fragment (Jackson ImmunoResearch #115-005-071)

Antigen: Human NRP2 (aa23-855) with C-terminal Avi-, Myc- and His-tags

Regeneration buffer: 10 mM glycine pH 1.5

Ligand blocking studies. SPR methods were used to demonstrate blocking of Fc-HRS(2-60), VEGF-C and SEMS3F binding to NRP2 by anti-NRP2 antibodies as shown in Table E3. SPR experiments were conducted on a Bio-Rad ProteOn XPR36 Protein Interaction Array instrument. Goat anti-mouse antibody was immobilized on ProteOn GLC sensor chips by amine coupling. Anti-NRP2 antibodies were flowed over and captured by the anti-mouse antibody. Human NRP2 protein was captured by the anti-NRP2 antibodies by flowing over at 400 nM. Either VEGF-C or SEMA3F-Fc was then flowed over the captured NRP2:anti-NRP2 complex at 50 nM. The signal upon ligand addition was referenced against addition of buffer only. If subsequent binding of the ligand (either VEGF-C or SEMA3F-Fc) was observed, that antibody was determined to not block NRP2 ligand binding. Conversely, if no binding of the ligand to the NRP2:anti-NRP2 complex was observed, that antibody was determined to block binding of that NRP2 ligand. Flow cytometry binding studies to 293 Epi NRP2 over expressing cells were conducted as described in Example 4.

Running buffer: 50 mM HEPES, 300 mM NaCl, 5 mM CaCl$_2$, 0.005% Tween-20, pH 7.4

Amine coupling: ProteOn Amine Coupling Kit (Bio-Rad #1762410)

Antibody coupling buffer: 10 mM sodium acetate pH 5.0

Immobilized antibody:

AffiniPure Goat Anti-Mouse IgG, Fcγ Fragment (Jackson ImmunoResearch #115-005-071)

Antigen: Human NRP2 (aa23-855) with C-terminal Avi-, Myc- and His-tags

Regeneration buffer: 10 mM glycine pH 1.5

NRP2 ligands: Human SEMA3F-Fc (R&D Systems #9878-S3)

VEGF-C (R&D Systems #9199-VC/CF)

TABLE E3

Antibody Characterization

| Clone | Epitope Domain (ELISA) | Binding NRP2 293Expi-NRP2 cells | Affinity by SPR: purified Ab (nM) | Ligand Blocking Fc-HRS(2-60) 293Expi-NRP2 cells | SPR | VEGF-C SPR | SEMA 3F SPR |
|---|---|---|---|---|---|---|---|
| 18B8 aNRP2-14 | a2 | Yes | 27 | Blocked | Blocked | Not blocked | Blocked |
| 8E2 aNRP2-6 | b1 | Yes | 0.4 | Blocked | Blocked | Blocked | Blocked |
| 5H11 aNRP2-7 | b1 | Yes | 0.3 | Blocked | Blocked | Blocked | Blocked |
| 7G10 aNRP2-8 | b1 | Yes | 1.4 | Blocked | Blocked | Blocked | Blocked |
| 9E7 aNRP2-9 | b1 | Yes | 8 | Blocked | Blocked | Blocked | Blocked |
| 1E3 aNRP2-10 | b1 | Yes | 0.8 | Blocked | Blocked | Blocked | Blocked |
| 19E8 aNRP2-15 | b1 | Yes | 2.7 | Blocked | Blocked | Blocked | Not Blocked |
| 17F7 aNRP2-1 | b2 | Yes | 41.8 | Blocked | Partial | Not blocked | Not blocked |
| 13D7 aNRP2-11 | b2 | Yes | 0.1 | Blocked | Blocked | Partial | Not blocked |
| 3F2 aNRP2-2 | c | Yes | 1.7 | Not blocked | Not blocked | Not blocked | Not blocked |
| 20F3 aNRP2-12 | c | Yes | 17.3 | Not blocked | Not blocked | Not blocked | Not blocked |

The results demonstrate that even among different a2, b1, b2 and c domain antibodies there are significant differences with respect to ligand blocking as determined by SPR. Importantly, the antibodies show significant specific with respect to the selectivity of blocking VEGF-C, Semaphorin 3F, and HRS polypeptide binding. For example, and without limitation, antibody clone18B8 (aNRP2-14) shows the ability to selectively block Sema 3F and HRS binding without blocking VEGF-C binding, and antibody 19E8 (aNRP2-15) shows the ability to selectively block VEGF-C without blocking Sema 3F binding.

EXAMPLE 3

Comparison of Antibody Binding Characteristics to Commercially Available Antibodies Using Wild Type A549 Cells Natively Expressing Human NRP2 Compared to NRP2 Null Cells Additionally, the specificity of the in-house anti-NRP2 antibodies binding to NRP2 was validated using A549 wildtype versus A549 NRP2 knockout clonal cells. The NRP2 knockout clonal cells were generated by CRISPR-Cas9 knock out, selection of single colonies, and validation for no NRP2 expression by western blots and cell surface immunostaining, following literature methods. Flow cytometry analysis was conducted essentially as described in Example 4 below. These in-house anti-NRP2 bound to A549 wildtype cells while showed no or little binding to the NRP2 knockout clonal cells (see Table E4).

TABLE E4

Comparison of signal to noise binding characteristics compared to commercially available antibodies

| Ab*/Clone | Domain Specificity | Fold change of a-NRP2 to Ctl^ (FC) A549 WT | NRP2 KO_107 | NRP2 KO_235 | KO/WT % |
|---|---|---|---|---|---|
| 18B8 aNRP2-14 | a2 | 232.8 | 1.1 | 1.1 | 0.5 |
| 19E8 aNRP2-15 | b1 | 521.3 | 1.1 | 1.0 | 0.2 |
| 1E3 aNRP2-10 | b1 | 410.2 | 1.6 | 1.4 | 0.4 |
| 5H11 aNRP2-7 | b1 | 397.6 | 1.5 | 1.4 | 0.4 |
| 7G10 aNRP2-8 | b1 | 390.9 | 1.2 | 1.1 | 0.3 |
| 8E2 aNRP2-6 | b1 | 431.5 | 1.3 | 1.2 | 0.3 |
| 9E7 aNRP2-9 | b1 | 461.9 | 1.2 | 1.1 | 0.2 |
| 13D7 aNRP2-11 | b2 | 286.6 | 1.2 | 1.5 | 0.5 |
| 17F7 aNRP2-1 | b2 | 246.6 | 1.5 | 1.3 | 0.6 |
| 20F3 aNRP2-12 | C | 61.1 | 1.2 | 1.4 | 2.1 |
| 3F2 aNRP2-2 | C | 348.9 | 2.1 | 2.0 | 0.6 |
| Commercial mabs | | | | | |
| R&D systems #AF567 | 23-857 | 57.6 | 5.4 | 5.4 | 9.4 |
| BAF2215 Boster | 25-855 | 137.2 | 8.6 | 7.3 | 5.8 |

TABLE E4-continued

Comparison of signal to noise binding characteristics compared to commercially available antibodies

| Ab*/Clone | Domain Specificity | Fold change of a-NRP2 to Ctl⁻ (FC) | | | KO/WT % |
|---|---|---|---|---|---|
| | | A549 WT | NRP2 KO_107 | NRP2 KO_235 | |
| C9-PE Santa Cruz Biotech | 560-858 hNRP2 | 6.0 | 1.7 | 1.7 | 27.9 |
| C9-AF647 Santa Cruz Biotech | 560-858 hNRP2 | 2.6 | 1.8 | 1.9 | 71.8 |
| C9-AF647 Santa Cruz Biotech | 560-858 hNRP2 | 1.8 | 1.3 | 1.7 | — |
| CS #3366 | Mouse N-terminus | 0.9 | 1.0 | 1.4 | — |

These results demonstrate that the claimed anti-NRP2 antibodies exhibit significantly superior specificity, and sensitivity to native NRP2 expressed on a cell line, compared to existing commercially available antibodies. These results are consistent with the idea that immunization of animals with NRP2 expressing cell lines results in the generation of an antibody response to the native NRP2 (non-denatured protein), which more accurately reflects the native conformation of the NRP2 protein found in vivo. As a result, the claimed antibodies would be anticipated to exhibit superior biological activity compared to antibodies raised recombinant proteins, as described further below.

EXAMPLE 4

Binding of Anti-Human Neuropilin 2 Antibodies to Human and Cynomolgus Monkey NRP2 Overexpressing Cells To assess the cross reactivity of the anti-NRP2 antibodies to human and cynomolgus monkey NRP2. NRP2 was expressed on the surface of HEK 293 cells, and flow cytometry studies were conducted as more fully described below. Establishing cross reactivity between cynomolgus monkey and human NRP2 is an important therapeutic development consideration to ensure that potential therapeutic candidates can be readily assessed for toxicity in animal studies; particularly if there is little or no cross reactivity of the antibodies between human and rodent NRP2.

Purification of plasmid DNA. Plasmids containing human or cynomolgus monkey NRP2 were purchased from Origene. To generate a large stock of plasmids and purify the DNA, each plasmid was transformed into chemically competent E. coli cells (One Shot TOP10) according to the manufacturer's instructions. The transformed bacteria were grown in the recommended liquid medium (Difco Dehydrated Miler Luria-Bertani medium powder resuspended in water) containing kanamycin monosulfate (50 µg/mL) as an antibiotic. The plasmid DNA was then purified using the QIAGEN DNA maxi prep kit according to the kit's instructions. DNA concentration and purity were measured on a spectrophotometer (Nanodrop 2000). An A260/A280 absorbance ratio between 1.8 and 2.0 was required for transfection.

Expi293 propagation and transient transfection. Expi293 cells, a HEK293 transient expression system maintained in suspension cultures, were used to express cynomolgus monkey NRP2. Cells were grown in 60 mL Expi293 medium within 250 mL vented suspension culture flasks. The propagation of cells was carried out in a Multitron Cell incubator at 37° C., with 8% $CO_2$, 80% humidity, and shaking at 225 rpm. During the maintenance and expansion phase, Expi293 cells were split twice a week at 0.3e6 cells/mL in order to keep the density within the optimal range for transfection and the viability high. Cell densities and viabilities were determined using a cell counter (Cedex HiRes Cell Analyzer).

The day prior to DNA transfection, the Expi293 cells were seeded at a density of 2.0e6 cells/mL in order to maintain high viability (>95%) and low density (not to exceed 3-5e6 cells/mL), thereby providing cells with fresh nutrients and avoiding transfection impediments caused by any secreted substances.

Prior to DNA transfection, Expi293 cells were counted and reseeded at 2.5e6 cells/mL in 50 mL shake flasks (TPP TubeSpin bioreactor tubes). The transfection procedure was performed using the Expifectamine kit. The manufacturer's protocol was adapted for a transfection in a total volume of 5 mL instead of 30 mL (i.e., all volumes were divided by a factor of 6). Five µg of each plasmid DNA was diluted in Opti-MEM reduced serum medium, complexed with Expifectamine transfection reagent, and transfected into Expi293 cells. The transfected pools were cultured with shaking at 225 rpm to ensure complete suspension of the cells within the 50 mL bioreactors. Following the manufacturer's protocol, Expifectamine kit enhancers were added after 16-18 hours, and the cultures analyzed by flow cytometry 2 days post-transfection.

Generation of Expi293-hNRP2 clonal cells stably overexpressing human NRP2. A plasmid (Origene Technologies Cat #RC220706) encoding the human NRP2 variant 2 transcript NM_003872 (hNRP2) fused to a Myc-DDK tag was purchased. The vector was PCR amplified using Q5 polymerase (New England Biolabs Cat #M0491) with the following primer pairs:

```
                                           (SEQ ID NO: 125)
5'-TGAGGATGACAAAGATTTGCAGCT-3'

(SEQ ID NO: 126)
5'-ACCGCGGCCGGCCGTTTATGCCTCGGAGCAGCACTT-3'

(SEQ ID NO: 127)
5'-AGTGCCAAGCAAGCAACTCAAA-3'

(SEQ ID NO: 128)
5'-AAGTGCTGCTCCGAGGCATAAACGGCCGGCCGCGGT-3'
```

The resulting PCR products were then fused, cut with MfeI/AgeI (New England Biolabs Cat #R3589, R3552), and ligated into a vector fragment of RC220706 cut with the same enzymes. This vector, containing an untagged hNRP2 transcript, was then linearized and re-suspended in 10 mM Tris-0.1 mM EDTA. Suspension Expi293 cells (ThermoFisher Cat #A14527), were grown in expression medium (ThermoFisher Cat #A1435101) at 37° C. and 8% $CO_2$. The linearized plasmid described above was transfected into Expi293 cells using an SF Cell Line 4D-Nucleofector® X Kit L (Lonza Cat #V4XC-2012) and standard protocol T-030 for suspension HEK293 cells. Cells were allowed to recover in static culture for 17 hours, transferred to suspension and recovered an additional 72 hours, and then were selected with 200-350 μg/mL G418 in 50 μg increments (ThermoFisher Cat #10131035). Cell densities and viabilities were monitored for a period of 3 weeks, with fresh media/antibiotic replacement every 2-3 days.

To select hNRP2 over-expressing clonal cells, cells were suspended into 96-well plates by limited dilution. Single colonies were transferred to falcon tubes for further expansion under maintained selection pressure. Clonal cells that over-express human NRP2 were validated by a-NRP2 staining followed with flow cytometry analysis.

Binding of a-NRP2 to Expi293-hNRP2 clonal cells or cynomolgus monkey NRP2-transfected Expi293 cells. Expi293-hNRP2 clonal cells or cynomolgus monkey (cyno) NRP2-transfected Expi293 cells were collected by centrifugation at 300 g for 5 minutes, and washed twice by DPBS with calcium and magnesium (ThermoFisher Cat #14040133). Washed cells were added to a 96-well V-bottom plate (ThermoFisher Cat #1424572) at 100,000 cells/well in 25 μL of DPBS with calcium and magnesium. 25 μL Zombie Violet viability stain (Biolegend Cat #423114, diluted at 1:250) was added to each well except the no-stain control. From this step on, cells were protected from light. Cells were kept at room temperature for 10 min and pelleted down at 300 g for 5 minutes at 4° C. Supernatants containing Zombie Violet were discarded, and without washing, 30 uL of antibodies diluted in the flow wash buffer (FWB, DPBS with calcium and magnesium plus 2% FBS) were added to the cells. For a-NRP2 staining on Expi293-hNRP2 clonal cells, in-house mouse anti-NRP2 antibodies were tested at final concentrations of 0.05-30 nM or 0.02-10 nM at 3-fold dilutions. For a-NRP2 staining on Cyno NRP2-transfected Expi293 cells, in-house a-NRP2 antibodies were tested at final concentrations of 0.01-200 nM at a 5-fold dilution. For each test, NRP2 over-expression on the cell surface was validated by a-NRP2 staining (in-house aNRP2-2v2-1327 at 5 μg/mL and/or 10 pg/mL R&D #AF567 a-NRP2) in separate wells. Binding was allowed to proceed on ice for 1 hour. Cells were then pelleted at 300 g for 5 minutes at 4° C., supernatants removed, and cells washed twice by adding 150 μL of FWB and centrifuging the cells again in the same conditions. To detect a-NRP2 binding on the cell surface, AF647-conjugated goat anti-mouse IgG or AF647-conjugated donkey anti-goat IgG (Jackson ImmunoResearch Cat #115606062 & 705605147) was added to the cells at a final concentration of 2.5 pg/mL in 30 μL of FWB. After 30-45 minutes of incubation on ice, cells were pelleted at 300 g for 5 minutes at 4° C. and supernatants removed, and the cells were washed twice as described previously. Cells were then resuspended in FWB before acquisition on the Cytoflex. Gains were set based on staining controls. Cells were collected with typically more than 10,000 events. Cells were then analyzed on FlowJo analysis software by excluding dead cells.

As additional controls, the following conditions were tested: 1) An isotype control mouse IgG1 (Biolgend Cat #400102) was used instead of the mouse anti-NRP2 antibody to demonstrate the specificity of the staining; and 2) Staining with aNRP2-2v2-1327 or R&D #AF567 a-NRP2 was also determined using mock- and non-transfected Expi293 cells to demonstrate over-expression of human or Cyno NRP2 on Expi293 cells. The statistical analysis was performed using GraphPad Prism. A four-parameter variable-slope curve was fitted to the data ([agonist] vs. response) using non-linear regression, and the $EC_{50}$ and r2 for each curve was determined.

The $EC_{50}$ of four anti-NRP2 antibodies, each against a distinct domain of NRP2, were measured for binding to both human and Cyno NRP2-transfected Expi293 cells (Table E5). They all showed specific binding to NRP2 with $EC_{50}$, in the nanomolar range. By contrast, no binding was observed by the isotype control mouse IgG1 antibody.

TABLE E5

Comparison of binding affinity to human and cynomolgus monkey NRP2

| Antibody clone | Domain Specificity | EC50 Human (nM) | EC50 Cyno (nM) |
|---|---|---|---|
| 18B8 aNRP2-14 | a2 | 0.9 | 5.5 |
| 1E3 aNRP2-10 | b1 | 0.4 | 1.2 |
| 13D7 aNRP2-11 | b2 | 0.9 | 4.5 |
| 3F2 aNRP2-2 | c | 2.0 | 1.8 |
| Isotype control antibody | n.d | n.d | No binding |

The results from these studies demonstrate that each of the tested antibodies showed comparable binding affinities to human and cyno NRP2, which affinities that were all low nanomolar and within about 5-6 fold of each other between species.

EXAMPLE 5

Binding of Anti-Human Neuropilin 2 Antibodies to Cells Natively Expressing NRP2

Figure 3:
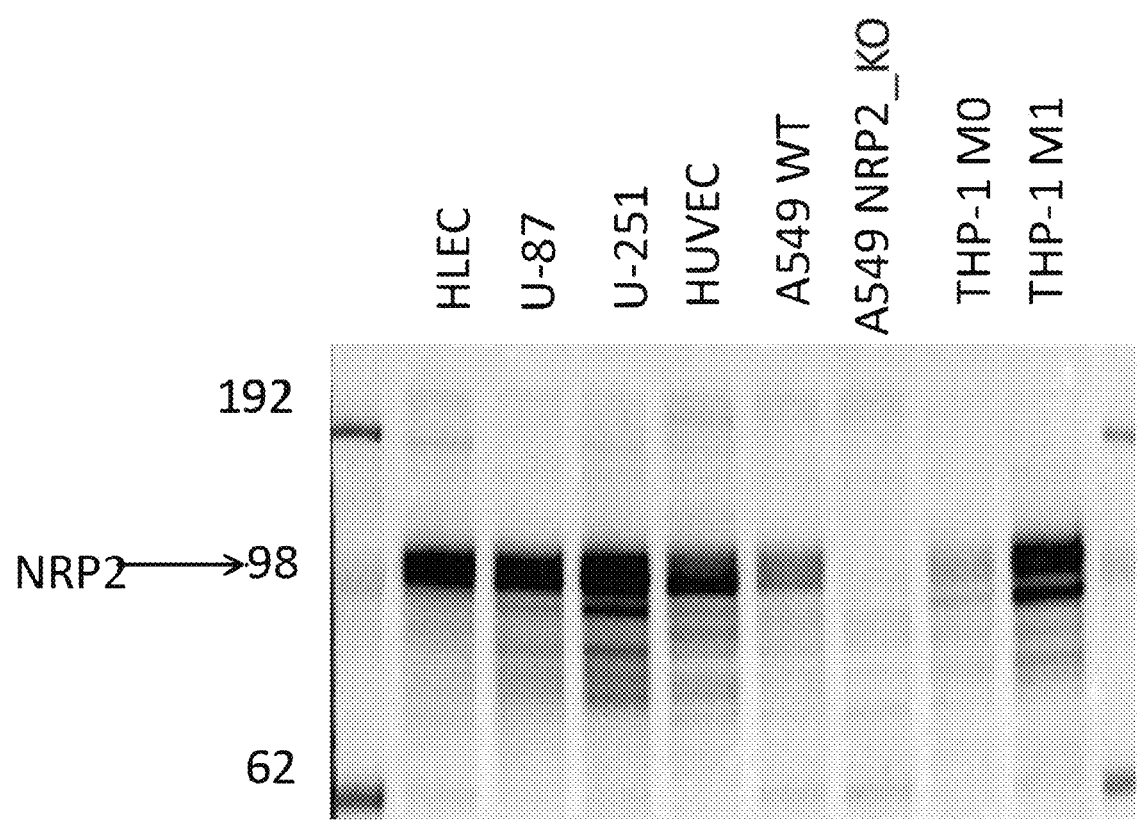
FIG. 3 shows a western blot of the indicated cell lines blotted with a commercially available antibody against human NRP2 (BAF2215, Boster, CA), using 6 µg of total cell lysate per lane. Molecular weight makers are shown in the outer lanes.
Figure 4A:
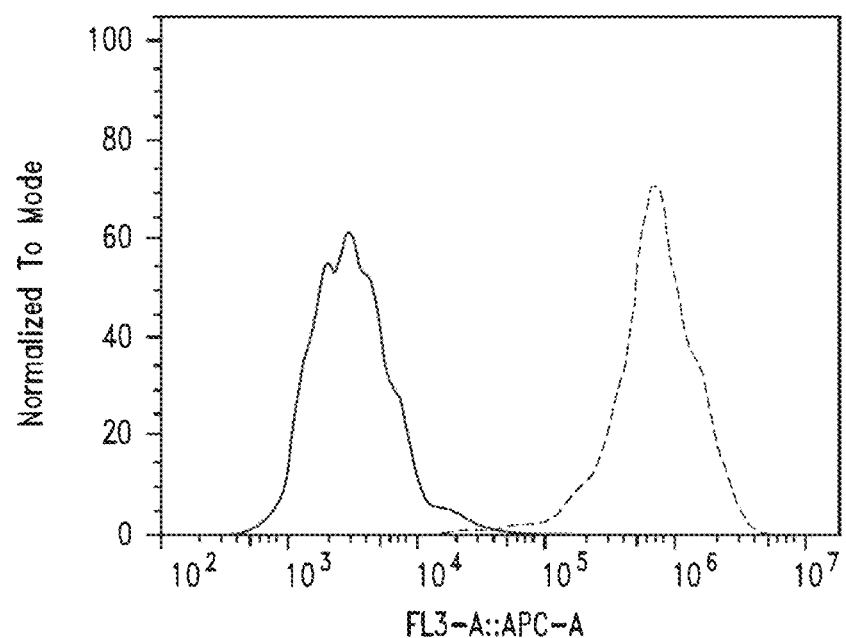
FIGS. 4A-4D show flow cytometry cell surface binding plots on the indicated cell lines using the c domain specific anti-NRP2 antibody 3F2 (aNRP2-2), which was detected using an AF647-conjugated goat anti-mouse IgG secondary antibody (GaM AF647). Binding of the secondary antibody alone is shown in lighter grey (left curve in each Figure).
Figure 4B:
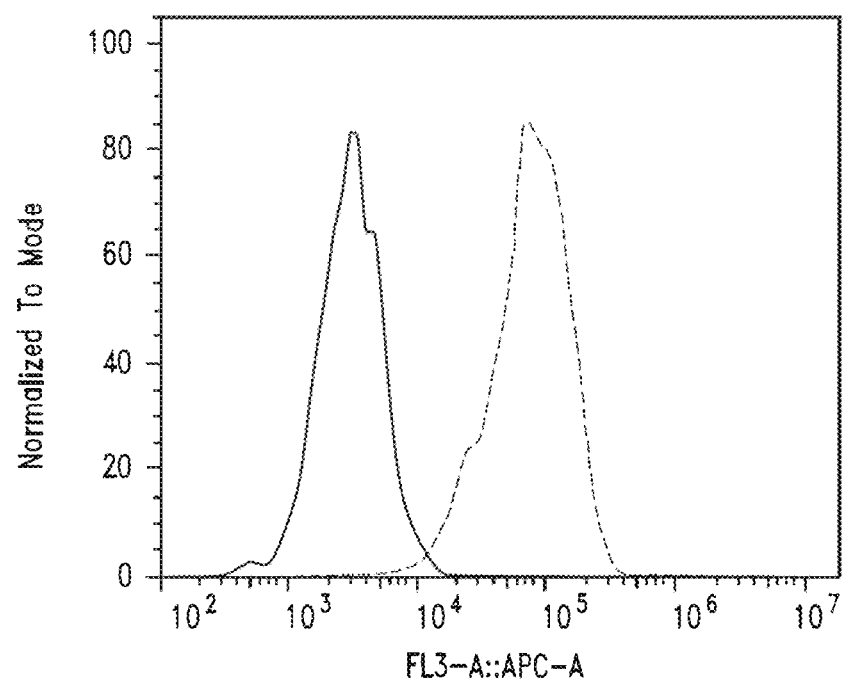
Figure 4C:
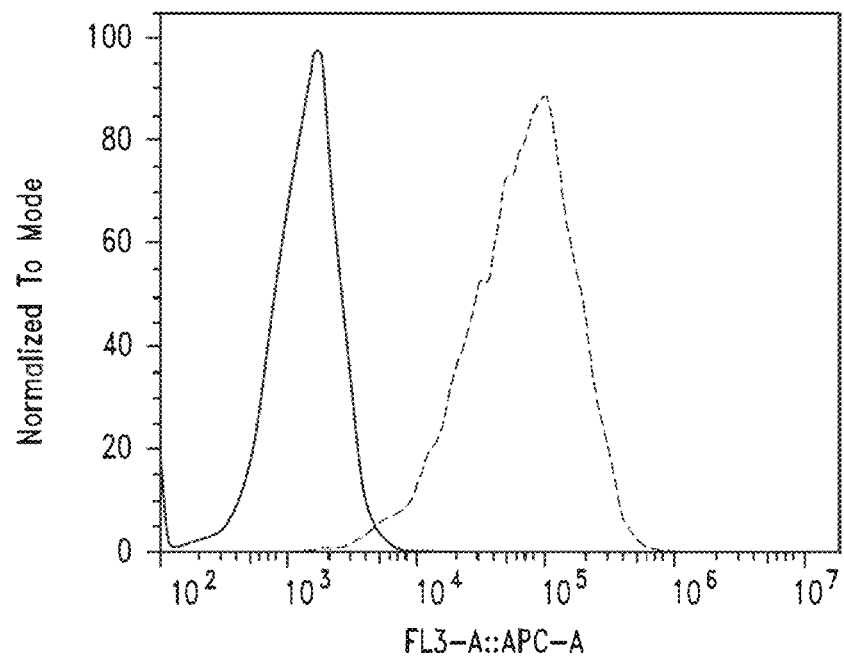
Figure 4D:
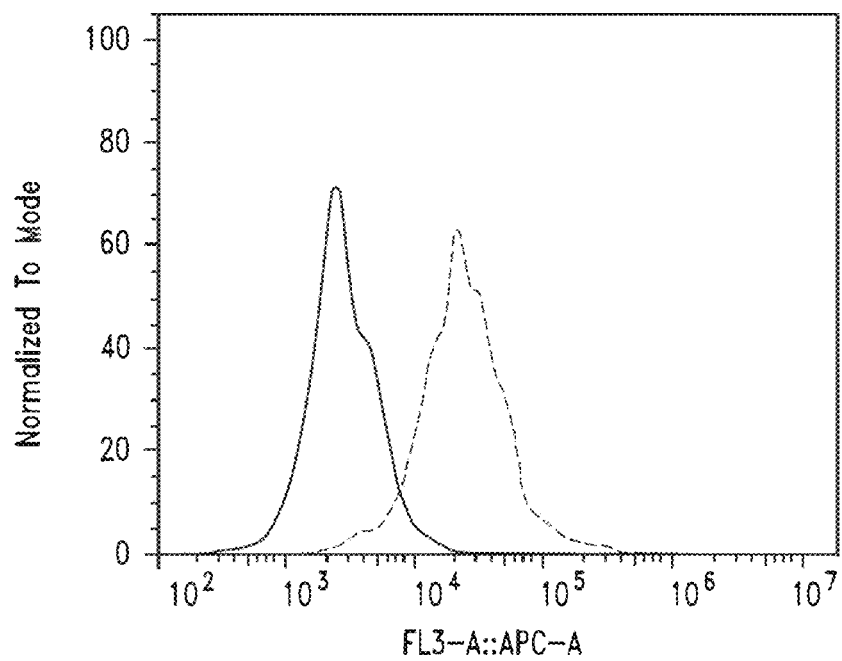
Figure 5A:
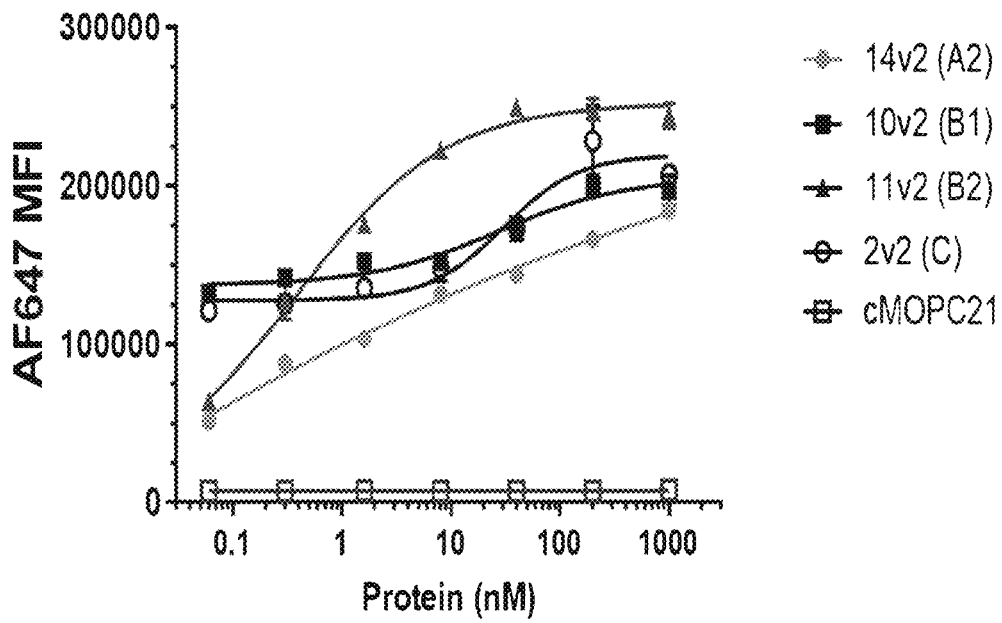
FIGS. 5A-5D show flow cytometry surface binding plots to various cell lines using the specified anti NRP2 antibodies. Antibody binding was detected using an AF647-conjugated goat anti-mouse IgG secondary antibody (GaM AF647).
Figure 5B:
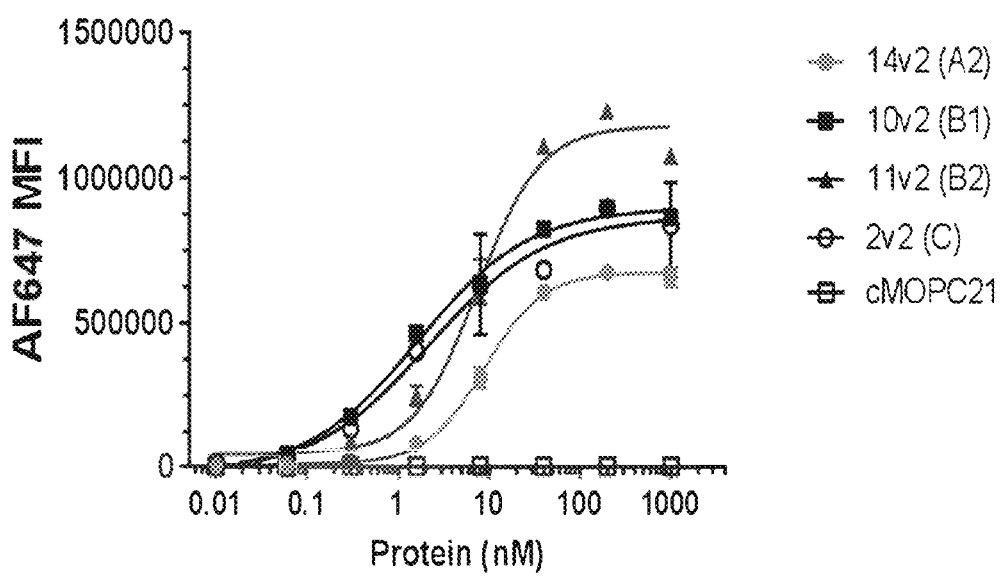
Figure 5C:
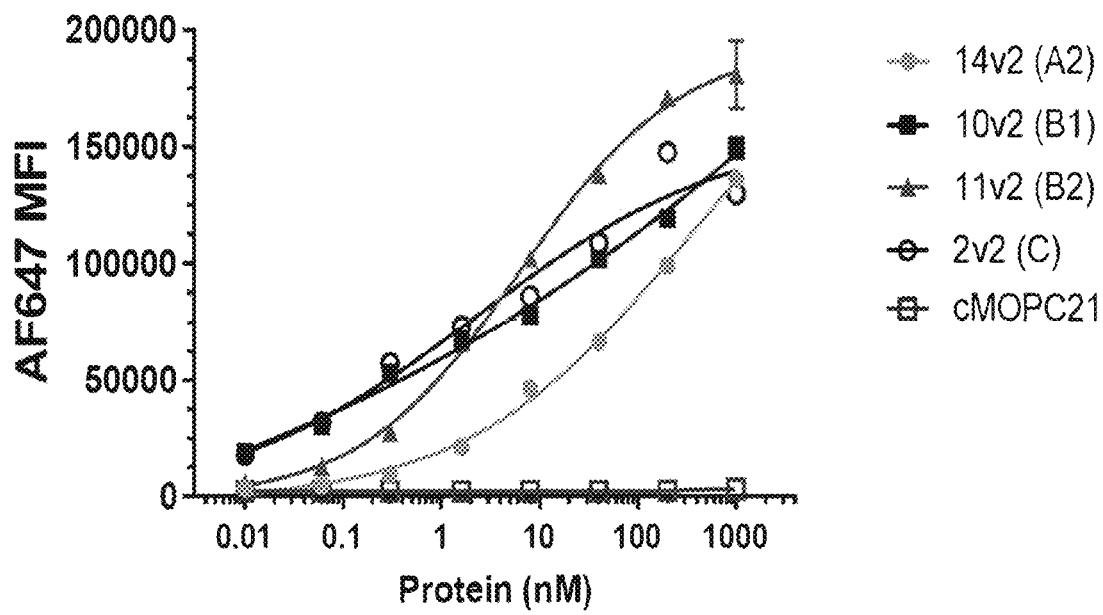
Figure 5D:
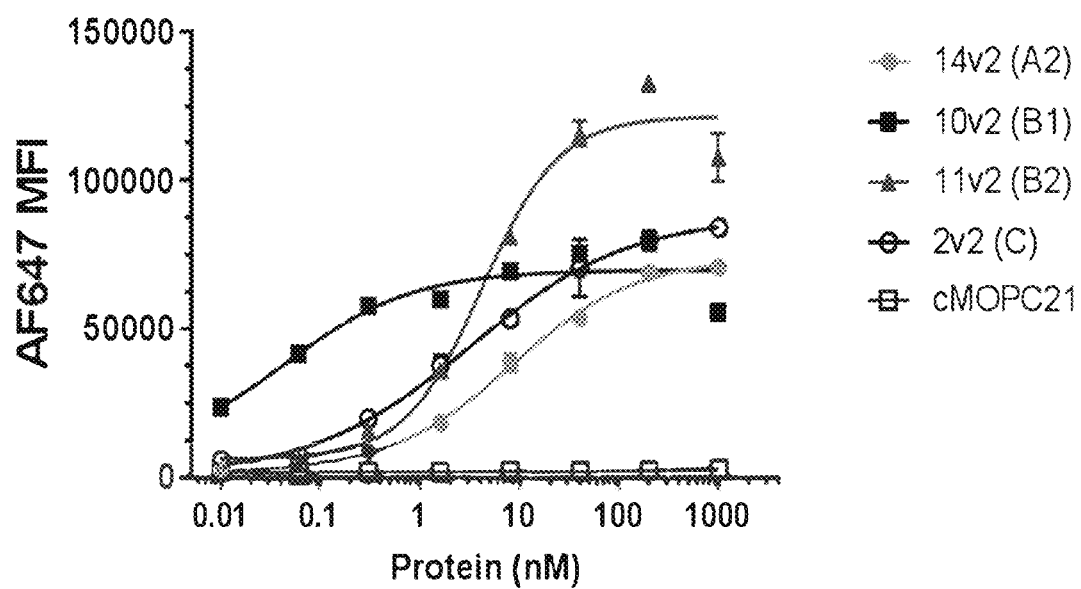

To evaluate binding of the anti-NRP2 antibodies to natively expressing cells, flow cytometry was conducted on a variety of cell lines known to endogenously express NRP2. To initially assess NRP2 expression levels western blots were conducted using 6 μg total cell lysate, and probed with the commercially available anti-NRP2 antibody BAF2215 (Boster Biological Technology, California, USA), following standard methodology. Cell lines tested included U251 (Glioblastoma), A549 (lung cancer), HUVECs (human umbilical vein cells), THP-1 (human macrophage cell line pre-differentiated towards an M1 phenotype), and HLEC (Human lymphatic endothelial cells). Flow cytometry analysis was conducted essentially as described in Example 4. Western blot results are shown in FIG. 3, and flow cytometry results are shown in FIGS. 4 and 5. Flow cytometry binding data is also summarized in Table E6 (below).

TABLE E6

BINDING OF ANTI-HUMAN NEUROPILIN 2 ANTIBODIES TO CELLS NATIVELY EXPRESSING NRP2.

| Cell Type | Tested Ab range (nM) | NRP2 level 3F2 vs Ctl FC* | a-NRP2 cell surface binding EC50 (nM) | | | | |
|---|---|---|---|---|---|---|---|
| | | | 18B8 aNRP2-14 | 1E3 aNRP2-10 | 13D7 aNRP2-11 | 3F2 aNRP2-2 | Isotype control |
| U251 | 0.01-1000 | 214.6 | 8.9 | 1.7 | 7.4 | 2.2 | No binding |
| HUVEC | 0.06-1000 | 21.9 | Not saturated | 27.1 | 0.4 | 30.3 | No binding |
| HLEC | 0.06-1000 | 8.6 | n.d | n.d | n.d | n.d | n.d |
| THP-1 M1 | 0.01-1000 | 33.7 | 8.4 | 0.1 | 4.2 | 3.3 | No binding |
| THP-1M0 | 0.01-1000 | 3.0 | n.d | n.d | n.d | n.d | n.d |
| THP-1 WT | 0.01-1000 | 25.2 | n.d | n.d | n.d | n.d | n.d |
| A549 | 0.01-1000 | 25.2 | Not saturated | Not saturated | 6.3 | 2.3 | No binding |

The results of these studies show that the anti-NRP2 antibodies show good specificity for a wide range of cells that endogenously express NRP2. The results confirm that the tested antibodies show high sensitivity to human NRP2 endogenous expressed on the cell surface on a broad range of cell types including cells derived from neuronal, epithelial, immune, lung, and cancer lineages.

EXAMPLE 6

Ligand Displacement Studies with Cells Overexpressing NRP2

To assess the ability of the anti-NRP2 antibodies to displace the binding of VEGF-C, Semaphorin 3F and HRS polypeptides, flow cytometry was used. Binding of recombinant human VEGF-C(R&D Cat #9199-VC-025, untagged), Sema3F-Fc (R&D Cat #9878-53-025, Fc chimera protein) or Sema3F-p95m (prepared In-house), Myc-tagged Sema3F-p95 R583A R586A-1359) to Expi293-hNRP2 cells over expressing human NRP2 were determined by immunostaining assay as described in Example 4. Studies were conducted with cells incubated with each of these proteins at 0.05-100 nM at 3-fold dilutions on ice for 1 hour. Cells were then washed and stained with secondary and/or detection antibodies as described previously. VEGF-C bound on the cell surface were stained by a rabbit anti VEGF-C antibody (Abcam Cat #AB9546), followed with the detection by an AF647-conjugated goat anti-rabbit IgG (Jackson ImmunoResearch Cat #111605144). Sema3F-Fc was detected by a Cy3-conjugated goat anti-human Fc IgG (Jackson ImmunoResearch Cat #109165098). Sema3F-p95m was detected by an AF555-conjugated anti-Myc antibody (ThermoFisher Cat #MA1980A555).

Binding curves were fit and $EC_{50}$ values determined as described above. VEGF-C was determined to bind to Expi293-hNRP2 cells with an $EC_{50}$ of 0.6 nM. Sema3F-Fc was determined to bind to Expi293-hNRP2 cells with an $EC_{50}$ of ~8.2 nM, and Sema3F-p95m bound to Expi293-hNRP2 cells with an with $EC_{50}$ of 5.7 nM.

For anti-NRP2 blocking of VEGF-C binding, Expi293-hNRP2 cells were first incubated with anti-NRP2 for 30 min on ice. Without washing, VEGF-C was added at 0.6 nM to the cells. After 1 hour of incubation on ice, cells were washed and then incubated with the rabbit anti VEGF-C antibody, followed with the detection by the AF647-conjugated goat anti-mouse IgG as described above.

For anti-NRP2 blocking of Sema3F binding, Expi293-hNRP2 cells were first incubated with anti-NRP2 for 30 min on ice. Without washing, Sema3F-p95m was added at 6 nM to the cells. After 1 hour of incubation on ice, cells were washed and then incubated with the AF555-conjugated anti-Myc antibody as described above.

Statistical analysis was performed using GraphPad Prism. A four-parameter variable-slope curve was fitted to the data ([Inhibitor] vs. response) using non-linear regression, and the $IC_{50}$ and r2 for each curve was determined.

Figure 6A:
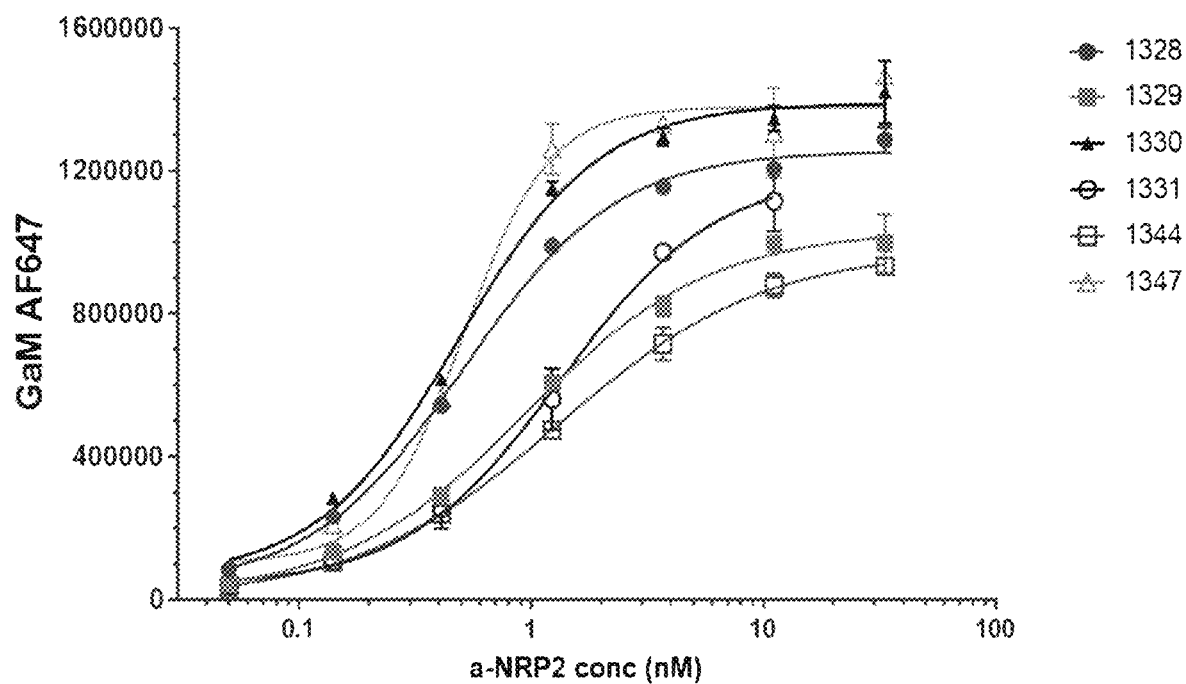
FIGS. 6A-6B show anti-NRP2 antibody binding curves to Expi293-hNRP2 clonal cells over-expressing human NRP2.
Figure 6B:
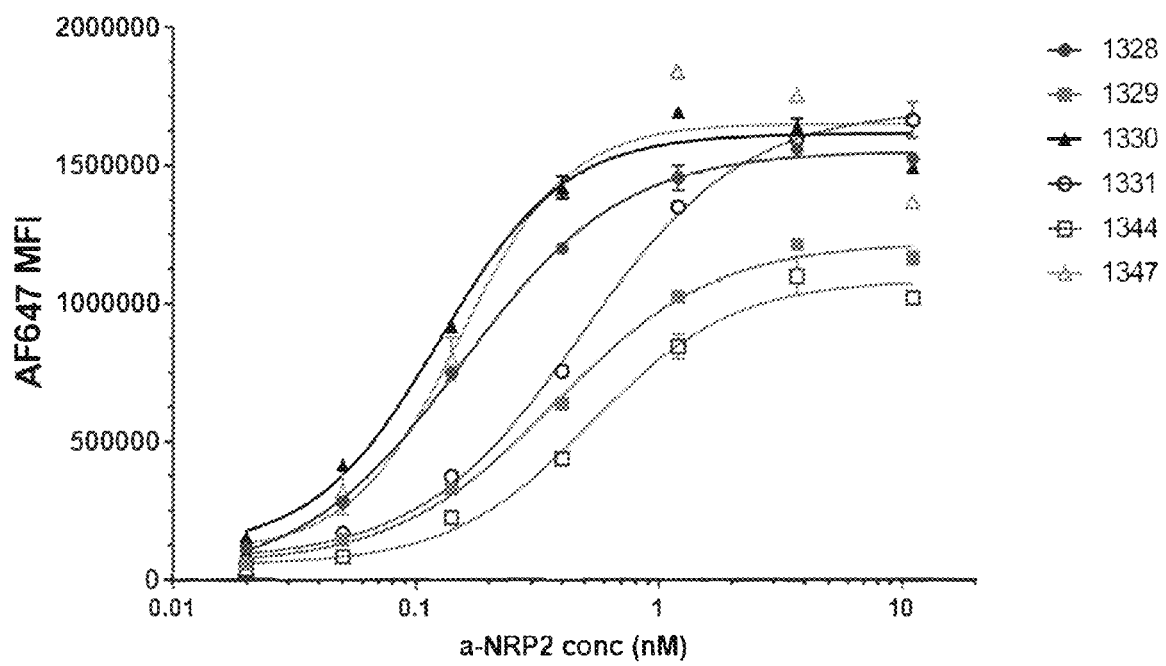
Figure 7A:
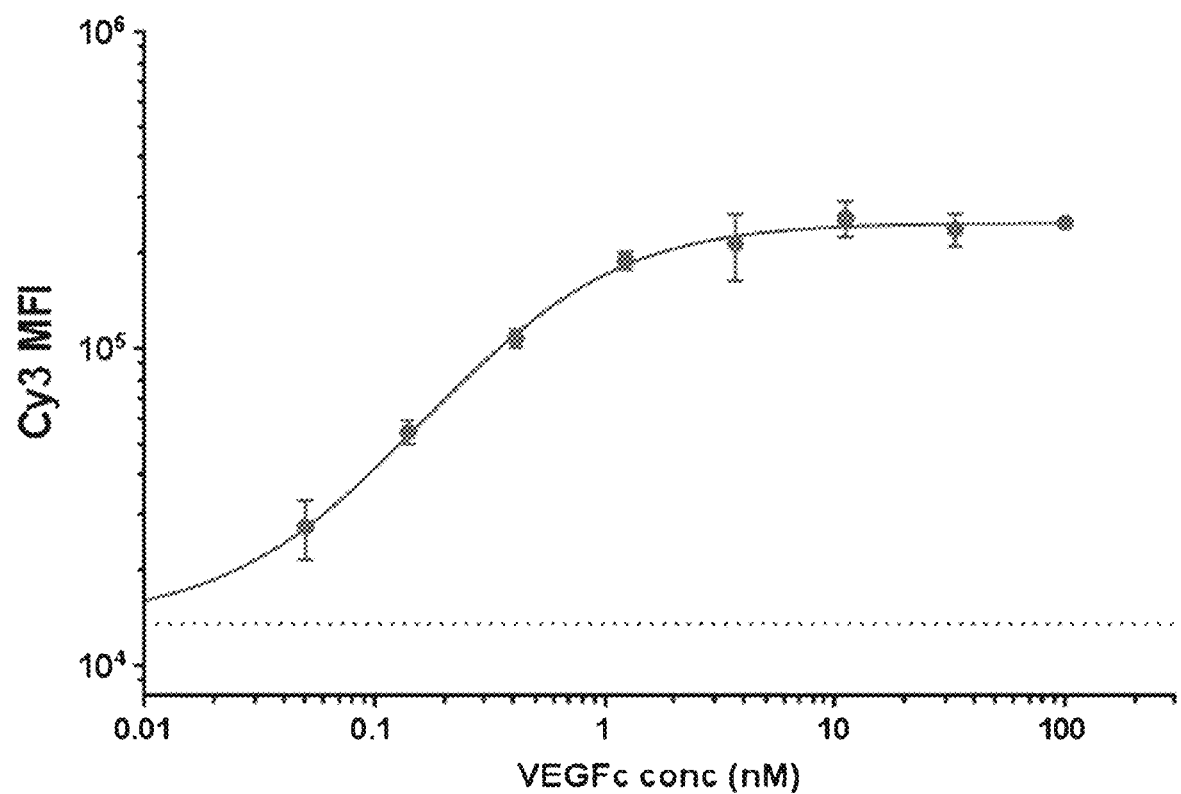
FIGS. 7A-7B show the binding of VEGF-C to Expi293-hNRP2 clonal cells over-expressing human NRP2.
Figure 7B:
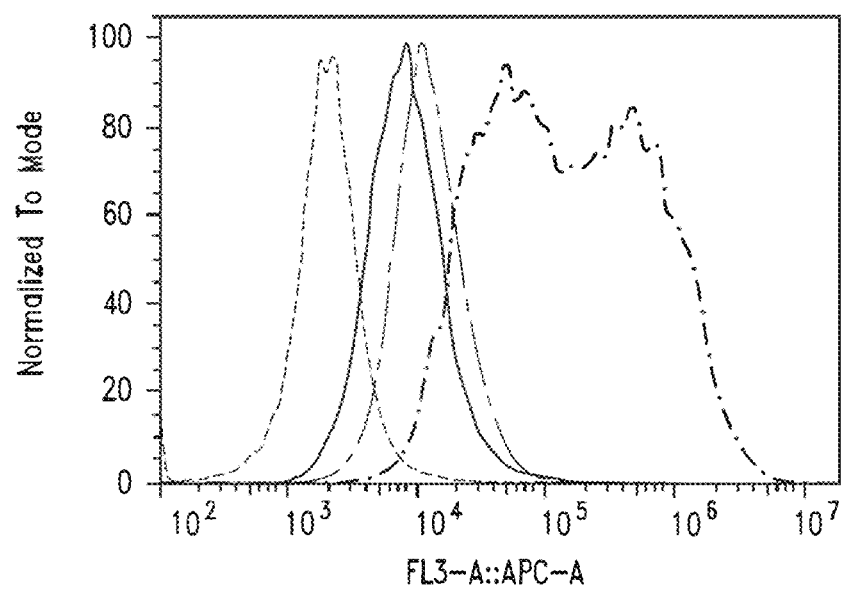
Figure 8F:
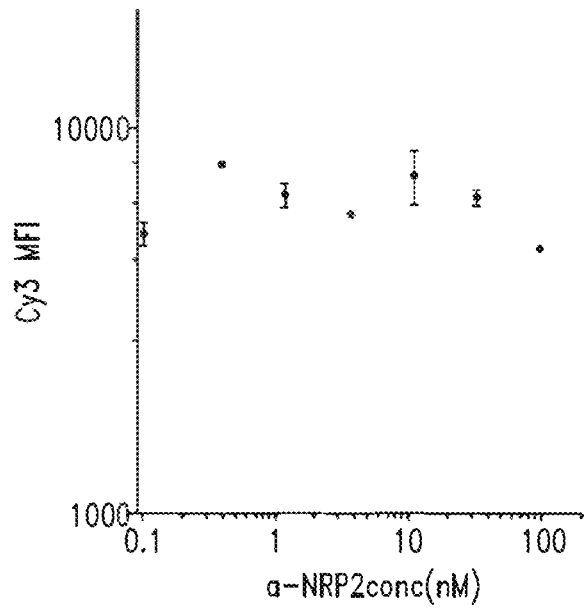
Figure 8G:
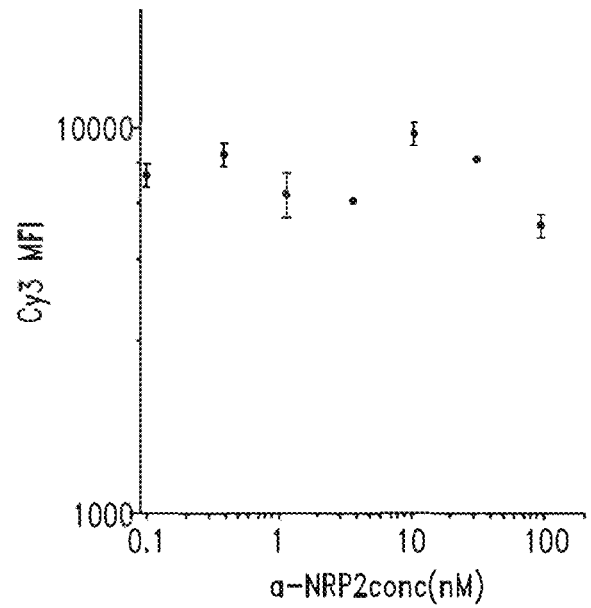
Figure 8H:
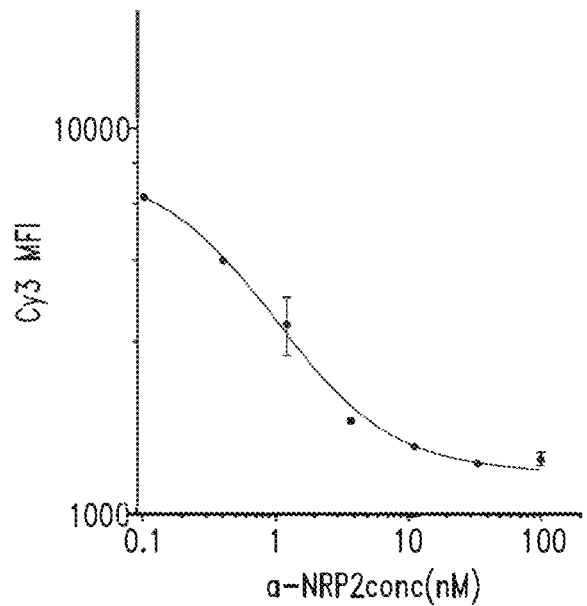
Figure 8I:
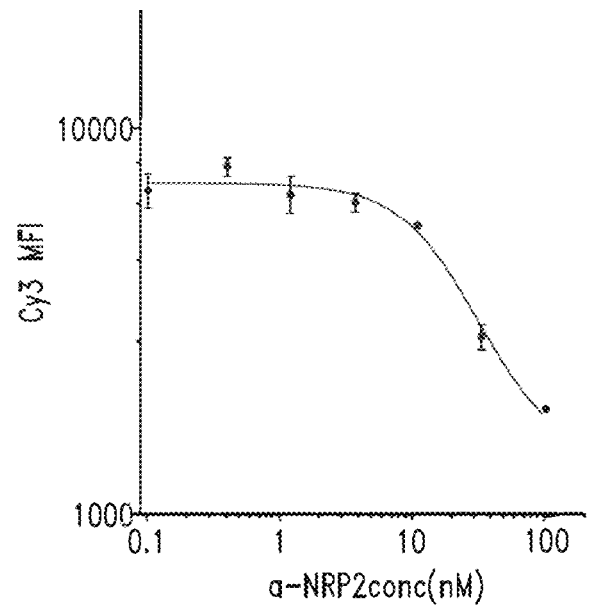
Figure 8J:
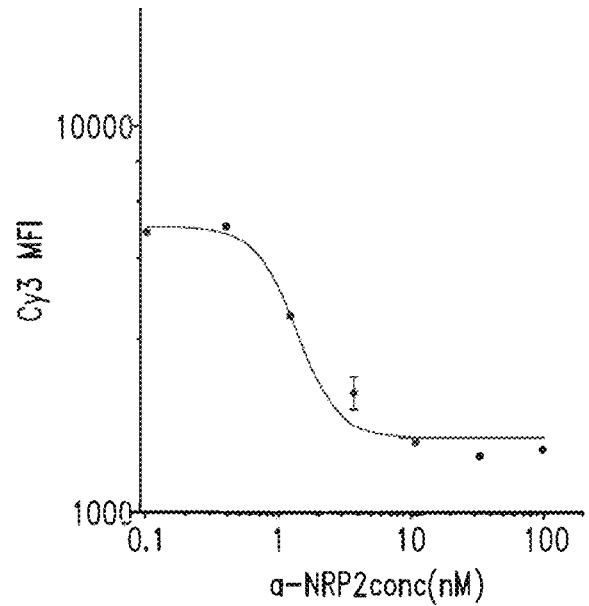
Figure 8K:
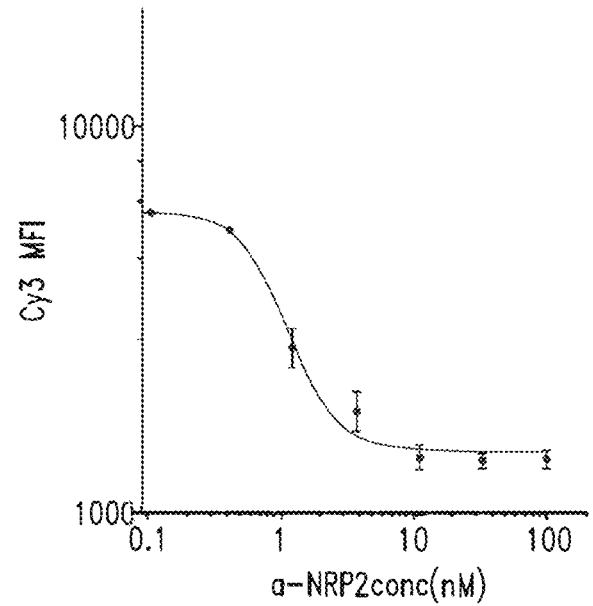
Figure 8L:
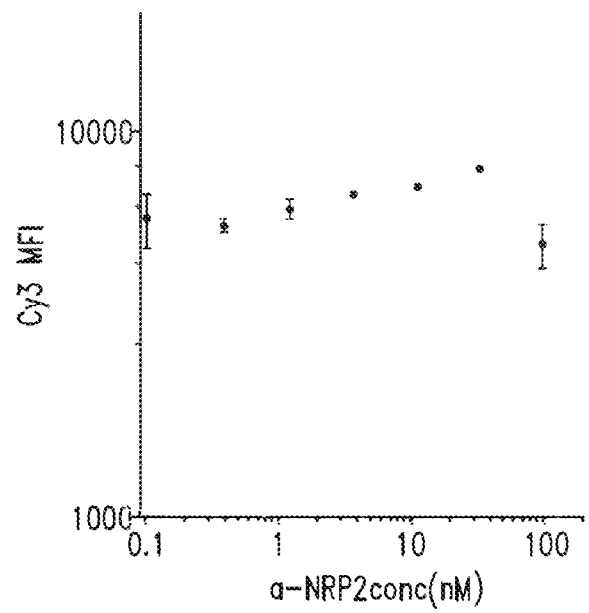
Figure 8M:
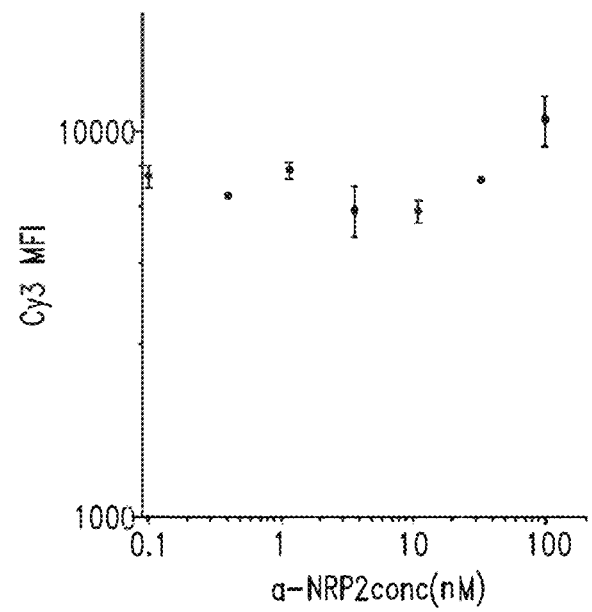
Figure 9:
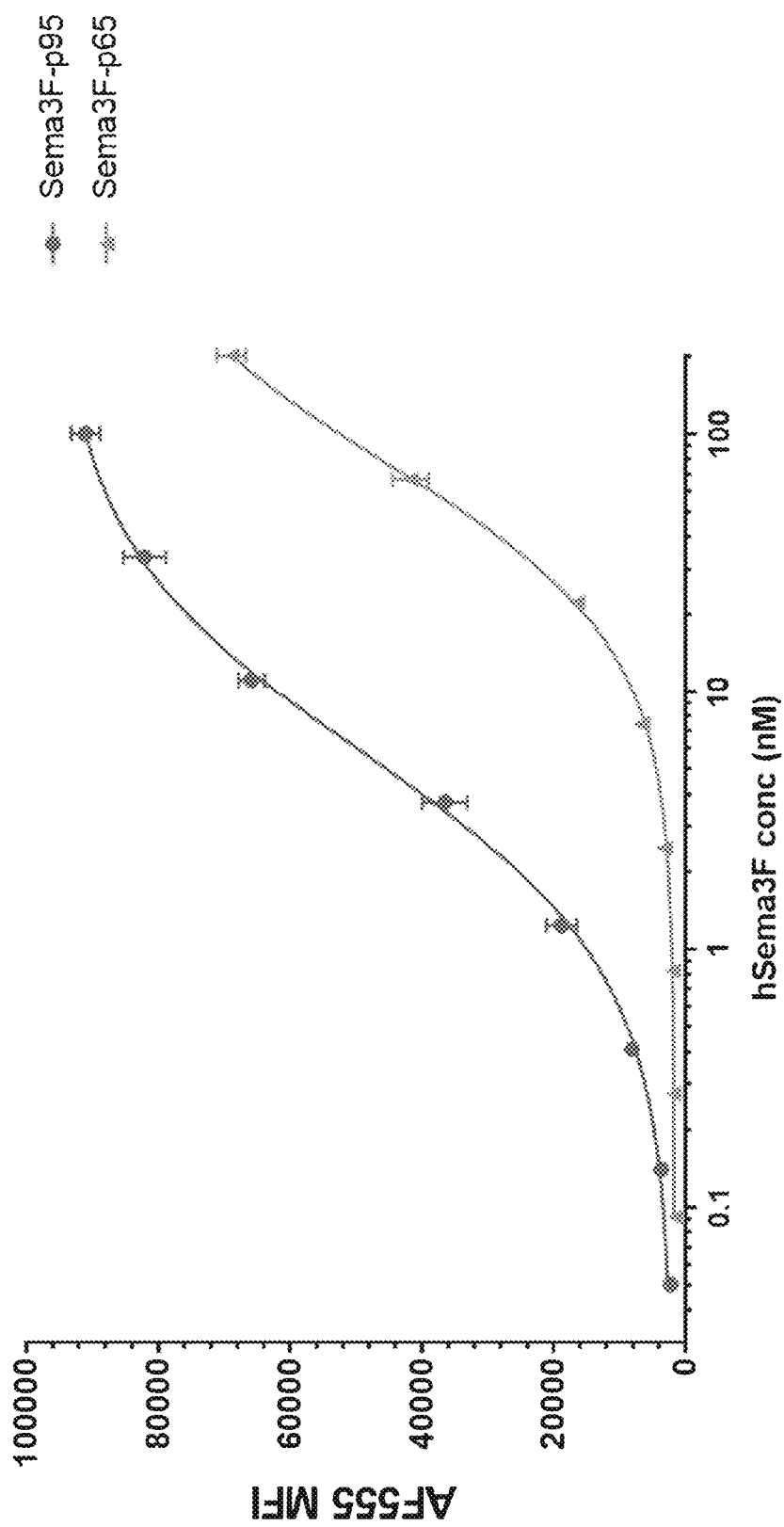
FIG. 9 shows the binding of Sema3F-p95 and Sema 3F-p65 (0.05-100 nM) to Expi293-hNRP2 clonal cells over-expressing human NRP2.
Figure 10A:
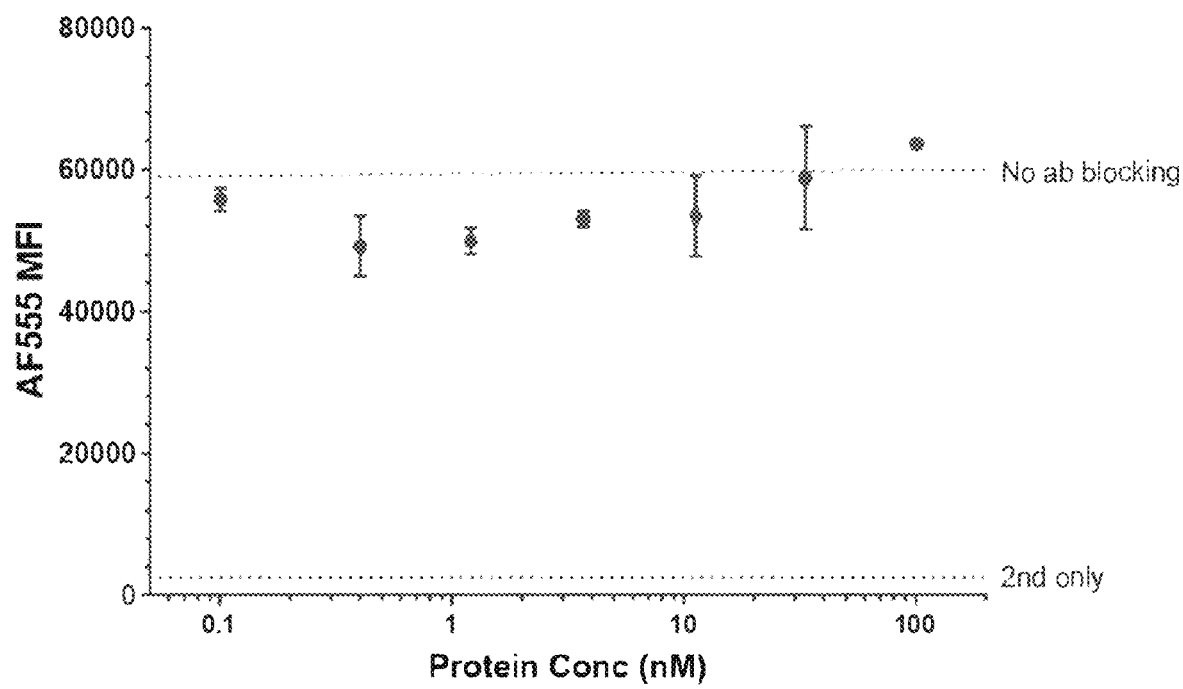
FIGS. 10A-10H show anti-NRP2 antibody blocking, displacement curves for the indicated antibodies on Sema 3F-p95 binding to Expi293-hNRP2 clonal cells over-expressing human NRP2.
Figure 10B:
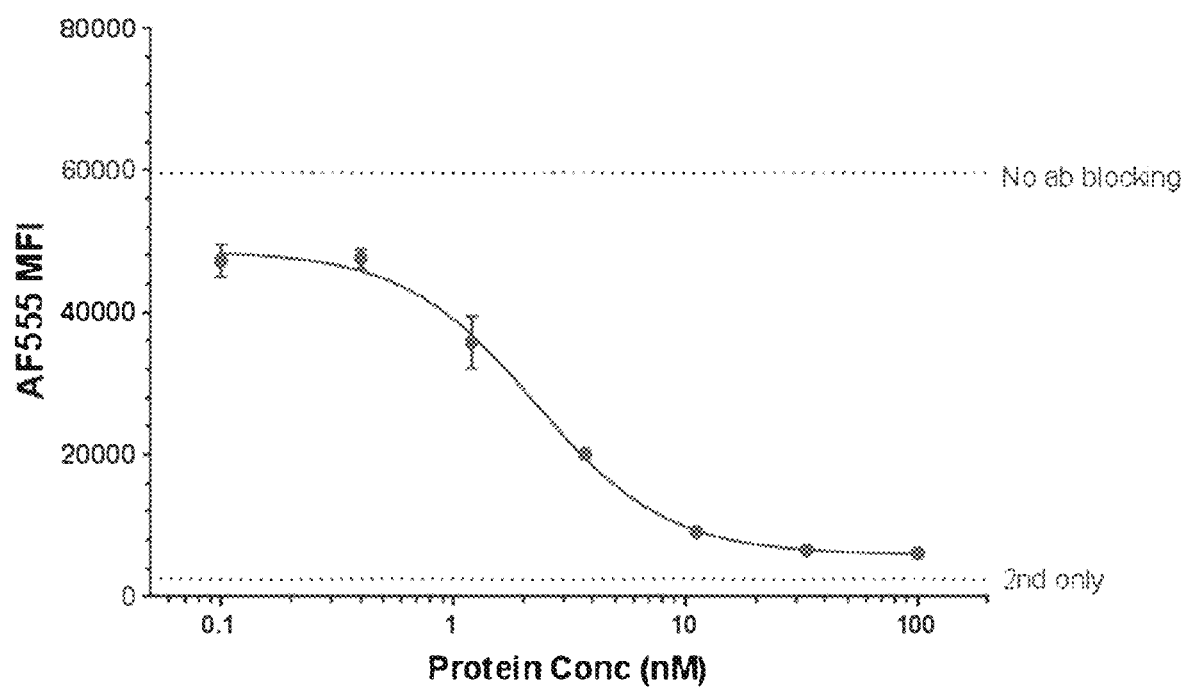
Figure 10C:
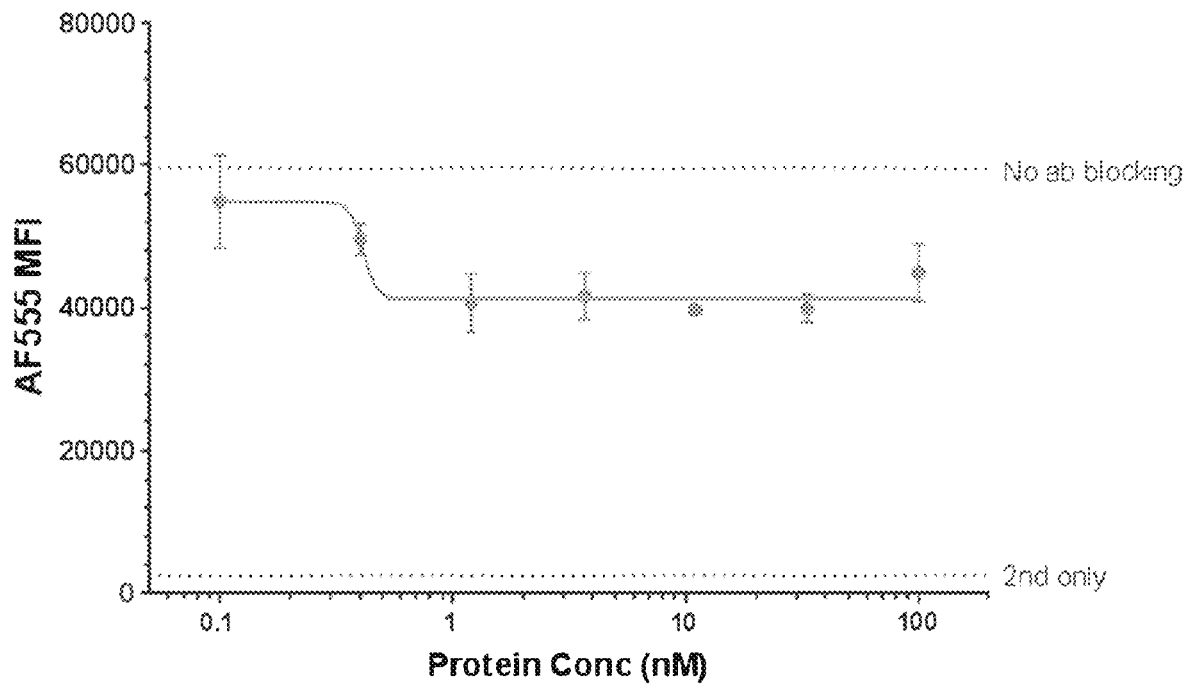
Figure 10D:
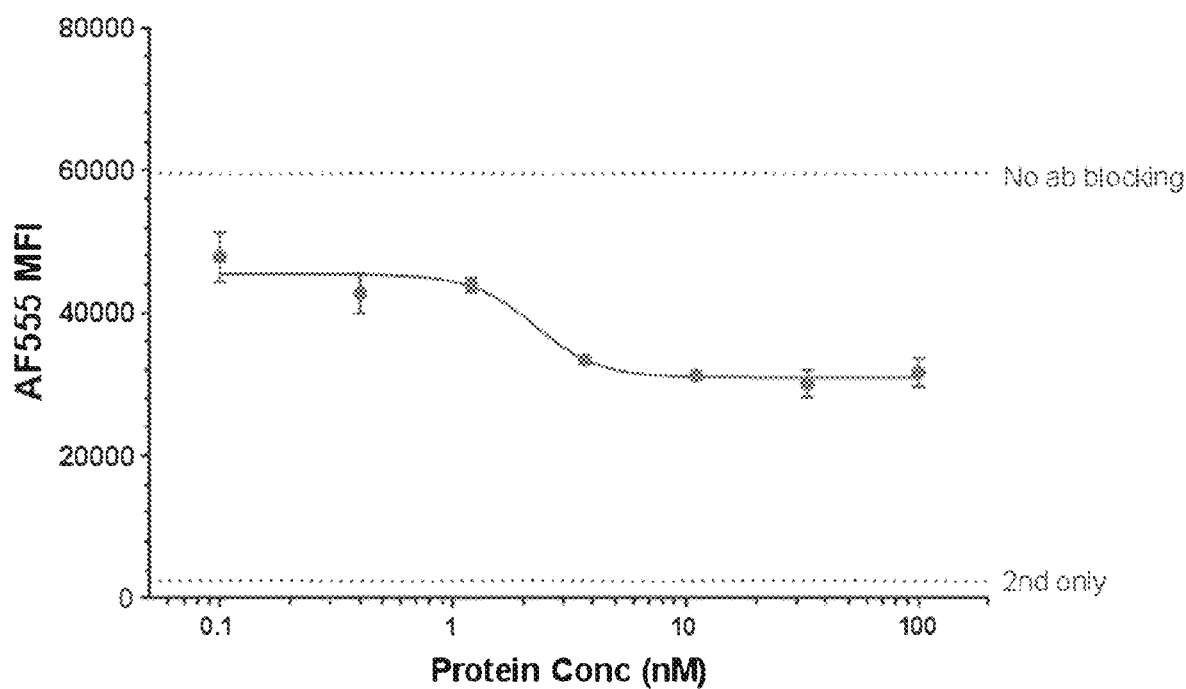
Figure 10E:
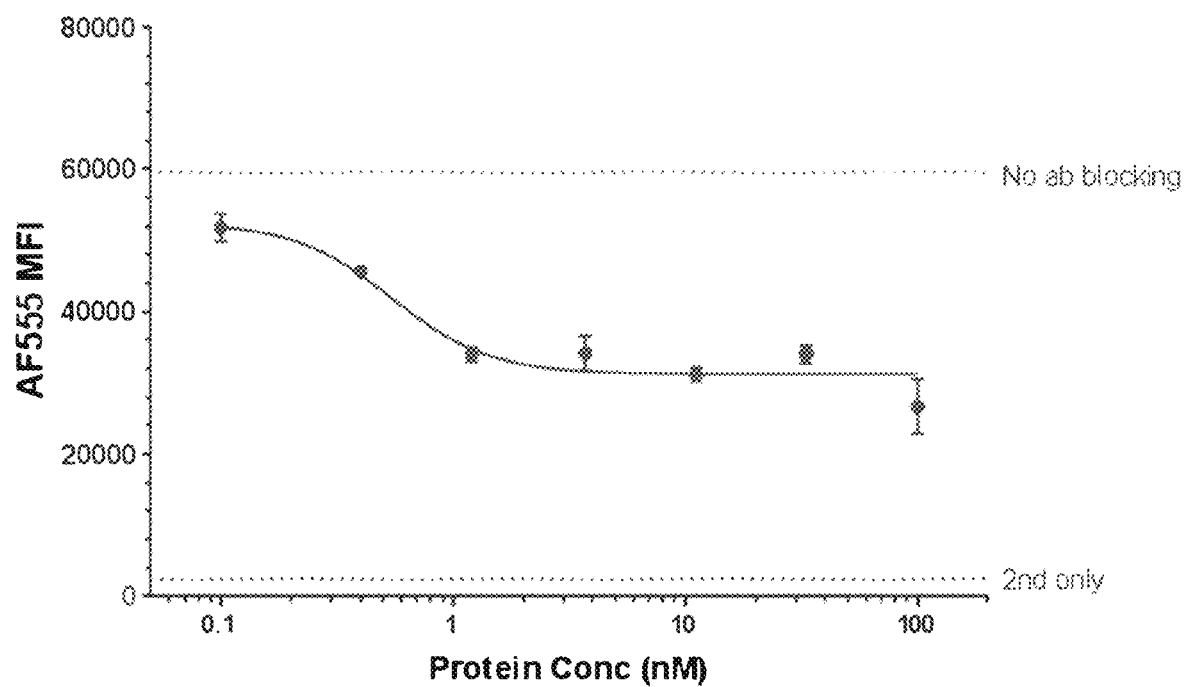
Figure 10F:
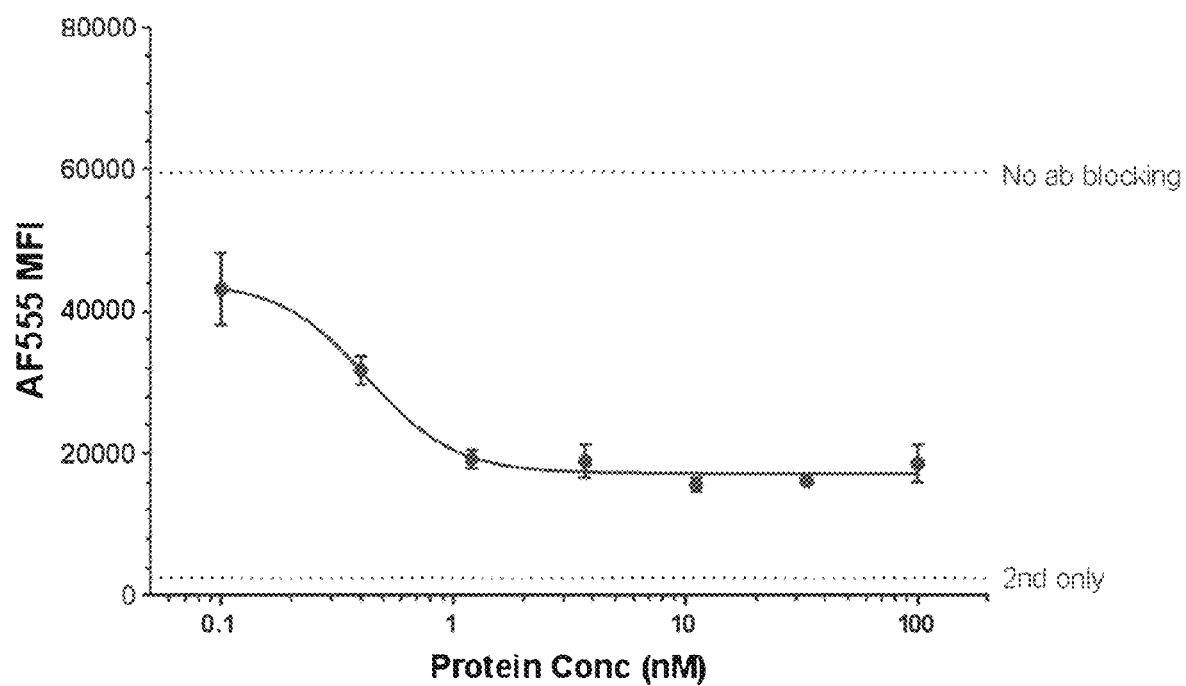
Figure 10G:
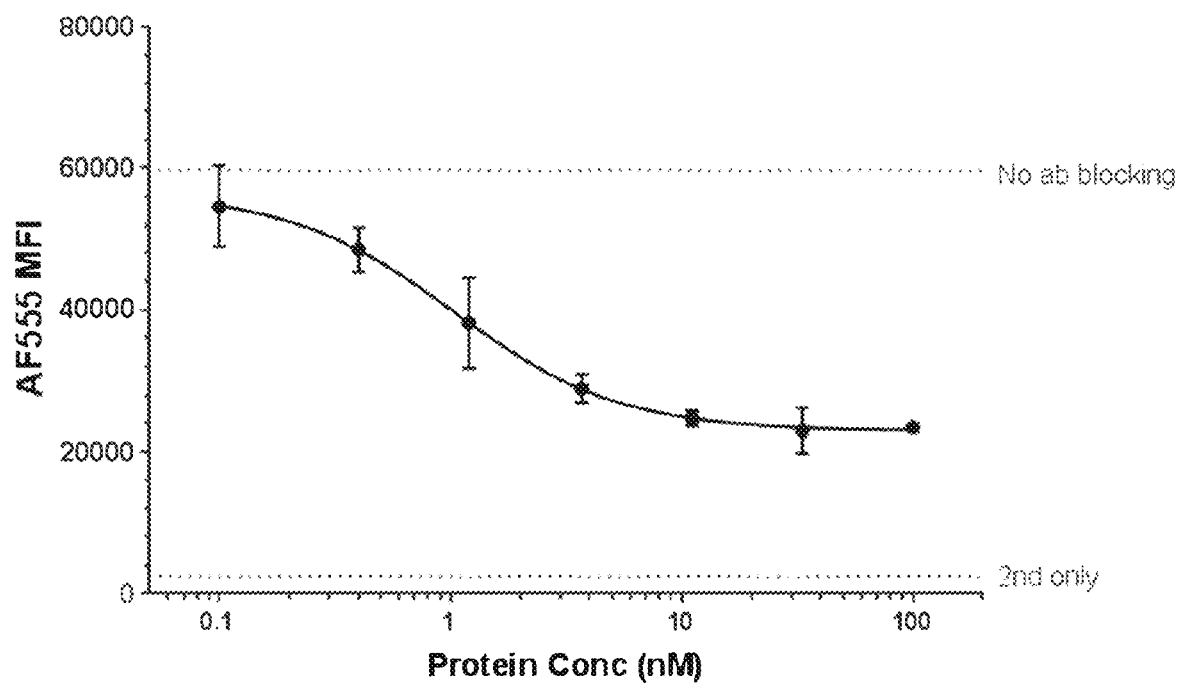
Figure 10H:
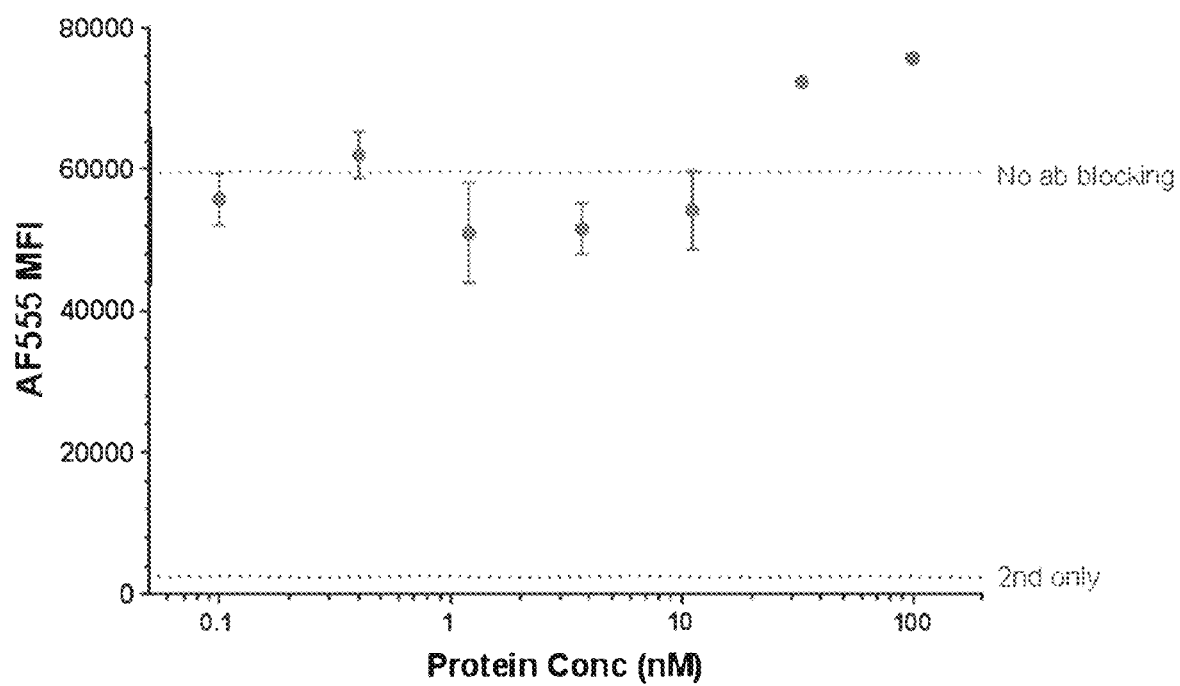
Figure 11A:
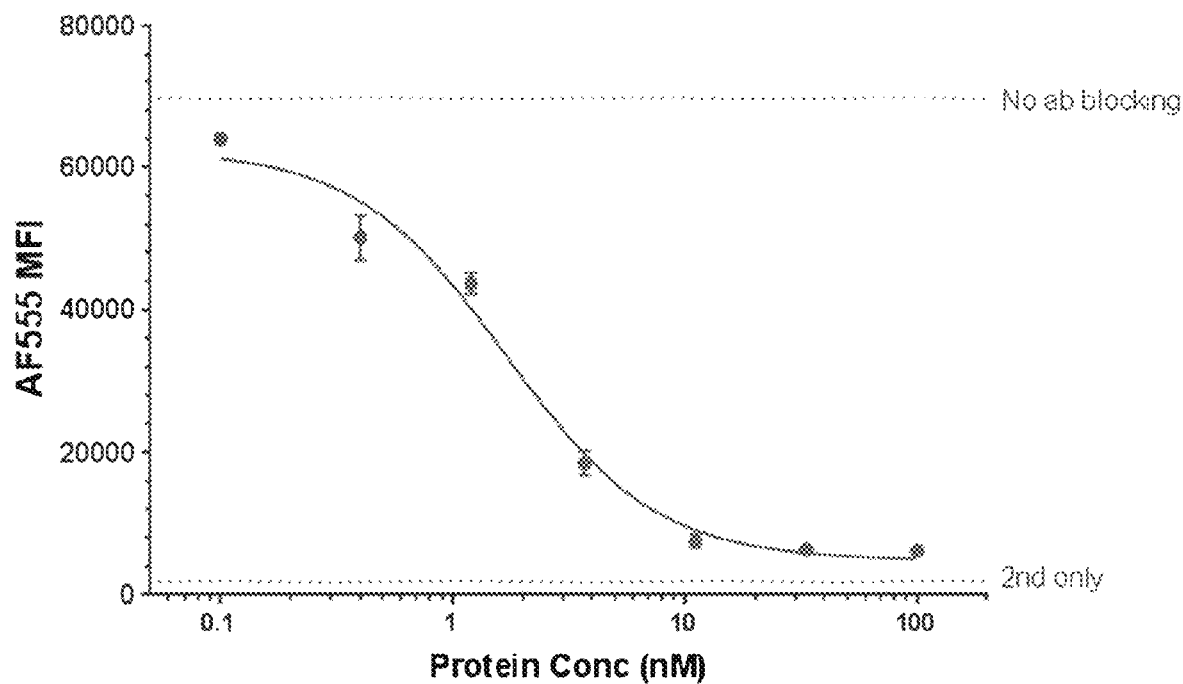
FIGS. 11A-11F show anti-NRP2 antibody blocking, displacement curves for the indicated antibodies on Sema 3F-p95 binding to Expi293-hNRP2 clonal cells over-expressing human NRP2.
Figure 11B:
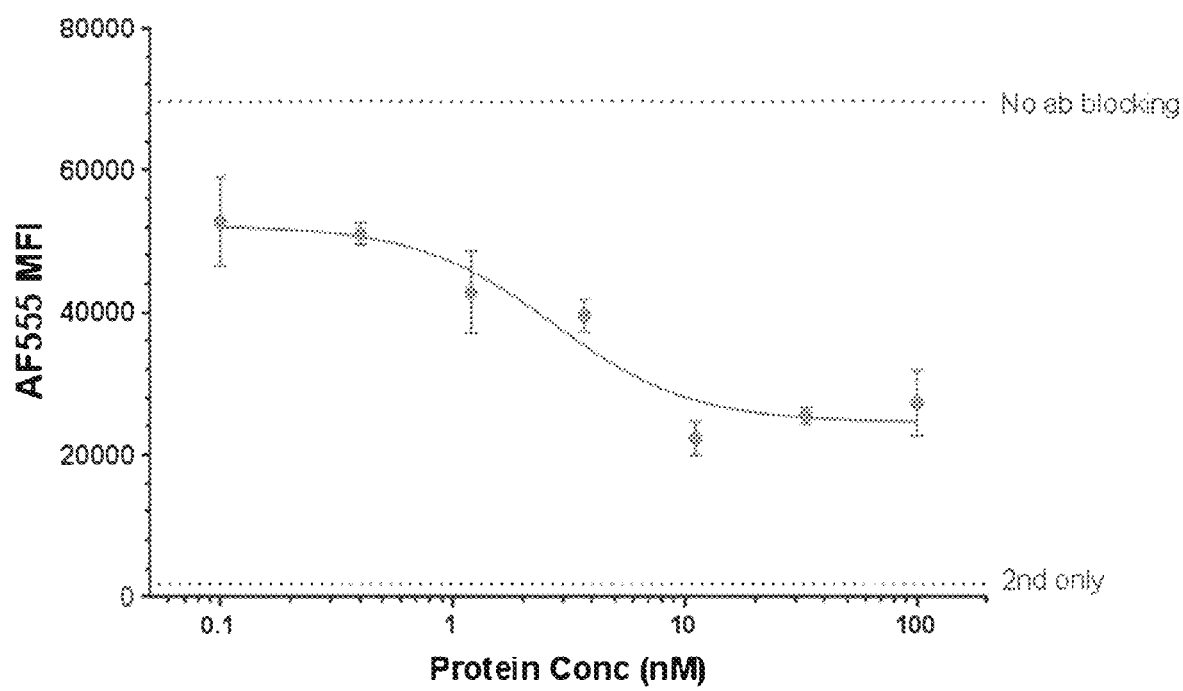
Figure 11C:
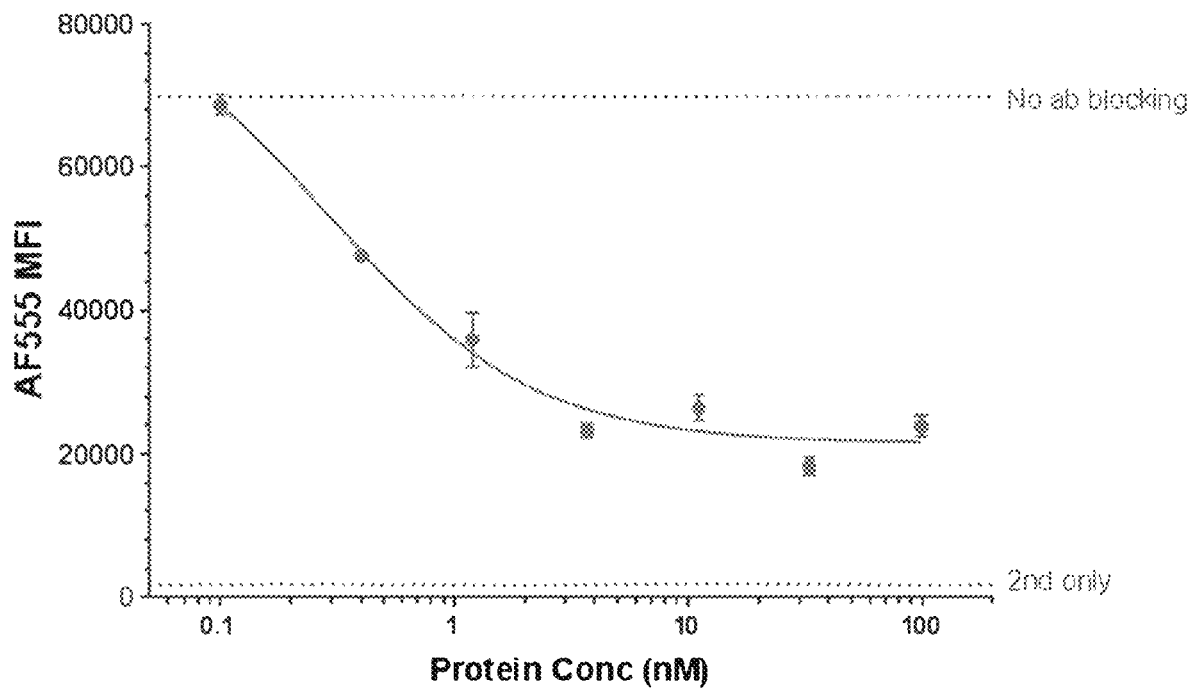
Figure 11D:
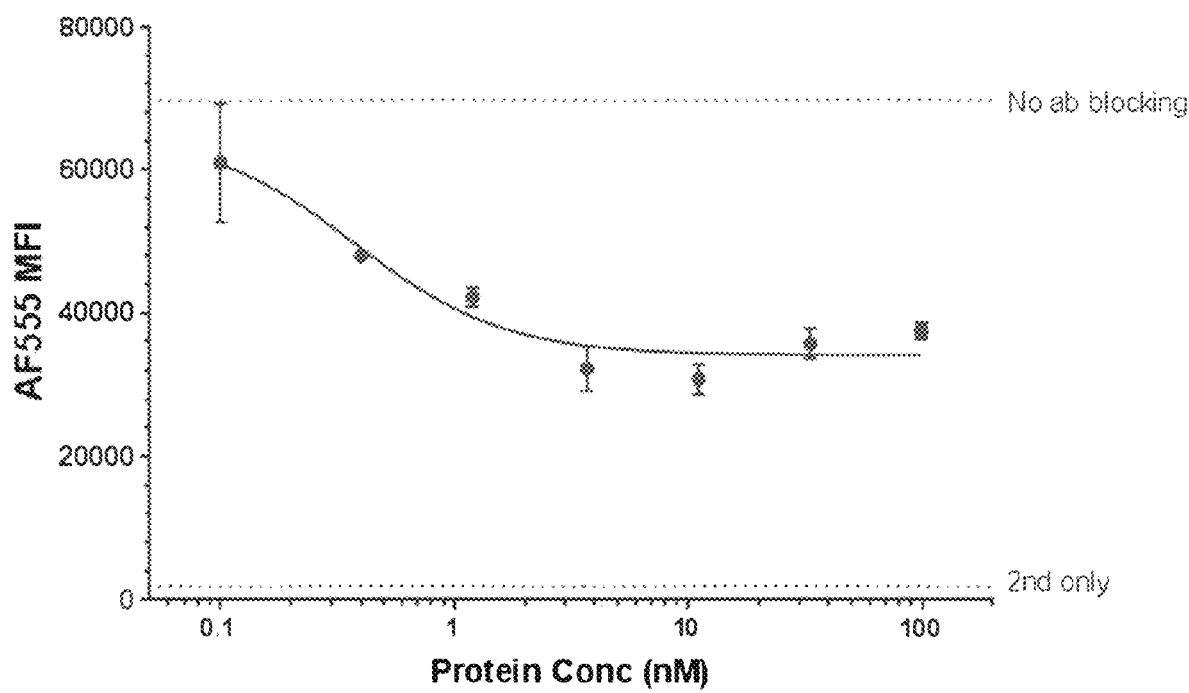
Figure 11E:
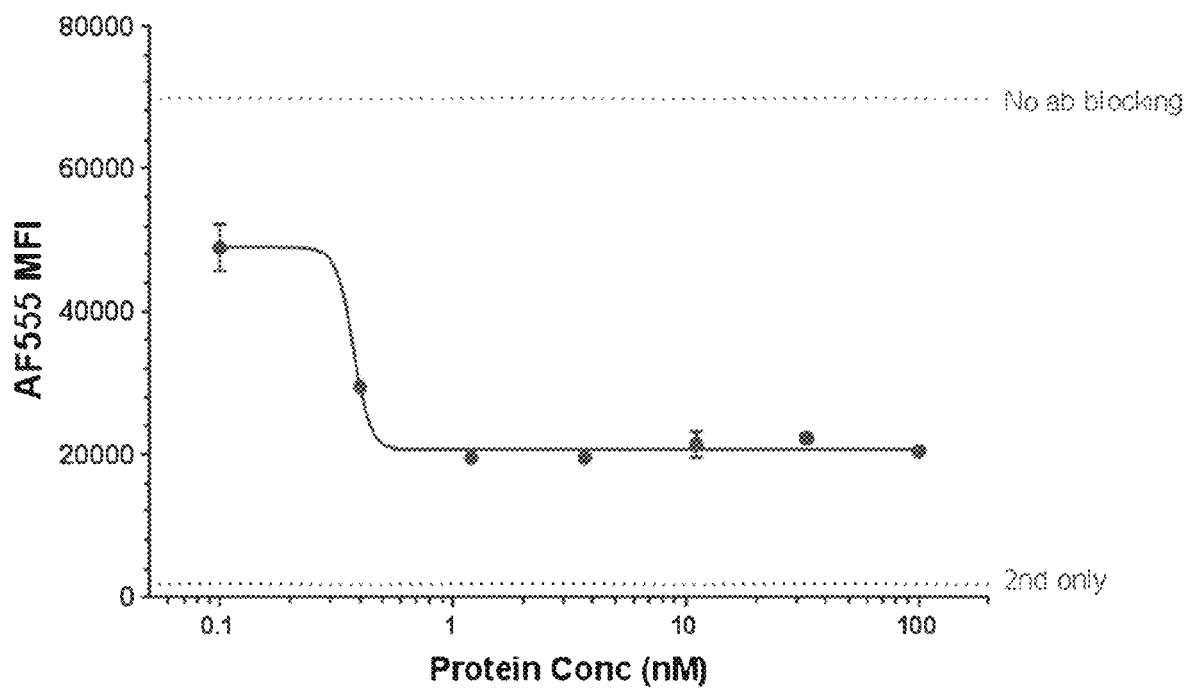
Figure 11F:
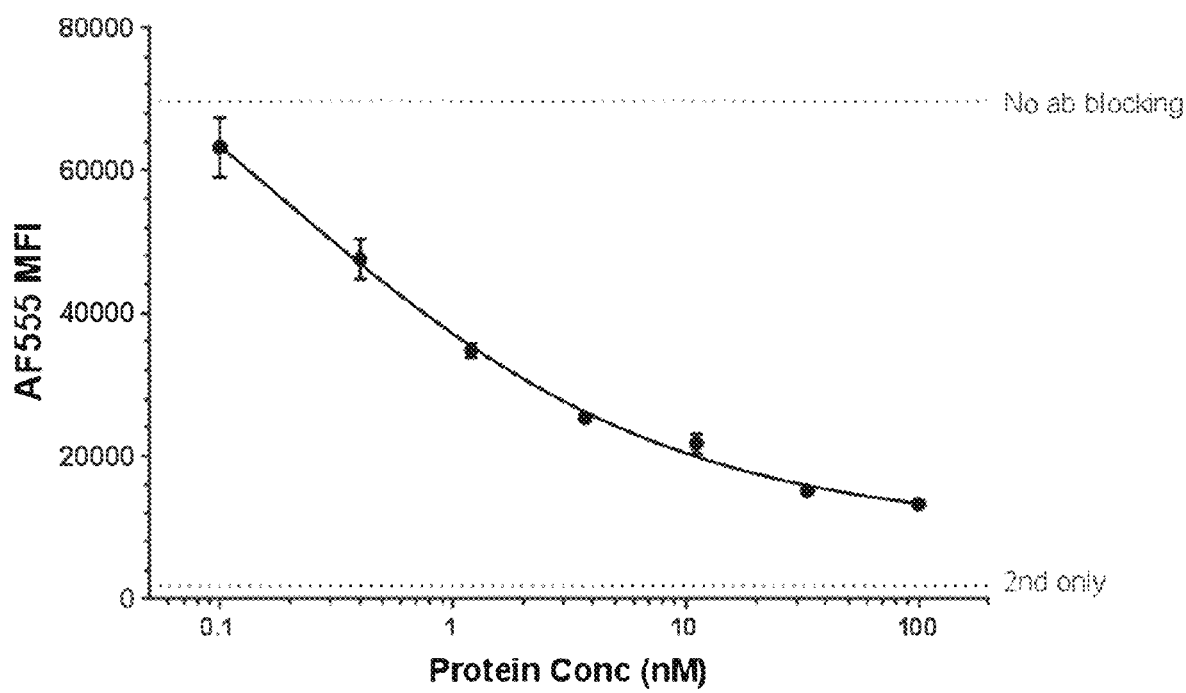

The tested anti-NRP2 showed different capabilities in blocking of VEGF-C or Sema3F-p95m binding to Expi293-hNRP2 cells, and were categorized as blockers (>90% inhibition), partial blockers (30-90% inhibition), or non-blockers (no obvious inhibition). Table E7 shows a summary of the binding data, including the calculated $IC_{50}$ values (within subnanomolar to nanomolar range) for these anti-NRP2 antibodies, while FIG. 6 shows the binding curves of the anti-NRP2 antibodies to Expi293-hNRP2 cells over expressing human NRP2 in the absence of added ligand. FIG. 7 shows the binding curves and FACS plots of the binding of human VEGF-C to Expi293-hNRP2 cells over expressing human NRP2. FIG. 8 shows the blocking and or displacement of VEGF-C binding to Expi293-hNRP2 cells over expressing human NRP2. FIG. 9 shows the binding of Sema3F-p95 and Sema 3F-p65 (0.05-100 nM) binding to Expi293-hNRP2 clonal cells over expressing human NRP2. FIGS. 10 and 11 shows anti-NRP2 antibody blocking, displacement curves for the indicated antibodies on Sema 3F-p95 binding to Expi293-hNRP2 clonal cells over expressing human NRP2.

TABLE E7

LIGAND DISPLACEMENT STUDIES WITH CELLS OVEREXPRESSING NRP2

| Clone | Epitope Domain (ELISA) | Binding 293F-hNRP2 (EC$_{50}$ nM) | Block ligand binding to 293F-hNRP2 | | | | | |
|---|---|---|---|---|---|---|---|---|
| | | | VEGF-C (IC$_{50}$ nM) | | Fc-HRS(2-60) (IC$_{50}$ nM) | | SEMA3F (IC$_{50}$ nM) | |
| 18B8 aNRP2-14 | a2 | Binding 0.9 | Partial | 6.7 | Not blocked | N/A | Blocked | 2.2 |
| 8E2 aNRP2-6 | b1 | N.D. N.D. | Blocked | 1.1 | Blocked | N.D. | N.D. | N.D. |
| 5H11 aNRP2-7 | b1 | N.D. N.D. | Blocked | 0.8 | Blocked | N.D. | N.D. | N.D. |
| 7G10 aNRP2-8 | b1 | Binding 0.3 | Blocked | 0.3 | Blocked | 0.3 | Partial | 2.7 |
| 9E7 aNRP2-9 | b1 | Binding 0.7 | Blocked | 0.7 | Blocked | 0.2 | Partial | 0.3 |
| 1E3 aNRP2-10 | b1 | Binding 0.3 | Blocked | 0.4 | Blocked | 0.5 | Partial | 0.4 |
| 19E8 aNRP2-15 | b1 | Binding 0.3 | N.D. | N.D. | N.D. | N.D. | Partial | 0.4 |
| 17F7 aNRP2-1 | b2 | N.D. N.D. | Not blocked | N/A | N.D. | N.D. | N.D. | N.D. |
| 13D7 aNRP2-11 | b2 | Binding 0.9 | Blocked | 5.8 | Partial | 34.3 | Partial | 0.2 |
| 3F2 aNRP2-2 | c | Binding N.D. | Not blocked | N/A | Not blocked | N/A | Not blocked | N/A |
| 20F3 aNRP2-12 | c | N.D. N.D. | Not blocked | N/A | N.D. | N.D. | N.D. | N.D. |

The results from these studies show specific and selective binding of specific antibodies with respect to displacing the binding of VEGF-C, Semaphorin 3F and HRS polypeptides. Importantly these results validate and extend the initial ligand displacement capacity of these bodies in the context of NRP2-ligand interactions in the native cellular environment. For example, the results show that clone 18138 (aNRP2-14) shows the ability selectively block Semaphorin binding, while only partially blocking VEGF-C binding, and HRS polypeptides binding, and that clones 7G10 (aNRP2-8), 9E7 (aNRP2-9), and 1E3 (aNRP2-10) shows the ability selectively block VEGF-C and HRS polypeptides while only partially blocking binding Semaphorin binding. Clone 13D7 (aNRP2-11) shows the ability selectively block VEGF-C, while only partially blocking binding Semaphorin binding and HRS polypeptides binding. Whereas clone 3F2 (aNRP2-2) showed the ability to bind to NRP2 without displacing any of the tested ligands—making it particularly useful as a diagnostic reagent for NRP2 expression, particularly for example in IHC applications.

EXAMPLE 7

Characterization of Anti-NRP2 Antibodies on Receptor NRP2 Dimerization

Figure 12:
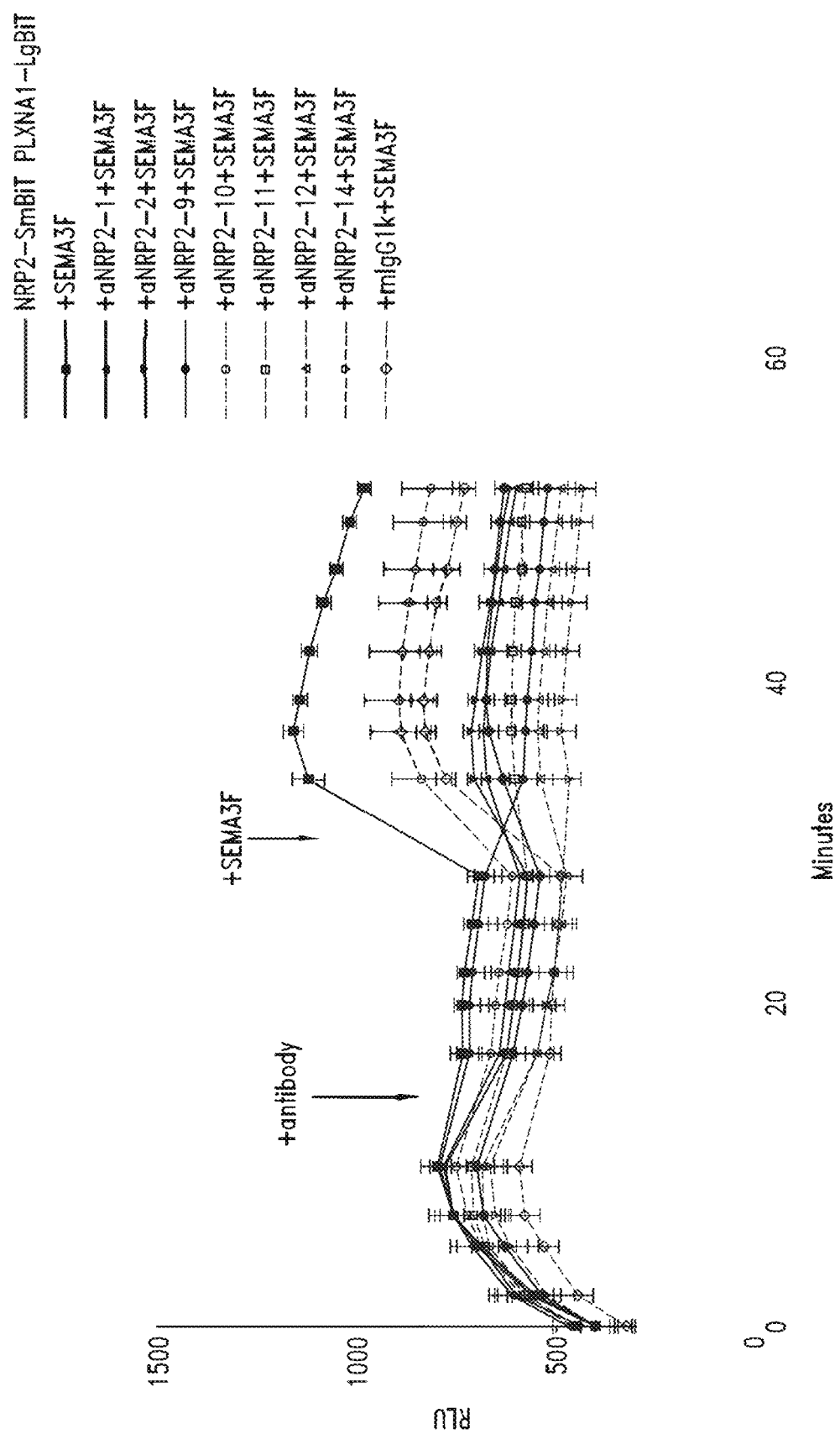
FIG. 12 shows the effects of anti-NRP2 antibody binding on NRP2-plexinA1 induced receptor hetero-dimerization as described in the examples, using the disclosed antibodies.
Figure 13:
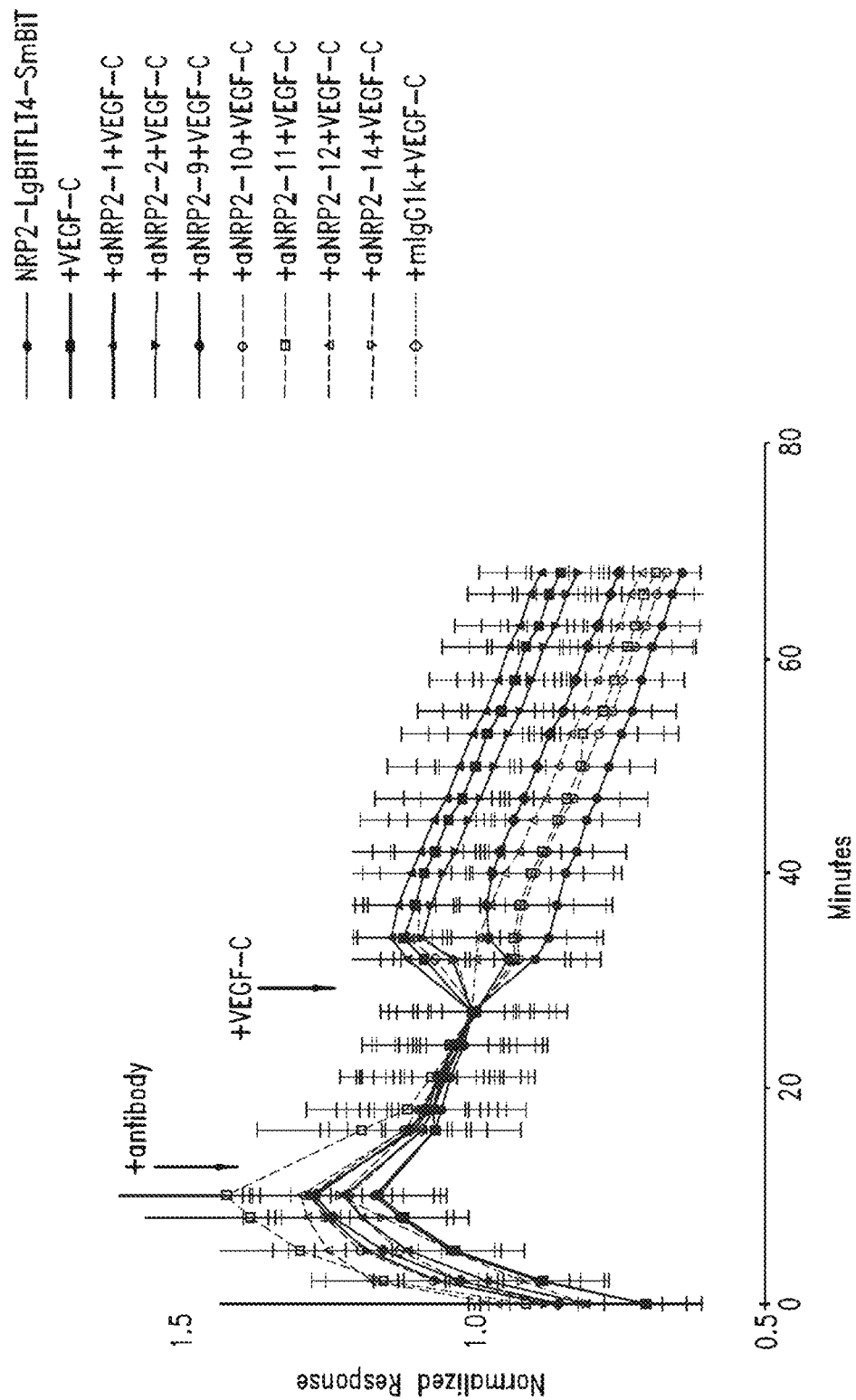
FIG. 13 shows the effects of anti-NRP2 antibody binding on NRP2-FLT4 (VEGFR3) induced receptor hetero dimerization as described in the examples, using the disclosed antibodies.

To further extend the assessment of the biological activity of the anti-NRP2 antibodies, their activity was assessed in a receptor dimerization assay. In brief, vectors encoding a split luciferase pBiT1.1 and pBiT2.1 were obtained from Promega corporation. The complete extracellular domain and transmembrane helices of NRP2v2, FLT4 (VEGFR3), and plexin A1 (PLXNA1) were cloned into the vectors and screened for optimal orientation, following established methods. Expi293 cells (Fisher) were transfected at 1 million cells/mL ~20 hours prior to the assay with NRP2v2 and a co-receptor at equal mass amounts. Cells were counted, and 100,000 live cells were plated in a well of a white luminometer plate in Optimem media (Fisher). Nano-Glo assay substrate (Promega) was added, and the plate was read on a MicroBeta luminometer at room temperature to establish baseline luminescence. Antibodies were added to the well at 100 nM and the plate was again read to establish a new baseline and monitor the effects of the antibodies on spontaneous receptor dimerization. Either SEMA3F-p95 (aTyr pharma) or VEGF-C(R&D systems) were then added, at 200 nM or 20 nM respectively and the plate was again read to measure dimerization of receptors. Raw response is shown for NRP2/PLXNA1 dimerization, due to weak response and high variability NRP2/FLT4 was normalized to the baseline prior to the addition of ligand. Results are summarized in Table E8 below, and graphically in FIGS. 12 and 13.

TABLE E8

Receptor Dimerization blocking summary:

| Antibody | Domain specificity | Ability to Block NRP2/PLXNA1 | Ability to Block NRP2/FLT4(VEGFR3) |
|---|---|---|---|
| aNRP2-14 | a2 | Very strong | None |
| aNRP2-9 | b1 | Partial | Partial |
| aNRP2-10 | b1 | Weak/None | Very strong |
| aNRP2-1 | b2 | Partial | None |
| aNRP2-11 | b2 | Strong | Very strong |
| aNRP2-2 | c | Partial | None |
| aNRP2-12 | c | Strong | Partial |

The results demonstrate that all of the tested antibodies show functional activity in these assays. Surprisingly specific antibodies show extremely specific and non obvious functional differentiation. For example, antibody aNRP2-14 is demonstrated to exhibit extremely potent inhibition of NRP2-plexin heterodimerization, while having no significant impact on NRP2-VEGFR3 heterodimerization. Additionally, antibody aNRP2-10 shows the ability to potently inhibit NRP2-VEGFR3 heterodimerization, without significantly inhibiting NRP2-plexin heterodimerization. By contrast antibody clone aNRP2-11 shows the ability to strongly inhibit the heterodimerization of NRP2 to both VEGFR3 and Plexin receptors. Further, antibody aNRP2-12 shows the surprising ability to strongly inhibit the heterodimerization of NRP2 to plexin receptors, while only partially impacting NRP2-VEGFR3 dimerization.

EXAMPLE 8

Characterization of Antibody Fab and NRP2 Complex Crystal Structure

Human NRP2 (aa25-595) with an N-terminal His-tag was expressed in Expi293 cells and purified by Ni-NTA affinity chromatography. a NRP2-14 Fab light chain and His-tagged heavy chain were co-expressed in ExpiCHO cells and purified by Ni-NTA affinity chromatography. Bound complex of NRP2 and aNRP2-14 Fab was obtained by mixing and purification by size exclusion chromatography. The protein complex was concentrated to 18.1 mg/ml in 1×PBS pH 7.4. The proteins were screened for crystallization hits by the sitting drop method (0.5 µl protein plus 0.5 µl precipitant) and incubated at 16° C. After 2-4 days of incubation, the complex crystal grew in the condition containing 30% v/v polyethylene glycol 300 and 0.1 M sodium acetate trihydrate pH 4.5. Crystals were cryoprotected in the same conditions with the addition of 15% v/v glycerol before being flash-cooled and stored in liquid nitrogen.

All the diffraction data were collected on a PILATUS3 6M detector at the Shanghai Synchrotron Radiation Facility beamline BL19U, at 100 K, and indexed and processed with the HKL3000 software (Minor et al, 2006). The structure of the complex was determined by molecular replacement with Phaser (McCoy et al, 2007) in the CCP4 suite (Winn et al, 2011) using previously published models as the search model [PDB code: NRP2 (2QQK), Fab (2D03)]. The final models were generated through multiple steps of building in Coot (Emsley et al, 2004) and refinement in Refmac (Murshudov et al, 2004) in the CCP4 suite. All the structure images and alignments were generated in PyMOL (DeLano, 2015). Buried surface areas were calculated by the EBI PISA server (www.ebi.ac.uk/msd-srv/prot_int/cgibin/piserver).

Figure 14:
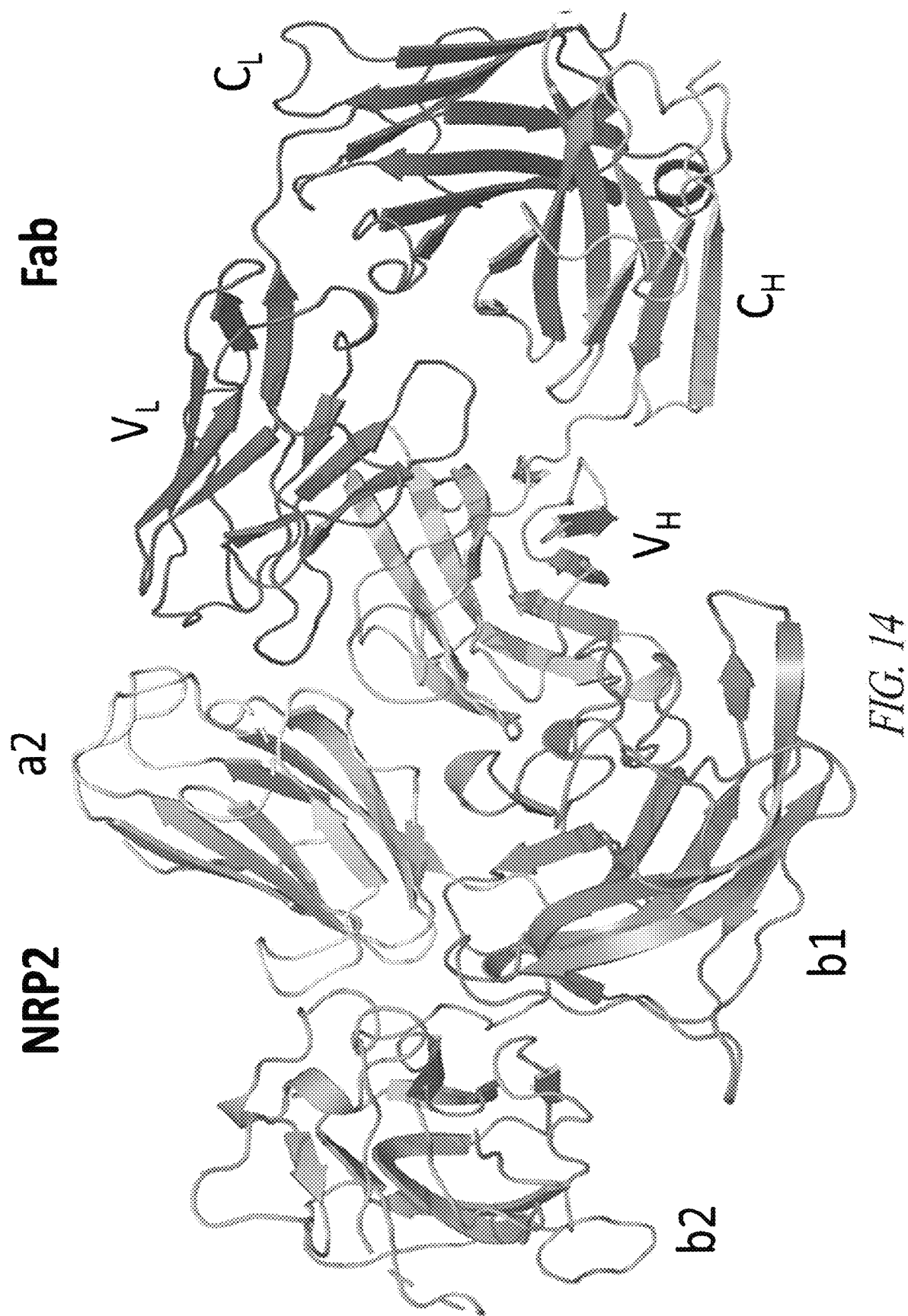
FIG. 14 shows the crystal structure of human NRP2, showing the a2 domain and b1/b2 domains in complex with variable heavy ($V_H$) and light ($V_L$) chains of the aNRP2-14 Fab.

Crystals of the NRP2/aNRP12-14 Fab had a space group of C2 with cell constants of a=89.5 Å, b=89.4 Å, c=130.9 Å and diffracted to a maximum resolution of 1.90 Å. The structure was refined to 1.90 A resolution with a final $R_{work}$ and $R_{free}$ of 19.71% and 23.46% respectively. While the Fab and the a2, b1 and b2 domain of NRP2 were well resolved (FIG. 14), Table E10, the electron density corresponding to the a1 domain of the NRP2 protein could not be detected.

Figure 15:
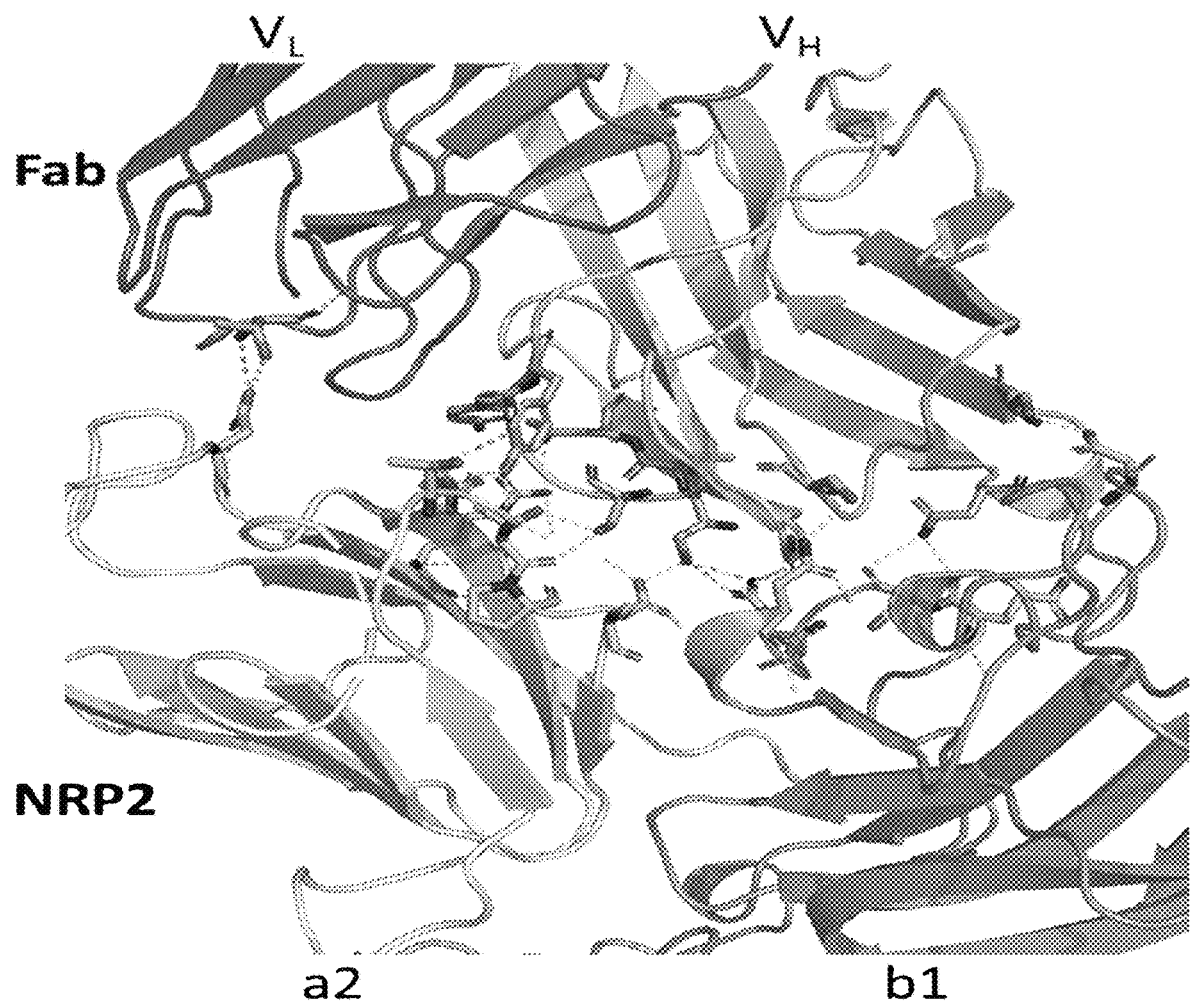
FIG. 15 shows the interaction surface between human NRP2 showing the a2 domain and b1 domains and heavy ($V_H$) and light ($V_L$) chains of the aNRP2-14 Fab, and interacting amino acids.
Figure 16:
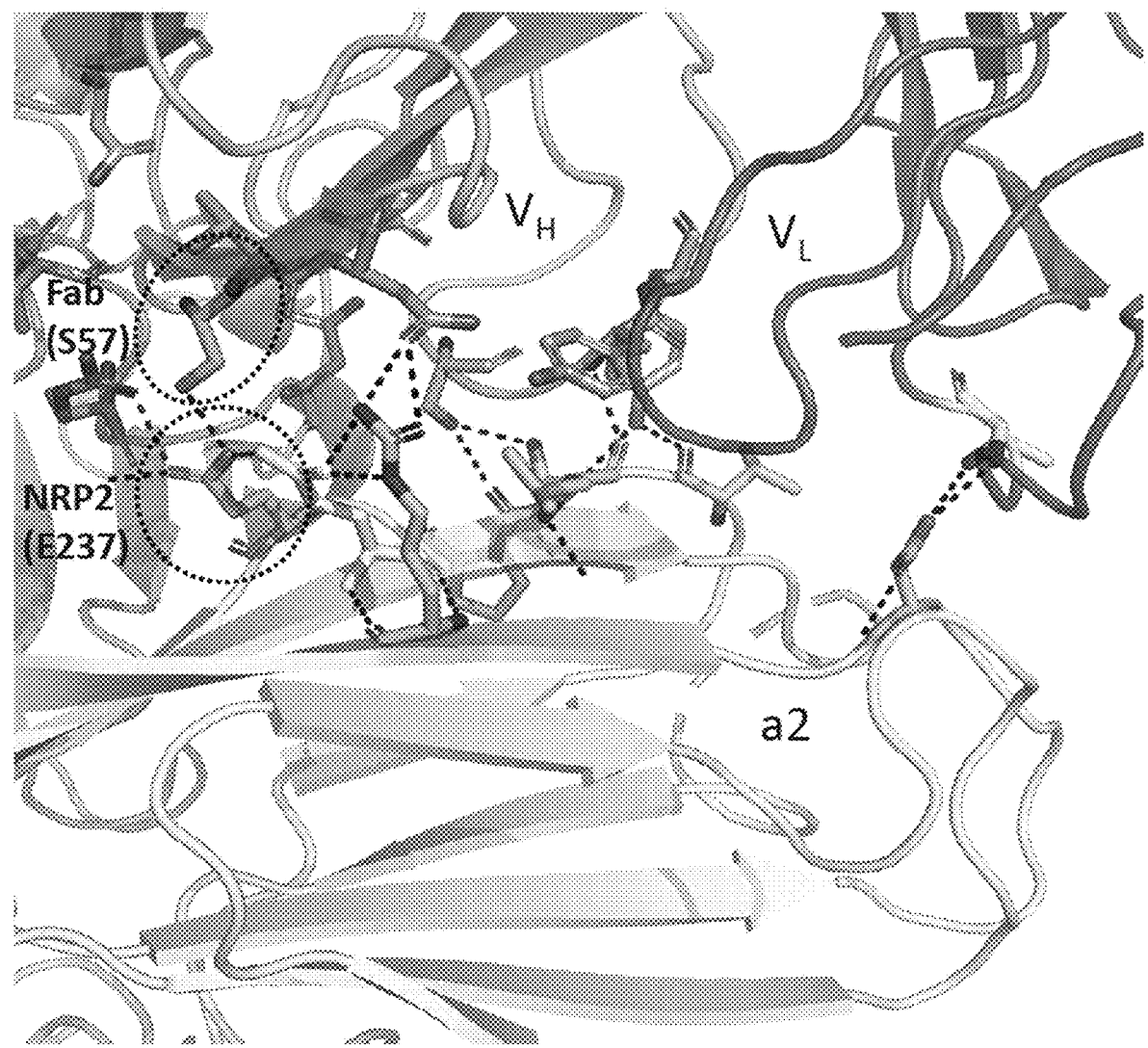
FIG. 16 shows a view of the interaction interface between human NRP2 a2 domain (lower) and the heavy (upper left) & light (upper right) chains of the aNRP2-14 Fab. Interacting residues E237 of human NRP2 and S57 of the Fab heavy chain are circled.

The aNRP2-14 antibody recognizes human NRP2 but not mouse NRP2. Among the NRP2 residues in the crystal structure that make contacts with the Fab (FIG. 15, Table E9), the only residue that is not conserved between human and mouse is residue 237, which is a glutamic acid in human and a lysine in mouse. This E237 residue in human NRP2 forms a hydrogen bond with the S57 residue in the CDR2 region of the antibody heavy chain (FIG. 16), and therefore plays a key role in the binding interaction.

TABLE E9

Summary of interacting residues between NRP2 and aNRP2-14 Fab

| NRP2 domain | NRP2 residue | Fab domain | Fab residue | Bond |
|---|---|---|---|---|
| a2 | D258 | VL | T32 | H-bond |
|  | L192 | VH | Y105 | H-bond |
|  | T232 | VH | Y106 | H-bond |
|  | T234 | VH | S103, Y106 | H-bond |
|  | P235 | VH | S103 | H-bond |
|  | E237 | VH | S57 | H-bond |
|  | R263 | VH | T58, D59, Y105 | H-bond |
|  |  | VH | D59 | Salt bridge |
| b1 | E284 | VH | N74 | H-bond |
|  | S285 | VH |  | H-bond |
|  | R287 | VH | G55,S57 | H-bond |
|  | N290 | VH | S32 | H-bond |
|  | D314 | VH | S77 | H-bond |

TABLE E10

Crystallographic data collection and refinement statistics

| Data collection | |
|---|---|
| Space group | C2 |
| Wavelength (Å) | 0.97915 |
| Unit cell parameters | 89.501Å 89.411Å 130.877Å 90° 94.18° 90° |
| Resolution range (Å) | 50-1.90 (1.93-1.90) |
| No. of unique reflections | 78778 (3849) |
| Redundancy | 5.9 (6.1) |
| I/σ | 23.3 (2.4) |
| Completeness (%) | 97.4 (96.1) |
| $R_{merge}^{a}$ (%) | 7.4 (59.0) |
| $CC_{1/2}$ (highest-resolution shell)$^b$ | 0.816 |
| Structure refinement | |
| Resolution (Å) | 1.90 |
| $R_{work}^{c}$ (%) | 19.71 |
| $R_{free}^{d}$ (%) | 23.46 |
| RMSD bonds (Å) | 0.009 |
| RMSD angles (°) | 1.555 |
| Average B factor (Å$^2$) | 40.2 |
| Ramachadran plot (%) | |
| Preferred | 95.68 |
| Allowed | 3.58 |
| Outliers | 6 |

Numbers in parentheses represent the values for the highest-resolution shell.
$^a R_{merge} = \Sigma|I_i - </>|/\Sigma I_i$, where $I_i$ is the intensity of measured reflection and $</>$ is the mean intensity of all symmetry-related reflections.
$^b CC_{1/2}$ was defined in [4].
$^c R_{work} = \Sigma_w| |F_{calc}| - |F_{obs}| |/\Sigma|F_{obs}|$, where $F_{obs}$ and $F_{calc}$ are observed and calculated structure factors. W is working dataset of about 95% of the total unique reflections randomly chosen and used for refinement.
$^d R_{free} = \Sigma_T| |F_{calc}| - |F_{obs}| |/\Sigma|F_{obs}|$, where T is a test dataset of about 5% of the total unique reflections randomly chosen and set aside prior to refinement.

All publications, patent applications, and issued patents cited in this specification are herein incorporated by reference as if each individual publication, patent application, or issued patent were specifically and individually indicated to be incorporated by reference.

The invention claimed is:

1. A therapeutic composition, comprising at least one antibody or antigen-binding fragment thereof that specifically binds to a human neuropilin-2 (NRP2) polypeptide (anti-NRP2 antibody) at an epitope in the neuropilin A2 domain of human NRP2 wherein the antibody or antigen-binding fragment thereof comprises a heavy chain variable region ($V_H$) sequence that comprises complementary determining region $V_H$CDR1, $V_H$CDR2, and $V_H$CDR3 sequences and a light chain variable region ($V_L$) sequence that comprises complementary determining region $V_L$CDR1, $V_L$CDR2, and $V_L$CDR3 sequences, wherein:
the $V_H$CDR1, $V_H$CDR2, and $V_H$CDR3 sequences comprise SEQ ID NOs: 77-79, respectively, and the $V_L$CDR1, $V_L$CDR2, and $V_L$CDR3 sequences comprise SEQ ID NOs: 80-82, respectively.

2. The therapeutic composition of claim 1, wherein the epitope comprises residues 190-265 of human NRP2 as defined by SEQ ID NO:1.

3. The therapeutic composition of claim 2, wherein the epitope comprises residues L192, T232, T234, P235, E237, D258, and R263 of human NRP2 as defined by SEQ ID NO: 1.

4. The therapeutic composition of claim 1, wherein the at least one antibody or antigen-binding fragment thereof antagonizes the binding/signaling activity between the NRP2 polypeptide and a plexin receptor and/or semaphorin 3F (SEMA 3F) without substantially modulating the binding/signaling activity between the NRP2 polypeptide and VEGFR3 or VEGF-C.

5. The therapeutic composition of claim 4, wherein the at least one antibody or antigen-binding fragment thereof selectively inhibits receptor dimerization between the NRP2 polypeptide and plexin A1 without substantially inhibiting dimerization between the NRP2 polypeptide and FLT4 (VEGFR3).

6. The therapeutic composition of claim 1, wherein the at least one antibody or antigen-binding fragment thereof comprises an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof.

7. The therapeutic composition of claim 6, wherein the at least one antibody or antigen-binding fragment thereof comprises an IgG Fc domain with high effector function in humans, optionally an IgG1 or IgG3 Fc domain.

8. The therapeutic composition of claim 6, wherein the at least one antibody or antigen-binding fragment thereof comprises an IgG Fc domain with low effector function in humans, optionally an IgG2 or IgG4 Fc domain.

9. The therapeutic composition of claim 8, wherein the at least one antibody or antigen-binding fragment thereof comprises an IgG1 or IgG4 Fc domain, optionally selected from SEQ ID NOs: 116-119.

10. The therapeutic composition of claim 1, wherein the at least one antibody or antigen-binding fragment thereof is a monoclonal antibody.

11. The therapeutic composition of claim 1, wherein the at least one antibody or antigen-binding fragment thereof is a humanized antibody.

12. The therapeutic composition of claim 1, wherein the at least one antibody or antigen-binding fragment thereof is an Fv fragment, a single chain Fv (scFv) polypeptide, an adnectin, an anticalin, an aptamer, an avimer, a camelid antibody, a designed ankyrin repeat protein (DARPin), a minibody, a nanobody, or a unibody.

13. The therapeutic composition of claim 1, wherein the composition has a purity of at least about 80%, 85%, 90%, 95%, 98%, or 99% on a protein basis with respect to the at least one antibody or antigen-binding fragment, and is substantially aggregate-free and substantially endotoxin-free.

14. The therapeutic composition of claim 1, wherein the therapeutic composition is a sterile, injectable solution, optionally suitable for intravenous, intramuscular, subcutaneous, or intraperitoneal administration.

15. The therapeutic composition of claim 1, further comprising at least one additional agent selected from one or more of a cancer immunotherapy agent, a chemotherapeutic agent, a hormonal therapeutic agent, and a kinase inhibitor.

* * * * *

SEQUENCE LISTING

```
Sequence total quantity: 128
SEQ ID NO: 1              moltype = AA   length = 931
FEATURE                   Location/Qualifiers
source                    1..931
                          mol_type = protein
                          organism = Homo sapiens
SEQUENCE: 1
MDMFPLTWVF LALYFSRHQV RGQPDPPCGG RLNSKDAGYI TSPGYPQDYP SHQNCEWIVY   60
APEPNQKIVL NFNPHFEIEK HDCKYDFIEI RDGDSESADL LGKHCGNIAP PTIISSGSML  120
YIRFTSDYAR QGAGFSLRYE IFKTGSEDCS KNFTSPNGTI ESPGFPEKYP HNLDCTFTIL  180
AKPKMEIILQ FLIFDLEHDP LQVGEGDCKY DWLDIWDGIP HVGPLIGKYC GTKTPSELRS  240
STGILSLTFH TDMAVAKDGF SARYYLVHQE PLENFQCNVP LGMESGRIAN EQISASSTYS  300
DGRWTPQQSR LHGDDNGWTP NLDSNKEYLQ VDLRFLTMLT AIATQGAISR ETQNGYYVKS  360
YKLEVSTNGE DWMVYRHGKN HKVFQANNDA TEVVLNKLHA PLLTRFVRIR PQTWHSGIAL  420
RLELFGCRVT DAPCSNMLGM LSGLIADSQI SASSTQEYLW SPSAARLVSS RSGWFPRIPQ  480
AQPGEEWLQV DLGTPKTVKG VIIQGARGGD SITAVEARAF VRKFKVSYSL NGKDWEYIQD  540
PRTQQPKLFE GNMHYDTPDI RRFDPIPAQY VRVYPERWSP AGIGMRLEVL GCDWTDSKPT  600
VETLGPTVKS EETTTPYPTE EEATECGENC SFEDDKDLQL PSGFNCNPDF LEEPCGWMYD  660
HAKWLRTTWA SSSSPNDRTF PDDRNFLRLQ SDSQREGQYA RLISPPVHLP RSPVCMEFQY  720
QATGGRGVAL QVVREASQES KLLWVIREDQ GGEWKHGRII LPSYDMEYQI VFEGVIGKGR  780
SGEIAIDDIR ISTDVPLENC MEPISAFAGE NFKVDIPEIH EREGYEDEID DEYEVDWSNS  840
SSATSGSGAP STDKEKSWLY TLDPILITII AMSSLGVLLG ATCAGLLLYC TCSYSGLSSR  900
SCTTLENYNF ELYDGLKHKV KMNHQKCCSE A                                931

SEQ ID NO: 2              moltype = AA   length = 926
FEATURE                   Location/Qualifiers
source                    1..926
                          mol_type = protein
                          organism = Homo sapiens
SEQUENCE: 2
MDMFPLTWVF LALYFSRHQV RGQPDPPCGG RLNSKDAGYI TSPGYPQDYP SHQNCEWIVY   60
APEPNQKIVL NFNPHFEIEK HDCKYDFIEI RDGDSESADL LGKHCGNIAP PTIISSGSML  120
YIKFTSDYAR QGAGFSLRYE IFKTGSEDCS KNFTSPNGTI ESPGFPEKYP HNLDCTFTIL  180
AKPKMEIILQ FLIFDLEHDP LQVGEGDCKY DWLDIWDGIP HVGPLIGKYC GTKTPSELRS  240
STGILSLTFH TDMAVAKDGF SARYYLVHQE PLENFQCNVP LGMESGRIAN EQISASSTYS  300
DGRWTPQQSR LHGDDNGWTP NLDSNKEYLQ VDLRFLTMLT AIATQGAISR ETQNGYYVKS  360
YKLEVSTNGE DWMVYRHGKN HKVFQANNDA TEVVLNKLHA PLLTRFVRIR PQTWHSGIAL  420
RLELFGCRVT DAPCSNMLGM LSGLIADSQI SASSTQEYLW SPSAARLVSS RSGWFPRIPQ  480
AQPGEEWLQV DLGTPKTVKG VIIQGARGGD SITAVEARAF VRKFKVSYSL NGKDWEYIQD  540
PRTQQPKLFE GNMHYDTPDI RRFDPIPAQY VRVYPERWSP AGIGMRLEVL GCDWTDSKPT  600
VETLGPTVKS EETTTPYPTE EEATECGENC SFEDDKDLQL PSGFNCNPDF LEEPCGWMYD  660
HAKWLRTTWA SSSSPNDRTF PDDRNFLRLQ SDSQREGQYA RLISPPVHLP RSPVCMEFQY  720
QATGGRGVAL QVVREASQES KLLWVIREDQ GGEWKHGRII LPSYDMEYQI VFEGVIGKGR  780
SGEIAIDDIR ISTDVPLENC MEPISAFAVD IPEIHEREGY EDEIDDEYEV DWSNSSSATS  840
GSGAPSTDKE KSWLYTLDPI LITIIAMSSL GVLLGATCAG LLLYCTCSYS GLSSRSCTTL  900
ENYNFELYDG LKHKVKMNHQ KCCSEA                                      926

SEQ ID NO: 3              moltype = AA   length = 909
FEATURE                   Location/Qualifiers
source                    1..909
                          mol_type = protein
                          organism = Homo sapiens
SEQUENCE: 3
MDMFPLTWVF LALYFSRHQV RGQPDPPCGG RLNSKDAGYI TSPGYPQDYP SHQNCEWIVY   60
APEPNQKIVL NFNPHFEIEK HDCKYDFIEI RDGDSESADL LGKHCGNIAP PTIISSGSML  120
YIKFTSDYAR QGAGFSLRYE IFKTGSEDCS KNFTSPNGTI ESPGFPEKYP HNLDCTFTIL  180
AKPKMEIILQ FLIFDLEHDP LQVGEGDCKY DWLDIWDGIP HVGPLIGKYC GTKTPSELRS  240
STGILSLTFH TDMAVAKDGF SARYYLVHQE PLENFQCNVP LGMESGRIAN EQISASSTYS  300
DGRWTPQQSR LHGDDNGWTP NLDSNKEYLQ VDLRFLTMLT AIATQGAISR ETQNGYYVKS  360
YKLEVSTNGE DWMVYRHGKN HKVFQANNDA TEVVLNKLHA PLLTRFVRIR PQTWHSGIAL  420
RLELFGCRVT DAPCSNMLGM LSGLIADSQI SASSTQEYLW SPSAARLVSS RSGWFPRIPQ  480
AQPGEEWLQV DLGTPKTVKG VIIQGARGGD SITAVEARAF VRKFKVSYSL NGKDWEYIQD  540
PRTQQPKLFE GNMHYDTPDI RRFDPIPAQY VRVYPERWSP AGIGMRLEVL GCDWTDSKPT  600
VETLGPTVKS EETTTPYPTE EEATECGENC SFEDDKDLQL PSGFNCNPDF LEEPCGWMYD  660
HAKWLRTTWA SSSSPNDRTF PDDRNFLRLQ SDSQREGQYA RLISPPVHLP RSPVCMEFQY  720
QATGGRGVAL QVVREASQES KLLWVIREDQ GGEWKHGRII LPSYDMEYQI VFEGVIGKGR  780
SGEIAIDDIR ISTDVPLENC MEPISAFADE YEVDWSNSSS ATSGSGAPST DKEKSWLYTL  840
DPILITIIAM SSLGVLLGAT CAGLLLYCTC SYSGLSSRSC TTLENYNFEL YDGLKHKVKM  900
NHQKCCSEA                                                         909

SEQ ID NO: 4              moltype = AA   length = 906
FEATURE                   Location/Qualifiers
source                    1..906
                          mol_type = protein
                          organism = Homo sapiens
SEQUENCE: 4
MDMFPLTWVF LALYFSRHQV RGQPDPPCGG RLNSKDAGYI TSPGYPQDYP SHQNCEWIVY   60
APEPNQKIVL NFNPHFEIEK HDCKYDFIEI RDGDSESADL LGKHCGNIAP PTIISSGSML  120
```

```
YIKFTSDYAR QGAGFSLRYE IFKTGSEDCS KNFTSPNGTI ESPGFPEKYP HNLDCTFTIL    180
AKPKMEIILQ FLIFDLEHDP LQVGEGDCKY DWLDIWDGIP HVGPLIGKYC GTKTPSELRS    240
STGILSLTFH TDMAVAKDGF SARYYLVHQE PLENFQCNVP LGMESGRIAN EQISASSTYS    300
DGRWTPQQSR LHGDDNGWTP NLDSNKEYLQ VDLRFLTMLT AIATQGAISR ETQNGYYVKS    360
YKLEVSTNGE DWMVYRHGKN HKVFQANNDA TEVVLNKLHA PLLTRFVRIR PQTWHSGIAL    420
RLELFGCRVT DAPCSNMLGM LSGLIADSQI SASSTQEYLW SPSAARLVSS RSGWFPRIPQ    480
AQPGEEWLQV DLGTPKTVKG VIIQGARGGD SITAVEARAF VRKFKVSYSL NGKDWEYIQD    540
PRTQQPKLFE GNMHYDTPDI RRFDPIPAQY VRVYPERWSP AGIGMRLEVL GCDWTDSKPT    600
VETLGPTVKS EETTTPYPTE EEATECGENC SFEDDKDLQL PSGFNCNPFDF LEEPCGWMYD   660
HAKWLRTTWA SSSSPNDRTF PDDRNFLRLQ SDSQREGQYA RLISPPVHLP RSPVCMEFQY    720
QATGGRGVAL QVVREASQES KLLWVIREDQ GGEWKHGRII LPSYDMEYQI VFEGVIGKGR    780
SGEIAIDDIR ISTDVPLENC MEPISAFAGE NFKGGTLLPG TEPTVDTVPM QPIPAYWYYV    840
MAAGGAVLVL VSVALALVLH YHRFRYAAKK TDHSITYKTS HYTNGAPLAV EPTLTIKLEQ    900
DRGSHC                                                              906

SEQ ID NO: 5              moltype = AA  length = 901
FEATURE                   Location/Qualifiers
source                    1..901
                          mol_type = protein
                          organism = Homo sapiens
SEQUENCE: 5
MDMFPLTWVF LALYFSRHQV RGQPDPPCGG RLNSKDAGYI TSPGYPQDYP SHQNCEWIVY    60
APEPNQKIVL NFNPHFEIEK HDCKYDFIEI RDGDSESADL LGKHCGNIAP PTIISSGSML   120
YIKFTSDYAR QGAGFSLRYE IFKTGSEDCS KNFTSPNGTI ESPGFPEKYP HNLDCTFTIL   180
AKPKMEIILQ FLIFDLEHDP LQVGEGDCKY DWLDIWDGIP HVGPLIGKYC GTKTPSELRS   240
STGILSLTFH TDMAVAKDGF SARYYLVHQE PLENFQCNVP LGMESGRIAN EQISASSTYS   300
DGRWTPQQSR LHGDDNGWTP NLDSNKEYLQ VDLRFLTMLT AIATQGAISR ETQNGYYVKS   360
YKLEVSTNGE DWMVYRHGKN HKVFQANNDA TEVVLNKLHA PLLTRFVRIR PQTWHSGIAL   420
RLELFGCRVT DAPCSNMLGM LSGLIADSQI SASSTQEYLW SPSAARLVSS RSGWFPRIPQ   480
AQPGEEWLQV DLGTPKTVKG VIIQGARGGD SITAVEARAF VRKFKVSYSL NGKDWEYIQD   540
PRTQQPKLFE GNMHYDTPDI RRFDPIPAQY VRVYPERWSP AGIGMRLEVL GCDWTDSKPT   600
VETLGPTVKS EETTTPYPTE EEATECGENC SFEDDKDLQL PSGFNCNPDF LEEPCGWMYD   660
HAKWLRTTWA SSSSPNDRTF PDDRNFLRLQ SDSQREGQYA RLISPPVHLP RSPVCMEFQY   720
QATGGRGVAL QVVREASQES KLLWVIREDQ GGEWKHGRII LPSYDMEYQI VFEGVIGKGR   780
SGEIAIDDIR ISTDVPLENC MEPISAFAGG TLLPGTEPTV DTVPMQPIPA YWYYVMAAGG   840
AVLVLVSVAL ALVLHYHRFR YAAKKTDHSI TYKTSHYTNG APLAVEPTLT IKLEQDRGSH   900
C                                                                  901

SEQ ID NO: 6              moltype = AA  length = 555
FEATURE                   Location/Qualifiers
source                    1..555
                          mol_type = protein
                          organism = Homo sapiens
SEQUENCE: 6
MDMFPLTWVF LALYFSRHQV RGQPDPPCGG RLNSKDAGYI TSPGYPQDYP SHQNCEWIVY    60
APEPNQKIVL NFNPHFEIEK HDCKYDFIEI RDGDSESADL LGKHCGNIAP PTIISSGSML   120
YIKFTSDYAR QGAGFSLRYE IFKTGSEDCS KNFTSPNGTI ESPGFPEKYP HNLDCTFTIL   180
AKPKMEIILQ FLIFDLEHDP LQVGEGDCKY DWLDIWDGIP HVGPLIGKYC GTKTPSELRS   240
STGILSLTFH TDMAVAKDGF SARYYLVHQE PLENFQCNVP LGMESGRIAN EQISASSTYS   300
DGRWTPQQSR LHGDDNGWTP NLDSNKEYLQ VDLRFLTMLT AIATQGAISR ETQNGYYVKS   360
YKLEVSTNGE DWMVYRHGKN HKVFQANNDA TEVVLNKLHA PLLTRFVRIR PQTWHSGIAL   420
RLELFGCRVT DAPCSNMLGM LSGLIADSQI SASSTQEYLW SPSAARLVSS RSGWFPRIPQ   480
AQPGEEWLQV DLGTPKTVKG VIIQGARGGD SITAVEARAF VRKFKVSYSL NGKDWEYIQD   540
PRTQQPKVGC SWRPL                                                   555

SEQ ID NO: 7              moltype = AA  length = 904
FEATURE                   Location/Qualifiers
source                    1..904
                          mol_type = protein
                          organism = Homo sapiens
SEQUENCE: 7
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDSKPTVE TLGPTVKSEE TTTPYPTEEE   600
ATECGENCSF EDDKDLQLPS GFNCNFDFLE EPCGWMYDHA KWLRTTWASS SSPNDRTFPD   660
DRNFLRLQSD SQREGQYARL ISPPVHLPRS PVCMEFQYQA TGGRGVALQV VREASQESKL   720
LWVIREDQGG EWKHGRIILP SYDMEYQIVF EGVIGKGRSG EIAIDDIRIS TDVPLENCME   780
PISAFAVDIP EIHEREGYED EIDDEYEVDW SNSSSATSGS GAPSTDKEKS WLYTLDPILI   840
TIIAMSSLGV LLGATCAGLL LYCTCSYSGL SSRSCTTLEN YNFELYDGLK HKVKMNHQKC   900
CSEA                                                               904
```

```
SEQ ID NO: 8           moltype = AA  length = 879
FEATURE                Location/Qualifiers
source                 1..879
                       mol_type = protein
                       organism = Homo sapiens
SEQUENCE: 8
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDSKPTVE TLGPTVKSEE TTTPYPTEEE   600
ATECGENCSF EDDKDLQLPS GFNCNFDFLE EPCGWMYDHA KWLRTTWASS SSPNDRTFPD   660
DRNFLRLQSD SQREGQYARL ISPPVHLPRS PVCMEFQYQA TGGRGVALQV VREASQESKL   720
LWVIREDQGG EWKHGRIILP SYDMEYQIVF EGVIGKGRSG EIAIDDIRIS TDVPLENCME   780
PISAFAGGTL LPGTEPTVDT VPMQPIPAYW YYVMAAGGAV LVLVSVALAL VLHYHRFRYA   840
AKKTDHSITY KTSHYTNGAP LAVEPTLTIK LEQDRGSHC                         879

SEQ ID NO: 9           moltype = AA  length = 533
FEATURE                Location/Qualifiers
source                 1..533
                       mol_type = protein
                       organism = Homo sapiens
SEQUENCE: 9
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKVGCSW RPL          533

SEQ ID NO: 10          moltype = AA  length = 114
FEATURE                Location/Qualifiers
source                 1..114
                       mol_type = protein
                       organism = Homo sapiens
SEQUENCE: 10
CGGRLNSKDA GYITSPGYPQ DYPSHQNCEW IVYAPEPNQK IVLNFNPHFE IEKHDCKYDF    60
IEIRDGDSES ADLLGKHCGN IAPPTIISSG SMLYIKFTSD YARQGAGFSL RYEI         114

SEQ ID NO: 11          moltype = AA  length = 117
FEATURE                Location/Qualifiers
source                 1..117
                       mol_type = protein
                       organism = Homo sapiens
SEQUENCE: 11
CSKNFTSPNG TIESPGFPEK YPHNLDCTFT ILAKPKMEII LQFLIFDLEH DPLQVGEGDC    60
KYDWLDIWDG IPHVGPLIGK YCGTKTPSEL RSSTGILSLT FHTDMAVAKD GFSARYY      117

SEQ ID NO: 12          moltype = AA  length = 147
FEATURE                Location/Qualifiers
source                 1..147
                       mol_type = protein
                       organism = Homo sapiens
SEQUENCE: 12
PLGMESGRIA NEQISASSTY SDGRWTPQQS RLHGDDNGWT PNLDSNKEYL QVDLRFLTML    60
TAIATQGAIS RETQNGYYVK SYKLEVSTNG EDWMVYRHGK NHKVFQANND ATEVVLNKLH   120
APLLTRFVRI RPQTWHSGIA LRLELFG                                      147

SEQ ID NO: 13          moltype = AA  length = 154
FEATURE                Location/Qualifiers
source                 1..154
                       mol_type = protein
                       organism = Homo sapiens
SEQUENCE: 13
LGMLSGLIAD SQISASSTQE YLWSPSAARL VSSRSGWFPR IPQAQPGEEW LQVDLGTPKT    60
VKGVIIQGAR GGDSITAVEA RAFVRKFKVS YSLNGKDWEY IQDPRTQQPK LFEGNMHYDT   120
PDIRRFDPIP AQYVRVYPER WSPAGIGMRL EVLG                              154

SEQ ID NO: 14          moltype = AA  length = 154
FEATURE                Location/Qualifiers
```

```
source                          1..154
                                mol_type = protein
                                organism = Homo sapiens
SEQUENCE: 14
PSGFNCNFDF LEEPCGWMYD HAKWLRTTWA SSSSPNDRTF PDDRNFLRLQ SDSQREGQYA     60
RLISPPVHLP RSPVCMEFQY QATGGRGVAL QVVREASQES KLLWVIREDQ GGEWKHGRII    120
LPSYDMEYQI VFEGVIGKGR SGEIAIDDIR ISTD                                154

SEQ ID NO: 15                   moltype = AA  length = 243
FEATURE                         Location/Qualifiers
source                          1..243
                                mol_type = protein
                                organism = Homo sapiens
SEQUENCE: 15
QPDPPCGGRL NSKDAGYITS PGYPQDYPSH QNCEWIVYAP EPNQKIVLNF NPHFEIEKHD     60
CKYDFIEIRD GDSESADLLG KHCGNIAPPT IISSGSMLYI KFTSDYARQG AGFSLRYEIF    120
KTGSEDCSKN FTSPNGTIES PGFPEKYPHN LDCTFTILAK PKMEIILQFL IFDLEHDPLQ    180
VGEGDCKYDW LDIWDGIPHV GPLIGKYCGT KTPSELRSST GILSLTFHTD MAVAKDGFSA    240
RYY                                                                  243

SEQ ID NO: 16                   moltype = AA  length = 278
FEATURE                         Location/Qualifiers
source                          1..278
                                mol_type = protein
                                organism = Homo sapiens
SEQUENCE: 16
CSKNFTSPNG TIESPGFPEK YPHNLDCTFT ILAKPKMEII LQFLIFDLEH DPLQVGEGDC     60
KYDWLDIWDG IPHVGPLIGK YCGTKTPSEL RSSTGILSLT FHTDMAVAKD GFSARYYLVH    120
QEPLENFQCN VPLGMESGRI ANEQISASST YSDGRWTPQQ SRLHGDDNGW TPNLDSNKEY    180
LQVDLRFLTM LTAIATQGAI SRETQNGYYV KSYKLEVSTN GEDWMVYRHG KNHKVFQANN    240
DATEVVLNKL HAPLLTRFVR IRPQTWHSGI ALRLELFG                            278

SEQ ID NO: 17                   moltype = AA  length = 404
FEATURE                         Location/Qualifiers
source                          1..404
                                mol_type = protein
                                organism = Homo sapiens
SEQUENCE: 17
QPDPPCGGRL NSKDAGYITS PGYPQDYPSH QNCEWIVYAP EPNQKIVLNF NPHFEIEKHD     60
CKYDFIEIRD GDSESADLLG KHCGNIAPPT IISSGSMLYI KFTSDYARQG AGFSLRYEIF    120
KTGSEDCSKN FTSPNGTIES PGFPEKYPHN LDCTFTILAK PKMEIILQFL IFDLEHDPLQ    180
VGEGDCKYDW LDIWDGIPHV GPLIGKYCGT KTPSELRSST GILSLTFHTD MAVAKDGFSA    240
RYYLVHQEPL ENFQCNVPLG MESGRIANEQ ISASSTYSDG RWTPQQSRLH GDDNGWTPNL    300
DSNKEYLQVD LRFLTMLTAI ATQGAISRET QNGYYVKSYK LEVSTNGEDW MVYRHGKNHK    360
VFQANNDATE VVLNKLHAPL LTRFVRIRPQ TWHSGIALRL ELFG                     404

SEQ ID NO: 18                   moltype = AA  length = 573
FEATURE                         Location/Qualifiers
source                          1..573
                                mol_type = protein
                                organism = Homo sapiens
SEQUENCE: 18
QPDPPCGGRL NSKDAGYITS PGYPQDYPSH QNCEWIVYAP EPNQKIVLNF NPHFEIEKHD     60
CKYDFIEIRD GDSESADLLG KHCGNIAPPT IISSGSMLYI KFTSDYARQG AGFSLRYEIF    120
KTGSEDCSKN FTSPNGTIES PGFPEKYPHN LDCTFTILAK PKMEIILQFL IFDLEHDPLQ    180
VGEGDCKYDW LDIWDGIPHV GPLIGKYCGT KTPSELRSST GILSLTFHTD MAVAKDGFSA    240
RYYLVHQEPL ENFQCNVPLG MESGRIANEQ ISASSTYSDG RWTPQQSRLH GDDNGWTPNL    300
DSNKEYLQVD LRFLTMLTAI ATQGAISRET QNGYYVKSYK LEVSTNGEDW MVYRHGKNHK    360
VFQANNDATE VVLNKLHAPL LTRFVRIRPQ TWHSGIALRL ELFGCRVTDA PCSNMLGMLS    420
GLIADSQISA SSTQEYLWSP SAARLVSSRS GWFPRIPQAQ PGEEWLQVDL GTPKTVKGVI    480
IQGARGGDSI TAVEARAFVR KFKVSYSLNG KDWEYIQDPR TQQPKLFEGN MHYDTPDIRR    540
FDPIPAQYVR VYPERWSPAG IGMRLEVLGC DWT                                 573

SEQ ID NO: 19                   moltype = AA  length = 451
FEATURE                         Location/Qualifiers
source                          1..451
                                mol_type = protein
                                organism = Homo sapiens
SEQUENCE: 19
GSEDCSKNFT SPNGTIESPG FPEKYPHNLD CTFTILAKPK MEIILQFLIF DLEHDPLQVG     60
EGDCKYDWLD IWDGIPHVGP LIGKYCGTKT PSELRSSTGI LSLTFHTDMA VAKDGFSARY    120
YLVHQEPLEN FQCNVPLGME SGRIANEQIS ASSTYSDGRW TPQQSRLHGD DNGWTPNLDS    180
NKEYLQVDLR FLTMLTAIAT QGAISRETQN GYYVKSYKLE VSTNGEDWMV YRHGKNHKVF    240
QANNDATEVV LNKLHAPLLT RFVRIRPQTW HSGIALRLEL FGCRVTDAPC SNMLGMLSGL    300
IADSQISASS TQEYLWSPSA ARLVSSRSGW FPRIPQAQPG EEWLQVDLGT PKTVKGVIIQ    360
GARGGDSITA VEARAFVRKF KVSYSLNGKD WEYIQDPRTQ QPKLFEGNMH YDTPDIRRFD    420
PIPAQYVRVY PERWSPAGIG MRLEVLGCDW T                                   451
```

```
SEQ ID NO: 20              moltype = AA   length = 320
FEATURE                    Location/Qualifiers
source                     1..320
                           mol_type = protein
                           organism = Homo sapiens
SEQUENCE: 20
QCNVPLGMES GRIANEQISA SSTYSDGRWT PQQSRLHGDD NGWTPNLDSN KEYLQVDLRF   60
LTMLTAIATQ GAISRETQNG YYVKSYKLEV STNGEDWMVY RHGKNHKVFQ ANNDATEVVL  120
NKLHAPLLTR FVRIRPQTWH SGIALRLELF GCRVTDAPCS NMLGMLSGLI ADSQISASST  180
QEYLWSPSAA RLVSSRSGWF PRIPQAQPGE EWLQVDLGTP KTVKGVIIQG ARGGDSITAV  240
EARAFVRKFK VSYSLNGKDW EYIQDPRTQQ PKLFEGNMHY DTPDIRRFDP IPAQYVRVYP  300
ERWSPAGIGM RLEVLGCDWT                                              320

SEQ ID NO: 21              moltype = AA   length = 1060
FEATURE                    Location/Qualifiers
REGION                     1..1060
                           note = Synthesized construct - NRP2 v2 - Fc fusion protein
source                     1..1060
                           mol_type = protein
                           organism = synthetic construct
SEQUENCE: 21
QPDPPCGGRL NSKDAGYITS PGYPQDYPSH QNCEWIVYAP EPNQKIVLNF NPHFEIEKHD   60
CKYDFIEIRD GDSESADLLG KHCGNIAPPT IISSGSMLYI KFTSDYARQG AGFSLRYEIF  120
KTGSEDCSKN FTSPNGTIES PGFPEKYPHN LDCTFTILAK PKMEIILQFL IFDLEHDPLQ  180
VGEGDCKYDW LDIWDGIPHV GPLIGKYCGT KTPSELRSST GILSLTFHTD MAVAKDGFSA  240
RYYLVHQEPL ENFQCNVPLG MESGRIANEQ ISASSTYSDG RWTPQQSRLH GDDNGWTPNL  300
DSNKEYLQVD LRFLTMLTAI ATQGAISRET QNGYYVKSYK LEVSTNGEDW MVYRHGKNHK  360
VFQANNDATE VVLNKLHAPL LTRFVRIRPQ TWHSGIALRL ELFGCRVTDA PCSNMLGMLS  420
GLIADSQISA SSTQEYLWSP SAARLVSSRS GWFPRIPQAQ PGEEWLQVDL GTPKTVKGVI  480
IQGARGGDSI TAVEARAFVR KFKVSYSLNG KDWEYIQDPR TQQPKLFEGN MHYDTPDIRR  540
FDPIPAQYVR VYPERWSPAG IGMRLEVLGC DWTDSKPTVE TLGPTVKSEE TTTPYPTEEE  600
ATECGENCSF EDDKDLQLPS GFNCNFDFLE EPCGWMYDHA KWLRTTWASS SSPNDRTFPD  660
DRNFLRLQSD SQREGQYARL ISPPVHLPRS PVCMEFQYQA TSGRGVALQV VREASQESKL  720
LWVIREDQGG EWKHGRIILP SYDMEYQIVF EGVIGKGRSG EIAIDDIRIS TDVPLENCME  780
PISAFAVDIP EIHEREGYED EIDDEYEVDW SNSSSATSGS GAPSTDKEKS WLYDKTHTCP  840
PCPAPELLGG PSVFLFPPKP KDTLMISRTP EVTCVVVDVS HEDPEVKFNW YVDGVEVHNA  900
KTKPREEQYN STYRVVSVLT VLHQDWLNGK EYKCKVSNKA LPAPIEKTIS KAKGQPREPQ  960
VYTLPPSRDE LTKNQVSLTC LVKGFYPSDI AVEWESNGQP ENNYKTTPPV LDSDGSFFLY 1020
SKLTVDKSRW QQGNVFSCSV MHEALHNHYT QKSLSLSPGK                       1060

SEQ ID NO: 22              moltype = AA   length = 678
FEATURE                    Location/Qualifiers
REGION                     1..678
                           note = Synthesized construct - NRP2 A2B1B2-Fc
source                     1..678
                           mol_type = protein
                           organism = synthetic construct
SEQUENCE: 22
GSEDCSKNFT SPNGTIESPG FPEKYPHNLD CTFTILAKPK MEIILQFLIF DLEHDPLQVG   60
EGDCKYDWLD IWDGIPHVGP LIGKYCGTKT PSELRSSTGI LSLTFHTDMA VAKDGFSARY  120
YLVHQEPLEN FQCNVPLGME SGRIANEQIS ASSTYSDGRW TPQQSRLHGD DNGWTPNLDS  180
NKEYLQVDLR FLTMLTAIAT QGAISRETQN GYYVKSYKLE VSTNGEDWMV YRHGKNHKVF  240
QANNDATEVV LNKLHAPLLT RFVRIRPQTW HSGIALRLEL FGCRVTDAPC SNMLGMLSGL  300
IADSQISASS TQEYLWSPSA ARLVSSRSGW FPRIPQAQPG EEWLQVDLGT PKTVKGVIIQ  360
GARGGDSITA VEARAFVRKF KVSYSLNGKD WEYIQDPRTQ QPKLFEGNMH YDTPDIRRFD  420
PIPAQYVRVY PERWSPAGIG MRLEVLGCDW TDKTHTCPPC PAPELLGGPS VFLFPPKPKD  480
TLMISRTPEV TCVVVDVSHE DPEVKFNWYV DGVEVHNAKT KPREEQYNST YRVVSVLTVL  540
HQDWLNGKEY KCKVSNKALP APIEKTISKA KGQPREPQVY TLPPSRDELT KNQVSLTCLV  600
KGFYPSDIAV EWESNGQPEN NYKTTPPVLD SDGSFFLYSK LTVDKSRWQQ GNVFSCSVMH  660
EALHNHYTQK SLSLSPGK                                                678

SEQ ID NO: 23              moltype = AA   length = 10
FEATURE                    Location/Qualifiers
REGION                     1..10
                           note = aNRP2-1 VH CDR1
source                     1..10
                           mol_type = protein
                           organism = synthetic construct
SEQUENCE: 23
GYTFTSYWMH                                                          10

SEQ ID NO: 24              moltype = AA   length = 19
FEATURE                    Location/Qualifiers
REGION                     1..19
                           note = aNRP2-1 VH CDR2
source                     1..19
                           mol_type = protein
                           organism = synthetic construct
```

```
SEQUENCE: 24
AIYPGNSDTS YNQQFKGKA                                                        19

SEQ ID NO: 25           moltype = AA  length = 8
FEATURE                 Location/Qualifiers
REGION                  1..8
                        note = aNRP2-1 VH CDR3
source                  1..8
                        mol_type = protein
                        organism = synthetic construct
SEQUENCE: 25
RGGGYFDY                                                                     8

SEQ ID NO: 26           moltype = AA  length = 11
FEATURE                 Location/Qualifiers
REGION                  1..11
                        note = aNRP2-1 VL CDR1
source                  1..11
                        mol_type = protein
                        organism = synthetic construct
SEQUENCE: 26
KASQNVGAAV A                                                                11

SEQ ID NO: 27           moltype = AA  length = 7
FEATURE                 Location/Qualifiers
REGION                  1..7
                        note = aNRP2-1 VL CDR2
source                  1..7
                        mol_type = protein
                        organism = synthetic construct
SEQUENCE: 27
SASNRYT                                                                      7

SEQ ID NO: 28           moltype = AA  length = 10
FEATURE                 Location/Qualifiers
REGION                  1..10
                        note = aNRP2-1 VL CDR3
source                  1..10
                        mol_type = protein
                        organism = synthetic construct
SEQUENCE: 28
QQYSSYPLLT                                                                  10

SEQ ID NO: 29           moltype = AA  length = 10
FEATURE                 Location/Qualifiers
REGION                  1..10
                        note = aNRP2-2 VH CDR1
source                  1..10
                        mol_type = protein
                        organism = synthetic construct
SEQUENCE: 29
GYTFTSYWMH                                                                  10

SEQ ID NO: 30           moltype = AA  length = 17
FEATURE                 Location/Qualifiers
REGION                  1..17
                        note = aNRP2-2 VH CDR2
source                  1..17
                        mol_type = protein
                        organism = synthetic construct
SEQUENCE: 30
VIHPNSASTF YNERFKT                                                          17

SEQ ID NO: 31           moltype = AA  length = 9
FEATURE                 Location/Qualifiers
REGION                  1..9
                        note = aNRP2-2 VH CDR3
source                  1..9
                        mol_type = protein
                        organism = synthetic construct
SEQUENCE: 31
PGTVRRSDY                                                                    9

SEQ ID NO: 32           moltype = AA  length = 16
FEATURE                 Location/Qualifiers
REGION                  1..16
                        note = aNRP2-2 VL CDR1
```

```
source                  1..16
                        mol_type = protein
                        organism = synthetic construct
SEQUENCE: 32
RSSQNIVHST GNTYLE                                                          16

SEQ ID NO: 33           moltype = AA   length = 7
FEATURE                 Location/Qualifiers
REGION                  1..7
                        note = aNRP2-2 VL CDR2
source                  1..7
                        mol_type = protein
                        organism = synthetic construct
SEQUENCE: 33
KVSNRFS                                                                     7

SEQ ID NO: 34           moltype = AA   length = 9
FEATURE                 Location/Qualifiers
REGION                  1..9
                        note = aNRP2-2 VL CDR3
source                  1..9
                        mol_type = protein
                        organism = synthetic construct
SEQUENCE: 34
FQGSHVPWT                                                                   9

SEQ ID NO: 35           moltype = AA   length = 10
FEATURE                 Location/Qualifiers
REGION                  1..10
                        note = aNRP2-6 VH CDR1
source                  1..10
                        mol_type = protein
                        organism = synthetic construct
SEQUENCE: 35
GFNIKDYYIH                                                                 10

SEQ ID NO: 36           moltype = AA   length = 17
FEATURE                 Location/Qualifiers
REGION                  1..17
                        note = aNRP2-6 VH CDR2
source                  1..17
                        mol_type = protein
                        organism = synthetic construct
SEQUENCE: 36
RIDVEDDETK YAPKFQG                                                         17

SEQ ID NO: 37           moltype = AA   length = 12
FEATURE                 Location/Qualifiers
REGION                  1..12
                        note = aNRP2-6 VH CDR3
source                  1..12
                        mol_type = protein
                        organism = synthetic construct
SEQUENCE: 37
PIYGSREAWF AY                                                              12

SEQ ID NO: 38           moltype = AA   length = 12
FEATURE                 Location/Qualifiers
REGION                  1..12
                        note = aNRP2-6 VL CDR1
source                  1..12
                        mol_type = protein
                        organism = synthetic construct
SEQUENCE: 38
TASSSVSSSY LH                                                              12

SEQ ID NO: 39           moltype = AA   length = 7
FEATURE                 Location/Qualifiers
REGION                  1..7
                        note = aNRP2-6 VL CDR2
source                  1..7
                        mol_type = protein
                        organism = synthetic construct
SEQUENCE: 39
RTSNLAS                                                                     7
```

```
SEQ ID NO: 40            moltype = AA  length = 9
FEATURE                  Location/Qualifiers
REGION                   1..9
                         note = aNRP2-6 VL CDR3
source                   1..9
                         mol_type = protein
                         organism = synthetic construct
SEQUENCE: 40
HQYYRSPPT                                                              9

SEQ ID NO: 41            moltype = AA  length = 10
FEATURE                  Location/Qualifiers
REGION                   1..10
                         note = aNRP2-7 VH CDR1
source                   1..10
                         mol_type = protein
                         organism = synthetic construct
SEQUENCE: 41
GFNIKDYYIH                                                            10

SEQ ID NO: 42            moltype = AA  length = 17
FEATURE                  Location/Qualifiers
REGION                   1..17
                         note = aNRP2-7 VH CDR2
source                   1..17
                         mol_type = protein
                         organism = synthetic construct
SEQUENCE: 42
RIDVEDDETK YAPKFQG                                                    17

SEQ ID NO: 43            moltype = AA  length = 12
FEATURE                  Location/Qualifiers
REGION                   1..12
                         note = aNRP2-7 VH CDR3
source                   1..12
                         mol_type = protein
                         organism = synthetic construct
SEQUENCE: 43
PIYGSREAFF AY                                                         12

SEQ ID NO: 44            moltype = AA  length = 12
FEATURE                  Location/Qualifiers
REGION                   1..12
                         note = aNRP2-7 VL CDR1
source                   1..12
                         mol_type = protein
                         organism = synthetic construct
SEQUENCE: 44
TASSSVSSSY LH                                                         12

SEQ ID NO: 45            moltype = AA  length = 7
FEATURE                  Location/Qualifiers
REGION                   1..7
                         note = aNRP2-7 VL CDR2
source                   1..7
                         mol_type = protein
                         organism = synthetic construct
SEQUENCE: 45
STSNLAS                                                                7

SEQ ID NO: 46            moltype = AA  length = 9
FEATURE                  Location/Qualifiers
REGION                   1..9
                         note = aNRP2-7 VL CDR3
source                   1..9
                         mol_type = protein
                         organism = synthetic construct
SEQUENCE: 46
HQYYRSPPT                                                              9

SEQ ID NO: 47            moltype = AA  length = 10
FEATURE                  Location/Qualifiers
REGION                   1..10
                         note = aNRP2-8 VH CDR1
source                   1..10
                         mol_type = protein
                         organism = synthetic construct
```

```
SEQUENCE: 47
GFNVKDYYVH                                                              10

SEQ ID NO: 48         moltype = AA  length = 17
FEATURE               Location/Qualifiers
REGION                1..17
                      note = aNRP2-8 VH CDR2
source                1..17
                      mol_type = protein
                      organism = synthetic construct
SEQUENCE: 48
RIDVEDDETK YAPKFQG                                                      17

SEQ ID NO: 49         moltype = AA  length = 12
FEATURE               Location/Qualifiers
REGION                1..12
                      note = aNRP2-8 VH CDR3
source                1..12
                      mol_type = protein
                      organism = synthetic construct
SEQUENCE: 49
PIYGAREAWF AY                                                           12

SEQ ID NO: 50         moltype = AA  length = 12
FEATURE               Location/Qualifiers
REGION                1..12
                      note = aNRP2-8 VL CDR1
source                1..12
                      mol_type = protein
                      organism = synthetic construct
SEQUENCE: 50
TANSSVSSSY LH                                                           12

SEQ ID NO: 51         moltype = AA  length = 7
FEATURE               Location/Qualifiers
REGION                1..7
                      note = aNRP2-8 VL CDR2
source                1..7
                      mol_type = protein
                      organism = synthetic construct
SEQUENCE: 51
STSNLAS                                                                  7

SEQ ID NO: 52         moltype = AA  length = 9
FEATURE               Location/Qualifiers
REGION                1..9
                      note = aNRP2-8 VL CDR3
source                1..9
                      mol_type = protein
                      organism = synthetic construct
SEQUENCE: 52
HQYHRSPPT                                                                9

SEQ ID NO: 53         moltype = AA  length = 10
FEATURE               Location/Qualifiers
REGION                1..10
                      note = aNRP2-9 VH CDR1
source                1..10
                      mol_type = protein
                      organism = synthetic construct
SEQUENCE: 53
GFSLTNYGVY                                                              10

SEQ ID NO: 54         moltype = AA  length = 16
FEATURE               Location/Qualifiers
REGION                1..16
                      note = aNRP2-9 VH CDR2
source                1..16
                      mol_type = protein
                      organism = synthetic construct
SEQUENCE: 54
VIWSGGSTDY NAAFIS                                                       16

SEQ ID NO: 55         moltype = AA  length = 14
FEATURE               Location/Qualifiers
REGION                1..14
                      note = aNRP2-9 VH CDR3
```

```
source                  1..14
                        mol_type = protein
                        organism = synthetic construct
SEQUENCE: 55
NGPNWDRGYY AMDY                                                      14

SEQ ID NO: 56           moltype = AA   length = 17
FEATURE                 Location/Qualifiers
REGION                  1..17
                        note = aNRP2-9 VL CDR1
source                  1..17
                        mol_type = protein
                        organism = synthetic construct
SEQUENCE: 56
KSSQSLLNSR NQKNYLA                                                   17

SEQ ID NO: 57           moltype = AA   length = 7
FEATURE                 Location/Qualifiers
REGION                  1..7
                        note = aNRP2-9 VL CDR2
source                  1..7
                        mol_type = protein
                        organism = synthetic construct
SEQUENCE: 57
FASTRES                                                               7

SEQ ID NO: 58           moltype = AA   length = 9
FEATURE                 Location/Qualifiers
REGION                  1..9
                        note = aNRP2-9 VL CDR3
source                  1..9
                        mol_type = protein
                        organism = synthetic construct
SEQUENCE: 58
QQHYSTPFT                                                             9

SEQ ID NO: 59           moltype = AA   length = 10
FEATURE                 Location/Qualifiers
REGION                  1..10
                        note = aNRP2-10 VH CDR1
source                  1..10
                        mol_type = protein
                        organism = synthetic construct
SEQUENCE: 59
GFNIKDYYIH                                                           10

SEQ ID NO: 60           moltype = AA   length = 17
FEATURE                 Location/Qualifiers
REGION                  1..17
                        note = aNRP2-10 VH CDR2
source                  1..17
                        mol_type = protein
                        organism = synthetic construct
SEQUENCE: 60
RIDVEDDETK YAPKFQG                                                   17

SEQ ID NO: 61           moltype = AA   length = 12
FEATURE                 Location/Qualifiers
REGION                  1..12
                        note = aNRP2-10 VH CDR3
source                  1..12
                        mol_type = protein
                        organism = synthetic construct
SEQUENCE: 61
PIYGSREAWF AY                                                        12

SEQ ID NO: 62           moltype = AA   length = 12
FEATURE                 Location/Qualifiers
REGION                  1..12
                        note = aNRP2-10 VL CDR1
source                  1..12
                        mol_type = protein
                        organism = synthetic construct
SEQUENCE: 62
TASSSVSSSY LH                                                        12
```

| | | |
|---|---|---|
| SEQ ID NO: 63<br>FEATURE<br>REGION<br><br>source | moltype = AA  length = 7<br>Location/Qualifiers<br>1..7<br>note = aNRP2-10 VL CDR2<br>1..7<br>mol_type = protein<br>organism = synthetic construct | |
| SEQUENCE: 63<br>STSNLAS | | 7 |
| SEQ ID NO: 64<br>FEATURE<br>REGION<br><br>source | moltype = AA  length = 9<br>Location/Qualifiers<br>1..9<br>note = aNRP2-10 VL CDR3<br>1..9<br>mol_type = protein<br>organism = synthetic construct | |
| SEQUENCE: 64<br>HQYYRSPPT | | 9 |
| SEQ ID NO: 65<br>FEATURE<br>REGION<br><br>source | moltype = AA  length = 10<br>Location/Qualifiers<br>1..10<br>note = aNRP2-11 VH CDR1<br>1..10<br>mol_type = protein<br>organism = synthetic construct | |
| SEQUENCE: 65<br>GYTFTSFGIS | | 10 |
| SEQ ID NO: 66<br>FEATURE<br>REGION<br><br>source | moltype = AA  length = 17<br>Location/Qualifiers<br>1..17<br>note = aNRP2-11 VH CDR2<br>1..17<br>mol_type = protein<br>organism = synthetic construct | |
| SEQUENCE: 66<br>EIYPRSGNTY YNENFKG | | 17 |
| SEQ ID NO: 67<br>FEATURE<br>REGION<br><br>source | moltype = AA  length = 12<br>Location/Qualifiers<br>1..12<br>note = aNRP2-11 VH CDR3<br>1..12<br>mol_type = protein<br>organism = synthetic construct | |
| SEQUENCE: 67<br>SSGYYGSTPF PY | | 12 |
| SEQ ID NO: 68<br>FEATURE<br>REGION<br><br>source | moltype = AA  length = 11<br>Location/Qualifiers<br>1..11<br>note = aNRP2-11 VL CDR1<br>1..11<br>mol_type = protein<br>organism = synthetic construct | |
| SEQUENCE: 68<br>RASQDISNYL N | | 11 |
| SEQ ID NO: 69<br>FEATURE<br>REGION<br><br>source | moltype = AA  length = 7<br>Location/Qualifiers<br>1..7<br>note = aNRP2-11 VL CDR2<br>1..7<br>mol_type = protein<br>organism = synthetic construct | |
| SEQUENCE: 69<br>YTSRLHS | | 7 |
| SEQ ID NO: 70<br>FEATURE<br>REGION<br><br>source | moltype = AA  length = 9<br>Location/Qualifiers<br>1..9<br>note = aNRP2-11 VL CDR3<br>1..9<br>mol_type = protein<br>organism = synthetic construct | |

```
SEQUENCE: 70
QQGNTLPWT                                                                9

SEQ ID NO: 71          moltype = AA  length = 10
FEATURE                Location/Qualifiers
REGION                 1..10
                       note = aNRP2-12 VH CDR1
source                 1..10
                       mol_type = protein
                       organism = synthetic construct
SEQUENCE: 71
GYTFTTSGMS                                                              10

SEQ ID NO: 72          moltype = AA  length = 17
FEATURE                Location/Qualifiers
REGION                 1..17
                       note = aNRP2-12 VH CDR2
source                 1..17
                       mol_type = protein
                       organism = synthetic construct
SEQUENCE: 72
WINTYSGVPT YADDFKG                                                      17

SEQ ID NO: 73          moltype = AA  length = 10
FEATURE                Location/Qualifiers
REGION                 1..10
                       note = aNRP2-12 VH CDR3
source                 1..10
                       mol_type = protein
                       organism = synthetic construct
SEQUENCE: 73
YYSYYVDFDY                                                              10

SEQ ID NO: 74          moltype = AA  length = 12
FEATURE                Location/Qualifiers
REGION                 1..12
                       note = aNRP2-12 VL CDR1
source                 1..12
                       mol_type = protein
                       organism = synthetic construct
SEQUENCE: 74
SASSSVSSSY LY                                                           12

SEQ ID NO: 75          moltype = AA  length = 7
FEATURE                Location/Qualifiers
REGION                 1..7
                       note = aNRP2-12 VL CDR2
source                 1..7
                       mol_type = protein
                       organism = synthetic construct
SEQUENCE: 75
STSNLAS                                                                  7

SEQ ID NO: 76          moltype = AA  length = 9
FEATURE                Location/Qualifiers
REGION                 1..9
                       note = aNRP2-12 VL CDR3
source                 1..9
                       mol_type = protein
                       organism = synthetic construct
SEQUENCE: 76
HQWSSYPRT                                                                9

SEQ ID NO: 77          moltype = AA  length = 10
FEATURE                Location/Qualifiers
REGION                 1..10
                       note = aNRP2-14 VH CDR1
source                 1..10
                       mol_type = protein
                       organism = synthetic construct
SEQUENCE: 77
GFSLTSYGVH                                                              10

SEQ ID NO: 78          moltype = AA  length = 16
FEATURE                Location/Qualifiers
REGION                 1..16
                       note = aNRP2-14 VH CDR2
```

```
source                   1..16
                         mol_type = protein
                         organism = synthetic construct
SEQUENCE: 78
LIWSGGSTDY SPAFIS                                                            16

SEQ ID NO: 79            moltype = AA  length = 12
FEATURE                  Location/Qualifiers
REGION                   1..12
                         note = aNRP2-14 VH CDR3
source                   1..12
                         mol_type = protein
                         organism = synthetic construct
SEQUENCE: 79
NSYSSGYYAM DY                                                                12

SEQ ID NO: 80            moltype = AA  length = 11
FEATURE                  Location/Qualifiers
REGION                   1..11
                         note = aNRP2-14 VL CDR1
source                   1..11
                         mol_type = protein
                         organism = synthetic construct
SEQUENCE: 80
KASQNVGTAV A                                                                 11

SEQ ID NO: 81            moltype = AA  length = 7
FEATURE                  Location/Qualifiers
REGION                   1..7
                         note = aNRP2-14 VL CDR2
source                   1..7
                         mol_type = protein
                         organism = synthetic construct
SEQUENCE: 81
SASNRYT                                                                       7

SEQ ID NO: 82            moltype = AA  length = 10
FEATURE                  Location/Qualifiers
REGION                   1..10
                         note = aNRP2-14 VL CDR3
source                   1..10
                         mol_type = protein
                         organism = synthetic construct
SEQUENCE: 82
QQYSSYPPYT                                                                   10

SEQ ID NO: 83            moltype = AA  length = 10
FEATURE                  Location/Qualifiers
REGION                   1..10
                         note = aNRP2-15 VH CDR1
source                   1..10
                         mol_type = protein
                         organism = synthetic construct
SEQUENCE: 83
GFNIKDSFIH                                                                   10

SEQ ID NO: 84            moltype = AA  length = 17
FEATURE                  Location/Qualifiers
REGION                   1..17
                         note = aNRP2-15 VH CDR2
source                   1..17
                         mol_type = protein
                         organism = synthetic construct
SEQUENCE: 84
RIDPEDDETK YAPKFQG                                                           17

SEQ ID NO: 85            moltype = AA  length = 12
FEATURE                  Location/Qualifiers
REGION                   1..12
                         note = aNRP2-15 VH CDR3
source                   1..12
                         mol_type = protein
                         organism = synthetic construct
SEQUENCE: 85
PIYGSREAWF AY                                                                12
```

```
SEQ ID NO: 86             moltype = AA  length = 12
FEATURE                   Location/Qualifiers
REGION                    1..12
                          note = aNRP2-15 VL CDR1
source                    1..12
                          mol_type = protein
                          organism = synthetic construct
SEQUENCE: 86
TASSSVSSSY LH                                                              12

SEQ ID NO: 87             moltype = AA  length = 7
FEATURE                   Location/Qualifiers
REGION                    1..7
                          note = aNRP2-15 VL CDR2
source                    1..7
                          mol_type = protein
                          organism = synthetic construct
SEQUENCE: 87
RTSNLAS                                                                    7

SEQ ID NO: 88             moltype = AA  length = 9
FEATURE                   Location/Qualifiers
REGION                    1..9
                          note = aNRP2-15 VL CDR3
source                    1..9
                          mol_type = protein
                          organism = synthetic construct
SEQUENCE: 88
HQYYRSPPT                                                                  9

SEQ ID NO: 89             moltype = AA  length = 357
FEATURE                   Location/Qualifiers
source                    1..357
                          mol_type = protein
                          organism = Homo sapiens
SEQUENCE: 89
LGMLSGLIAD SQISASSTQE YLWSPSAARL VSSRSGWFPR IPQAQPGEEW LQVDLGTPKT    60
VKGVIIQGAR GGDSITAVEA RAFVRKFKVS YSLNGKDWEY IQDPRTQQPK LFEGNMHYDT    120
PDIRRFDPIP AQYVRVYPER WSPAGIGMRL EVLGCDWTDS KPTVETLGPT VKSEETTTPY    180
PTEEEATECG ENCSFEDDKD LQLPSGFNCN FDFLEEPCGW MYDHAKWLRT TWASSSSPND    240
RTFPDDRNFL RLQSDSQREG QYARLISPPV HLPRSPVCME FQYQATGRG  VALQVVREAS    300
QESKLLWVIR EDQGGEWKHG RIILPSYDME YQIVFEGVIG KGRSGEIAID DIRISTD       357

SEQ ID NO: 90             moltype = AA  length = 519
FEATURE                   Location/Qualifiers
source                    1..519
                          mol_type = protein
                          organism = Homo sapiens
SEQUENCE: 90
QCNVPLGMES GRIANEQISA SSTYSDGRWT PQQSRLHGDD NGWTPNLDSN KEYLQVDLRF    60
LTMLTAIATQ GAISRETQNG YYVKSYKLEV STNGEDWMVY RHGKNHKVFQ ANNDATEVVL    120
NKLHAPLLTR FVRIRPQTWH SGIALRLELF GCRVTDAPCS NMLGMLSGLI ADSQISASST    180
QEYLWSPSAA RLVSSRSGWF PRIPQAQPGE EWLQVDLGTP KTVKGVIIQG ARGGDSITAV    240
EARAFVRKFK VSYSLNGKDW EYIQDPRTQQ PKLFEGNMHY DTPDIRRFDP IPAQYVRVYP    300
ERWSPAGIGM RLEVLGCDWT DSKPTVETLG PTVKSEETTT PYPTEEEATE CGENCSFEDD    360
KDLQLPSGFN CNFDFLEEPC GWMYDHAKWL RTTWASSSSP NDRTFPDDRN FLRLQSDSQR    420
EGQYARLISP PVHLPRSPVC MEFQYQATGG RGVALQVVRE ASQESKLLWV IREDQGGEWK    480
HGRIILPSYD MEYQIVFEGV IGKGRSGEIA IDDIRISTD                           519

SEQ ID NO: 91             moltype = AA  length = 509
FEATURE                   Location/Qualifiers
source                    1..509
                          mol_type = protein
                          organism = Homo sapiens
SEQUENCE: 91
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKLIYDLKDQ    120
GGELLSLRYD LTVPFARYLA MNKLTNIKRY HIAKVYRRDN PAMTRGRYRE FYQCDFDIAG    180
NFDPMIPDAE CLKIMCEILS SLQIGDFLVK VNDRRILDGM FAICGVSDSK FRTICSSVDK    240
LDKVSWEEVK NEMVGEKGLA PEVADRIGDY VQQHGGVSLV EQLLQDPKLS QNKQALEGLG    300
DLKLLFEYLT LFGIDDKISF DLSLARGLDY YTGVIYEAVL LQTPAQAGEE PLGVGSVAAG    360
GRYDGLVGMF DPKGRKVPCV GLSIGVERIF SIVEQRLEAL EEKIRTTETQ VLVASAQKKL    420
LEERLKLVSE LWDAGIKAEL LYKKNPKLLN QLQYCEEAGI PLVAIIGEQE LKDGVIKLRS    480
VTSREEVDVR REDLVEEIKR RTGQPLCIC                                     509

SEQ ID NO: 92             moltype = AA  length = 141
FEATURE                   Location/Qualifiers
source                    1..141
```

```
                        mol_type = protein
                        organism = Homo sapiens
SEQUENCE: 92
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKLIYDLKDQ   120
GGELLSLRYD LTVPFARYLA M                                             141

SEQ ID NO: 93           moltype = AA  length = 408
FEATURE                 Location/Qualifiers
source                  1..408
                        mol_type = protein
                        organism = Homo sapiens
SEQUENCE: 93
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKLIYDLKDQ   120
GGELLSLRYD LTVPFARYLA MNKLTNIKRY HIAKVYRRDN PAMTRGRYRE FYQCDFDIAG   180
NFDPMIPDAE CLKIMCEILS SLQIGDFLVK VNDRRILDGM FAICGVSDSK FRTICSSVDK   240
LDKVSWEEVK NEMVGEKGLA PEVADRIGDY VQQHGGVSLV EQLLQDPKLS QNKQALEGLG   300
DLKLLFEYLT LFGIDDKISF DLSLARGLDY YTGVIYEAVL LQTPAQAGEE PLGVGSVAAG   360
GRYDGLVGMF DPKGRKVPCV GLSIGVERIF SIVEQRLEAL EEKIRTTE               408

SEQ ID NO: 94           moltype = AA  length = 113
FEATURE                 Location/Qualifiers
source                  1..113
                        mol_type = protein
                        organism = Homo sapiens
SEQUENCE: 94
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKL          113

SEQ ID NO: 95           moltype = AA  length = 60
FEATURE                 Location/Qualifiers
source                  1..60
                        mol_type = protein
                        organism = Homo sapiens
SEQUENCE: 95
MAERAALEEL VKLQGERVRG LKQQKASAEL IEEEVAKLLK LKAQLGPDES KQKFVLKTPK    60

SEQ ID NO: 96           moltype = AA  length = 270
FEATURE                 Location/Qualifiers
source                  1..270
                        mol_type = protein
                        organism = Homo sapiens
SEQUENCE: 96
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKLIYDLKDQ   120
GGELLSLRYD LTVPFARYLA MNKLTNIKRY HIAKVYRRDN PAMTRGRYRE FYQCDFDIAG   180
NFDPMIPDAE CLKIMCEILS SLQIGDFLVK VNDRRILDGM FAICGVSDSK FRTICSSVDK   240
LDKVGYPWWN SCSRILNYPK TSRPWRAWET                                    270

SEQ ID NO: 97           moltype = AA  length = 105
FEATURE                 Location/Qualifiers
source                  1..105
                        mol_type = protein
                        organism = Homo sapiens
SEQUENCE: 97
RTTETQVLVA SAQKKLLEER LKLVSELWDA GIKAELLYKK NPKLLNQLQY CEEAGIPLVA    60
IIGEQELKDG VIKLRSVTSR EEVDVRREDL VEEIKRRTGQ PLCIC                   105

SEQ ID NO: 98           moltype = AA  length = 395
FEATURE                 Location/Qualifiers
source                  1..395
                        mol_type = protein
                        organism = Homo sapiens
SEQUENCE: 98
MAERAALEEL VKLQGERVRG LKQQKASAEL IEEEVAKLLK LKAQLGPDES KQKFVLKTPK    60
DFDIAGNFDP MIPDAECLKI MCEILSSLQI GDFLVKVNDR RILDGMFAIC GVSDSKFRTI   120
CSSVDKLDKV SWEEVKNEMV GEKGLAPEVA DRIGDYVQQH GGVSLVEQLL QDPKLSQNKQ   180
ALEGLGDLKL LFEYLTLFGI DDKISFDLSL ARGLDYYTGV IYEAVLLQTP AQAGEEPLGV   240
GSVAAGGRYD GLVGMFDPKG RKVPCVGLSI GVERIFSIVE QRLEALEEKI RTTETQVLVA   300
SAQKKLLEER LKLVSELWDA GIKAELLYKK NPKLLNQLQY CEEAGIPLVA IIGEQELKDG   360
VIKLRSVTSR EEVDVRREDL VEEIKRRTGQ PLCIC                             395

SEQ ID NO: 99           moltype = AA  length = 399
FEATURE                 Location/Qualifiers
source                  1..399
                        mol_type = protein
                        organism = Homo sapiens
```

```
SEQUENCE: 99
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK VNDRRILDGM FAICGVSDSK   120
FRTICSSVDK LDKVSWEEVK NEMVGEKGLA PEVADRIGDY VQQHGGVSLV EQLLQDPKLS   180
QNKQALEGLG DLKLLFEYLT LFGIDDKISF DLSLARGLDY YTGVIYEAVL LQTPAQAGEE   240
PLGVGSVAAG GRYDGLVGMF DPKGRKVPCV GLSIGVERIF SIVEQRLEAL EEKIRTTETQ   300
VLVASAQKKL LEERLKLVSE LWDAGIKAEL LYKKNPKLLN QLQYCEEAGI PLVAIIGEQE   360
LKDGVIKLRS VTSREEVDVR REDLVEEIKR RTGQPLCIC                          399

SEQ ID NO: 100          moltype = AA  length = 473
FEATURE                 Location/Qualifiers
source                  1..473
                        mol_type = protein
                        organism = Homo sapiens
SEQUENCE: 100
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ETLMGKYGED SKLIYDLKDQ   120
GGELLSLRYD LTVPFARYLA MNKLTNIKRY HIAKVYRRDN PAMTRGRYRE FYQCVNDRRI   180
LDGMFAICGV SDSKFRTICS SVDKLDKVSW EEVKNEMVGE KGLAPEVADR IGDYVQQHGG   240
VSLVEQLLQD PKLSQNKQAL EGLGDKLLF EYLTLFGIDD KISFDLSLAR GLDYYTGVIY    300
EAVLLQTPAQ AGEEPLGVGS VAAGGRYDGL VGMFDPKGRK VPCVGLSIGV ERIFSIVEQR   360
LEALEEKIRT TETQVLVASA QKKLLEERLK LVSELWDAGI KAELLYKKNP KLLNQLQYCE   420
EAGIPLVAII GEQELKDGVI KLRSVTSREE VDVRREDLVE EIKRRTGQPL CIC           473

SEQ ID NO: 101          moltype = AA  length = 469
FEATURE                 Location/Qualifiers
source                  1..469
                        mol_type = protein
                        organism = Homo sapiens
SEQUENCE: 101
MAERAALEEL VKLQGERVRG LKQQKASAEL IEEEVAKLLK LKAQLGPDES KQKFVLKTPK    60
ETLMGKYGED SKLIYDLKDQ GGELLSLRYD LTVPFARYLA MNKLTNIKRY HIAKVYRRDN   120
PAMTRGRYRE FYQCDFDIAG NFDPMIPDAE CLKIMCEILS SLQIGDFLVK VNDRRILDGM   180
FAICGVSDSK FRTICSSVDK LDKVSWEEVK NEMVGEKGLA PEVADRIGDY VQQHGGVSLV   240
EQLLQDPKLS QNKQALEGLG DLKLLFEYLT LFGIDDKISF DLSLARGLDY YTGVIYEAVL   300
LQTPAQAGEE PLGVGSVAAG GRYDGLVGMF DPKGRKVPCV GLSIGVERIF SIVEQRLEAL   360
EEKIRTTETQ VLVASAQKKL LEERLKLVSE LWDAGIKAEL LYKKNPKLLN QLQYCEEAGI   420
PLVAIIGEQE LKDGVIKLRS VTSREEVDVR REDLVEEIKR RTGQPLCIC                469

SEQ ID NO: 102          moltype = AA  length = 435
FEATURE                 Location/Qualifiers
source                  1..435
                        mol_type = protein
                        organism = Homo sapiens
SEQUENCE: 102
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK DFDIAGNFDP MIPDAECLKI   120
MCEILSSLQI GDFLVKVNDR RILDGMFAIC GVSDSKFRTI CSSVDKLDKV SWEEVKNEMV   180
GEKGLAPEVA DRIGDYVQQH GGVSLVEQLL QDPKLSQNKQ ALEGLGDLKL LFEYLTLFGI   240
DDKISFDLSL ARGLDYYTGV IYEAVLLQTP AQAGEEPLGV GSVAAGGRYD GLVGMFDPKG   300
RKVPCVGLSI GVERIFSIVE QRLEALEEKI RTTETQVLVA SAQKKLLEER LKLVSELWDA   360
GIKAELLYKK NPKLLNQLQY CEEAGIPLVA IIGEQELKDG VIKLRSVTSR EEVDVRREDL   420
VEEIKRRTGQ PLCIC                                                    435

SEQ ID NO: 103          moltype = AA  length = 171
FEATURE                 Location/Qualifiers
source                  1..171
                        mol_type = protein
                        organism = Homo sapiens
SEQUENCE: 103
MAERAALEEL VKLQGERVRG LKQQKASAEL IEEEVAKLLK LKAQLGPDES KQKFVLKTPK    60
ALEEKIRTTE TQVLVASAQK KLLEERLKLV SELWDAGIKA ELLYKKNPKL LNQLQYCEEA   120
GIPLVAIIGE QELKDGVIKL RSVTSREEVD VRREDLVEEI KRRTGQPLCI C             171

SEQ ID NO: 104          moltype = AA  length = 211
FEATURE                 Location/Qualifiers
source                  1..211
                        mol_type = protein
                        organism = Homo sapiens
SEQUENCE: 104
MAERAALEEL VKLQGERVRG LKQQKASAEL IEEEVAKLLK LKAQLGPDES KQKFVLKTPK    60
GTRDYSPRQM AVREKVFDVI IRCFKRHGAE VIDTPVFELK ALEEKIRTTE TQVLVASAQK   120
KLLEERLKLV SELWDAGIKA ELLYKKNPKL LNQLQYCEEA GIPLVAIIGE QELKDGVIKL   180
RSVTSREEVD VRREDLVEEI KRRTGQPLCI C                                  211
```

```
SEQ ID NO: 105          moltype = AA  length = 141
FEATURE                 Location/Qualifiers
source                  1..141
                        mol_type = protein
                        organism = Homo sapiens
SEQUENCE: 105
MFDPKGRKVP CVGLSIGVER IFSIVEQRLE ALEEKIRTTE TQVLVASAQK KLLEERLKLV    60
SELWDAGIKA ELLYKKNPKL LNQLQYCEEA GIPLVAIIGE QELKDGVIKL RSVTSREEVD   120
VRREDLVEEI KRRTGQPLCI C                                             141

SEQ ID NO: 106          moltype = AA  length = 143
FEATURE                 Location/Qualifiers
source                  1..143
                        mol_type = protein
                        organism = Homo sapiens
SEQUENCE: 106
CLKIMCEILS SLQIGDFLVK VNDRRILDGM FAICGVSDSK FRTICSSVDK LDKVSWEEVK    60
NEMVGEKGLA PEVADRIGDY VQQHGGVSLV EQLLQDPKLS QNKQALEGLG DLKLLFEYLT   120
LFGIDDKISF DLSLARGLDY YTG                                           143

SEQ ID NO: 107          moltype = AA  length = 506
FEATURE                 Location/Qualifiers
REGION                  1..506
                        note = MISC_FEATURE - Mitochondrial
source                  1..506
                        mol_type = protein
                        organism = Homo sapiens
SEQUENCE: 107
MPLLGLLPRR AWASLLSQLL RPPCASCTGA VRCQSQVAEA VLTSQLKAHQ EKPNFIIKTP    60
KGTRDLSPQH MVVREKILDL VISCFKRHGA KGMDTPAFEL KETLTEKYGE DSGLMYDLKD   120
QGGELLSLRY DLTVPFARYL AMNKVKKMKR YHVGKVWRRE SPTIVQGRYR EFCQCDFDIA   180
GQFDPMIPDA ECLKIMCEIL SGLQLGDFLI KVNDRRIVDG MFAVCGVPES KFRAICSSID   240
KLDKMAWKDV RHEMVVKKGL APEVADRIGD YVQCHGGVSL VEQMFQDPRL SQNKQALEGL   300
GDLKLLFEYL TLFGIADKIS FDLSLARGLD YYTGVIYEAV LLQTPTQAGE EPLNVGSVAA   360
GGRYDGLVGM FDPKGHKVPC VGLSIGVERI FYIVEQRMKT KGEKVRTTET QVFVATPQKN   420
FLQERLKLIA ELWDSGIKAE MLYKNNPKLL TQLHYCESTG IPLVVIIGEQ ELKEGVIKIR   480
SVASREEVAI KRENFVAEIQ KRLSES                                        506

SEQ ID NO: 108          moltype = AA  length = 247
FEATURE                 Location/Qualifiers
source                  1..247
                        mol_type = protein
                        organism = Homo sapiens
SEQUENCE: 108
HVGKVWRRES PTIVQGRYRE FCQCDFDIAG QFDPMIPDAE CLKIMCEILS GLQLGDFLIK    60
VNDRRIVDGM FAVCGVPESK FRAICSSIDK LDKMAWKDVR HEMVVKKGLA PEVADRIGDY   120
VQCHGGVSLV EQMFQDPRLS QNKQALEGLG DLKLLFEYLT LFGIADKISF DLSLARGLDY   180
YTGVIYEAVL LQTPTQAGEE PLNVGSVAAG GRYDGLVGMF DPKGHKVPCV GLSIGVERIF   240
YIVEQRM                                                             247

SEQ ID NO: 109          moltype = AA  length = 79
FEATURE                 Location/Qualifiers
source                  1..79
                        mol_type = protein
                        organism = Homo sapiens
SEQUENCE: 109
QALEGLGDLK LLFEYLTLFG IDDKISFDLS LARGLDYYTG VIYEAVLLQT PAQAGEEPLG    60
VGSVAAGGRY DGLVGMFDP                                                 79

SEQ ID NO: 110          moltype = AA  length = 456
FEATURE                 Location/Qualifiers
source                  1..456
                        mol_type = protein
                        organism = Homo sapiens
SEQUENCE: 110
FVLKTPKGTR DYSPRQMAVR EKVFDVIIRC FKRHGAEVID TPVFELKETL MGKYGEDSKL    60
IYDLKDQGGE LLSLRYDLTV PFARYLAMNK LTNIKRYHIA KVYRRDNPAM TRGRYREFYQ   120
CDFDIAGNFD PMIPDAECLK IMCEILSSLQ IGDFLVKVND RRILDGMFAI CGVSDSKFRT   180
ICSSVDKLDK VSWEEVKNEM VGEKGLAPEV ADRIGDYVQQ HGGVSLVEQL LQDPKLSQNK   240
QALEGLGDLK LLFEYLTLFG IDDKISFDLS LARGLDYYTG VIYEAVLLQT PAQAGEEPLG   300
VGSVAAGGRY DGLVGMFDPK GRKVPCVGLS IGVERIFSIV EQRLEALEEK IRTTETQVLV   360
ASAQKKLLEE RLKLVSELWD AGIKAELLYK KNPKLLNQLQ YCEEAGIPLV AIIGEQELKD   420
GVIKLRSVTS REEVDVRRED LVEEIKRRTG QPLCIC                             456
```

```
SEQ ID NO: 111          moltype = AA   length = 345
FEATURE                 Location/Qualifiers
source                  1..345
                        mol_type = protein
                        organism = Homo sapiens
SEQUENCE: 111
FVLKTPKGTR DYSPRQMAVR EKVFDVIIRC FKRHGAEVID TPVFELKETL MGKYGEDSKL   60
IYDLKDQGGE LLSLRYDLTV PFARYLAMNK LTNIKRYHIA KVYRRDNPAM TRGRYREFYQ  120
CDFDIAGNFD PMIPDAECLK IMCEILSSLQ IGDFLVKVND RRILDGMFAI CGVSDSKFRT  180
ICSSVDKLDK VSWEEVKNEM VGEKGLAPEV ADRIGDYVQQ HGGVSLVEQL LQDPKLSQNK  240
QALEGLGDLK LLFEYLTLFG IDDKISFDLS LARGLDYYTG VIYEAVLLQT PAQAGEEPLG  300
VGSVAAGGRY DGLVGMFDPK GRKVPCVGLS IGVERIFSIV EQRLE                 345

SEQ ID NO: 112          moltype = AA   length = 338
FEATURE                 Location/Qualifiers
source                  1..338
                        mol_type = protein
                        organism = Homo sapiens
SEQUENCE: 112
GTRDYSPRQM AVREKVFDVI IRCFKRHGAE VIDTPVFELK ETLMGKYGED SKLIYDLKDQ   60
GGELLSLRYD LTVPFARYLA MNKLTNIKRY HIAKVYRRDN PAMTRGRYRE FYQCDFDIAG  120
NFDPMIPDAE CLKIMCEILS SLQIGDFLVK VNDRRILDGM FAICGVSDSK FRTICSSVDK  180
LDKVSWEEVK NEMVGEKGLA PEVADRIGDY VQQHGGVSLV EQLLQDPKLS QNKQALEGLG  240
DLKLLFEYLT LFGIDDKISF DLSLARGLDY YTGVIYEAVL LQTPAQAGEE PLGVGSVAAG  300
GRYDGLVGMF DPKGRKVPCV GLSIGVERIF SIVEQRLE                         338

SEQ ID NO: 113          moltype = AA   length = 111
FEATURE                 Location/Qualifiers
source                  1..111
                        mol_type = protein
                        organism = Homo sapiens
SEQUENCE: 113
ALEEKIRTTE TQVLVASAQK KLLEERLKLV SELWDAGIKA ELLYKKNPKL LNQLQYCEEA   60
GIPLVAIIGE QELKDGVIKL RSVTSREEVD VRREDLVEEI KRRTGQPLCI C           111

SEQ ID NO: 114          moltype = AA   length = 96
FEATURE                 Location/Qualifiers
source                  1..96
                        mol_type = protein
                        organism = Homo sapiens
SEQUENCE: 114
TTETQVLVAS AQKKLLEERL KLVSELWDAG IKAELLYKKN PKLLNQLQYC EEAGIPLVAI   60
IGEQELKDGV IKLRSVTSRE EVDVRREDLV EEIKRR                            96

SEQ ID NO: 115          moltype = AA   length = 138
FEATURE                 Location/Qualifiers
VARIANT                 1..50
                        note = Xaa can be absent or any amino acid
source                  1..138
                        mol_type = protein
                        organism = synthetic construct
VARIANT                 52..56
                        note = Xaa can be any naturally occuring amino acid
VARIANT                 57..58
                        note = Xaa can be absent or any amino acid
VARIANT                 61..62
                        note = Xaa is any amino acid
VARIANT                 65
                        note = Xaa is any amino acid
VARIANT                 68..69
                        note = Xaa is any amino acid
VARIANT                 72..78
                        note = Xaa can be any naturally occurring amino acid
VARIANT                 79..80
                        note = Xaa is any amino acid or absent
VARIANT                 82..83
                        note = Xaa is any amino acid
VARIANT                 86
                        note = Xaa is any amino acid
VARIANT                 89..138
                        note = Xaa is any amino acid or absent
SEQUENCE: 115
XXXXXXXXXX XXXXXXXXXX XXXXXXXXXX XXXXXXXXXX XXXXXXXXXX LXXXXXXXQG   60
XXVRXLKXXK AXXXXXXXXX VXXLLXLKXX XXXXXXXXXX XXXXXXXXXX XXXXXXXXXX  120
XXXXXXXXXX XXXXXXXX                                                138

SEQ ID NO: 116          moltype = AA   length = 327
FEATURE                 Location/Qualifiers
```

```
source                  1..327
                        mol_type = protein
                        organism = Homo sapiens
SEQUENCE: 116
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 117          moltype = AA  length = 327
FEATURE                 Location/Qualifiers
REGION                  1..327
                        note = Synthesized IgG4 variant
source                  1..327
                        mol_type = protein
                        organism = synthetic construct
SEQUENCE: 117
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 118          moltype = AA  length = 330
FEATURE                 Location/Qualifiers
source                  1..330
                        mol_type = protein
                        organism = Homo sapiens
SEQUENCE: 118
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 119          moltype = AA  length = 107
FEATURE                 Location/Qualifiers
source                  1..107
                        mol_type = protein
                        organism = Homo sapiens
SEQUENCE: 119
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 120          moltype = AA  length = 800
FEATURE                 Location/Qualifiers
REGION                  1..800
                        note = Synthesized construct - NRP2 (23-595 Fc fusion
                         protein
source                  1..800
                        mol_type = protein
                        organism = synthetic construct
SEQUENCE: 120
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDKTHTCP PCPAPELLGG PSVFLFPPKP   600
KDTLMISRTP EVTCVVVDVS HEDPEVKFNW YVDGVEVHNA KTKPREEQYN STYRVVSVLT   660
VLHQDWLNGK EYKCKVSNKA LPAPIEKTIS KAKGQPREPQ VYTLPPSRDE LTKNQVSLTC   720
LVKGFYPSDI AVEWESNGQP ENNYKTTPPV LDSDGSFFLY SKLTVDKSRW QQGNVFSCSV   780
MHEALHNHYT QKSLSLSPGK                                              800

SEQ ID NO: 121          moltype = AA  length = 654
FEATURE                 Location/Qualifiers
source                  1..654
                        mol_type = protein
                        organism = Homo sapiens
```

```
SEQUENCE: 121
CSKNFTSPNG TIESPGFPEK YPHNLDCTFT ILAKPKMEII LQFLIFDLEH DPLQVGEGDC    60
KYDWLDIWDG IPHVGPLIGK YCGTKTPSEL RSSTGILSLT FHTDMAVAKD GFSARYYLVH   120
QEPLENFQCN VPLGMESGRI ANEQISASST YSDGRWTPQQ SRLHGDDNGW TPNLDSNKEY   180
LQVDLRFLTM LTAIATQGAI SRETQNGYYV KSYKLEVSTN GEDWMVYRHG KNHKVFQANN   240
DATEVVLNKL HAPLLTRFVR IRPQTWHSGI ALRLELFGCR VTDAPCSNML GMLSGLIADS   300
QISASSTQEY LWSPSAARLV SSRSGWFPRI PQAQPGEEWL QVDLGTPKTV KGVIIQGARG   360
GDSITAVEAR AFVRKFKVSY SLNGKDWEYI QDPRTQQPKL FEGNMHYDTP DIRRFDPIPA   420
QYVRVYPERW SPAGIGMRLE VLGCDWTDSK PTVETLGPTV KSEETTTPYP TEEEATECGE   480
NCSFEDDKDL QLPSGFNCNF DFLEEPCGWM YDHAKWLRTT WASSSSPNDR TFPDDRNFLR   540
LQSDSQREGQ YARLISPPVH LPRSPVCMEF QYQATGGRGV ALQVVREASQ ESKLLWVIRE   600
DQGGEWKHGR IILPSYDMEY QIVFEGVIGK GRSGEIAIDD IRISTDVPLE NCME         654

SEQ ID NO: 122         moltype = AA  length = 780
FEATURE                Location/Qualifiers
source                 1..780
                       mol_type = protein
                       organism = Homo sapiens
SEQUENCE: 122
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDSKPTVE TLGPTVKSEE TTTPYPTEEE   600
ATECGENCSF EDDKDLQLPS GFNCNFDFLE EPCGWMYDHA KWLRTTWASS SSPNDRTFPD   660
DRNFLRLQSD SQREGQYARL ISPPVHLPRS PVCMEFQYQA TGGRGVALQV VREASQESKL   720
LWVIREDQGG EWKHGRIILP SYDMEYQIVF EGVIGKGRSG EIAIDDIRIS TDVPLENCME   780

SEQ ID NO: 123         moltype = AA  length = 837
FEATURE                Location/Qualifiers
source                 1..837
                       mol_type = protein
                       organism = Homo sapiens
SEQUENCE: 123
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDSKPTVE TLGPTVKSEE TTTPYPTEEE   600
ATECGENCSF EDDKDLQLPS GFNCNFDFLE EPCGWMYDHA KWLRTTWASS SSPNDRTFPD   660
DRNFLRLQSD SQREGQYARL ISPPVHLPRS PVCMEFQYQA TGGRGVALQV VREASQESKL   720
LWVIREDQGG EWKHGRIILP SYDMEYQIVF EGVIGKGRSG EIAIDDIRIS TDVPLENCME   780
PISAFAVDIP EIHEREGYED EIDDEYEVDW SNSSSATSGS GAPSTDKEKS WLYTLDP      837

SEQ ID NO: 124         moltype = AA  length = 809
FEATURE                Location/Qualifiers
source                 1..809
                       mol_type = protein
                       organism = Homo sapiens
SEQUENCE: 124
QPDPPCGGRL NSKDAGYITS PGYPQDYPSH QNCEWIVYAP EPNQKIVLNF NPHFEIEKHD    60
CKYDFIEIRD GDSESADLLG KHCGNIAPPT IISSGSMLYI KFTSDYARQG AGFSLRYEIF   120
KTGSEDCSKN FTSPNGTIES PGFPEKYPHN LDCTFTILAK PKMEIILQFL IFDLEHDPLQ   180
VGEGDCKYDW LDIWDGIPHV GPLIGKYCGT KTPSELRSST GILSLTFHTD MAVAKDGFSA   240
RYYLVHQEPL ENFQCNVPLG MESGRIANEQ ISASSTYSDG RWTPQQSRLH GDDNGWTPNL   300
DSNKEYLQVD LRFLTMLTAI ATQGAISRET QNGYYVKSYK LEVSTNGEDW MVYRHGKNHK   360
VFQANNDATE VVLNKLHAPL LTRFVRIRPQ TWHSGIALRL ELFGCRVTDA PCSNMLGMLS   420
GLIADSQISA SSTQEYLWSP SAARLVSSRS GWFPRIPQAQ PGEEWLQVDL GTPKTVKGVI   480
IQGARGGDSI TAVEARAFVR KFKVSYSLNG KDWEYIQDPR TQQPKLFEGN MHYDTPDIRR   540
FDPIPAQYVR VYPERWSPAG IGMRLEVLGC DWTDSKPTVE TLGPTVKSEE TTTPYPTEEE   600
ATECGENCSF EDDKDLQLPS GFNCNFDFLE EPCGWMYDHA KWLRTTWASS SSPNDRTFPD   660
DRNFLRLQSD SQREGQYARL ISPPVHLPRS PVCMEFQYQA TGGRGVALQV VREASQESKL   720
LWVIREDQGG EWKHGRIILP SYDMEYQIVF EGVIGKGRSG EIAIDDIRIS TDVPLENCME   780
PISAFAGGTL LPGTEPTVDT VPMQPIPAY                                     809

SEQ ID NO: 125         moltype = DNA  length = 24
FEATURE                Location/Qualifiers
misc_feature           1..24
                       note = Primer
```

```
source                1..24
                      mol_type = other DNA
                      organism = synthetic construct
SEQUENCE: 125
tgaggatgac aaagatttgc agct                                              24

SEQ ID NO: 126        moltype = DNA  length = 36
FEATURE               Location/Qualifiers
misc_feature          1..36
                      note = Primer
source                1..36
                      mol_type = other DNA
                      organism = synthetic construct
SEQUENCE: 126
accgcggccg gccgtttatg cctcggagca gcactt                                 36

SEQ ID NO: 127        moltype = DNA  length = 22
FEATURE               Location/Qualifiers
misc_feature          1..22
                      note = Primer
source                1..22
                      mol_type = other DNA
                      organism = synthetic construct
SEQUENCE: 127
agtgccaagc aagcaactca aa                                                22

SEQ ID NO: 128        moltype = DNA  length = 36
FEATURE               Location/Qualifiers
misc_feature          1..36
                      note = Primer
source                1..36
                      mol_type = other DNA
                      organism = synthetic construct
SEQUENCE: 128
aagtgctgct ccgaggcata aacggccggc cgcggt                                 36
```